United States Patent
Lam et al.

(10) Patent No.: US 8,901,115 B2
(45) Date of Patent: Dec. 2, 2014

(54) CYCLIC P1 LINKERS AS FACTOR XIA INHIBITORS

(75) Inventors: Patrick Y. S. Lam, Chadds Ford, PA (US); Charles G. Clark, Cherry Hill, NJ (US); James R. Corte, Lawrenceville, NJ (US); William R. Ewing, Yardley, PA (US); Paul J. Gilligan, Wilmington, DE (US); Yoon Jeon, Belle Mead, NJ (US); Wu Yang, Princeton Junction, NJ (US); Leon M. Smith, II, Somerset, NJ (US); Yufeng Wang, North Brunswick, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/236,968

(22) PCT Filed: Aug. 6, 2012

(86) PCT No.: PCT/US2012/049698
§ 371 (c)(1),
(2), (4) Date: Feb. 4, 2014

(87) PCT Pub. No.: WO2013/022814
PCT Pub. Date: Feb. 14, 2013

(65) Prior Publication Data
US 2014/0163002 A1 Jun. 12, 2014

Related U.S. Application Data

(60) Provisional application No. 61/515,404, filed on Aug. 5, 2011.

(51) Int. Cl.
C07D 471/06 (2006.01)
C07D 487/06 (2006.01)
A61K 31/505 (2006.01)
A61K 31/5365 (2006.01)
A61K 31/4985 (2006.01)
A61P 7/00 (2006.01)
C07D 498/06 (2006.01)

(52) U.S. Cl.
CPC ............ C07D 498/06 (2013.01); C07D 471/06 (2013.01); C07D 487/06 (2013.01)
USPC .................. 514/228.8; 514/252.13; 514/256; 514/290; 514/292; 514/317; 514/318; 514/319; 514/321; 514/322; 540/460; 540/461; 540/463; 540/472; 540/479

(58) Field of Classification Search
USPC .......................... 540/460, 461, 463, 472, 479; 514/228.8, 252.13, 256, 290, 292, 317, 514/318, 319, 321, 322
See application file for complete search history.

(56) References Cited

FOREIGN PATENT DOCUMENTS

| WO | WO 03/011222 | 2/2003 |
|---|---|---|
| WO | WO 2004/080971 | 9/2004 |
| WO | WO 2004/094372 | 11/2004 |
| WO | WO 2005/099709 | 10/2005 |
| WO | WO 2005/123050 | 12/2005 |
| WO | WO 2005/123680 | 12/2005 |
| WO | WO 2006/076575 | 7/2006 |
| WO | WO 2006/089005 | 8/2006 |
| WO | WO 2007/070816 | 6/2007 |
| WO | WO 2007/070818 | 6/2007 |
| WO | WO 2007/070826 | 6/2007 |
| WO | WO 2007/076431 | 7/2007 |
| WO | WO 2008/076805 | 6/2008 |
| WO | WO 2008/157162 | 12/2008 |
| WO | WO 2009/114677 | 9/2009 |
| WO | WO 2011/100401 | 8/2011 |
| WO | WO 2011/100402 | 8/2011 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2014/022766 | 2/2014 |
| WO | WO 2014/022767 | 2/2014 |
| WO | WO 2014/059202 | 4/2014 |
| WO | WO 2014/059203 | 4/2014 |
| WO | WO 2014/059214 | 4/2014 |

*Primary Examiner* — Bruck Kifle
(74) *Attorney, Agent, or Firm* — Hong Liu

(57) ABSTRACT

The present invention provides compounds of Formula (Ia): or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

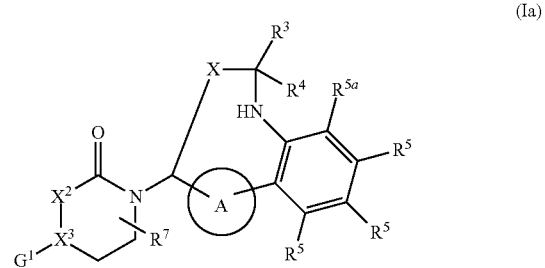

(Ia)

12 Claims, No Drawings

CYCLIC P1 LINKERS AS FACTOR XIA INHIBITORS

FIELD OF THE INVENTION

The present invention relates generally to novel macrocyclic compounds, and their analogues thereof, which are inhibitors of factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for antithrombotic therapy.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (Ia):

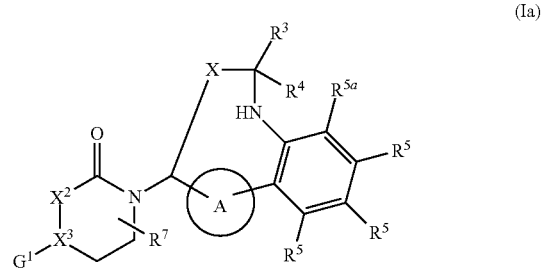

(Ia)

or stereoisomers, tautomers, pharmaceutically acceptable salts, solvates, or prodrugs thereof, wherein:

$G^1$ is selected from the group consisting of a 6-membered aryl and a 5- to 6-membered heteroaryl wherein said aryl and heteroaryl are substituted with 1-5 $R^8$;

ring A is selected from the group consisting of a 6-membered aryl and a 5- to 6-membered heterocycle, wherein said aryl and heterocycle are substituted with 1-3 $R^{13}$;

X is selected from the group consisting of $C_{4-8}$ alkylene and $C_{4-8}$ alkenylene, wherein said alkylene and alkenylene are substituted with $R^1$, $R^{2t}$ and $R^6$; alternatively one or more of the carbon atoms of said alkylene and alkenylene may be replaced by O, C=O, S(O)$_p$, NH, and N(C$_{1-4}$ alkyl);

$X^2$ is selected from the group consisting of $CHR^{11}$, C=O, O, NH, and N(C$_{1-4}$ alkyl);

$X^3$ is $CR^{12}$ or N, provided $X^3$ is $CR^{12}$ when $X^2$ is O, NH, or N(C$_{1-4}$ alkyl);

$R^1$ and $R^2$ are independently selected from the group consisting of H, halogen, $C_{1-6}$ alkyl, OH, NH$_2$, —CH$_2$NH$_2$, $C_{1-4}$ haloalkyl, —OCH$_2$F, —OCHF$_2$, —OCF$_3$, NH($C_{1-4}$ alkyl), N($C_{1-4}$ alkyl)$_2$, $C_{1-4}$ alkoxy, —CH$_2$OH, and —CH$_2$O($C_{1-4}$ alkyl); alternatively, $R^1$ and $R^2$ are taken together with the carbon atoms to which they are attached to form a carbocycle;

$R^3$ is selected from the group consisting of H, haloalkyl, —C(=O)OH, —C(=O)O—$C_{1-4}$ alkyl, and —C(=O)NR$^9$R$^{10}$;

$R^4$ is selected from the group consisting of H and $C_{1-6}$ alkyl; alternatively, $R^3$ and $R^4$ together are =O;

$R^5$ is independently selected from the group consisting of H, halogen, $C_{1-4}$alkyl, OH, CN, NR$^9$R$^{10}$, NO$_2$, $C_{1-4}$ alkoxy, —C(=O)OH, —C(=O)O($C_{1-4}$ alkyl), —C(=O)NH$_2$, C(=O)NR$^9$($C_{1-4}$ alkyl), —C(=O)NR$^9$—$C_{1-4}$ alkylene-O ($C_{1-4}$ alkyl), —NR$^9$C(=O)$C_{1-4}$ alkyl, —NR$^9$C(=O)OC$_{1-4}$ alkyl, —NR$^9$C(=O)$C_{1-4}$ alkylene-O($C_{1-4}$ alkyl), —NR$^9$C (=O)OC$_{1-4}$ alkylene-O($C_{1-4}$ alkyl), —NR$^9$C(=O)NH($C_{1-4}$ alkyl), $R^{15}$, —C(=O)O$R^{15}$, —C(=O)N$R^9R^{15}$, —N$R^9R^{15}$, —N$R^9$C(=O)$R^{15}$, and —N$R^9$C(=O)O$R^{15}$;

$R^{5a}$ is selected from the group consisting of H, halogen, and methyl;

$R^6$ is selected from the group consisting of H, $C_{1-6}$ alkyl, and OH;

$R^7$ is selected from the group consisting of H, $^2$H, F, =O, OH, and $C_{1-4}$ alkyl;

$R^8$ is selected from the group consisting of H, halogen, OH, CN, $C_{1-6}$ alkyl, haloalkyl, alkoxy, haloalkoxy, and —C(=O)$C_{1-3}$ alkyl;

$R^9$ is selected from the group consisting of H and $C_{1-6}$ alkyl;

$R^{10}$ is selected from the group consisting of H and $C_{1-6}$ alkyl;

alternatively, $R^9$ and $R^{10}$ are taken together with the nitrogen atom to which they are attached to form a 4- to 7-membered heterocycle substituted with $R^{14}$;

$R^{11}$ is selected from the group consisting of H and $C_{1-6}$ alkyl;

$R^{12}$ is selected from the group consisting of H, $^2$H, and $C_{1-6}$ alkyl;

$R^{13}$ is selected from the group consisting of H, OH, halogen, CN, $C_{1-6}$ alkyl, alkoxy, haloalkyl, haloalkoxy, and $C_{3-6}$ cycloalkyl;

$R^{14}$ is selected from the group consisting of H, OH, halogen, and $C_{1-6}$ alkyl;

$R^{15}$ is selected from the group consisting of: —(CH$_2$)$_n$—$C_{3-10}$ carbocycle and —(CH$_2$)$_n$-4-10 membered heterocycle, wherein said carbocycle and heterocycle are optionally substituted with $C_{1-6}$ alkyl, $C_{3-6}$ cycloalkyl, —(CH$_2$)$_n$—C(=O)O$C_{1-4}$ alkyl, —(CH$_2$)$_n$—O$C_{1-4}$ alkyl, and =O;

n, at each occurrence, is selected from 0, 1, 2, 3 and 4; and
p, at each occurrence, is selected from 0, 1, and 2.

In another aspect, the present invention provides compounds of Formula (IIa):

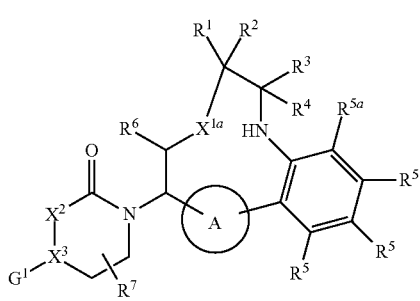

(IIa)

or stereoisomers, tautomers, pharmaceutically acceptable salts, solvates, or prodrugs thereof, wherein:

$G^1$ is selected from the group consisting of a 6-membered aryl and heteroaryl comprising carbon atoms and 1-2 heteroatoms selected from N, NH, and N($C_{1-4}$ alkyl), wherein said aryl and heterocycle are substituted with 1-4 $R^8$;

$X^{1a}$ is selected from the group consisting of $C_{2-4}$ alkylene and $C_{2-4}$ alkenylene wherein said $C_{2-4}$ alkylene and $C_{2-4}$ alkenylene are optionally substituted with $R^1$ and $R^2$; alternatively one or more of the carbon atoms of said alkylene may be replaced by O and C=O;

$R^1$ and $R^2$ are independently selected from the group consisting of H, halogen, $C_{1-6}$ alkyl, OH, NH$_2$, $C_{1-4}$ haloalkyl, —OCHF$_2$, —OCF$_3$;

$R^3$ is selected from the group consisting of H, haloalkyl, —C(=O)OH, —C(=O)O—$C_{1-4}$ alkyl, and —C(=O)N$R^9R^{10}$;

$R^4$ is selected from the group consisting of H and $C_{1-4}$ alkyl; optionally, $R^3$ and $R^4$ together are =O;

$R^5$ is independently selected from the group consisting of H, halogen, —NHC(=O)O—$C_{1-4}$ alkyl, —NHC(=O)O(CH$_2$)$_{1-4}$—O$C_{1-4}$ alkyl, —C(=O)NH$_2$, —C(=O)O—$C_{1-4}$ alkyl, —C(=O)OH, CN, OH, and —O—$C_{1-4}$ alkyl, $R^{15}$, and —N$R^9R^{15}$;

$R^{5a}$ is selected from the group consisting of H, halogen, and methyl;

$R^7$ is selected from the group consisting of H, F, =O, OH, methyl, ethyl, and isopropyl;

$R^8$ is selected from the group consisting of H, halogen, OH, CN, $C_{1-4}$ alkyl, haloalkyl, alkoxy, haloalkoxy, and —C(=O)$C_{1-3}$ alkyl;

$R^9$ is selected from the group consisting of H and $C_{1-6}$ alkyl;

$R^{10}$ is selected from the group consisting of H and $C_{1-6}$ alkyl;

$R^9$ and $R^{10}$ are taken together with the nitrogen atom to which they are attached to form a 4- to 7-membered heterocycle; and $R^{15}$ is selected from the group consisting of —(CH$_2$)$_n$—$C_{3-10}$ carbocycle and —(CH$_2$)$_n$-4-10 membered heterocycle comprising carbon atoms and 1-4 heteroatoms selected from the group consisting of N, NH, N($C_{1-4}$ alkyl), O, and S(O)$_p$; wherein said carbocycle and heterocycle are optionally substituted with $C_{1-6}$ alkyl, $C_{3-6}$ cycloalkyl, —(CH$_2$)$_n$—C(=O)O$C_{1-4}$ alkyl, —(CH$_2$)$_n$—O$C_{1-4}$ alkyl, and =O.

In another aspect, the present invention provides compounds of Formula (IIa) or stereoisomers, tautomers, pharmaceutically acceptable salts, solvates, or prodrugs thereof, wherein:

$G^1$ is selected from the group consisting of

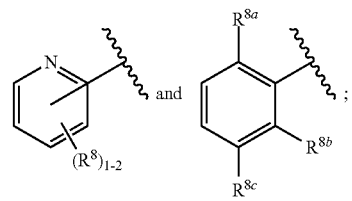

$R^8$ is selected from the group consisting of H, halogen, $C_{1-4}$ alkyl, and haloalkyl;

$R^{8a}$ and $R^{8c}$ are each independently selected from the group consisting of H, halogen, CN, $C_{1-4}$ alkyl, haloalkyl, alkoxy, haloalkoxy, and —C(=O)$C_{1-3}$ alkyl; and $R^{8b}$ is selected from the group consisting of H and halogen.

In another aspect, the present invention provides compounds of Formula (IIa) or stereoisomers, tautomers, pharmaceutically acceptable salts, solvates, or prodrugs thereof, wherein:

ring A is selected from the group consisting of phenyl, imidazole, pyridine, pyridazine, pyrimidine, pyridone, and pyridazinone.

In another aspect, the present invention provides compounds of Formula (IIIa):

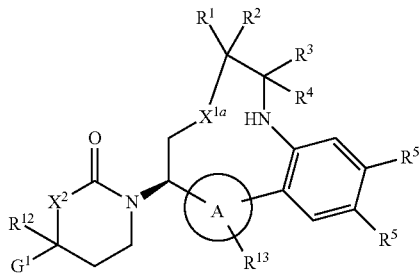
(IIIa)

or stereoisomers, tautomers, pharmaceutically acceptable salts, solvates, or prodrugs thereof, wherein:

$G^1$ is selected from the group consisting of

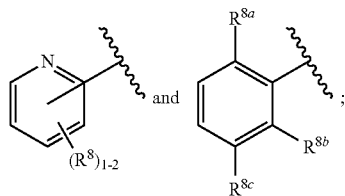

ring A is selected from the group consisting of

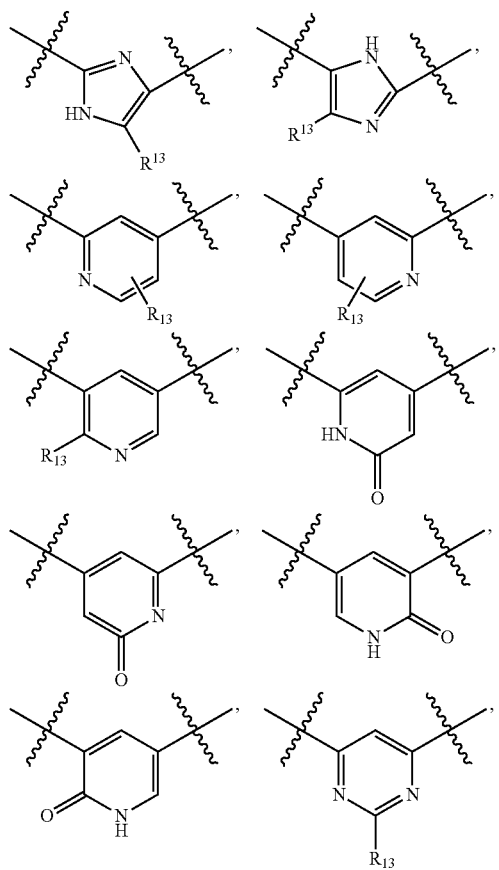

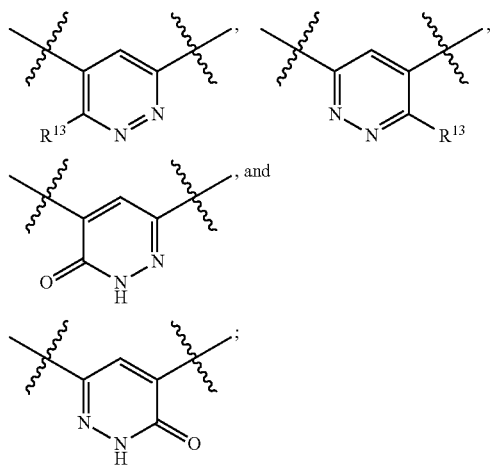

$X^{1a}$ is selected from the group consisting of —$CR^1R^2$—$CR^1R^2$—, —$CR^1R^2$—$CR^1R^2$—$CR^1R^2$—, and —$CR^1$=$CR^2CR^1R^2$—, wherein one or more —$CR^1R^2$— may be replaced by O or C=O;

$X^2$ is selected from the group consisting of $CH_2$, O, NH, and $N(C_{1-4}$ alkyl);

$R^1$ and $R^2$ are independently selected from the group consisting of H, F, $C_{1-6}$ alkyl, OH, $CF_3$, $OCHF_2$, $OCF_3$;

$R^3$ is selected from the group consisting of H, haloalkyl, C(=O)OH, C(=O)O—$C_{1-4}$ alkyl, and C(=O)$NR^9R^{10}$;

$R^4$ is selected from the group consisting of H and $C_{1-6}$ alkyl; optionally, $R^3$ and $R^4$ together are =O;

$R^5$ is selected from the group consisting of H, halogen, NHC(=O)O—$C_{1-4}$ alkyl, NHC(=O)O(CH$_2$)$_2$—$OC_{1-4}$ alkyl, C(=O)$NH_2$, C(=O)O—$C_{1-4}$ alkyl, C(=O)OH, $R^{15}$, and —$NHR^{15}$;

$R^8$ is selected from the group consisting of H, F, Cl, Br, $CH_3$ and $CF_3$;

$R^{8a}$ and $R^{8c}$ are each independently selected from the group consisting of H, halogen, CN, $CH_3$, $OCH_3$, $CF_3$, and $OCHF_2$;

$R^{8b}$ is selected from the group consisting of H, F, and Cl;

$R^9$ is selected from the group consisting of H and $C_{1-6}$ alkyl;

$R^{10}$ is selected from the group consisting of H and $C_{1-6}$ alkyl;

alternatively, $R^9$ and $R^{10}$ are taken together with the nitrogen atom to which they are attached to form a 4- to 7-membered heterocycle optionally substituted with $R^{14}$; and $R^{12}$ is selected from the group consisting of H, $^2H$, and methyl;

$R^{13}$ is selected from the group consisting of H, OH, halogen, CN, $C_{1-4}$ alkyl, and $OC_{1-4}$ alkyl;

$R^{14}$ is selected from the group consisting of H, OH, halogen, and $C_{1-6}$ alkyl;

$R^{15}$ is a 4- to 10-membered heterocycle comprising carbon atoms and 1-4 heteroatoms selected from the group consisting of N, NH, $N(C_{1-4}$ alkyl), O, and $S(O)_p$ optionally substituted with $C_{1-6}$ alkyl, $C_{3-6}$ cycloalkyl, —$(CH_2)_n$—C(=O)$OC_{1-4}$ alkyl, —$(CH_2)_n$—$OC_{1-4}$ alkyl, and =O.

In another aspect, the present invention provides compounds of Formula (IVa):

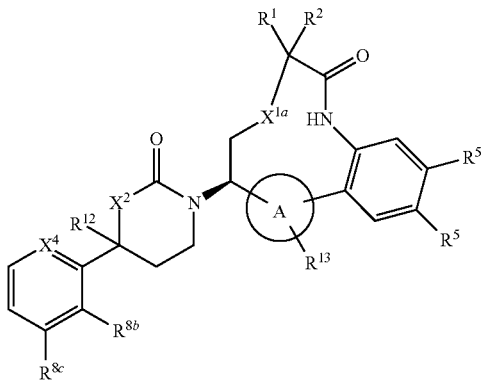

(IVa)

or stereoisomers, tautomers, pharmaceutically acceptable salts, solvates, or prodrugs thereof, wherein:
ring A is selected from the group consisting of

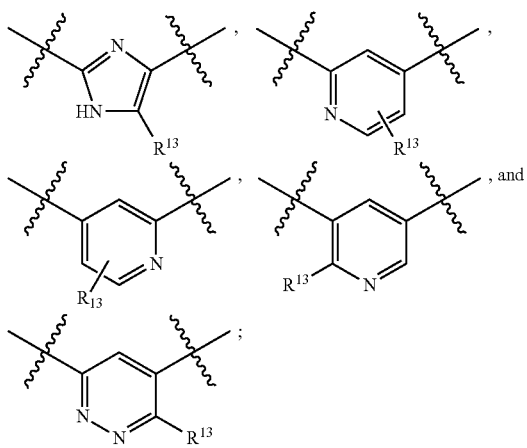

$X^{1a}$ is selected from the group consisting of $CH_2CH_2$ and $CH=CHCH_2$;
$X^2$ is selected from the group consisting of $CH_2$, O, and NH;
$X^4$ is selected from the group consisting of $CR^{8a}$ and N;
$R^1$ is selected from the group consisting of H, F, methyl, ethyl, and isopropyl;
$R^2$ is selected from the group consisting of H and F;
$R^{12}$ is selected from the group consisting of H, $^2$H, and methyl;
$R^5$ is selected from the group consisting of H, halogen, —NHC(=O)O—$C_{1-4}$ alkyl, —NHC(=O)O($CH_2$)$_2$—O$C_{1-4}$ alkyl, —C(=O)NH$_2$, —C(=O)O—$C_{1-4}$ alkyl, —C(=O)OH, and NH—$R^{15}$;
$R^{8a}$ is selected from the group consisting of H, F, Cl, Br, CN, OCH$_3$, CF$_3$, and OCHF$_2$;
$R^{8b}$ is selected from the group consisting of H and F;
$R^{8c}$ is selected from the group consisting of H, F, Cl, OH, CH$_3$, OCH$_3$, and CF$_3$;
$R^{12}$ is selected from the group consisting of H and $^2$H;
$R^{13}$ is selected from the group consisting of H, OH, F, Cl, O$C_{1-4}$ alkyl, and CN;

$R^{15}$ is a 5- to 10-membered heterocycle comprising carbon atoms and 1-4 heteroatoms selected from the group consisting of N, NH, N($C_{1-4}$ alkyl), O, and S(O)$_p$ optionally substituted with $C_{1-6}$ alkyl, $C_{3-6}$ cycloalkyl, —$CH_2C(=O)OC_{1-4}$ alkyl, —$CH_2OC_{1-4}$ alkyl, and =O.

In another aspect, the present invention provides compounds of Formula (Va):

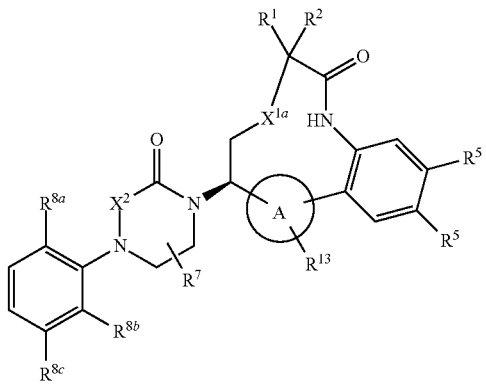

(Va)

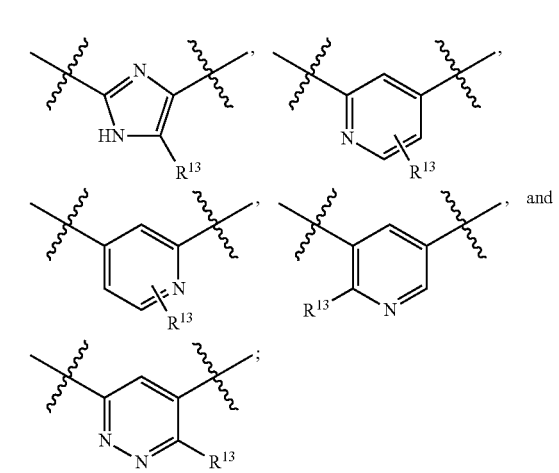

or stereoisomers, tautomers, pharmaceutically acceptable salts, solvates, or prodrugs thereof, wherein:
ring A is selected from the group consisting of $X^{1a}$ is selected from the group consisting of $CH_2CH_2$ and $CH=CHCH_2$;
$X^2$ is selected from the group consisting of $CHR^{11}$, and C=O;
$R^1$ is selected from the group consisting of H, methyl, ethyl;
$R^2$ is H;
$R^5$ is selected from the group consisting of NHC(O)OMe, C(O)OH and NH—$R^{15}$;
$R^7$ is selected from the group consisting of H, =O, OH, and methyl;
$R^{8a}$ is selected from the group consisting of H, F, Cl, methyl, and CF$_3$;
$R^{8b}$ is selected from the group consisting of H and F
$R^{8c}$ is selected from the group consisting of H and Cl;
$R^{11}$ is selected from the group consisting of H and $C_{1-4}$ alkyl;

$R^{13}$ is selected from the group consisting of H, F, Cl, and CN; and $R^{15}$ is a 5- to 10-membered heterocycle comprising carbon atoms and 1-4 heteroatoms selected from the group consisting of N, NH, N($C_{1-4}$ alkyl), O, and S(O)$_p$ optionally substituted with $C_{1-6}$ alkyl, $C_{3-6}$ cycloalkyl, —$CH_2C$(=O)O$C_{1-4}$ alkyl, —$CH_2OC_{1-4}$ alkyl, and =O.

In another aspect, the present invention provides compounds of Formula (IIa) or stereoisomers, tautomers, pharmaceutically acceptable salts, solvates, or prodrugs thereof, wherein:

$G^1$ is selected from the group consisting of

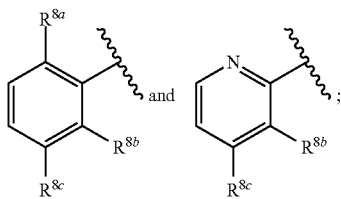

ring A is selected from the group consisting of

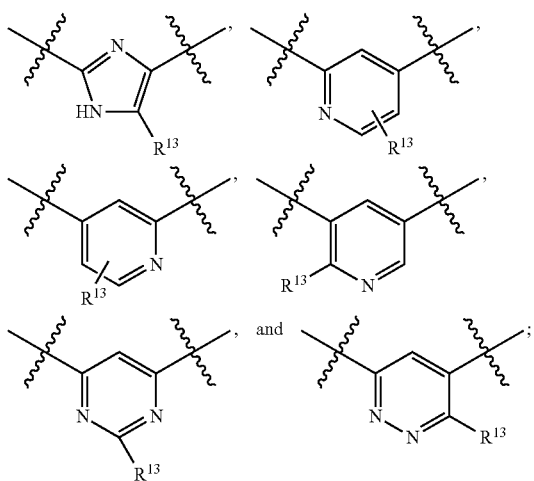

$X^{1a}$ is selected from the group consisting of $CH_2CH_2$ and CH=CHCH$_2$;

$X^2$ is selected from the group consisting of $CH_2$, C=O, O, and NH;

$X^3$ is CH or N; provided when $X^2$ is O or NH, $X^3$ is CH;

$R^1$ is selected from the group consisting of H, methyl, and ethyl;

$R^2$ is H;

$R^3$ is selected from the group consisting of C(=O)OH and C(=O)OMe;

$R^4$ is H; or $R^3$ and $R^4$ together are =O;

$R^5$ is selected from the group consisting of NHC(=O)OMe, C(=O)OH, and NHC(=O)O(CH$_2$)$_2$OCH$_3$;

$R^7$ is selected from the group consisting of H, methyl, =O, and OH;

$R^{8a}$ is selected from the group consisting of H, F, Cl, Br, CN, CH$_3$, OCH$_3$, CF$_3$, and OCHF$_2$;

$R^{8b}$ is selected from the group consisting of H and F;

$R^{8c}$ is selected from the group consisting of H, Cl, CH$_3$, and OCH$_3$;

$R^{12}$ is selected from the group consisting of H, and $^2$H; and $R^{13}$ is selected from the group consisting of H, F, Cl, OCH$_3$, and CN.

In still another aspect, the present invention provides compounds of Formula (I):

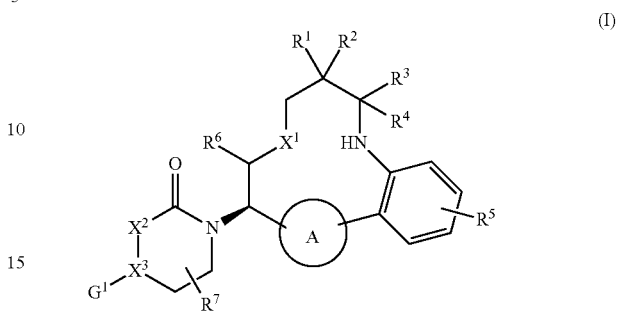

or stereoisomers, tautomers, pharmaceutically acceptable salts, solvates, or prodrugs thereof, wherein:

$G^1$ is selected from the group consisting of a 6-membered aryl and a 5- to 6-membered heteroaryl wherein said aryl and heteroaryl are optionally substituted with 1-4 $R^8$;

ring A is selected from the group consisting of a 6-membered aryl and a 5- to 6-membered heterocycle, wherein said aryl and heterocycle are optionally substituted with 1-3 $R^{13}$;

$X^1$ is selected from the group consisting of $C_{1-4}$ alkylene and $C_{2-4}$ alkenylene; optionally one or more of the carbon atoms of said alkylene may be replaced by O, S(O)$_p$, NH, and N($C_{1-4}$ alkyl);

$X^2$ is selected from the group consisting of CHR$^{11}$, O, NH, and N($C_{1-4}$ alkyl);

$X^3$ is CR$^{12}$ or N, provided when $X^2$ is O, NH, and N($C_{1-4}$ alkyl), $X^3$ is CR$^{12}$;

$R^1$ is selected from the group consisting of H, halogen, CF$_3$, $C_{1-6}$ alkyl, and hydroxyl;

$R^2$ is selected from the group consisting of H and $C_{1-6}$ alkyl;

$R^3$ is selected from the group consisting of H, haloalkyl, C(O)OH, C(O)O—$C_{1-4}$ alkyl, and C(O)NR$^9$R$^{10}$;

$R^4$ is selected from the group consisting of H and $C_{1-6}$ alkyl; optionally, $R^3$ and $R^4$ together are =O;

$R^5$ is selected from the group consisting of H, halogen, NHC(O)O—$C_{1-4}$ alkyl, CONH$_2$, CO$_2$—$C_{1-4}$ alkyl, COOH, CN, OH, and O—$C_{1-4}$ alkyl;

$R^6$ is selected from the group consisting of H, $C_{1-6}$ alkyl, and OH;

$R^7$ is selected from the group consisting of H, F, methyl, ethyl, and isopropyl;

$R^8$ is selected from the group consisting of H, halogen, OH, CN, $C_{1-6}$ alkyl, haloalkyl, alkoxy, and haloalkoxy;

$R^9$ is selected from the group consisting of H and $C_{1-6}$ alkyl;

$R^{10}$ is selected from the group consisting of H and $C_{1-6}$ alkyl;

alternatively, $R^9$ and $R^{10}$ are taken together with the nitrogen atom to which they are attached to form a 4- to 7-membered heterocycle optionally substituted with $R^{14}$;

$R^{11}$ is selected from the group consisting of H and $C_{1-6}$ alkyl;

$R^{12}$ is selected from the group consisting of H and $C_{1-6}$ alkyl;

$R^{13}$ is selected from the group consisting of H, =O, halogen, $C_{1-6}$ alkyl, CF$_3$ and CN;

$R^{14}$ is selected from the group consisting of H, OH, halogen, and $C_{1-6}$ alkyl; and p, at each occurrence, is selected from 0, 1, and 2.

In still another aspect, the present invention provides compounds of Formula (II):

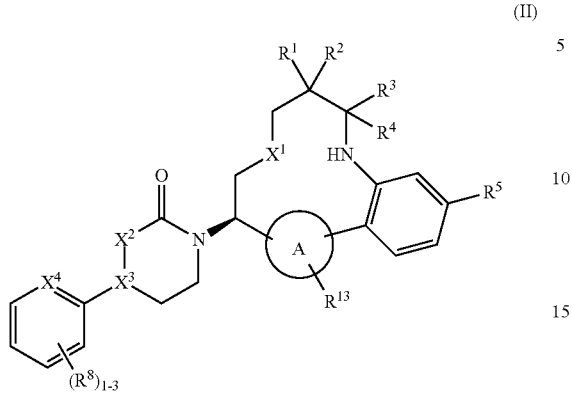
(II)

or stereoisomers, tautomers, pharmaceutically acceptable salts, solvates, or prodrugs thereof, within the scope of the first aspect, wherein:

$X^1$ is selected from the group consisting of $CH_2$ and $CH=CH$;

$X^4$ is selected from the group consisting of CH, $CR^8$, and N; and $R^8$ is selected from the group consisting of H, halogen, $C_{1-6}$ alkyl, alkoxy, haloalkyl, and haloalkoxy.

In still another aspect, the present invention provides compounds of Formula (II), or stereoisomers, tautomers, pharmaceutically acceptable salts, solvates, or prodrugs thereof, within the scope of the second aspect, wherein:

ring A is selected from the group consisting of imidazole, pyridine, pyridone, pyridazine, pyridazinone, and pyrimidine.

In still another aspect, the present invention provides compounds of Formula (III):

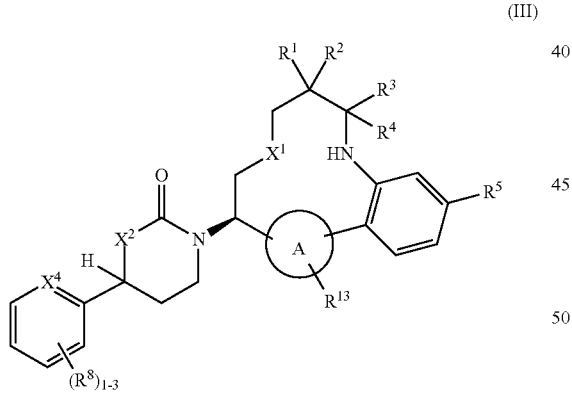
(III)

or stereoisomers, tautomers, pharmaceutically acceptable salts, solvates, or prodrugs thereof, within the scope of the third aspect, wherein:

ring A is selected from the group consisting of

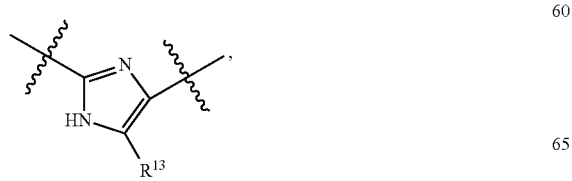

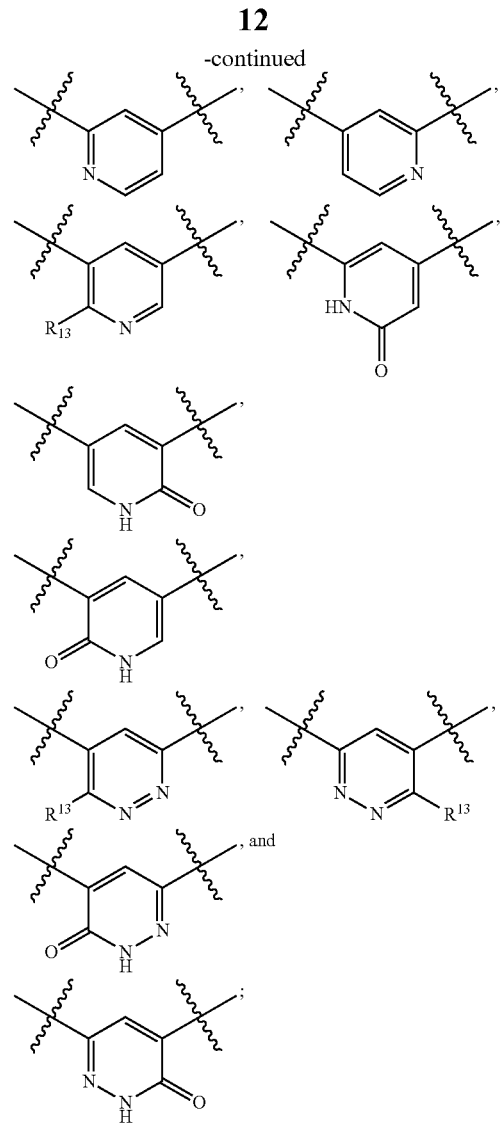

and $R^{13}$ is selected from the group consisting of H, $C_{1-4}$ alkyl, halogen, and CN.

In still another aspect, the present invention provides compounds of Formula (IV):

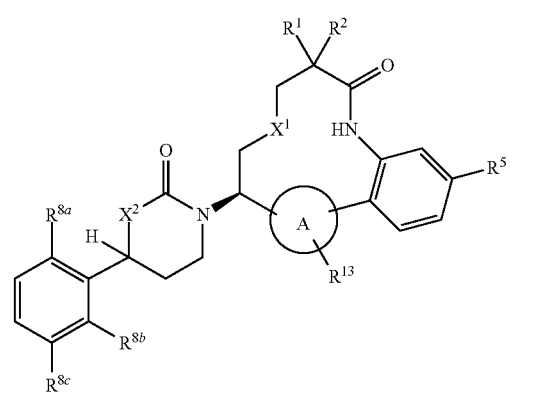
(IV)

or stereoisomers, tautomers, pharmaceutically acceptable salts, solvates, or prodrugs thereof, within the scope of the fourth aspect, wherein:

ring A is selected from the group consisting of

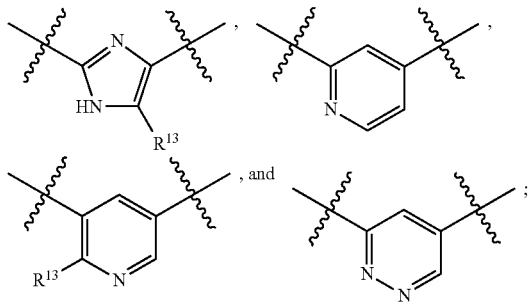

$X^1$ is selected from the group consisting of $CH_2$ and CH=CH;

$X^2$ is selected from the group consisting of $CH_2$, O, and NH;

$R^1$ is selected from the group consisting of H, methyl, ethyl, and isopropyl;

$R^2$ is H;

$R^5$ is NHC(O)OMe;

$R^{8a}$, $R^{8b}$, and $R^{8c}$ are independently selected from the group consisting of H, F, Cl, $OCH_3$, $CF_3$ and $OCHF_2$; and $R^{13}$ is selected from the group consisting of H, F, Cl, and CN.

In still another aspect, the present invention provides compounds of Formula (V):

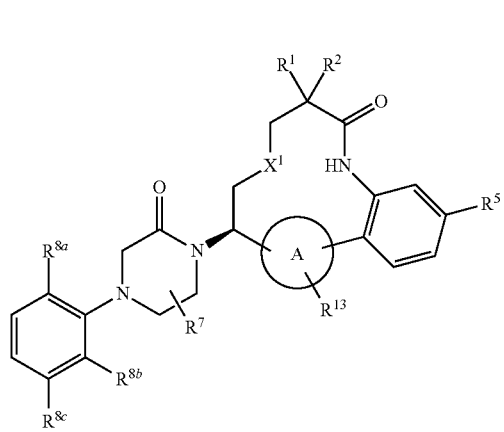

(V)

or stereoisomers, tautomers, pharmaceutically acceptable salts, solvates, or prodrugs thereof, within the scope of the second aspect, wherein:

ring A is selected from the group consisting of

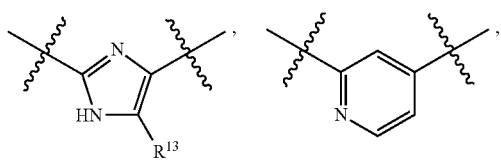

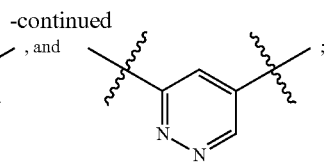

$X^1$ is selected from the group consisting of $CH_2$ and CH=CH;

$R^1$ is selected from the group consisting of H and methyl;

$R^2$ is H;

$R^5$ is NHC(O)OMe;

$R^7$ is selected from the group consisting of H and methyl;

$R^{8a}$, $R^{8b}$, and $R^{8c}$ are independently selected from the group consisting of H, F, Cl, and methyl; and $R^{13}$ is selected from the group consisting of H, F, Cl, and CN.

In still another aspect, the present invention provides compounds of Formula (I) or stereoisomers, tautomers, pharmaceutically acceptable salts, solvates, or prodrugs thereof, wherein:

$G^1$ is selected from the group consisting of

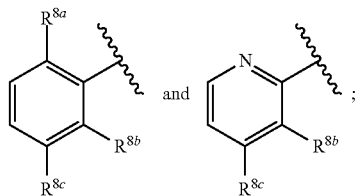

ring A is selected from the group consisting of

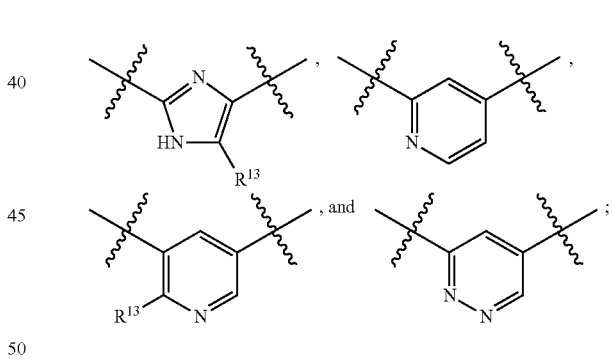

$X^1$ is selected from the group consisting of $CH_2$ and CH=CH;

$X^2$ is selected from the group consisting of $CH_2$, O, and NH;

$X^3$ is CH or N; provided when $X^2$ is O or NH, $X^3$ is CH;

$R^1$ is selected from the group consisting of H and methyl;

$R^2$ is H;

$R^3$ is selected from the group consisting of C(O)OH and C(O)OMe;

$R^4$ is H; or $R^3$ and $R^4$ together are =O;

$R^5$ is NHC(O)OMe;

$R^{8a}$, $R^{8b}$, and $R^{8c}$ are independently selected from the group consisting of H, F, Cl, $OCH_3$, $CF_3$, and $OCHF_2$; and $R^{13}$ is selected from the group consisting of H, F, Cl, and CN.

In one embodiment, $G^1$ is selected from the group consisting of

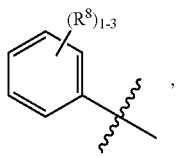

wherein $R^8$ is, independently at each occurrence, selected from the group consisting of H, halogen, OH, CN, $C_{1-6}$ alkyl, haloalkyl, alkoxy, and haloalkoxy.

In another embodiment, $G^1$ is

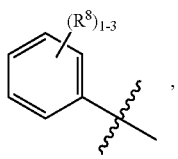

wherein $R^8$ is, independently at each occurrence, selected from the group consisting of H, halogen, OH, CN, methyl, ethyl, $CF_3$, $CHF_2$, OMe, OEt, $OCF_3$, $OCHF_2$, and —C(=O)$C_{1-3}$ alkyl.

In another embodiment, $G^1$ is

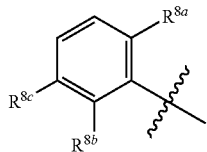

and selected from the group consisting of

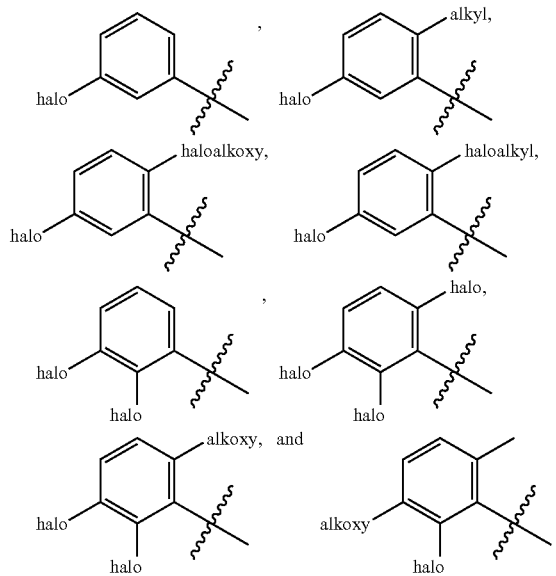

In another embodiment, $G^1$ is

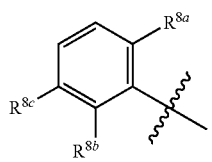

wherein $R^{8a}$, $R^{8b}$, and $R^{8c}$ are independently selected from the group consisting of H, F, Cl, $OCH_3$, $CF_3$, $OCHF_2$, and —C(=O)$C_{1-3}$ alkyl.

In another embodiment, $R^{8a}$ is selected from the group consisting of H, F, $OCH_3$, $OCHF_2$, and —C(=O)$C_{1-3}$ alkyl.

In another embodiment, $R^{8b}$ is selected from the group consisting of H, F and Cl.

In another embodiment, $R^{8b}$ is selected from the group consisting of H and F.

In another embodiment, $R^{8c}$ is Cl.

In another embodiment, $G^1$ is

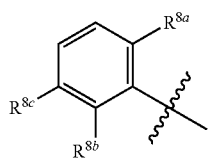

and selected from the group consisting of

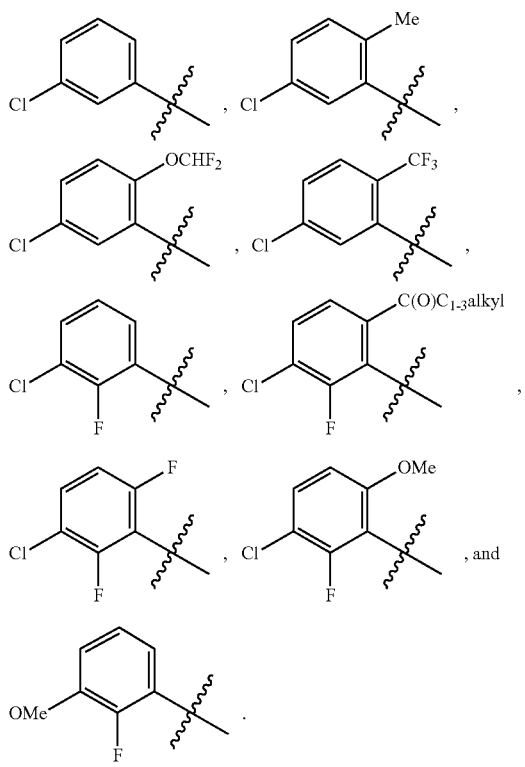

In another embodiment, $G^1$ is

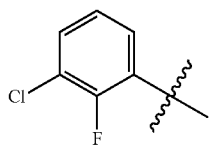.

In one embodiment, the present invention provides compounds of Formulae (Ia), (IIa), (IIIa), (IVa), (Va), (I), (II), (III), (IV), and (V), or stereoisomers, tautomers, pharmaceutically acceptable salts, solvates, or prodrugs thereof, wherein ring A is independently selected from the group consisting of imidazole, oxadiazole, pyridine, pyridinone, pyrimidine, pyridazine, pyridazinone, and phenyl.

In another embodiment,

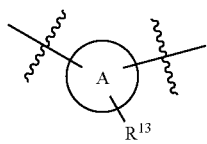

is independently selected from the group consisting of

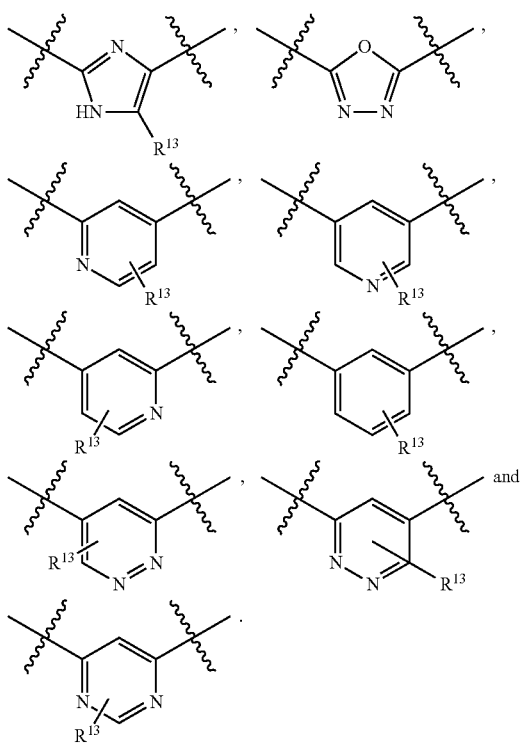

In another embodiment,

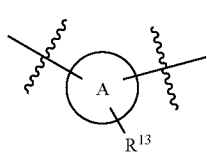

is independently selected from the group consisting of ring A is selected from the group consisting of

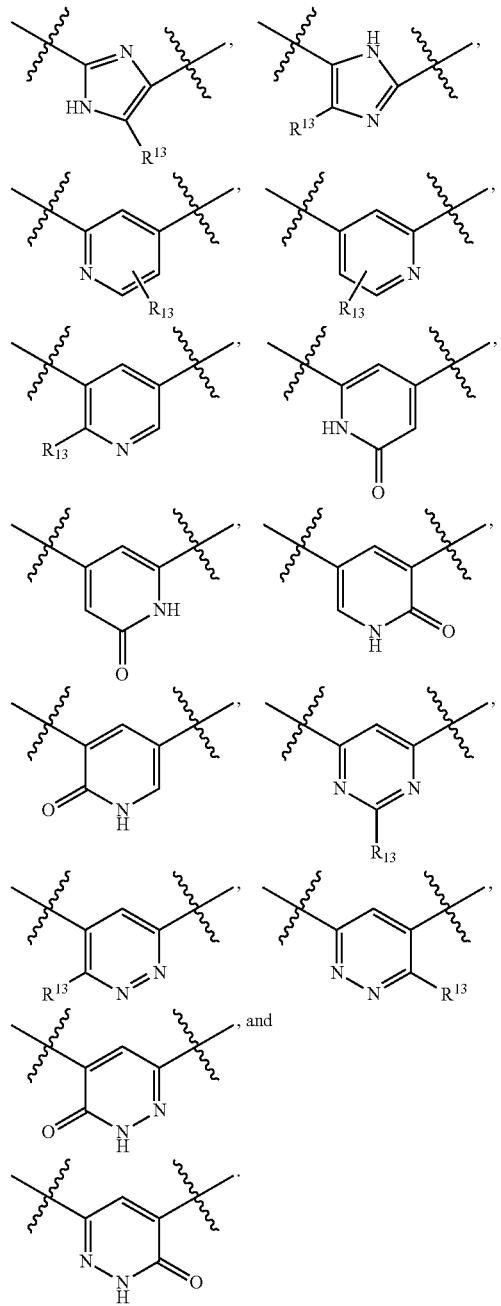

In another embodiment,

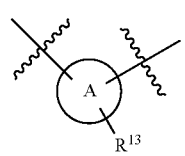

is independently selected from the group consisting of
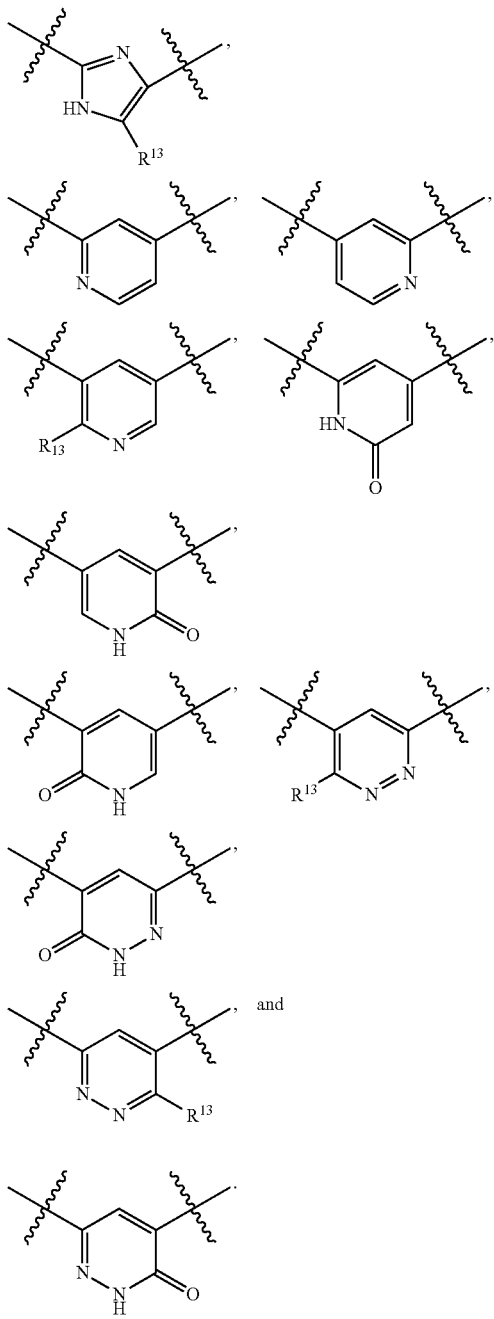
and
In another embodiment,
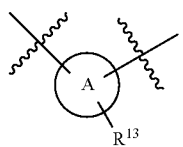
is independently selected from the group consisting of
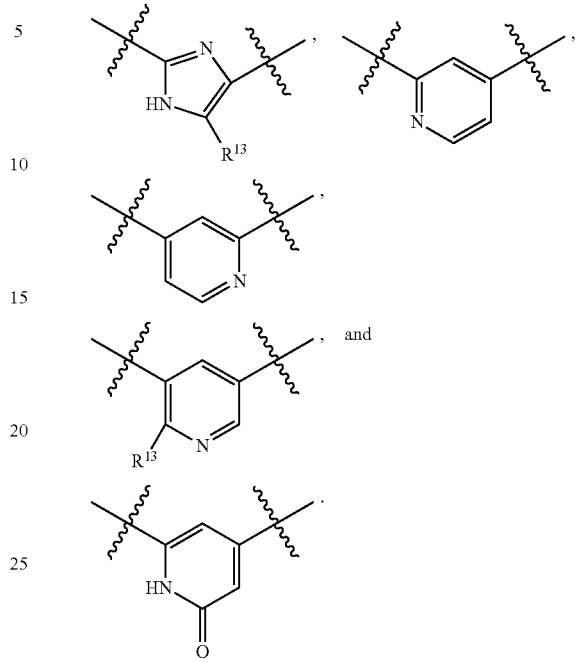
and
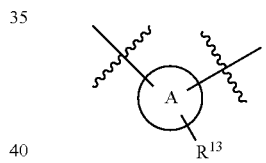
In still another embodiment,
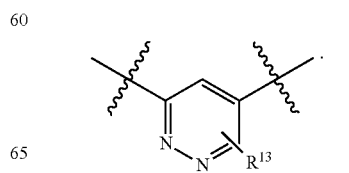
is selected from the group consisting of In another embodiment,

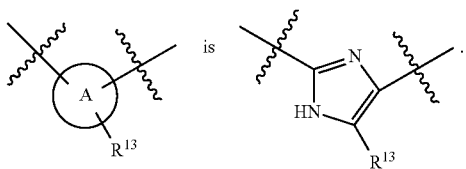

In another embodiment,

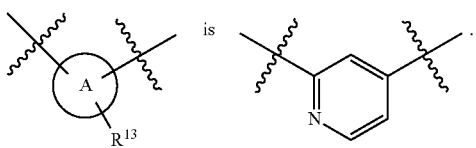

In another embodiment,

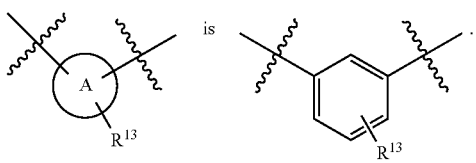

In another embodiment,

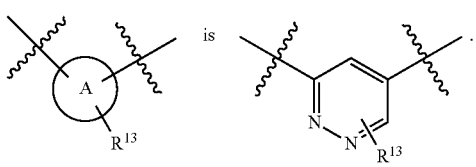

In another embodiment,

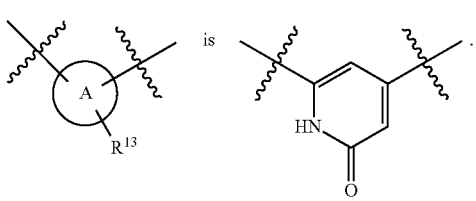

In another embodiment,

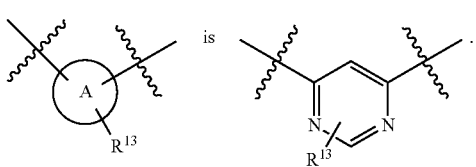

In one embodiment, $X^1$ is selected from the group consisting of $C_{1-3}$ alkylene and $C_{2-4}$ alkenylene; wherein said alkylene and alkenylene are optionally substituted with OH and $C_{1-4}$ alkyl; alternatively, one or two of the carbon atoms of said alkylene and alkenylene may be replaced by O, $S(O)_p$, NH, $N(C_{1-4}$ alkyl), CONH, or CON($C_{1-4}$ alkyl).

In another embodiment, $X^1$ is selected from the group consisting of —$CH_2$—, —$CH(C_{1-4}$ alkyl), —$CH_2$—$CH_2$—, —CH=CH—, —CH=C($C_{1-4}$ alkyl)-, —C($C_{1-4}$ alkyl)=CH—, —$OCH_2$—, —$CH_2O$—, —$CF_2$—, —$(CH_2)_4$—CH($CF_3$)—, —$CH_2NHCO$—, —$CH_2NHCH_2$—, —$CH_2N(C_{1-4}$ alkyl)$CH_2$—, —$CH_2CONH$—, —$CH_2$—CONH—$CH_2$—, —$CH_2$—CON($C_{1-4}$ alkyl)-, —$CH_2$—CON($C_{1-4}$ alkyl)-($CH_2)_3$—, and —$CH_2CH(OH)(CH_2)_2$—.

In another embodiment, $X^1$ is selected from the group consisting of —$CH_2$—, —CH=CH—, —C(Me)=CH—, and —$CH_2NH$—.

In another embodiment, $X^1$ is selected from the group consisting of —$CH_2$—, —CH=CH—, and —C(Me)=CH.

In another embodiment, $X^1$ is selected from the group consisting of —$CH_2$— and —CH=CH—.

In another embodiment, $X^1$ is —$CH_2$—;

$X^{1a}$ is selected from the group consisting of $C_{2-4}$ alkylene and $C_{2-4}$ alkenylene wherein said $C_{2-4}$ alkylene and $C_{2-4}$ alkenylene are optionally substituted with $R^1$ and $R^2$; alternatively one or more of the carbon atoms of said alkylene may be replaced by O and C=O;

$R^1$ and $R^2$ are independently selected from the group consisting of H, halogen, $C_{1-6}$ alkyl, OH, $NH_2$, $C_{1-4}$ haloalkyl, —$OCHF_2$, —$OCF_3$.

In another embodiment, $X^{1a}$ is selected from the group consisting of $X^{1a}$ is selected from the group consisting of —$CR^1R^2$—$CR^1R^2$—, —$CR^1R^2$—$CR^1R^2$—$CR^1R^2$—, and —$CR^1$=$CR^2CR^1R^2$—, wherein one or more —$CR^1R^2$— may be replaced by O or C=O.

In another embodiment, $X^{1a}$ is selected from the group consisting of —$CH_2CH_2$—, —$CH(C_{1-4}$ alkyl)$CH_2$, —$CH_2$—$CH_2$—$CH_2$—, —CH=$CHCH_2$—, —CH=C($C_{1-4}$ alkyl)$CH_2$—, —C($C_{1-4}$ alkyl)=$CHCH_2$—, —$CH_2OCH_2$—, —$CH_2CH_2O$—, —$OCH_2CH_2$—, —$CH_2CF_2$—, —$(CH_2)_3$CH($CF_3$)—, —$CH_2NHCO$—, —$CH_2NHCH_2$—, —$CH_2N(C_{1-4}$ alkyl)$CH_2$—, —$CH_2CONH$—, —$CH_2$—CONH—$CH_2$—, —$CH_2$—CON($C_{1-4}$ alkyl)-, —$CH_2$—CON($C_{1-4}$ alkyl)-($CH_2)_3$—, and —$CH_2CH(OH)(CH_2)_2$—.

In another embodiment, $X^{1a}$ is selected from the group consisting of $CH_2CH_2$ and CH=$CHCH_2$.

In another embodiment, $X^{1a}$ is —$CH_2CH_2$—.

In one embodiment, $X^2$ is selected from the group consisting of $CHR^{11}$, O, NH, and $N(C_{1-4}$ alkyl).

In one embodiment, $X^3$ is $CR^{12}$ or N, provided when $X^2$ is O, NH, and $N(C_{1-4}$ alkyl), $X^3$ is $CR^{12}$.

In another embodiment, $X^2$ is $CHR^{11}$, $X^3$ is $CR^{12}$ or N.

In another embodiment, $X^2$ and $X^3$ are both $CH_2$.

In another embodiment, $X^2$ is $CH_2$, or $CHCH_3$, $X^3$ is N.

In another embodiment, $X^2$ is O, $X^3$ is $CH_2$ or $CHCH_3$.

In another embodiment, $X^2$ is NH, $X^3$ is $CH_2$ or $CHCH_3$.

In one embodiment, $X^2$ is selected from the group consisting of $CHR^{11}$, C=O, O, NH, and $N(C_{1-4}$ alkyl).

In another embodiment, $X^2$ is C=O, $X^3$ is N.

In another embodiment, $X^2$ is C=O, $X^3$ is $CH_2$.

In another embodiment, $X^2$ is NMe, $X^3$ is $CH_2$.

In another embodiment, $X^3$ is N, $R^7$ is C=O.

In one embodiment, $R^1$ is selected from the group consisting of H, $C_{1-4}$ alkyl, and hydroxyl.

In another embodiment, $R^1$ is selected from the group consisting of H and $C_{1-4}$ alkyl.

In another embodiment, $R^1$ is selected from the group consisting of H and methyl, ethyl, and isopropyl.

In one embodiment, $R^2$ is, independently at each occurrence, selected from the group consisting of H and $C_{1-4}$ alkyl.

In another embodiment, $R^2$ is, independently at each occurrence, selected from the group consisting of H and methyl.

In one embodiment, $R^3$ is selected from the group consisting of H, halogen, haloalkyl, C(O)OH, C(O)O—$R^{15}$, C(O)NR$^9$R$^{10}$, C(O)NHR$^9$, C(O)N(C$_{1-4}$ alkyl)R$^9$, wherein $R^9$ and $R^{10}$ are independently selected from the group consisting of H and C$_{1-6}$ alkyl; or $R^9$ and $R^{10}$ are taken together with the nitrogen atom to which they are attached to form a 4- to 7-membered heterocycle optionally substituted with $R^{14}$; $R^{15}$ is selected from the group consisting of C$_{1-4}$ alkyl, C$_{3-6}$ cycloalkyl, 5- to 6-membered heteroaryl, 4- to 7-membered heterocycle, and benzyl, said groups being optionally substituted with OH, OMe, and halogen.

In another embodiment, $R^3$ is selected from the group consisting of H, halogen, haloalkyl, C(O)OH, and C(O)O (C$_{1-4}$ alkyl).

In another embodiment, $R^4$ is selected from the group consisting of H and C$_{1-4}$ alkyl; alternatively, $R^3$ and $R^4$ together are =O.

In one embodiment, $R^5$ is selected from the group consisting of H, halogen, NHC(O)O—C$_{1-4}$ alkyl, CN, OH, O—C$_{1-4}$ alkyl; CF$_3$, CO$_2$H, CO$_2$—C$_{1-4}$ alkyl, —CH$_2$CO$_2$H, —(CH$_2$)$_2$CO$_2$H, —CH$_2$CO$_2$(C$_{1-4}$ alkyl), —(CH$_2$)$_2$CO$_2$(C$_{1-4}$ alkyl), NH$_2$, —CH$_2$NH$_2$, —NHCO(C$_{1-4}$ alkyl), —NHCO$_2$(CH$_2$)$_2$O(C$_{1-4}$ alkyl), —NHCO$_2$(CH$_2$)$_{1-3}$O(C$_{1-4}$ alkyl), NHCO$_2$CH$_2$CH(C$_{1-4}$ alkyl)O(C$_{1-4}$ alkyl), —NHCO$_2$(CH$_2$)$_{1-2}$OH, —NHCO$_2$CH$_2$CO$_2$H, —CH$_2$NHCO$_2$(C$_{1-4}$ alkyl), —NHC(O)NH(C$_{1-4}$ alkyl), —NHC(O)N(C$_{1-4}$ alkyl)$_2$, NHC(O)NH(C$_{1-4}$ alkyl)N[5- to 6-membered heterocycle], —NHSO$_2$(C$_{1-4}$ alkyl), —CONH$_2$, —CONH(C$_{1-4}$ alkyl), —CON(C$_{1-4}$ alkyl)$_2$, and —CH$_2$CONH$_2$.

In another embodiment, $R^5$ is selected from the group consisting of H, halogen, NHC(O)O—C$_{1-4}$ alkyl, CONH$_2$, CO$_2$—C$_{1-4}$ alkyl, COOH, CN, OH, and O—C$_{1-4}$ alkyl.

In another embodiment, $R^5$ is NHC(O)O—C$_{1-4}$ alkyl.

In another embodiment, $R^5$ is NHC(O)OMe.

In another aspect, the present invention provides compounds of Formula (VI):

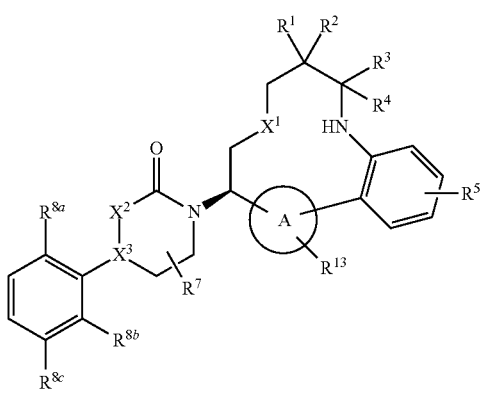

(VI)

or stereoisomers, tautomers, pharmaceutically acceptable salts, solvates, or prodrugs thereof, wherein:

ring A is selected from the group consisting of phenyl and a 5- to 6-membered heterocycle;

$X^1$ is selected from the group consisting of C$_{1-4}$ alkylene, and C$_{2-4}$ alkenylene; optionally one or more of the carbon atoms of said alkylene and alkenylene may be replaced by O, S(O)$_p$, NH, and N(C$_{1-4}$ alkyl);

$X^2$ is selected from the group consisting of CHR$^{11}$, O, NH, and N(C$_{1-4}$ alkyl);

$X^3$ is CR$^{12}$ or N, provided when $X^2$ is O, NH, and N(C$_{1-4}$ alkyl), $X^3$ is CR$^{12}$;

$R^1$ is selected from the group consisting of H, halogen, CF$_3$, C$_{1-6}$ alkyl, and hydroxyl;

$R^2$ is selected from the group consisting of H and C$_{1-6}$ alkyl;

$R^3$ is selected from the group consisting of H, halogen, haloalkyl, C(O)OH, C(O)O—R$^{15}$, C(O)NR$^9$R$^{10}$, C(O)NHR$^9$, C(O)N(C$_{1-4}$ alkyl)R$^9$;

$R^5$ is, independently at each occurrence, selected from the group consisting of H, halogen, NHC(O)O—C$_{1-4}$ alkyl, CN, OH, O—C$_{1-4}$ alkyl; CF$_3$, CO$_2$H, CO$_2$—C$_{1-4}$ alkyl, —CH$_2$CO$_2$H, —(CH$_2$)$_2$CO$_2$H, —CH$_2$CO$_2$(C$_{1-4}$ alkyl), —(CH$_2$)$_2$CO$_2$(C$_{1-4}$ alkyl), NH$_2$, —CH$_2$NH$_2$, —NHCO(C$_{1-4}$ alkyl), —NHCO$_2$(CH$_2$)$_{1-2}$O(C$_{1-4}$ alkyl), —NHCO$_2$(CH$_2$)$_{1-3}$O(C$_{1-4}$ alkyl), NHCO$_2$CH$_2$CH(C$_{1-4}$ alkyl)O(C$_{1-4}$ alkyl), —NHCO$_2$(CH$_2$)$_{1-2}$OH, —NHCO$_2$CH$_2$CO$_2$H, —CH$_2$NHCO$_2$(C$_{1-4}$ alkyl), —NHC(O)NH(C$_{1-4}$ alkyl), —NHC(O)N(C$_{1-4}$ alkyl)$_2$, NHC(O)NH(C$_{1-4}$ alkyl)N[5- to 6-membered heterocycle], —NHSO$_2$(C$_{1-4}$ alkyl), —CONH$_2$, —CONH(C$_{1-4}$ alkyl), —CON(C$_{1-4}$ alkyl)$_2$, and —CH$_2$CONH$_2$;

$R^6$ is selected from the group consisting of H, C$_{1-6}$ alkyl, and OH;

$R^7$ is selected from the group consisting of H, F, methyl, ethyl, and isopropyl;

$R^{8a}$, $R^{8b}$, and $R^{8c}$ are independently selected from the group consisting of H, halogen, OH, CN, C$_{1-6}$ alkyl, haloalkyl, alkoxy, and haloalkoxy;

$R^9$ is selected from the group consisting of H and C$_{1-6}$ alkyl;

$R^{10}$ is selected from the group consisting of H and C$_{1-6}$ alkyl;

alternatively, $R^9$ and $R^{10}$ are taken together with the nitrogen atom to which they are attached to form a 4- to 7-membered heterocycle optionally substituted with $R^{14}$;

$R^{11}$ is selected from the group consisting of H and C$_{1-6}$ alkyl;

$R^{12}$ is selected from the group consisting of H and C$_{1-6}$ alkyl;

$R^{13}$ is selected from the group consisting of H, =O, halogen, C$_{1-6}$ alkyl, CF$_3$ and CN;

$R^{14}$ is selected from the group consisting of H, OH, halogen, and C$_{1-6}$ alkyl; and $R^{15}$ is selected from the group consisting of C$_{1-4}$ alkyl, C$_{3-6}$ cycloalkyl, 5- to 6-membered heteroaryl, 4- to 7-membered heterocycle, and benzyl, said groups being optionally substituted with OH, OMe, and halogen;

p, at each occurrence, is selected from 0, 1, and 2.

In another aspect, the present invention provides compounds of Formula (VII):

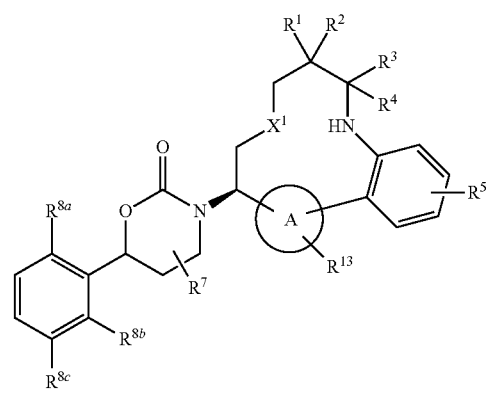

(VII)

or stereoisomers, tautomers, pharmaceutically acceptable salts, solvates, or prodrugs thereof, wherein the variables have the meaning as defined in Formula (VI).

In another aspect, the present invention provides compounds of Formula (VIII):

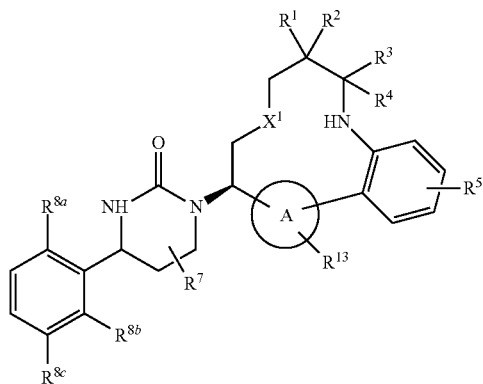

(VIII)

or stereoisomers, tautomers, pharmaceutically acceptable salts, solvates, or prodrugs thereof, wherein the variables have the meaning as defined in Formula (VI).

In another aspect, the present invention provides compounds of Formula (IX):

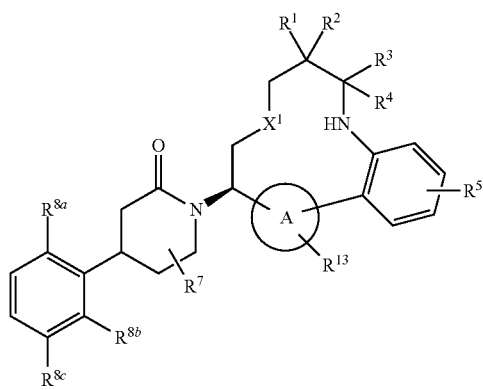

(IX)

or stereoisomers, tautomers, pharmaceutically acceptable salts, solvates, or prodrugs thereof, wherein the variables have the meaning as defined in Formula (VI).

In another aspect, the present invention provides compounds of Formulae (VI), (VII), (VIII), and (IX) or stereoisomers, tautomers, pharmaceutically acceptable salts, solvates, or prodrugs thereof, wherein:

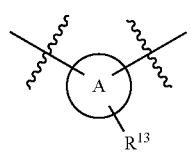

is selected from the group consisting of

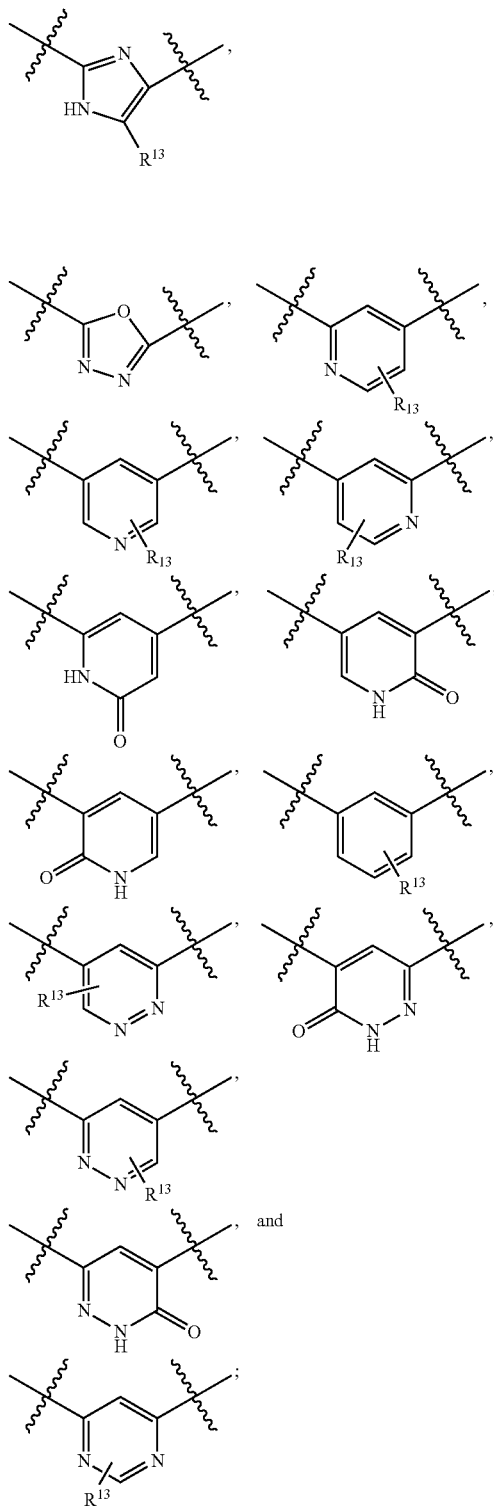

$X^1$ is selected from the group consisting of —CH$_2$—, —CH(C$_{1-4}$ alkyl), —CH$_2$—CH$_2$—, —CH=CH—, —CH=C(C$_{1-4}$ alkyl)-, —C(C$_{1-4}$ alkyl)=CH—, —OCH$_2$—, —CH$_2$O—, —CH$_2$NH—, and —NHCH$_2$—;

$R^{8a}$ is selected from the group consisting of H, F, OCH$_3$, and OCHF$_2$;

$R^{8b}$ is selected from the group consisting of H and F;
$R^{8c}$ is Cl;
$R^1$ is selected from the group consisting of H and $C_{1-4}$ alkyl;
$R^2$ is selected from the group consisting of H and $C_{1-4}$ alkyl;
$R^3$ is selected from the group consisting of H, halogen, C(O)OH, and C(O)O($C_{1-4}$ alkyl);
$R^4$ is selected from the group consisting of H and $C_{1-4}$ alkyl;
alternatively, $R^3$ and $R^4$ together are =O;
$R^5$ is selected from the group consisting of H, halogen, NHC(O)O—$C_{1-4}$ alkyl, $CONH_2$, $CO_2$—$C_{1-4}$ alkyl, COOH, CN, OH, and O—$C_{1-4}$ alkyl; preferably, $R^5$ is NHC(O)O—$C_{1-4}$ alkyl.

In another aspect, the present invention provides a compound selected from any subset list of compounds exemplified in the present application.

In another embodiment, the compounds of the present invention have Factor XIa Ki values ≤10 μM.

In another embodiment, the compounds of the present invention have Factor XIa Ki values ≤1 μM.

In another embodiment, the compounds of the present invention have Factor XIa Ki values ≤0.5 μM.

In another embodiment, the compounds of the present invention have Factor XIa Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary* (13th Edition), John Wiley & Sons, New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(\!=\!O)CH_3$, $SCH_3$, $S(\!=\!O)CH_3$, $S(\!=\!O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(\!=\!O)CH_3$, $SCH_3$, $S(\!=\!O)CH_3$, $S(\!=\!O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→0 and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzisoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl

Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
SEM-Cl 2-(trimethysilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P propane phosphonic acid anhydride
TRIS tris(hydroxymethyl)aminomethane The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice,* 5th Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of a venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood,* 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood,* 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis,* pp. 103-122, Lippincott Williams & Wilkins (2001); Schmaier, A. H., "Contact Activation", *Thrombosis and Hemorrhage,* pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.,* 202:271-281 (2005); Kleinschmitz et al., *J. Exp. Med.,* 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.,* 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.,* 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.,* 87:774-777 (2002); Wang et al., *J. Thromb. Haemost.,* 3:695-702 (2005)). Also, factor XI deficiency rescues the perinatal lethal phenotype of complete protein C deficiency (Chan et al., *Amer. J. Pathology,* 158:469-479 (2001)). Furthermore, baboon cross-reactive, function blocking antibodies to human factor XI protect against baboon arterial-venous shunt thrombosis (Gruber et al., *Blood,* 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis*, pp. 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, 3(Suppl. 1): P1228 (2005); Schumacher, W. A. et al., *European Journal of Pharmacology*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s = I/(K_i(1+S/K_m)) \text{ for a competitive inhibitor with one binding site; or}$$

$$v_s/v_o = A+((B-A)/(1+((IC_{50}/(I))^n))); \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=K$_i$ for protease P/K$_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or INNOVIN®, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of ≤10 µM (10000 nM) was observed. Table 1 below lists Factor XIa Ki values measured for the following examples.

TABLE 1

| Example No. | Factor XIa Ki (nM) |
|---|---|
| 4 | 3396.00 |
| 5 | 12.24 |
| 7 | 41.77 |
| 9 | <5.00 |
| 13 | <5.00 |
| 18 | 6.83 |
| 20 | 7.46 |
| 26 | <5.00 |
| 32 | 2461.00 |
| 37 | <5.00 |
| 40 | 24.42 |
| 48 | <5.00 |
| 58 | <5.00 |
| 70 | <5.00 |
| 71 | 329.80 |
| 72 | 28.79 |
| 77 | 7.46 |

TABLE 1-continued

| Example No. | Factor XIa Ki (nM) |
|---|---|
| 79 | 13.35 |
| 99 | 1926.00 |
| 100 | <5.00 |
| 119 | 9.60 |
| 133 | 69.32 |
| 147 | 9.48 |
| 152 | <5.00 |
| 158 | 983.80 |

B. In Vivo Assays

The effectiveness of compounds of the present invention as antithrombotic agents can be determined using relevant in vivo thrombosis models, including In vivo Electrically-induced Carotid Artery Thrombosis Models and In vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The ED$_{50}$ (dose that increased average carotid blood flow over 90 min to 50% of the control) of compounds are estimated by a nonlinear least square regression program using the Hill sigmoid E$_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, P2Y$_1$ receptor antagonists, P2Y$_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentanyl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors P2Y$_1$ and P2Y$_{12}$, with P2Y$_{12}$ being even more preferred. Preferred P2Y$_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa, XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1): 35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

Certain 2-bromoacetophenone analogs (1b) that are not commercially available but used in the current invention may be synthesized from commercially available starting materials as described in Scheme 1. Acetophenone derivatives 1a can be treated with a brominating reagent such as bromine in a solvent such as chloroform to give 1b. Alternatively, acetophenone derivatives 1a can be treated with either copper (II) bromide in a solvent such as ethyl acetate at elevated temperature or phenyltrimethylammonium tribromide in a solvent such as THF at low temperature to provide 1b. Benzoic acid derivatives 1c can then be treated sequentially with oxalyl chloride in a suitable solvent, such as DCM, containing a few drops of DMF, and then treated with trimethylsilyldiazomethane in a suitable solvent or solvent combination, such as ACN and hexane. The intermediate diazoketone is isolated and treated with aqueous hydrobromic acid and DCM to provide 1b. Alternatively the benzoic acid derivatives 1c can be converted to the acetophenone derivatives 1a in three steps as described in Scheme 1. Alternatively, Stille coupling between a suitably substituted aryl halide or triflate and tributyl-(1-ethoxyvinyl) stannane with a palladium catalyst, such as bis-(triphenylphosphine)palladium dichloride, in a suitable solvent, such as toluene, at elevated temperature yields the enol ether 1e, which can then be converted to 1b with N-bromosuccinimide.

Scheme 1

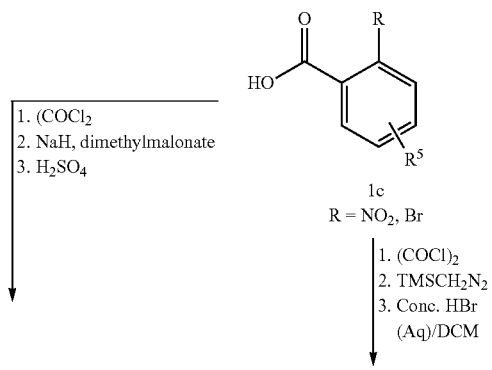

-continued

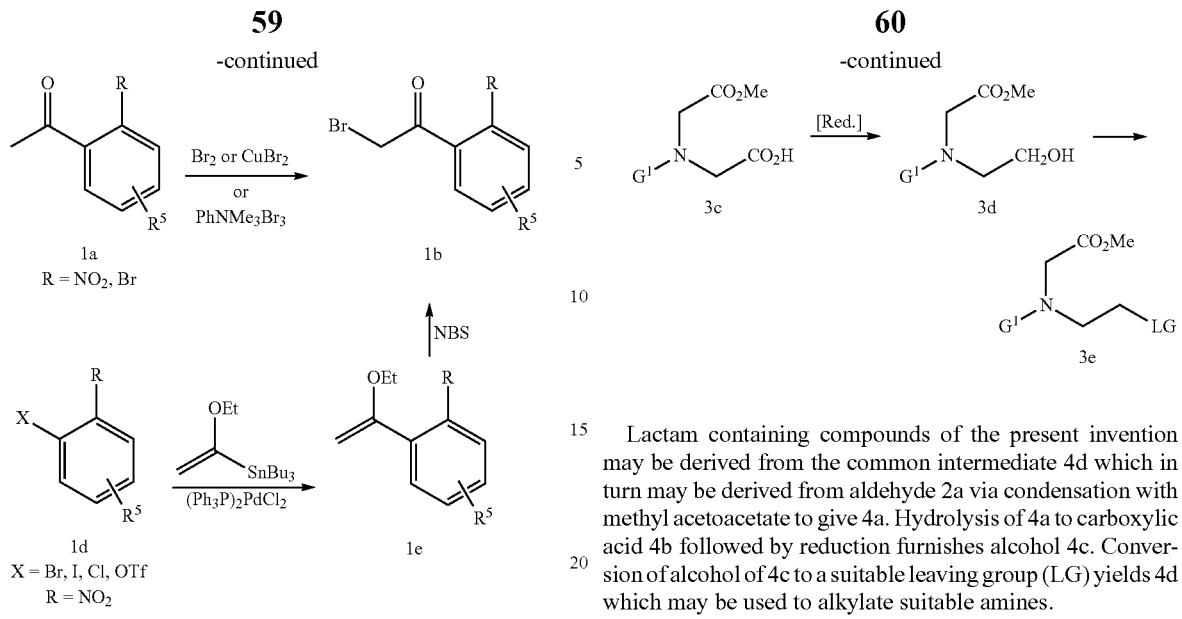

Cyclic carbamates of the present invention may be derived from intermediate 2e which in turn may be derived from aldehyde 2a via treatment with vinyl Grignard followed by oxidation to give 2-propenone 2c. Michael addition of iodine to 2c followed by reduction furnishes 3-iodo-1-propanol 2e which is used to alkylate primary and secondary amines.

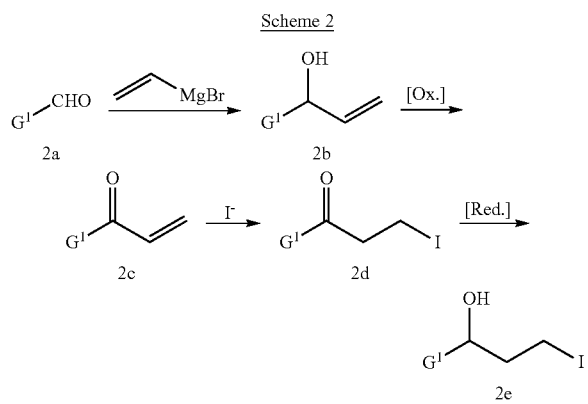

Keto-piperazine containing compounds of the present invention may be derived from the common intermediate 3e which in turn may be derived from amine 3a via alkylation with methyl bromoacetate to give 3b. Hydrolysis of 3b to carboxylic acid 3c followed by reduction furnishes alcohol 3d. Conversion of alcohol of 3d to a suitable leaving group (LG) yields 3e which can be used to alkylate appropriate amines.

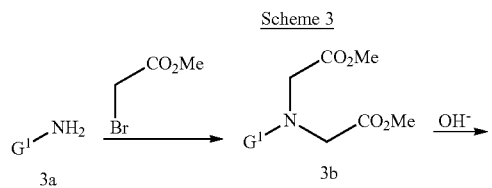

-continued

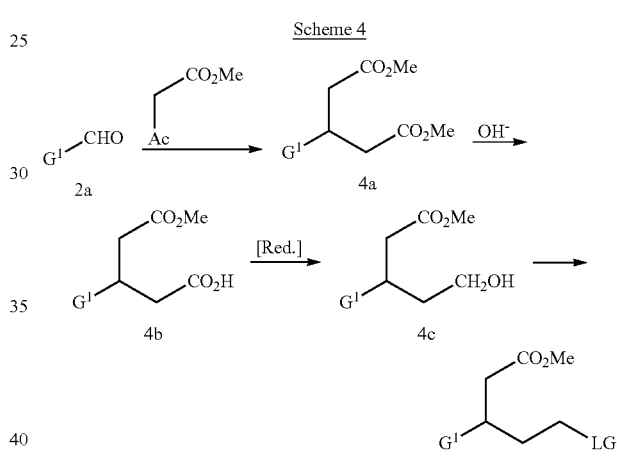

Lactam containing compounds of the present invention may be derived from the common intermediate 4d which in turn may be derived from aldehyde 2a via condensation with methyl acetoacetate to give 4a. Hydrolysis of 4a to carboxylic acid 4b followed by reduction furnishes alcohol 4c. Conversion of alcohol of 4c to a suitable leaving group (LG) yields 4d which may be used to alkylate suitable amines.

Scheme 4

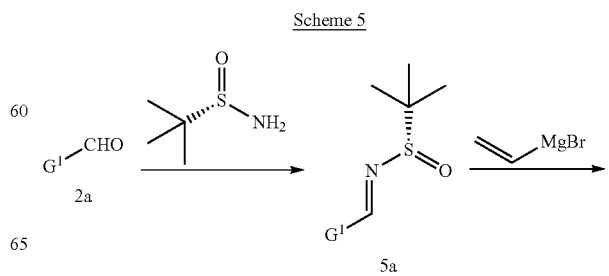

Cyclic ureas of the type described in the present invention may be derived from aldehyde 2a via treatment with racemic or chiral 2-methylpropane-2-sulfinamide followed by addition of vinyl Grignard reagent to provide sulfinamide 5b. Treatment of 5b with acid followed by protection of the amino group with Boc$_2$O provides 5c. Hydroboration of olefin 5c then affords the alcohol 5d. Treatment of the resulting alcohol 5d with methanesulfonyl chloride and sodium iodide provides iodide intermediate 5e, which is then employed to alkylate suitable amines.

Scheme 5

-continued

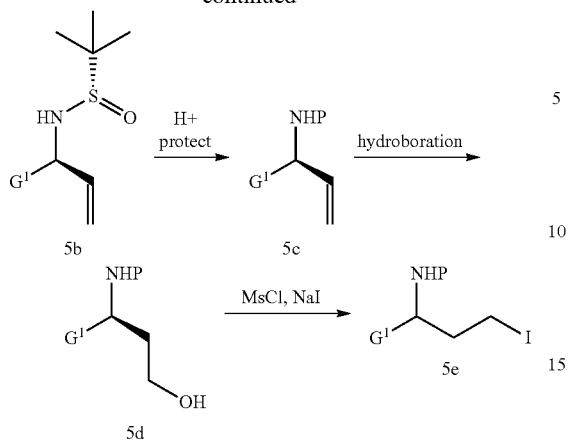

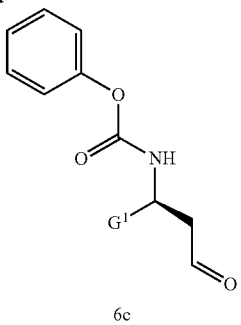

Intermediates for preparation of compounds of the present invention wherein ring A is an imidazole ring, can be prepared from an appropriately N-protected allylglycine (7a) according to the general method outlined in Scheme 7 (Contour-Galcera et al., *Bioorg. Med. Chem. Lett.*, 11(5):741-745 (2001)). Condensation of 7a with a suitably substituted bromoacetophenone (1b) in the presence of a suitable base such as potassium bicarbonate, potassium carbonate or cesium carbonate in a suitable solvent such as DMF provides a keto ester intermediate which can be cyclized to afford an imidazole (7c) by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate (7c) is then protected by treatment with SEM-Cl in the presence of a base such as sodium hydride or dicyclohexylmethylamine in a solvent such as THF or dichloromethane. The resulting aryl bromide (7d) is then converted to the corresponding aniline (7e) by heating in a sealed vessel with excess ammonium hydroxide, in the presence of copper iodide, a base such as potassium carbonate and a catalytic amount of proline in DMSO as solvent. Acylation of 7e with the appropriate alkenoic acid and a coupling agent such as T3P or BOP reagent, or alternately, by treatment with an alkenoic acid chloride in the presence of a base such as TEA, DIPEA, or pyridine provides diene 7f, which undergoes ring closing metathesis by heating in dilute solution in the presence of p-toluene sulfonic acid and Grubbs II catalyst in a suitable solvent such as DCM or DCE to provide the corresponding macrocycle (7g). Alternately, the RCM can be run in a microwave at elevated temperatures without pTsOH. Chlorination on the imidazole ring with N-chlorosuccinimide, or initial reduction of the double bond followed by chlorination, and subsequent removal of the amine protecting group (PG) provides intermediates 7h and 7i, respectively. Alternately, for compounds wherein $R^{13}$ is CN, catalytic hydrogenation of 7g followed by bromination with NBS at room temperature and subsequent palladium-catalyzed cyanation and removal of the protecting group (PG), provides intermediate 7j. Intermediates 7h-j can be converted to compounds of the present invention following the steps described in Scheme 14.

Alternatively, cyclic ureas described in the present invention may be derived from 6a. Treatment of 6a with acid followed by treatment with phenyl chloroformate and oxidation to provide the aldehyde 6c. The aldehyde 6c can then be subjected to reductive amination with suitable amines.

Scheme 6

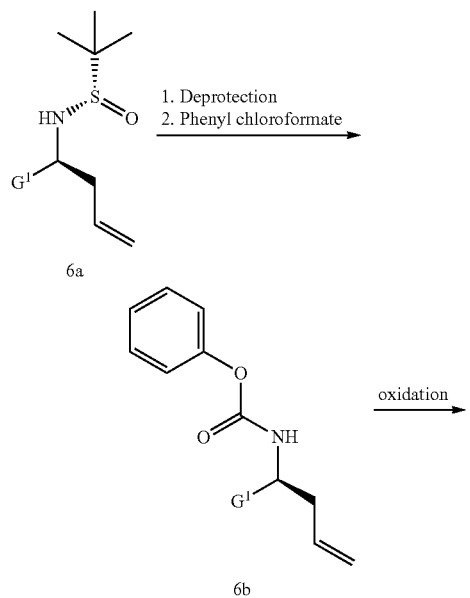

Scheme 7

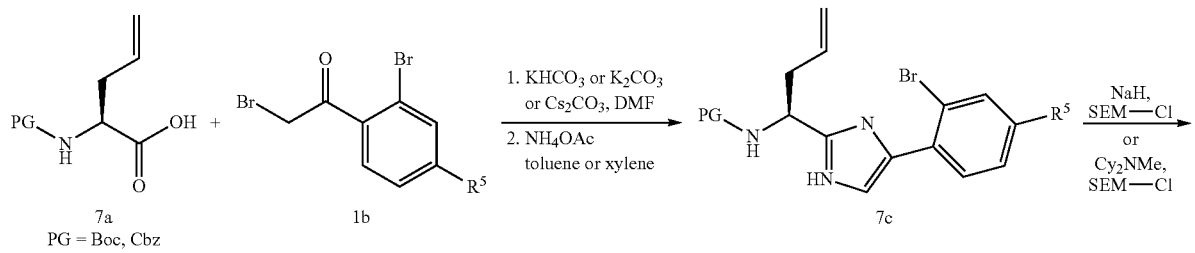

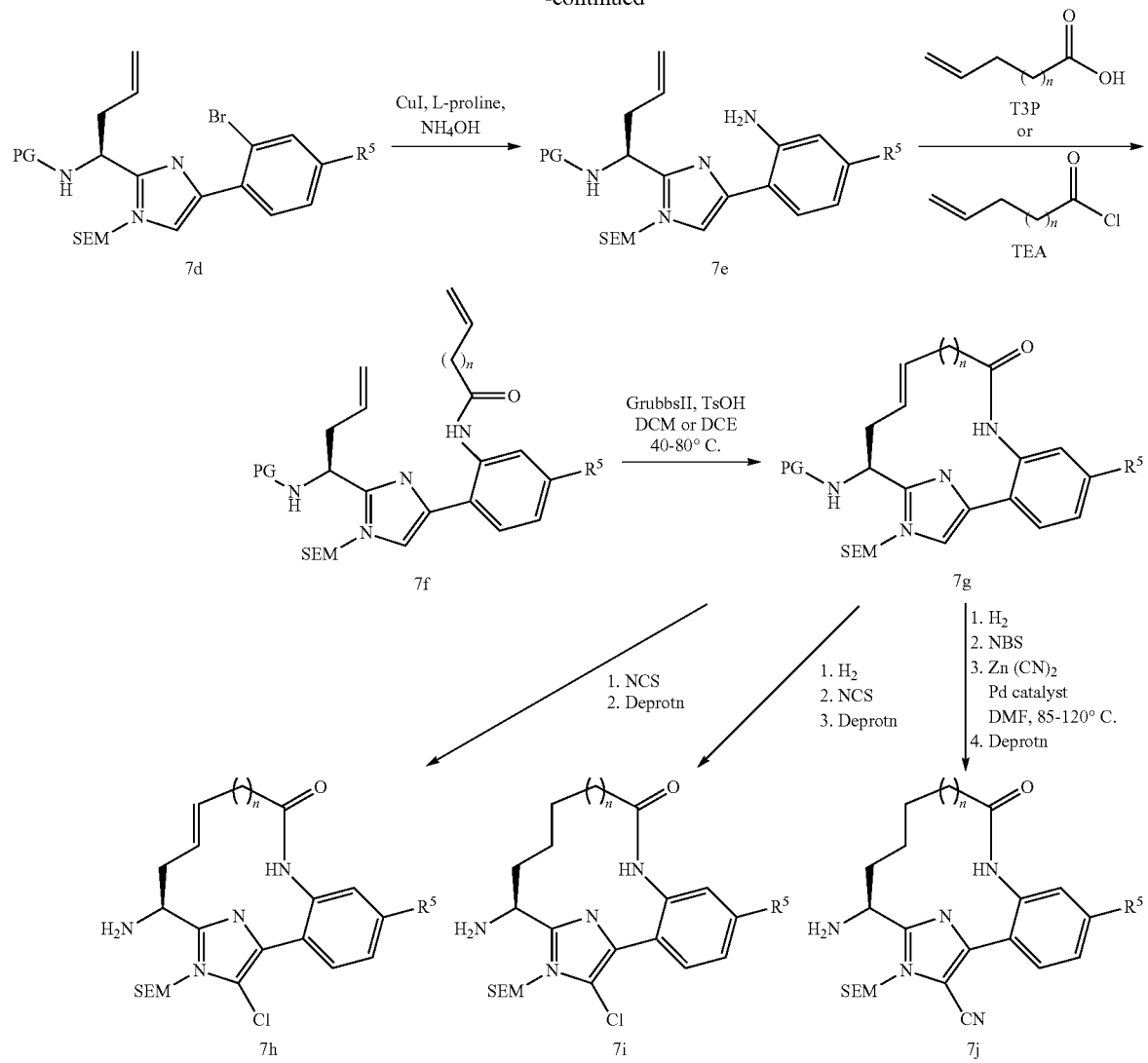

Additional representative imidazole-containing amide macrocycle intermediates useful for the synthesis of compounds of this invention are described in Scheme 8. Aniline 7e can be coupled with an appropriately substituted carboxylic acid 8a using propane phosphonic acid anhydride (T3P) to give the amide 8b (n=0) and 8c (n=1). Using a modified procedure described by Lovely (*Tetrahedron Letters*, 44:1379 (2003)), 8b and 8c, following pretreatment with p-toluenesulfonic acid to form the imidazolium ion, can be cyclized via ring-closing metathesis using a catalyst, such as Grubbs (II), in a suitable solvent, such as dichloromethane, dichloroethane, or toluene at elevated temperature, to give the imidazole-containing macrocycles 8d (n=0) and 8e (n=1). The alkene can then be reduced with hydrogen over either palladium on carbon or platinum oxide, and subsequent deprotection with TFA in dichloromethane provides amine 8f and 8g. Compounds of the formulae 8f and 8g can be converted to compounds in this invention according to Scheme 14.

Scheme 8

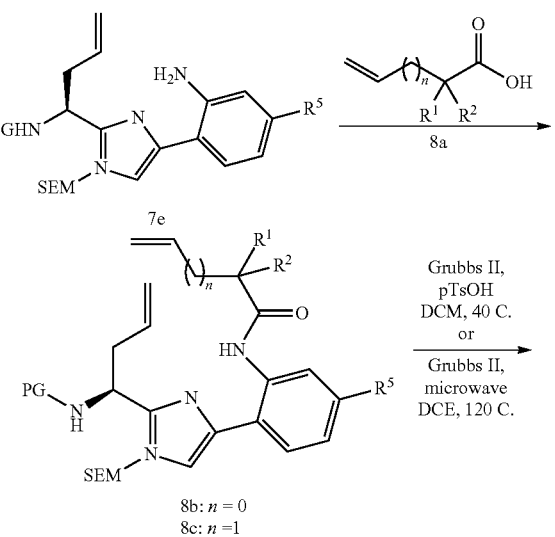

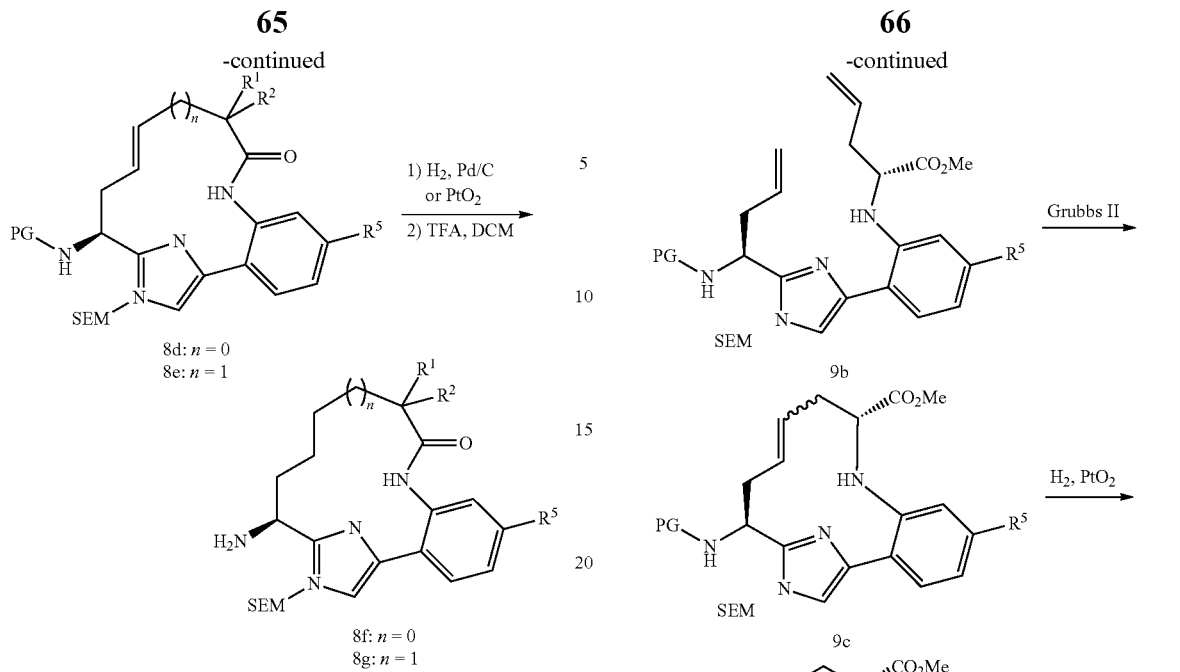

Alternatively, imidazole-containing macrocycles of this invention can be derived from intermediate 9e according to Scheme 9. Ullmann type coupling reaction of compound 7d and allyl glycine, followed by methylation of the acid provides the extended aniline analog 9b. Ring closing metathesis of the diene 9b using Grubbs II catalyst provides the macrocyclic olefin 9c. Then, the macrocyclic olefin 9c may be converted to the key intermediate 9e via hydrogenation and selective deprotection of the Boc group from compound 9d. The amine 9e may be converted to the corresponding cyclic carbamate or other analogs following the procedures described in Scheme 14. The other diastereomer at the methyl ester position can also be made in the same way as described above.

Scheme 9

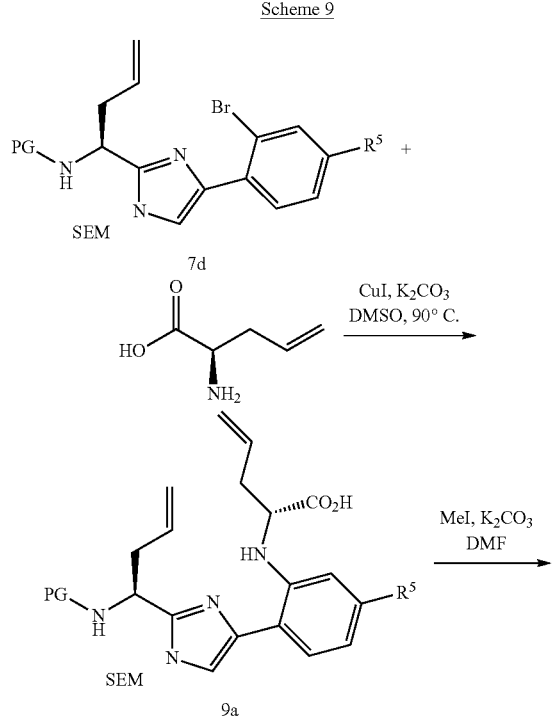

The cyano or chloro imidazole analog of intermediate 9e may be obtained by a slightly modified sequence of Scheme 9. The aniline nitrogen in compound 9b may be protected with a trifluoroacetyl group (TFA) in order to suppress bromination/chlorination on the phenyl group during conversion of compound 10b to 10c. Following the same sequence as outlined in Scheme 9, the resulting protected aniline 10a may be converted to macrocyclic compound 10b. Bromination or chlorination of 10b with NBS or NCS, respectively provides intermediates 10c. For compounds wherein $R^{13}$ is CN, bromide 10c is converted to cyanoimidazole 10d by palladium-catalyzed cyanation as described in Scheme 7 above. Selective removal of the amine protecting group from compound 10d provides amine intermediates 10e. For example a Boc protecting group can be selectively removed either under mild acidic conditions or thermally by heating in HFIP in a microwave at 150° C. for 2 h. Intermediate 10e can be converted to the final compounds described in this invention according to Scheme 14.

Scheme 10

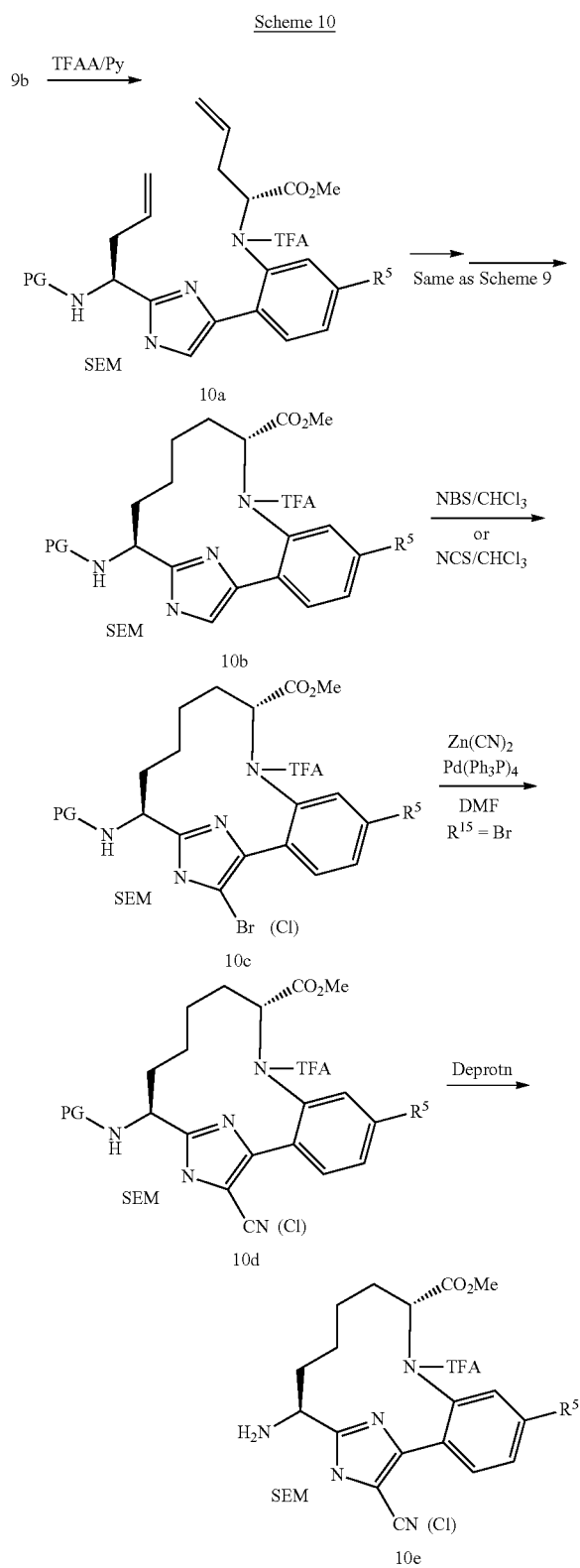

hemiacetal provides the aminal 11a. Treatment of 11a with allyl Grignard reagent, provides aniline 11b, which is then converted to the target compound 11c via the sequence described in Scheme 7.

Scheme 11

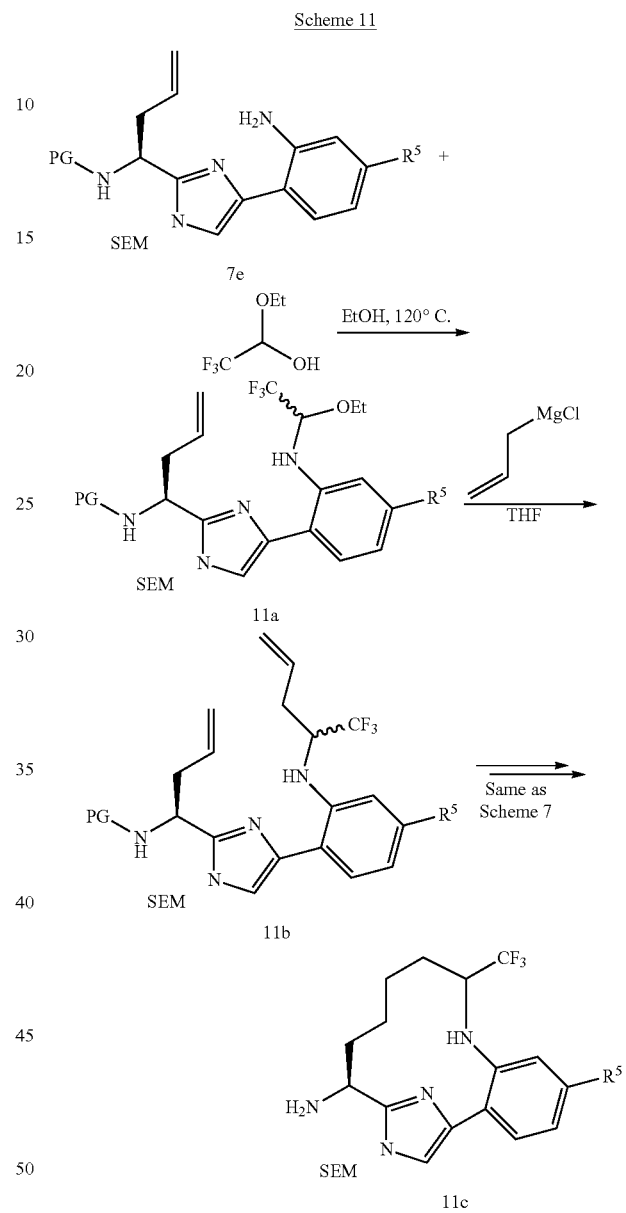

Alternatively, imidazole compounds of this invention can be derived from trifluoromethyl substituted macrocycle intermediates, 11c which can be prepared from aniline 7e following the sequence described in Scheme 11. A condensation reaction of the aniline 7e with trifluoroacetaldehyde ethyl Representative compounds of this invention where ring A is a 6-membered heterocycle (example—pyridine) can be derived from intermediates 12j, the synthesis of which are described in Scheme 12. Condensation of aldehyde 12a (X=N) prepared according to a modified procedure described by Negi (*Synthesis,* 991 (1996)), with (S or R)-2-methylpropane-2-sulfinamide in the presence of anhydrous copper sulfate in a solvent such as DCM gives the sulfinimine 12b (Ellman, J., *J. Org. Chem.*, 64:1278 (1999)). Using a modified procedure described by Kuduk (*Tetrahedron Letters,* 45:6641 (2004)), suitably substituted Grignard reagents, for example allylmagnesium bromide, can be added to sulfinimine 12b to give a sulfinamide 12c, as a mixture of diastereomers which can be separated at various stages of the sequence. The diastereoselectivity for the addition of allymagnesium bromide to sulfinimine 12b can be improved by employing indium according to a modified procedure of Xu (Xu, M-H, *Organic Letters*, 10 (6):1259 (2008)). Suzuki-Miyaura coupling between 4-chloropyridine 12c and an appropriately substituted aryl or heteroaryl boronic acid or ester 12d in the presence of a base such as potassium phosphate, in a solvent mixture, such as DMSO and $H_2O$, or DMF, using a precatalyst such as $Pd(dppf)Cl_2 \cdot CH_2Cl_2$ complex provides 12e. Protecting group interconversion can be accomplished in two steps to give 12f. Alternatively, the protecting group interconversion can take place initially on 12c followed by the Suzuki Miyaura coupling. The aniline 12f can then be coupled with an appropriately substituted carboxylic acid 12g using T3P to give the amide 12h. Using a modified procedure described by Lovely (*Tetrahedron Letters*, 44:1379 (2003)), 12h, following pretreatment with p-toluenesulfonic acid to form the pyridinium ion, can be cyclized via ring-closing metathesis using a catalyst, such as Grubbs (II), in a suitable solvent, such as DCM, DCE, or toluene at elevated temperature, to give the pyridine-containing macrocycle 12i. The alkene can be reduced with hydrogen over either palladium on carbon or platinum oxide, and subsequent deprotection with TFA in DCM provides amine 12j. Compounds of the formulae 12j can be converted to compounds in this invention according to Scheme 14.

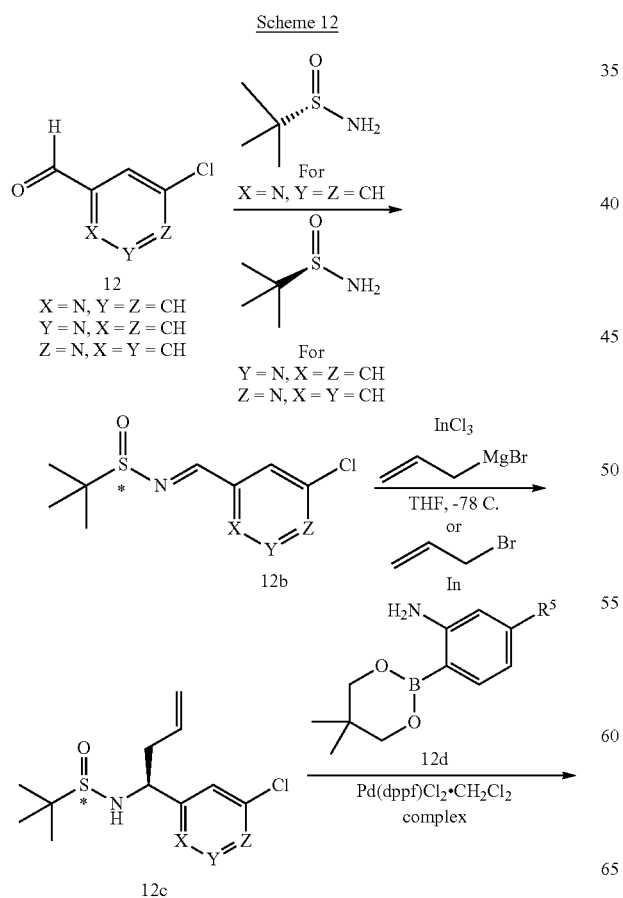

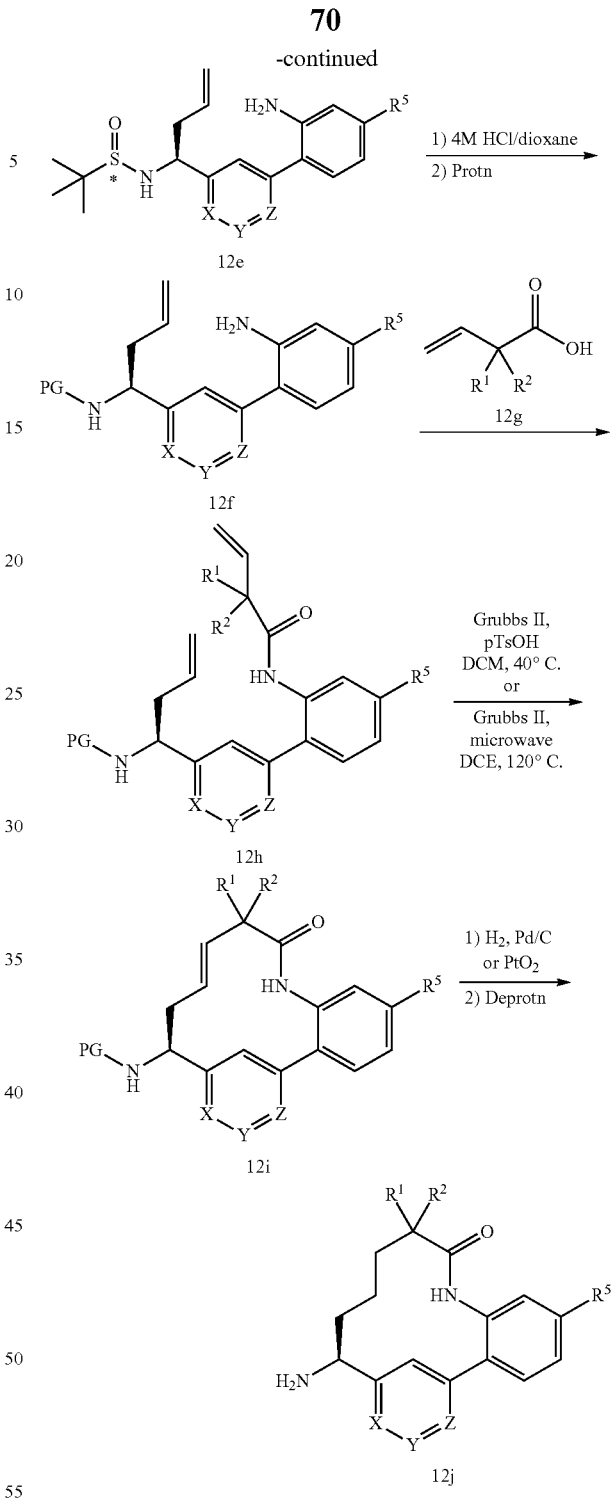

Additional pyridine containing macrocycles useful for the synthesis of compounds of this invention can also be prepared according to Scheme 12. Intermediates of formula 12e where $R^5$=$NO_2$ may be modified further to give intermediates where $R^5$=NH $CO_2$—$C_{1-4}$ alkyl either before coupling with acid 12g or after coupling with acid. Reduction of the nitro group to an amino group may be accomplished with a reducing agent (e.g., Zn—$NH_4Cl$) in an inert solvent (e.g., MeOH) to give an intermediate of formula 12e where $R^5$=$NH_2$. These anilino derivatives may be coupled with chloroalkanoates of the formula $ClCO_2$—$C_{1-4}$ alkyl in the presence of a base (e.g., DIEA) in an inert solvent (e.g., DCM) to give intermediates where $R^5$=NH $CO_2$—$C_{1-4}$ alkyl.

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., *Synthesis*, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato)diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23): 7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Additional pyridazine and pyridazinone-containing macrocycles can be prepared according to Scheme 13. Condensation of the potassium salt of 13a with a suitably substituted α-ketoester 13b, which is either commercially available or prepared using a modified procedure described by Domagala (*Tetrahedron Lett.*, 21:4997-5000), in a solvent such as THF generates the α,β-unsaturated ketone derivative which can then be condensed with a suitably substituted hydrazine derivative to give pyridazinone 13c. The nitro group can then be reduced to the aniline 13f with zinc and ammonium chloride in MeOH. The pyridazinone 13c can be converted to chloro-pyridazine 13d by deprotection of Boc, followed by treatment with $POCl_3$, then reprotection with Boc group. The nitro group can be reduced to the aniline 13e with iron and acetic acid. The anilines 13e and 13f can then be coupled with an appropriately substituted carboxylic acid 12g using T3P to give the amide 13g ($R^{13a}$=Cl) and 13h ($R^{13a}$=OH), respectively. 13g and 13h can then be cyclized via ring-closing metathesis using a catalyst, such as Grubbs (II), in a suitable solvent, such as DCM, DCE, or toluene at elevated temperature, to give the macrocycle 13i ($R^{13a}$=Cl) and 13j ($R^{13a}$=OH), respectively. The resulting alkenes can then be reduced with hydrogen over either palladium on carbon or platinum oxide to give 13k and 13l. Compound 13k can be reduced with ammonium acetate and palladium on carbon to give 13m. Subsequent deprotection of 13m and 13l with HCl provides amines 13n ($R^{13a}$=H) and 13o ($R^{13a}$=OH). Compounds of formulae 13n and 13o can be converted to compounds in this invention according to Scheme 14.

Scheme 13

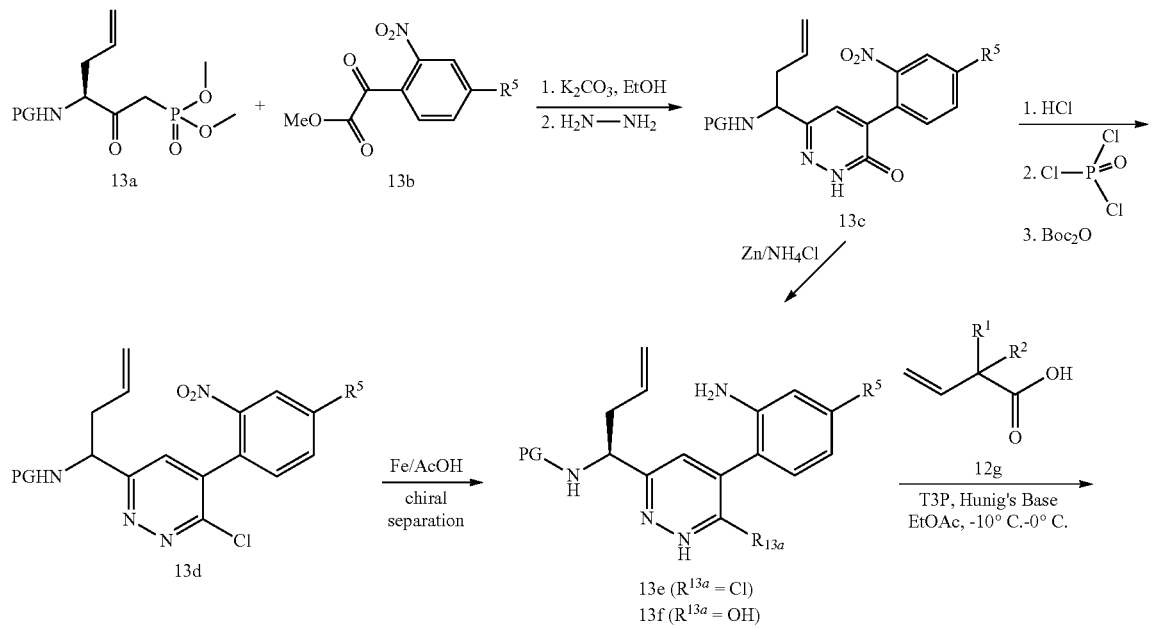

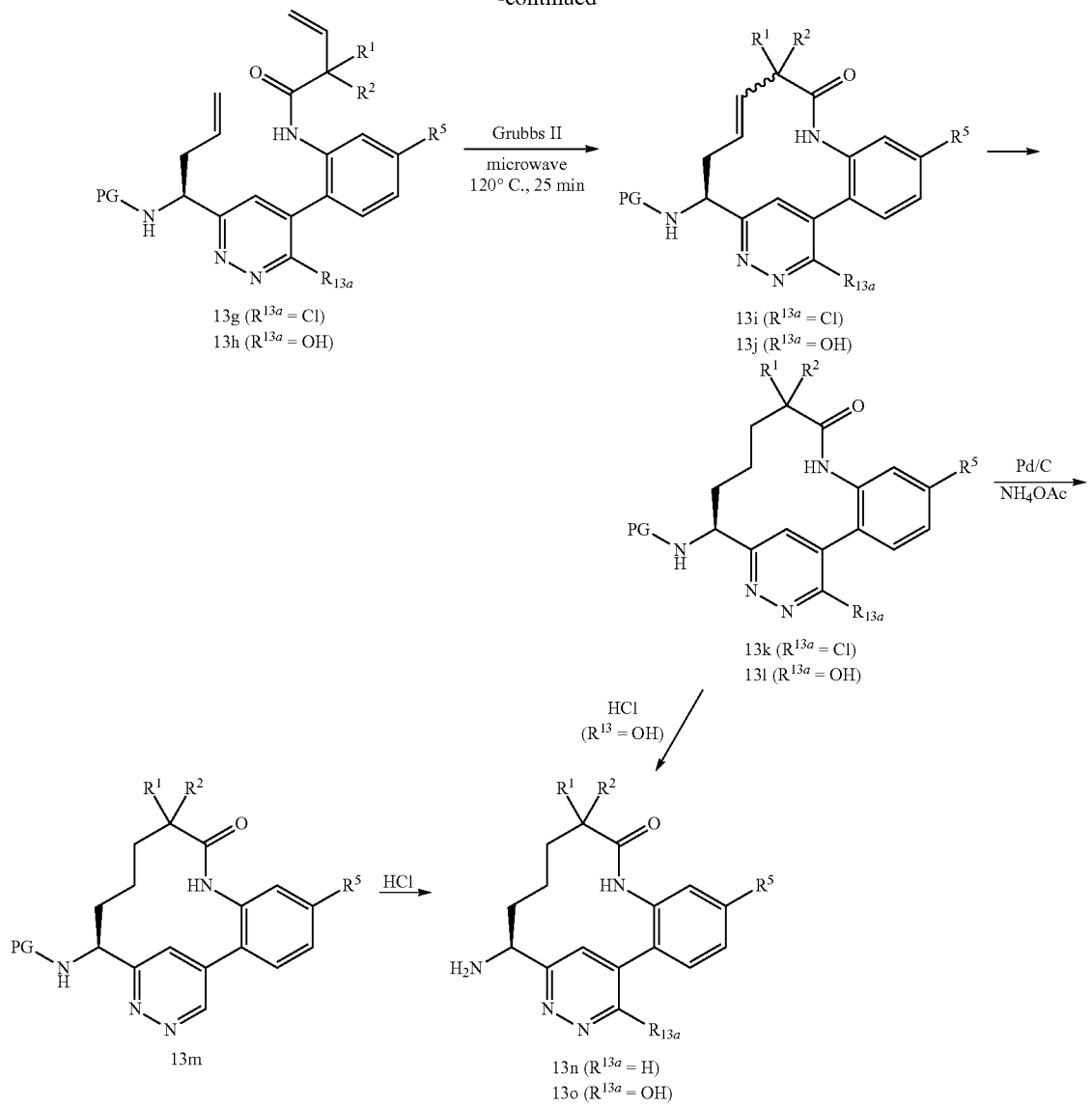

Representative compounds of this invention can then be made as shown in Scheme 14 using intermediates made in Schemes 2 to 13. Cyclic carbamate of the type 14b of this invention may be derived from intermediate 3-iodo-1-propanol 2e which can be used to alkylate suitable amines to yield 14a. Further treatment of amino-alcohol 14a with CDI gives cyclic carbamate 14b. Keto-piperazine of formula 14d may be prepared by alkylation of suitable amine intermediates with 3e to yield aminoester 14c. Hydrolysis and cyclization of aminoester 14c provides ketopiperazines 14d. Lactams of formula 14f may be prepared by alkylation of suitable amine intermediates with 4d to provide intermediate 14e. Cyclization of 14e provides lactam 14f. Cyclic urea of formula 14h may be prepared by alkylation of suitable amine intermediates with iodide 5e to provide diamine 14g. Deprotection and cyclization of 14g with CDI provides the cyclic urea 14h. Alternatively, cyclic ureas of formula 14h may be derived from the aldehyde 6b via reductive amination with suitable amine intermediates followed by deprotection and cyclization and deprotection (in case of imidazole) to provide cyclic urea 14h.

Scheme 14

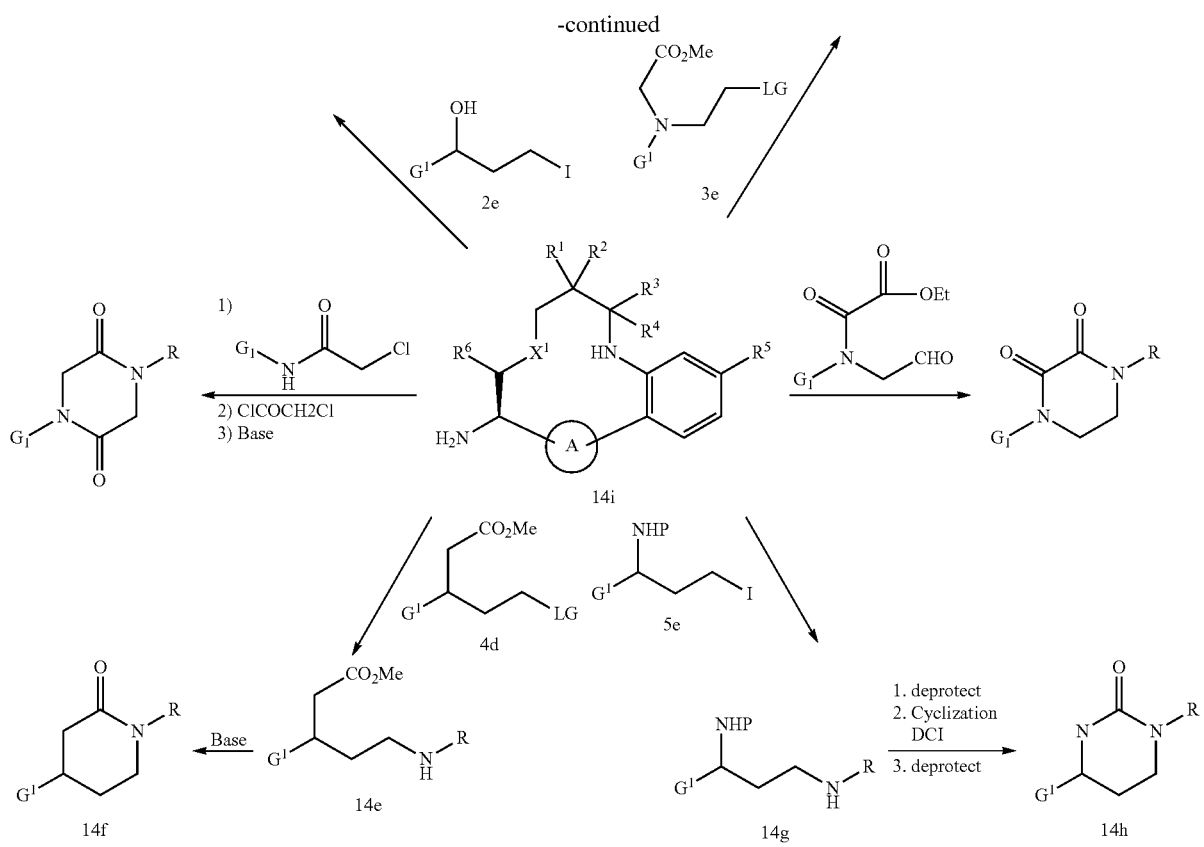

Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) Sunfire Prep C18 OBD 5u 30×100 mm, 25 min gradient from 0-100% B. A=$H_2O$/ACN/TFA 90:10:0.1. B=ACN/$H_2O$/TFA 90:10:0.1.

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN-to 95:5 ACN/$H_2O$—0.05% TFA).

Method B: ZORBAX® (4.6×75 mm) (8 min gradient—10: 90 MeOH/$H_2O$ to 90:10 MeOH/$H_2O$, 0.2% $H_3PO_4$).

Method C: SunFire column (3.5 μm C18, 3.0×150 mm). Gradient elution (1.0 mL/min) from 10-100% Solvent B for 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

A majority of mass spectra runs were: LCMS (ESI) m/z: [M+H]+ PHENOMENEX® Luna C18 (2×30 mm) (2 min gradient 90% $H_2O$/10% MeOH/0.1% TFA to 90% MeOH/ 10% $H_2O$/0.1% TFA) (or) BEH C18 2.1×50 mm—2 min gradient from 0-100% B. (A: 90/10/0.1 $H_2O$/ACN/TFA; B: 90/10/0.1 ACN/$H_2O$/TFA).

Intermediate 1

1-(3-Chlorophenyl)-3-iodopropan-1-ol

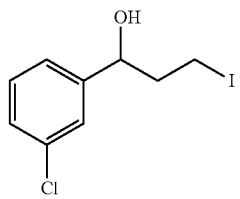 [SMILES: OC(CCI)c1cccc(Cl)c1]

Intermediate 1A

3-Chloro-1-(3-chlorophenyl)propan-1-one: To a solution of zinc chloride (0.5 M in THF, 20.40 mL, 10.20 mmol) was added a solution of (3-chlorophenyl) magnesium bromide (0.5 M in THF, 20.00 mL, 10 mmol) and the mixture was stirred at ambient temperature for 20 min. Pd(PPh$_3$)$_4$ (578 mg, 0.500 mmol) was added to the above mixture and the reaction was then cooled to 0° C. A solution of 3-chloropropanoyl chloride (1.008 mL, 10.50 mmol) in THF (anhydrous) (10 mL) was added and the reaction was stirred at 0° C. for 2 h. After this time, the mixture was acidified with 3 N HCl and extracted with $Et_2O$ (3×). The combined organic layer was washed with saturated aqueous NaHCO$_3$, brine, dried (Na$_2$SO$_4$), filtered and evaporated to an oil which was purified using silica gel chromatography to give the desired product (635 mg, 31%). MS (ESI) m/z: 202.9 (M+H)$^+$.

Intermediate 1B

3-Chloro-1-(3-chlorophenyl)propan-1-ol: To a solution of Intermediate 1A (389.6 mg, 1.919 mmol) in THF (5 mL) and water (0.294 mL) was added sodium borohydride (80 mg, 2.110 mmol), and the mixture was stirred overnight at ambient temperature. Water (5 mL) was then added, and the volume of the resulting solution was reduced under a stream of nitrogen to ~5 mL. EtOAc was added and the phases were separated. The aqueous phase was extracted twice with EtOAc, and the combined extracts were washed with brine, dried (Na$_2$SO$_4$), filtered, and evaporated. The residue was purified using silica gel chromatography to give the desired product (278 mg, 71%) as colorless oil.

Intermediate 1

1-(3-Chlorophenyl)-3-iodopropan-1-ol: (Ref: *J. Med. Chem.*, 31:1412-1417 (1988)). Intermediate 1B (114.5 mg, 0.558 mmol) was treated with sodium iodide solution (2.66 M in dry acetone, 21 mL, 55.9 mmol), and the mixture was heated overnight under nitrogen. The reaction mixture was cooled to rt, and the solvent was removed under reduced pressure. The residue was partitioned between Et$_2$O and water, and layers were separated. The organic layer was washed with water and brine, dried (Na$_2$SO$_4$), filtered, and evaporated to yield the desired product as a colorless oil (139 mg, 84%).

Intermediate 2

(R)-1-(3-Chloro-2,6-difluorophenyl)-3-iodopropan-1-ol

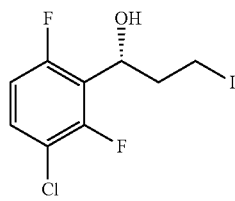 [SMILES: O[C@H](CCI)c1c(F)ccc(Cl)c1F]

Intermediate 2A 1-(3-Chloro-2,6-difluorophenyl)prop-2-en-1-ol: 3-Chloro-2,6-difluorobenzaldehyde (1.0 g, 5.66 mmol) was dissolved in THF (28.3 mL) under an atmosphere of argon, and the solution was cooled to −78° C. To the cold solution was then added vinyl magnesium bromide, 1.0 M in THF (8.50 mL, 8.50 mmol) dropwise over 10-15 min. Stirring was continued at −78° C. for 1 h. The reaction was warmed to rt, then cooled to 0° C. and carefully quenched with saturated NH$_4$Cl solution. The mixture was diluted with water and extracted with EtOAc. The organic extracts were combined and washed with water and brine, dried over anhydrous MgSO$_4$, filtered and evaporated to yield the desired product as a light yellow oil (1.19 g, 98%). MS (ESI) m/z: 187.0 (M−H$_2$O)$^+$. $^1$H NMR (500 MHz, CDCl$_3$) δ 7.36-7.30 (m, 1H), 6.88 (td, J=9.2, 1.9 Hz, 1H), 6.21 (dddt, J=17.1, 10.3, 5.8, 1.1 Hz, 1H), 5.59 (dd, J=7.4, 6.6 Hz, 1H), 5.33 (dd, J=17.1, 0.8 Hz, 1H), 5.26 (dt, J=10.3, 1.2 Hz, 1H), 2.35 (dt, J=8.5, 1.8 Hz, 1H).

Intermediate 2B 1-(3-Chloro-2,6-difluorophenyl)prop-2-en-1-one: To a solution of Intermediate 2A (0.300 g, 1.466 mmol) in acetone (7.33 mL) at 0° C. was added Jones reagent (1.094 mL, 2.93 mmol) dropwise. The reaction mixture turned orange/brown and stirring was continued at 0° C. for 30 min. Excess reagent was quenched by addition of isopropanol (5 mL) and the resultant solution was allowed to stir at rt for 5 min. After this time, the reaction was diluted with EtOAc and water. The layers were separated, and the EtOAc layer was extracted with water, dried over MgSO$_4$, filtered, and concentrated to yield a light yellow oil which was purified using silica gel chromatography to give the desired product (0.177 g, 59%) as a colorless liquid. MS (ESI) m/z: 203.0 (M+H)$^+$. $^1$H NMR (400 MHz, CDCl$_3$) δ 7.49 (td, J=8.5, 5.5 Hz, 1H), 6.96 (td, J=8.5, 1.6 Hz, 1H), 6.70 (dd, J=17.6, 10.4 Hz, 1H), 6.24-6.17 (m, 2H) ppm.

Intermediate 2C 1-(3-Chloro-2,6-difluorophenyl)-3-iodopropan-1-one: (Ref: *Synthesis*, 366-399 (1998)) To a stirred solution of NaI (0.153 g, 1.019 mmol) in ACN (0.637 ml) was added TMS-Cl (0.130 mL, 1.019 mmol) dropwise. A precipitate was formed, and the mixture turned yellow. Water (0.015 mL, 0.849 mmol) was added (which re-dissolved the precipitate), followed by addition of Intermediate 2B (0.172 g, 0.849 mmol). The mixture was diluted with additional ACN (0.637 mL), and stirred at rt under argon for 15 min. The reaction mixture was diluted with water and extracted with EtOAc (3×). The combined organic layers were washed with 10% Na$_2$S$_2$O$_3$ and brine, dried over anhydrous MgSO$_4$, filtered, and concentrated to yield the desired product as a light yellow oil (0.265 g, 94%), MS (ESI) m/z: 330.7 (M+H)$^+$. $^1$H NMR (400 MHz, CDCl$_3$) δ 7.50 (ddd, J=8.9, 8.1, 5.7 Hz, 1H), 6.96 (td, J=8.8, 1.8 Hz, 1H), 3.59-3.53 (m, 2H), 3.45-3.40 (m, 2H).

Intermediate 2

(R)-1-(3-Chloro-2,6-difluorophenyl)-3-iodopropan-1-ol: A solution of R-5,5-diphenyl-2-methyl-3,4-propano-1,3,2-oxazaborlidine (1 M in toluene) (0.787 mL, 0.787 mmol) and BH$_3$.THF (1 M in THF) (7.87 mL, 7.87 mmol) was stirred at rt under Ar. Then two separate solutions of Intermediate 2C (13 g, 39.3 mmol) in THF (19.67 mL) and borane-tetrahydrofuran complex (1 M in THF) (19.67 mL, 19.67 mmol) were added dropwise to the reaction mixture over 45 min. After 1 h, the reaction mixture was quenched with MeOH at 0° C. The resulting solution was concentrated to yield a colorless oil, which was purified by silica gel chromatography to yield a white solid product as a mixture of (R)-1-(3-chloro-2,6-difluorophenyl)-3-iodopropan-1-ol and (S)-1-(3-chloro-2,6-difluorophenyl)-3-iodopropan-1-ol, with ratio of 2.1:1 by chiral OJ HPLC. The product was then used as a mixture or alternatively as a chirally pure material. Intermediate 2 was obtained as a single enantiomer by chiral chromatography separation and was the late eluting enantiomer by chiral OJ column. MS (ESI) m/z: 314.8 (M−H$_2$O)$^+$. $^1$H NMR (400 MHz, CDCl$_3$) δ 7.34 (td, J=8.5, 5.7 Hz, 1H), 6.89 (td, J=9.3, 1.8 Hz, 1H), 5.21 (td, J=8.6, 4.8 Hz, 1H), 3.31 (dd, J=7.7, 6.4 Hz, 2H), 2.61-2.50 (m, 1H), 2.34-2.22 (m, 1H), 2.19 (dt, J=8.3, 1.8 Hz, 1H).

Intermediate 3

Methyl 3-(3-chlorophenyl)-5-((methylsulfonyl)oxy)pentanoate

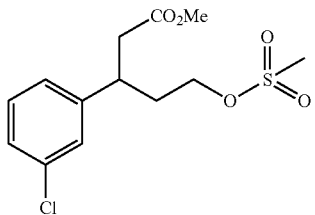 [SMILES: COC(=O)CC(CCOS(C)(=O)=O)c1cccc(Cl)c1]

Intermediate 3A

Dimethyl 3-(3-chlorophenyl)pentanedioate: 3-Chlorobenzaldehyde (5 mL, 44.1 mmol), methyl 3-oxobutanoate (9.53 mL, 88 mmol), piperidine (0.654 mL, 6.62 mmol) in MeOH (14.71 mL) were stirred at rt. Over time, the yellow solution turned cloudy, and finally too thick to stir. The solid-like reaction mixture was kept at rt overnight. MeOH (20 mL) was then added, and the yellow solid was broken apart using a spatula, chilled in an ice-water bath and filtered. The solid was washed with cold MeOH (2×10 mL) and then air-dried. A yellowish solid was obtained and the solid was suspended in MeOH (10 mL), then NaOMe (41 mL, 179 mmol, 25% wt in MeOH), followed by water (3.4 mL, 189 mmol) were added. The reaction was warmed to reflux (80-85° C.). During the course of reaction, the suspension became very hard to stir, and additional MeOH (40 mL) was added. After 7 h, the reaction was cooled to rt, and left at rt for 2 days. Water was added to the solid-like reaction mixture to give a brown solution. The reaction mixture was concentrated to remove MeOH, and the residue extracted with EtOAc. The aqueous layer was acidified with concentrated HCl to pH<3, then extracted with EtOAc (3×). The combined organic layers were dried over $Na_2SO_4$, filtered and concentrated. The orange oil obtained was dissolved in MeOH (50 mL), then concentrated HCl (0.63 mL) was added, and the mixture was heated at reflux (80° C. in an oil bath). After 6 h, the reaction was cooled to rt and then the reaction was concentrated to remove ⅔ of the MeOH. Water was then added, and a brown oil separated out. The solution was concentrated to remove all organics. The brown oil at the bottom solidified overnight. The solid was filtered, washed with water, air-dried and then dried in a vacuum oven (50° C.) for 2 h, to give a brown solid. The crude solid was purified by silica gel chromatography to give the desired product as a yellow oil (6.23 g, 52%). MS (ESI) m/z: 292.9 (M+Na)$^+$.

Intermediate 3B 3-(3-Chlorophenyl)-5-methoxy-5-oxopentanoic acid: To the solution of Intermediate 3A (0.35 g, 1.293 mmol) in MeOH (5 mL) was added 1 N NaOH (1.293 mL, 1.293 mmol). The reaction was stirred at rt. The solution was concentrated to remove the MeOH. Next, 1N HCl (1.5 mL) was then added to give a white suspension. MeOH was added to give a solution (8 mL), and resultant solution was purified by reverse phase chromatography. A colorless oil was obtained as 3-(3-chlorophenyl)-5-methoxy-5-oxopentanoic acid (0.228 g, 69%). MS (ESI) m/z: 278.9 (M+Na)$^+$.

Intermediate 3C

Methyl 3-(3-chlorophenyl)-5-hydroxypentanoate: To the solution of Intermediate 3B (0.228 g, 0.888 mmol) in THF (8.88 mL) was added $BH_3$-methyl sulfide complex (1.332 ml, 2.66 mmol, 2 M in THF), and the reaction was stirred at rt. After 3 h, the reaction was cooled to 0° C., quenched with MeOH (1 mL), followed by water (1 mL), and saturated $NaHCO_3$ (1 mL). The reaction mixture was extracted with EtOAc. The organic layer was washed with brine, dried over $Na_2SO_4$, filtered, and concentrated to yield the desired product as a colorless oil (0.2 g, 93%). MS (ESI) m/z: 264.9 (M+Na)$^+$. The enantiomers can be separated by chiral SFC preparatory HPLC (CHIRALPAK® IC; 15% Isopropanol/85% $CO_2$) to give Intermediate 3C (enantiomer A) and Intermediate 3C (enantiomer B).

Intermediate 3

Methyl 3-(3-chlorophenyl)-5-((methylsulfonyl)oxy)pentanoate: To a stirred solution of Intermediate 3C (0.085 g, 0.350 mmol) in DCM (5 mL) and $Et_3N$ (0.146 mL, 1.051 mmol) at 0° C. was added $MeSO_2Cl$ (0.041 mL, 0.525 mmol). The reaction was stirred at rt. After 20 h, the reaction mixture was diluted with EtOAc and washed with 1 N HCl, saturated $NaHCO_3$ and brine. The organic layer was dried over anhydrous $Na_2SO_4$, filtered and concentrated to give Intermediate 3 (0.1 g, 89%) as a yellow oil. Alternatively, Intermediate 3 (enantiomer A) can be prepared from Intermediate 3C (enantiomer A) and Intermediate 3 (enantiomer B) can be prepared from Intermediate 3C (enantiomer B). $^1$H NMR (500 MHz, CDCl$_3$) δ7.31-7.19 (m, 3H), 7.14-7.10 (m, 1H), 4.18-4.11 (m, 1H), 3.98 (ddd, J=10.1, 8.5, 5.6 Hz, 1H), 3.62 (s, 3H), 3.35-3.27 (m, 1H), 2.95 (s, 3H), 2.71-2.60 (m, 2H), 2.26-2.16 (m, 1H), 2.04-1.95 (m, 1H) ppm. MS (ESI) m/z: 342.9 (M+Na)$^+$.

Intermediate 4

(R)-1-(5-Chloro-2-(difluoromethoxy)phenyl)-3-iodopropan-1-ol

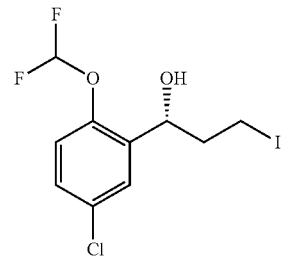 [SMILES: O[C@H](CCI)c1cc(Cl)ccc1OC(F)F]

Intermediate 4A 1-(5-Chloro-2-(difluoromethoxy)phenyl)prop-2-en-1-ol: 5-Chloro-2-(difluoromethoxy)benzaldehyde (0.480 g, 2.324 mmol) was dissolved in dry THF (11.62 mL) and the reaction was cooled to −78° C. under argon. Vinyl magnesium bromide (3.49 mL, 3.49 mmol) was then added dropwise. After the reaction was complete, the ice bath was removed and reaction was allowed to warm to rt and stirred for an additional 2 h. The reaction was cooled to 0° C. and then carefully quenched with saturated ammonium chloride. The mixture was then diluted with water and extracted with EtOAc (3×). The combined organic phases were dried over $Na_2SO_4$, filtered and concentrated to yield 1-(5-chloro-2-(difluoromethoxy)phenyl)prop-2-en-1-ol (561 mg, 103%) as a clear oil. MS (ESI) m/z: 236.9 (M+H, Chlorine isotope peak)$^+$.

Intermediate 4B 1-(5-Chloro-2-(difluoromethoxy)phenyl)prop-2-en-1-one: To a solution of Intermediate 4A (0.400 g, 1.705 mmol) in acetone (10 mL) at 0° C. was added Jones Reagent (1.272 mL, 3.41 mmol) dropwise. The reaction mixture turned brown. The reaction was allowed to stir at 0° C. and gradually raised to rt and stirred overnight. The reaction was quenched by addition of isopropanol (5 mL), stirred at rt for 5 min, and then diluted with EtOAc and water. The EtOAc layer was washed with water (3×), dried with sodium sulfate, filtered, and concentrated to yield 321 mg of crude material which was purified by silica gel chromatography to give the desired product (189 mg, 48%) as a yellow oil. $^1$H NMR (500 MHz, $CDCl_3$) δ 7.57 (d, J=2.8 Hz, 1H), 7.49 (dd, J=8.8, 2.8 Hz, 1H), 7.22 (d, J=8.8 Hz, 1H), 6.84 (dd, J=17.3, 10.5 Hz, 1H), 6.69-6.35 (m, 1H), 6.28 (dd, J=17.3, 1.1 Hz, 1H), 6.04 (dd, J=10.6, 1.0 Hz, 1H).

Intermediate 4C 1-(5-Chloro-2-(difluoromethoxy)phenyl)-3-iodopropan-1-one: To a stirred solution of NaI (107 mg, 0.717 mmol) in 1.5 mL of ACN was added TMS-Cl (0.092 ml, 0.717 mmol) dropwise. A precipitate formed and the reaction mixture turned yellow. Water (0.022 ml, 1.195 mmol) was added followed by a solution of Intermediate 4B (204 mg, 0.566 mmol) in 1.5 mL of ACN. The reaction was stirred at rt for 20 min. The reaction was then diluted with 10% sodium thiosulfate (color turned clear) and extracted with EtOAc (3×). The combined organics were washed with brine, dried over sodium sulfate, filtered, and concentrated to yield Intermediate 4C (204 mg, 95%) as a clear oil. $^1$H NMR (500 MHz, $CDCl_3$) δ 7.75 (d, J=2.8 Hz, 1H), 7.52 (dd, J=8.8, 2.5 Hz, 1H), 7.18 (d, J=8.8 Hz, 1H), 6.78-6.43 (m, 1H), 3.67-3.59 (m, 1H), 3.50-3.39 (m, 1H).

Intermediate 4

(R)-1-(5-Chloro-2-(difluoromethoxy)phenyl)-3-iodopropan-1-ol: A solution of (S)-MeCBS (1 M in toluene) (0.015 ml, 0.015 mmol) and $BH_3$.THF (1 M in THF) (0.079 ml, 0.079 mmol) in THF (1 mL) was stirred at rt under argon. Then two separate solutions of Intermediate 4C (0.136 g, 0.377 mmol) in THF (1 mL) and $BH_3$.THF (1 M in THF) (0.189 mL, 0.189 mmol) were simultaneously added dropwise to the reaction mixture over ~2 min. After addition of the reagents, the reaction was allowed to stir at rt under argon for 2 h. The reaction was carefully quenched at 0° C. with MeOH and concentrated. The crude reaction mixture was then purified using silica gel chromatography. The desired fractions were combined and concentrated to yield Intermediate 4 (0.126 g, 92%) as a clear oil. MS (ESI) m/z: 384.7 (M+H)$^+$. $^1$H NMR (500 MHz, $CDCl_3$) δ 7.57 (d, J=2.8 Hz, 1H), 7.35-

7.23 (m, 1H), 7.09 (d, J=8.8 Hz, 1H), 6.77-6.25 (m, 1H), 5.15 (dt, J=8.5, 4.2 Hz, 1H), 3.42-3.28 (m, 2H), 2.31-2.13 (m, 2H), 2.12-2.06 (m, 1H).

Intermediate 5

1-(3-Chloro-2-fluoro-6-(trifluoromethyl)phenyl)-3-iodopropan-1-ol

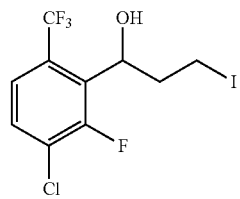

Intermediate 5A 1-(3-Chloro-2-fluoro-6-(trifluoromethyl)phenyl)prop-2-en-1-ol: To a solution of 3-chloro-2-fluoro-6-(trifluoromethyl)benzaldehyde (2.052 g, 9.06 mmol) in THF (30 mL) under nitrogen at −78° C. was added dropwise vinyl magnesium bromide (1 M in THF) (11.77 mL, 11.77 mmol). The mixture was stirred for 15 minutes at this temperature then the cooling bath was removed allowing the solution to warm to ambient temperature where it was stirred for 1 h. The reaction was cooled to 0° C. and quenched with 20 mL of aqueous $NH_4Cl$ (saturated) and the solvent was removed under a stream of nitrogen. The solid residue was taken up in water/ethyl acetate and phases were separated. The aqueous layer was extracted twice with ethyl acetate and the combined organic extracts were washed with brine, dried ($Na_2SO_4$), filtered and concentrated to give an oil. The oil was then purified using silica gel chromatography. The desired fractions were combined together to give 1-(3-chloro-2-fluoro-6-(trifluoromethyl)phenyl)prop-2-en-1-ol (1.322 g, 57%) as a faint yellow colored oil.

Intermediate 5B 1-(3-Chloro-2-fluoro-6-(trifluoromethyl)phenyl)prop-2-en-1-one: To a solution of Intermediate 5A (794.7 mg, 3.12 mmol) in acetone (15 mL) at 0° C. was added dropwise Jones reagent (2.329 mL, 6.24 mmol). The resulting reaction was then stirred at 0° C. for 30 min. The reaction was quenched with i-PrOH (4 mL), filtered through CELITE®, partially evaporated and partitioned with $NaHCO_3$/EtOAc. The aqueous layer was further extracted with EtOAc (3×) and the combined organics were washed with brine, dried ($Na_2SO_4$), filtered and evaporated to give a light yellow oil. The oil was dissolved in a small amount of DCM and purified using silica gel chromatography. Appropriate fractions were combined and evaporated to give the desired product 1-(3-chloro-2-fluoro-6-(trifluoromethyl)phenyl)prop-2-en-1-one (295 mg, 37%) as a light yellow colored oil.

Intermediate 5C 1-(3-Chloro-2-fluoro-6-(trifluoromethyl)phenyl)-3-iodopropan-1-one: To a round bottomed flask was added NaI (210 mg, 1.401 mmol) and ACN (5 mL). To this mixture was added TMS-Cl (0.179 mL, 1.401 mmol) dropwise followed by addition of water (0.021 mL, 1.167 mmol). A solution of Intermediate 5B (294.8 mg, 1.167 mmol) in ACN (5 mL) was added and the mixture was stirred for 20 min at ambient temperature. The reaction mixture was diluted with water, extracted with ethyl acetate (3×), and the combined organics were washed with 10% Na$_2$S$_2$O$_3$, brine, dried (Na$_2$SO$_4$), filtered and evaporated to provide Intermediate 5C as an oil (366.4 mg, 83%).

Intermediate 5

1-(3-Chloro-2-fluoro-6-(trifluoromethyl)phenyl)-3-iodopropan-1-ol: To a solution of Intermediate 5C (364 mg, 0.957 mmol) in THF (5 mL) and water (0.146 mL, 8.13 mmol) was added sodium borohydride (39.8 mg, 1.052 mmol) and the mixture stirred for overnight at ambient temperature. Water (5 mL) and EtOAc were added and the phases were separated. The aqueous phase was extracted three times with EtOAc. The combined organic extracts were washed with brine, dried (Na$_2$SO$_4$), filtered and evaporated to a colorless oil which was purified using silica gel chromatography. Appropriate fractions were combined and concentrated to give 1-(3-chloro-2-fluoro-6-(trifluoromethyl)phenyl)-3-iodopropan-1-ol (79.5 mg, 22%) as a colorless solid. $^1$H NMR (400 MHz, CDCl$_3$) δ 7.52-7.40 (m, 2H), 5.23-5.13 (m, 1H), 3.45-3.38 (m, 1H), 3.34 (m, 1H), 2.63-2.52 (m, 1H), 2.30-2.16 (m, 2H).

Intermediate 6

(R)-tert-Butyl (1-(3-chloro-2-fluorophenyl)-3-iodopropyl)carbamate

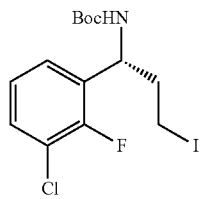 [SMILES: CC(C)(C)OC(=O)N[C@H](CCI)c1cccc(Cl)c1F]

Intermediate 6A (R,E)-N-(3-Chloro-2-fluorobenzylidene)-2-methylpropane-2-sulfinamide: (Ref: *Angew. Chem. Int. Ed.,* 48:914-917 (2009)). To a stirred suspension of 3-chloro-2-fluorobenzaldehyde (1.308 g, 8.25 mmol) and Cs$_2$CO$_3$ (4.03 g, 12.38 mmol) in DCM (10 mL) was added a solution of (R)-2-methylpropane-2-sulfinamide (1 g, 8.25 mmol) in DCM (50 mL) dropwise for 10 min. The solution was then stirred for 2 h at rt. LC/MS indicated that the reaction was complete. The reaction mixture was then diluted with EtOAc (50 mL) and washed with brine (20 mL×3). The organic layers were dried over Na$_2$SO$_4$ and concentrated in vacuo to give (R,E)-N-(3-chloro-2-fluorobenzylidene)-2-methylpropane-2-sulfinamide (2.3 g, 107%) as a clear oil. MS (ESI) m/z: 262.1 (M+H)$^+$.

Intermediate 6B (R)—N—((R)-1-(3-Chloro-2-fluorophenyl)allyl)-2-methylpropane-2-sulfinamide: To a cooled (−78° C.) solution of Intermediate 6A (1.24 g, 4.74 mmol) in THF (50 mL) was added vinyl magnesium bromide (1 M in THF) (6.16 mL, 6.16 mmol) ~0.5 ml at a time. The resulting solution was stirred for 0.5 h at −78° C. After this time, the dry ice was removed and the reaction was allowed to slowly reach to rt. The mixture was stirred at rt for 0.5 h. LCMS analysis indicated incomplete reaction and more Grignard reagent (1 mL) was then added and the reaction was then stirred at rt overnight. The reaction mixture was cooled in an ice bath, quenched with saturated NH$_4$Cl followed by extraction with EtOAc (3×). The combined organic layers were then concentrated to give the crude product, (R)—N—((R)-1-(3-chloro-2-fluorophenyl)allyl)-2-methylpropane-2-sulfinamide (1.44 g, 105%) as a yellow oil which was taken onto the next step as is. MS (ESI) m/z: 290.0 (M+H)$^+$. $^1$H NMR (400 MHz, CDCl$_3$) δ 7.36-7.28 (m, 1H), 6.88 (td, J=9.2, 2.0 Hz, 1H), 6.27-6.13 (m, 1H), 5.44-5.36 (m, 1H), 5.32-5.19 (m, 3H), 3.83 (d, J=7.8 Hz, 1H), 1.20-1.13 (m, 9H) ppm. (3:1 diastereomer ratio).

Intermediate 6C (R)-tert-Butyl(1-(3-chloro-2-fluorophenyl)allyl)carbamate: To a solution of crude Intermediate 6B (1.44 g, 4.97 mmol) in MeOH (10 mL) was added HCl (7 mL, 28.0 mmol) and stirred at rt for 1 h. Aliquot LCMS indicates that the starting material had been consumed. The reaction mixture was concentrated and coevaporated with toluene (2×). The crude product was then triturated with ether, filtered and then washed with ether to give (R)-1-(3-chloro-2-fluorophenyl)prop-2-en-1-amine as beige solid. The solid was dissolved in ACN (25 mL) and TEA (3.46 mL, 24.85 mmol) and to this solution was added Boc$_2$O (1.50 mL, 6.46 mmol). The reaction was then stirred at rt overnight. The reaction mixture was diluted with EtOAc and washed with water followed by brine. The crude product was then purified using silica gel chromatography to give (R)-tert-butyl (1-(3-chloro-2-fluorophenyl)allyl)carbamate (835 mg, 59%) as a white solid. MS (ESI) m/z: 271.0 (M+H)$^+$. $^1$H NMR (400 MHz, CDCl$_3$) δ 7.35-7.30 (m, 1H), 7.17 (td, J=7.0, 1.5 Hz, 1H), 7.09-7.03 (m, 1H), 6.03-5.92 (m, 1H), 5.48 (br. s., 1H), 5.26-5.11 (m, 2H), 1.49-1.35 (m, 9H) ppm.

Intermediate 6D (R)-tert-Butyl (1-(3-chloro-2-fluorophenyl)-3-hydroxypropyl)carbamate: (Ref: *J. Org. Chem.,* 69(8):2773-2784 (2004).) To a microwave vial containing Intermediate 6C (300 mg, 1.050 mmol) was added 9-BBN (0.5 M) in THF (6.30 mL, 3.15 mmol) and the microwave vial was capped. The reaction mixture was then heated at 100° C. overnight. The reaction mixture was cooled to rt, then 0° C. followed by addition of EtOH (1 mL), NaOH (1.575 mL, 3.15 mmol) and then hydrogen peroxide (0.919 mL, 10.50 mmol). The reaction mixture was further heated at 45° C. for 1 h (add balloon on syringe to relieve pressure). To the reaction mixture after cooling to rt was added sodium thiosulfate (Na$_2$S$_2$O$_2$) solution to remove excess peroxide. The reaction mixture was then extracted with EtOAc (3×). The organic layers were combined and dried over MgSO$_4$. The crude product was then subjected to silica gel chromatography. Desired fractions were pooled together and concentrated to give (R)-tert-butyl (1-(3-chloro-2-fluorophenyl)-3-hydroxypropyl)carbamate (173 mg, 54%) as clear oil. MS (ESI) m/z: 304.1 (M+H)$^+$.

Intermediate 6

(R)-tert-Butyl (1-(3-chloro-2-fluorophenyl)-3-iodopropyl)carbamate: To a solution of Intermediate 6D (50 mg, 0.165 mmol) in DCM (5 mL) was added DIEA (0.060 mL, 0.344 mmol) followed by MeSO₂Cl (0.020 mL, 0.257 mmol). The reaction mixture was stirred at rt for 0.5 h. LC/MS analysis indicated the starting material had been consumed. The reaction mixture was concentrated. The residue was dissolved in EtOAc and washed with aqueous NaHCO₃ solution followed by brine. The organic layer was dried over MgSO₄ and concentrated in vacuo to yield a yellow oil. To a solution of the yellow oil (79 mg, 0.207 mmol) in acetone (5.00 mL) was added sodium iodide (99 mg, 0.658 mmol). The yellow suspension was heated to 65° C. for ~4 h followed by stirring at rt for two more days. After this time, the reaction mixture was concentrated and then to the crude product was added small amount of water and DCM. The reaction mixture was then extracted with DCM (2×) and the organic layers were dried over MgSO₄. The organic layers were then concentrated and purified using silica gel chromatography to yield the desired product (R)-tert-butyl (1-(3-chloro-2-fluorophenyl)-3-iodopropyl)carbamate (48 mg, 71%) as a yellow oil. MS (ESI) m/z: 398.1 (M+H)⁺. ¹H NMR (400 MHz, CDCl₃) δ 7.37-7.30 (m, 1H), 7.24-7.17 (m, 1H), 7.11-7.03 (m, 1H), 5.15-4.83 (m, 2H), 3.21-2.97 (m, 2H), 2.33 (br. s., 2H), 1.51-1.34 (m, 9H) ppm.

Intermediate 7

(R)-1-(5-Chloro-2-fluorophenyl)-3-iodopropan-1-ol

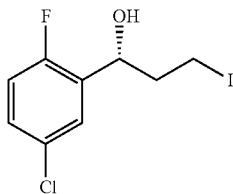 [SMILES: O[C@H](CCI)c1cc(Cl)ccc1F]

Intermediate 7A

3-Chloro-1-(5-chloro-2-fluorophenyl)propan-1-one: In a flame-dried 3-neck flask, 2-bromo-4-chloro-1-fluorobenzene (2.0 g, 9.55 mmol) was dissolved in THF (anhydrous) (28.9 mL) under argon. Isopropylmagnesium chloride (2 M in THF) (5.01 mL, 10.03 mmol) was added, and the reaction was stirred at rt. To this solution was added zinc chloride (0.5 M in THF) (20.44 mL, 10.22 mmol) and the mixture was stirred at ambient temperature for 40 min. To the reaction was then added Pd(PPh₃)₄ (0.276 g, 0.239 mmol), and the mixture was cooled to 0° C. A solution of 3-chloropropanoyl chloride (0.981 mL, 10.22 mmol) in THF (2.89 mL) was added, and the reaction was stirred for 2 h at 0° C. The reaction mixture was then quenched with 3 N HCl, diluted with water, and extracted with Et₂O (3×). The combined organics were dried (MgSO₄), filtered and evaporated to yield a grainy yellow liquid, which was purified using silica gel chromatography to obtain a colorless oil, 3-chloro-1-(5-chloro-2-fluorophenyl)propan-1-one (0.405 g, 19%). MS (ESI) m/z: 221.0 (M+H)⁺. ¹H NMR (400 MHz, CDCl₃) δ 7.88 (dd, J=6.3, 2.8 Hz, 1H), 7.51 (ddd, J=8.8, 4.3, 2.8 Hz, 1H), 7.13 (dd, J=10.2, 8.7 Hz, 1H), 3.94-3.88 (m, 2H), 3.46 (td, J=6.6, 3.2 Hz, 2H) ppm.

Intermediate 7B (R)-3-Chloro-1-(5-chloro-2-fluorophenyl)propan-1-ol: A solution of (S)-MeCBS (0.037 mL, 0.037 mmol) and BH₃.THF (1M in THF) (0.384 mL, 0.384 mmol) was stirred at rt under argon. Then two separate solutions of Intermediate 7A (0.404 g, 1.828 mmol) in THF (0.914 mL) and BH₃.THF (1 M in THF) (0.914 mL, 0.914 mmol) were simultaneously added dropwise to the reaction mixture over 5 min. After addition of the reagents, the reaction was allowed to stir under argon at rt for another 2 h. The reaction mixture was quenched with slow dropwise addition of MeOH (careful—very exothermic) and then allowed to stir at rt for two days. The reaction was concentrated to dryness and residue purified by silica gel chromatography to yield a colorless oil, (R)-3-chloro-1-(5-chloro-2-fluorophenyl)propan-1-ol (0.294 g, 72% yield). ¹H NMR (500 MHz, CDCl₃) δ 7.50 (dd, J=6.1, 2.5 Hz, 1H), 7.24 (ddd, J=8.8, 4.4, 2.8 Hz, 1H), 7.00 (dd, J=9.6, 8.8 Hz, 1H), 5.27-5.22 (m, 1H), 3.78 (ddd, J=11.0, 8.3, 6.1 Hz, 1H), 3.66 (dt, J=11.1, 5.6 Hz, 1H), 2.24-2.13 (m, 2H), 2.07 (d, J=4.7 Hz, 1H) ppm.

Intermediate 7

(R)-1-(5-Chloro-2-fluorophenyl)-3-iodopropan-1-ol: To Intermediate 7B (0.2914 g, 1.306 mmol) was added sodium iodide solution (2.66 M in dry acetone) (1.964 mL, 5.23 mmol) (made from 0.784 mg of NaI and 1.96 mL of dry acetone) and the mixture was placed under argon and brought to reflux at 60° C. for 20 h. To the reaction mixture was added EtOAc and water and the two phases separated. The aqueous layer was extracted again with EtOAc. The combined organic layers were washed with water followed by brine. The organic layer was dried (MgSO₄), filtered and evaporated to a colorless oil, (R)-1-(5-chloro-2-fluorophenyl)-3-iodopropan-1-ol (0.377 g, 92%). MS (ESI) m/z: 336.9 (M+H)⁺. ¹H NMR (500 MHz, CDCl₃) δ 7.49 (dd, J=6.2, 2.6 Hz, 1H), 7.24 (ddd, J=8.8, 4.4, 2.8 Hz, 1H), 6.99 (dd, J=9.6, 8.8 Hz, 1H), 5.12 (dt, J=7.2, 4.9 Hz, 1H), 3.38-3.31 (m, 1H), 3.31-3.26 (m, 1H), 2.27-2.21 (m, 2H), 2.00 (d, J=4.4 Hz, 1H) ppm. (7.5:2.5 enantiomers (52% ee)).

Intermediate 8 tert-Butyl (1-(4-chloropyridin-2-yl)-3-oxopropyl)carbamate

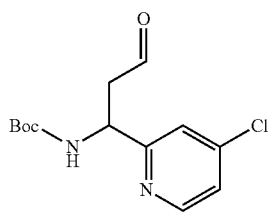 [SMILES: CC(C)(C)OC(=O)NC(CC=O)c1cc(Cl)ccn1]

Intermediate 8A

Methyl 3-((tert-butoxycarbonyl)amino)-3-(4-chloropyridin-2-yl)propanoate: To a solution of methyl 3-(4-chloropyridin-2-yl)-3-((R)-1,1-dimethylethylsulfinamido)propanoate (400 mg, 1.255 mmol) in MeOH (2 mL) was added 4 N HCl in dioxane. The reaction was stirred at rt for 1 h and evaporated to dryness. The reaction mixture was then treated with saturated NaHCO₃ solution until the pH of the solution turned basic. The aqueous layer was then extracted with EtOAc (2×15 mL). The combined organic layers were washed with brine, dried over MgSO₄ and concentrated to give brownish oil (270 mg, 100%). To a solution of brownish oil in ACN (5 mL) was added TEA (0.525 mL, 3.76 mmol) followed by Boc₂O (0.350 mL, 1.506 mmol). The reaction mixture was then stirred at rt for 1 h. The reaction mixture was concentrated and diluted with EtOAc. The organic layer was washed with brine and dried over MgSO₄ to give Intermediate 8A (410 mg, 104%) as yellow oil. The above crude product was used in the next step without further purification. MS (ESI) m/z: 315.0; 317.0 (M+H, Chlorine isotope)⁺.

Intermediate 8 tert-Butyl (1-(4-chloropyridin-2-yl)-3-oxopropyl)carbamate: A solution of Intermediate 8A (70 mg, 0.222 mmol) in DCM (3 mL) was cooled to −78° C. To this solution was added DIBAL-H (1 M solution in toluene) (0.445 mL, 0.445 mmol) dropwise. After 1 h, the reaction mixture was quenched with MeOH (0.5 mL) and H₂O (0.1 mL) at −78° C. and then allowed to warm to rt. The aqueous layer was extracted with EtOAc (2×). The combined organic layers were washed with brine, dried over MgSO₄, filtered and concentrated to give the desired product. MS (ESI) m/z: 285.1 (M+H)⁺.

Intermediate 9 tert-Butyl (1-(3-chlorophenyl)-3-iodopropyl)carbamate

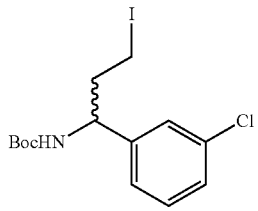 [SMILES: CC(C)(C)OC(=O)NC(CCI)c1cccc(Cl)c1]

Intermediate 9A (S)—N—((S)-1-(4-Chloropyridin-2-yl)but-3-en-1-yl)-2-methylpropane-2-sulfinamide: To a cooled (−78° C.) solution of (S,E)-N-(3-chlorobenzylidene)-2-methylpropane-2-sulfinamide (4 g, 16.34 mmol) in THF (50 mL) was added vinyl magnesium bromide (21.25 mL, 21.25 mmol) ~0.5 mL at a time. The resulting solution was stirred for 0.5 h at −78° C. and then the dry ice was removed, and the acetone bath was used to allow the reaction to slowly reach to rt. The reaction was then stirred at rt for 0.5 h. The dry ice is again added to the acetone bath and the reaction was quenched with saturated NH₄Cl solution. The aqueous layer was extracted with EtOAc (3×) and the combined organic layers were concentrated and the resultant crude material was purified by chromatography to give the desired product (4.12 g, 88%) MS (ESI) m/z: 272.0 (M+H)⁺.

Intermediate 9B (S)-tert-Butyl (1-(3-chlorophenyl)allyl)carbamate: To a solution of Intermediate 9A (1.38 g, 5.08 mmol) in MeOH (10 mL) was added 4 N HCl (6.35 mL, 25.4 mmol) in dioxane and the resulting reaction was stirred at rt for 1 h. After this time, the reaction mixture was concentrated and coevaporated with toluene (2×). The crude product was then triturated with ether, filtered and washed with additional ether to give (S)-1-(3-chlorophenyl)prop-2-en-1-amine (0.8 g, 94%) as a beige solid. MS (ESI) m/z: 150.8 (M+H-NH₃)⁺. The beige solid was dissolved in ACN (25 mL) and TEA (4 mL, 28.7 mmol) and to this solution was added Boc₂O (1.415 mL, 6.09 mmol). The reaction mixture was stirred at rt overnight. The reaction mixture was diluted with EtOAc and washed with water followed by brine. The crude product was then purified by silica gel chromatography to give the desired product, Intermediate 9B (546 mg, 40%) as a clear oil. MS (ESI) m/z: 290.0 (M+Na)⁺.

Intermediate 9C tert-Butyl (1-(3-chlorophenyl)-3-hydroxypropyl)carbamate: (Reference: *J. Org. Chem.*, 69(8):2773-2784 (2004); *Chemistry—A European Journal*, 15(41):10809-10817, S10809/1-S10809/18 (2009).) A microwave vial was charged with Intermediate 9B (226 mg, 0.844 mmol) and to the microwave vial was added 9-BBN (0.5 M in THF) (5064 μL, 2.53 mmol). The reaction mixture was heated at 100° C. overnight. The reaction mixture was then cooled to rt, and further cooled to 0° C. To this cooled solution was added 2 mL of EtOH followed by NaOH (1300 μl, 2.60 mmol) and then hydrogen peroxide (800 μL, 9.14 mmol). The reaction mixture was then heated at 45° for 1 h. The reaction mixture was capped with a balloon to relieve any pressure build up. After 1 h, to the reaction mixture was added sodium thiosulfate solution to remove excess peroxide. The aqueous layer was then extracted EtOAc (3×). The combined organic layers were concentrated and purified using silica gel chromatography. The desired product, tert-butyl (1-(3-chlorophenyl)-3-hydroxypropyl)carbamate (175 mg, 73%) was obtained as clear oil. MS (ESI) m/z: 286.1 (M+H)⁺.

Intermediate 9 tert-Butyl (1-(3-chlorophenyl)-3-iodopropyl)carbamate: To a solution of Intermediate 9C (61 mg, 0.213 mmol) in DCM (5 mL) was added DIEA (0.080 mL, 0.458 mmol) followed by the addition of MeSO₂Cl (0.030 mL, 0.385 mmol). The reaction mixture was then stirred at rt for 0.5 h. After 30 min., the reaction mixture was concentrated. The residue was dissolved in EtOAc and washed with aqueous NaHCO₃ solution followed by brine. The organic layers were then dried over MgSO₄ and concentrated in vacuo to yield a clear oily residue, which was subjected to the next step without further purification. To a solution of 3-((tert-butoxycarbonyl)amino)-3-(3-chlorophenyl)propyl methanesulfonate in acetone (5 mL) was added sodium iodide (128 mg, 0.854 mmol). The yellow suspension was refluxed for ~4 h, and then stirred at rt for overnight. The reaction mixture was then concentrated followed by addition of small amount of water and DCM. The aqueous layer was then re-extracted with DCM (2×). The combined organic layers were concentrated and then purified by chromatography to give tert-butyl (1-(3-chlorophenyl)-3-iodopropyl)carbamate (68 mg, 81%) as yellow oil which solidified upon standing. MS (ESI) m/z: 395.9 (M+H)⁺.

Intermediate 10

[3-Bromo-4-(2-bromo-acetyl)-phenyl]-carbamic acid methyl ester

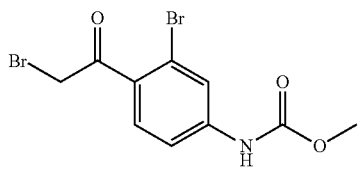 [SMILES: COC(=O)Nc1ccc(C(=O)CBr)c(Br)c1]

Intermediate 10A

2-Bromo-4-nitro-benzoic acid: To a warm (80° C.) solution of pyridine (500 mL) and water (1 L) was added 4-nitro-2-bromo toluene (100 g, 0.46 mol). The resulting suspension was stirred until it became a clear solution. To the above reaction mixture was then added $KMnO_4$ (600 g, 3.8 mol) in portions over 1.5 h and stirring was continued overnight. The reaction mixture was then cooled to rt and then 10% aqueous NaOH (200 mL) was added. After 15 min, the reaction was filtered to remove the solids. The solids were then rinsed with 10% aqueous NaOH (5×100 mL). The filtrate was extracted with MTBE (3×250 mL). The clear aqueous layer was cooled to 10° C. and then it was acidified with concentrated HCl. The aqueous layer was again extracted with MTBE (4×500 mL). The organic layers were combined, dried over $Na_2SO_4$, filtered and concentrated to afford 72 g of Intermediate 10A. $^1H$ NMR (400 MHz, DMSO-$d_6$) δ 7.96 (d, J=8 Hz, 1H), 8.28-8.48 (m, 1H), 8.49 (d, J=2.4 Hz, 1H), 14.1 (br. s, 1H) ppm.

Intermediate 10B 2-(2-Bromo-4-nitro-benzoyl)-malonic acid diethyl ester: To a solution of Intermediate 10A (50 g, 0.2 mol) in toluene (500 mL) was added TEA (24.6 g, 0.24 mol). The reaction was cooled to 15° C. and ethyl chloroformate (24 g, 0.22 mol) was added. After 45 min, the mixed anhydride solution was cooled to 0° C. In a separate flask: To a suspension of Mg turnings (5.4 g) in dry ether (300 mL) was added EtOH (3.0 mL), $CCl_4$ (2.0 mL), and diethyl malonate (34 mL, 0.22 mol). The mixture was stirred at 40° C. for an hour to ensure that the magnesium dissolved completely. After the reaction became a clear solution, it was added to the cooled solution of the mixed anhydride. After 2 h, the reaction was quenched with 2 N sulfuric acid (200 mL) and then extracted with EtOAc (4×100 mL). The combined organic layers were dried over $Na_2SO_4$, filtered and concentrated to afford 80 g of Intermediate 10B. This was used in the next step without further purification.

Intermediate 10C 1-(2-Bromo-4-nitro-phenyl)-ethanone: A mixture of Intermediate 10B (80 g, 0.2 mol) in acetic acid (400 mL) and sulfuric acid (400 mL) was stirred at 105° C. After 3 h, the reaction mixture was cooled to rt and then extracted with ethyl acetate (2×500 mL). The combined organic layers were washed with 20% aqueous NaOH solution. The organic layer was dried over $Na_2SO_4$, filtered and concentrated to give 43.0 g of Intermediate 10C. $^1H$ NMR (400 MHz, $CDCl_3$) δ 2.66 (s, 3H), 7.57 (d, J=8 Hz, 1H), 8.21-8.24 (dd, 1H), 8.48 (d, J=2.0 Hz, 1H) ppm.

Intermediate 10D 1-(4-Amino-2-bromophenyl)ethanone: To a solution of Intermediate 10C (19 g, 0.077 mol) in EtOH (400 mL) was added in portions tin(II) chloride (74 g, 0.39 mol). Following the addition, the reaction was heated to refluxing temperature overnight. The reaction mixture was then concentrated and the residue was dissolved in 10% aqueous NaOH (200 mL). The aqueous solution was extracted with ethyl acetate (2×200 mL). The combined organic layers were washed with brine and concentrated to afford an oil. Petroleum ether (25 mL) was added to the oil to afford a suspension that was decanted and the solid was suspended in 20% ethyl acetate/petroleum ether. The organic layer was filtered and the solids were collected to afford 14 g of Intermediate 10D.

Intermediate 10E (4-Acetyl-3-bromo-phenyl)-carbamic acid methyl ester: To a cooled (10° C.) mixture of alternative Intermediate 10D (14 g, 0.065 mol) and Hunig's base (12.7 g, 0.098 mol) in dry dioxane (140 mL) was added methyl chloroformate (7.4 g, 0.078 m) dropwise. After 3 h, the reaction mixture was quenched with water (100 mL) and then extracted with ethyl acetate (2×150 mL). The combined organic layers were washed with brine, dried over $Na_2SO_4$, filtered, and concentrated. Purification by trituration from isopropanol provided 14 g of the alternative Intermediate 10E. MS (ESI) m/z: 271.7 $(M+H)^+$. $^1H$ NMR (400 MHz, DMSO-$d_6$) 2.50 (s, 3H), 3.71 (s, 3H), 7.53-7.56 (m, 1H), 7.78 (d, J=8.8 Hz, 1H), 7.86 (d, J=2.0 Hz, 1H), 10.14 (s, 1H) ppm.

Intermediate 10

[3-Bromo-4-(2-bromo-acetyl)-phenyl]-carbamic acid methyl ester: To a cooled (10° C.) solution of alternative Intermediate 10E (90 g, 0.33 mol) in dry dioxane (900 mL) was added a solution of bromine (52.9 g, 0.33 mol) in dioxane (430 mL) dropwise over 1 h. After 2 h, ice cold water (500 mL) was added and the reaction was extracted with ethyl acetate (2×500 mL). The combined organic layers were washed with brine, dried over $Na_2SO_4$, filtered, and concentrated to afford 110 g of crude product. A suspension of the crude product in EtOH (1 L) was warmed to 50° C. After a clear solution had formed, water (1.0 L) was added dropwise and the mixture was gradually cooled to 35° C. The precipitated solid was collected by filtration, washed with EtOH (200 mL), air-dried, and then dried at 50° C. under vacuum for 30 min to yield 70 g of alternative Intermediate 10.

Intermediate 11

Methyl 4-(2-bromoacetyl)-3-nitrophenylcarbamate

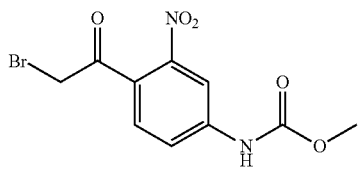 [SMILES: COC(=O)Nc1ccc(C(=O)CBr)c([N+](=O)[O-])c1]

Intermediate 11A

Methyl 4-iodo-3-nitrophenylcarbamate: To a cooled (0° C.), yellow suspension of 4-iodo-3-nitroaniline (8.46 g, 32.0 mmol) in DCM (320 mL) and pyridine (2.85 mL, 35.2 mmol) was added methyl chloroformate (2.61 mL, 33.6 mmol) dropwise. The reaction mixture turned to light yellow solution and stirring was continued for 1.5 h. After 1.5 h, the reaction mixture was diluted with DCM, washed with saturated NaHCO₃ solution followed by brine. The organic layers were dried over MgSO₄, filtered and concentrated to obtain a residue. The residue was then dissolved in DCM (~100 mL), then hexane (600 mL) was added to give a yellow suspension. The above suspension was filtered and the filtered solid was rinsed with hexane and air-dried to obtain the desired product as yellow solid (10.3 g, 100%). MS (ESI) m/z: 321.3 (M−H)$^+$.

Intermediate 11B

Methyl 4-acetyl-3-nitrophenylcarbamate: A solution of Intermediate 11A (1 g, 3.11 mmol), tributyl(1-ethoxyvinyl) stannane (2.098 mL, 6.21 mmol), and bis(triphenylphosphine)palladium(II) chloride (0.218 g, 0.311 mmol) in toluene (6.21 mL) was heated at 110° C. in a sealed tube. After 3 h, the reaction was cooled to rt and concentrated to dryness. The residue was then dissolved in THF (5 mL), and to the solution was added 1 N HCl (15.53 mL, 15.53 mmol). The reaction mixture was stirred at rt for 1 h and then diluted with EtOAc. The organic layer was washed with brine, dried over Na₂SO₄, filtered and concentrated to give the crude product. The crude product was then purified by silica gel chromatography to yield the desired product as brown solid (0.544 g, 74%). MS (ESI) m/z: 239.3 (M+H)$^+$.

Intermediate 11

Methyl 4-(2-bromoacetyl)-3-nitrophenylcarbamate: To a yellow solution of Intermediate 11B (0.544 g, 2.284 mmol) in EtOAc (18.27 mL) was added copper (II) bromide (1.020 g, 4.57 mmol). The flask was equipped with a reflux condenser and then the reaction was warmed to 70° C. at stirred for 3 h. After 3 h, the stirring was stopped and the reaction mixture was cooled to rt. The reaction mixture was then filtered through a sintered glass funnel eluting with EtOAc. The green organic solution was washed with water (3×), brine, dried over Na₂SO₄, filtered and concentrated to yield the desired product as brown foam (0.724 g, 100%). MS (ESI) m/z: 317.4 (M+H)$^+$, 319.4 (M+2H)$^+$. The crude product was carried forward without any further purification.

An alternative procedure for Intermediate 11 is highlighted here.

Alternative Intermediate 11B. Methyl 4-(1-ethoxyvinyl)-3-nitrophenylcarbamate: A solution of Intermediate 11A (1 g, 3.11 mmol), tributyl(1-ethoxyvinyl)stannane (1.574 mL, 4.66 mmol), and bis(triphenylphosphine)palladium(II) chloride (0.109 g, 0.155 mmol) in toluene (6.21 mL) was heated at 110° C. for 2 h. After 2 h, the reaction was cooled to rt, filtered through a 0.45μ GMF filter and rinsed with EtOAc. The filtrate concentrated to dryness and purified by silica gel chromatography to obtain the desired product as brown solid (0.56 g, 68%). MS (ESI) m/z: 267.3 (M+H)$^+$.

Alternative Intermediate 11. Methyl 4-(2-bromoacetyl)-3-nitrophenylcarbamate: (Reference: *J. Med. Chem.*, 45:2127-2130 (2002)) To a solution of alternative Intermediate 11B (0.56 g, 2.103 mmol) in THF (3.12 mL) and water (1.091 mL) was added NBS (0.374 g, 2.103 mmol). After stirring at rt for 20 min, the reaction mixture was partitioned between EtOAc and brine. The organic layer was washed with brine, dried over Na₂SO₄, filtered, and concentrated to yield the desired product as yellow oil (0.667 g, 100%). MS (ESI) m/z: 317.2 (M+H)$^+$, 319.2 (M+2H)$^+$.

Intermediate 12

(R)-1-(3-Chlorophenyl)-3-iodopropan-1-ol

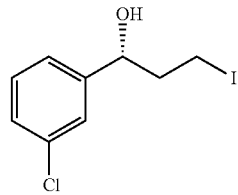 [SMILES: O[C@H](CCI)c1cccc(Cl)c1]

Intermediate 12A 1-(3-Chlorophenyl)-3-iodopropan-1-ol: To 3-chloro-1-(3-chlorophenyl)propan-1-ol (2.85 g, 13.90 mmol) was added sodium iodide (2.66 M in dry acetone) (21 mL, 55.9 mmol) and the mixture was placed under nitrogen and brought to reflux for overnight. After overnight stirring, the solvent was removed under reduced pressure. The residue was taken up in Et₂O and water and the phases separated. The organic layer was washed further with water and brine. The organic layer was then dried (Na₂SO₄), filtered and evaporated to give the desired product as colorless oil (3.9 g, 94%).

Intermediate 12B 1-(3-Chlorophenyl)-3-iodopropan-1-one: Intermediate 12A (2.415 g, 8.14 mmol) was dissolved in acetone (40.7 mL) and the above solution was cooled to 0° C. and Jones Reagent (6.08 ml, 16.29 mmol) was added dropwise. The reaction mixture turned orange/brown and was allowed to stir at 0° C. for 30 min. To the mixture was added 10 mL of isoproponal (reaction mixture turned green) and was then allowed to stir at rt for 10 min. The reaction mixture was then diluted with EtOAc and water. The organic layer was washed with water (3×) and brine, dried with magnesium sulfate, filtered and concentrated to yield a light yellow oil (which solidified into long yellow needles). The crude product was then purified using silica gel chromatography to yield the desired product as a white solid (2.16 g, 90%). MS (ESI) m/z: 294.8 (M+H)$^+$. $^1$H NMR (400 MHz, CDCl₃) δ 7.93 (t, J=1.6 Hz, 1H), 7.85-7.81 (m, 1H), 7.59-7.56 (m, 1H), 7.47-7.42 (m, 1H), 3.65-3.60 (m, 2H), 3.49-3.43 (m, 2H) ppm.

Intermediate 12

(R)-1-(3-Chlorophenyl)-3-iodopropan-1-ol: A solution of (S)-MeCBS (1 M in toluene) (0.139 ml, 0.139 mmol) and BH$_3$.THF (1 M in THF) (1.462 ml, 1.462 mmol) was stirred at rt under argon. Then two separate solutions of Intermediate 12B (2.05 g, 6.96 mmol) in THF (3.48 mL) and BH$_3$.THF (1 M in THF) (3.48 mL, 3.48 mmol) were added dropwise to the reaction mixture over 15 min. After addition of the reagents, the reaction mixture was allowed to stir under argon at rt for another hour. The reaction mixture was then carefully quenched with MeOH. The solution was allowed to stir at rt overnight under argon. The reaction mixture was then concentrated to yield a colorless oil which was purified by silica gel chromatography to yield the desired product as a colorless oil (1.81 g, 88%). Chiral HPLC using CHIRALCEL® OJ analytical column and a 50/50 mixture of heptane and EtOH/MeOH (50/50) solvent showed a mixture of enantiomers in the ratio of (11:89) with the major isomer being the desired product. The mixture was used as is. MS (ESI) m/z: 278.8 (M+H-H$_2$O)$^+$. $^1$H NMR (500 MHz, CDCl$_3$) δ 7.39 (t, J=1.7 Hz, 1H), 7.32-7.27 (m, 2H), 7.26-7.23 (m, 1H), 4.84 (dt, J=8.0, 4.1 Hz, 1H), 3.34 (ddd, J=9.8, 8.2, 6.7 Hz, 1H), 3.21 (ddd, J=9.9, 6.9, 5.8 Hz, 1H), 2.28-2.20 (m, 1H), 2.20-2.12 (m, 1H), 1.95 (dd, J=3.7, 1.0 Hz, 1H) ppm.

Intermediate 13

Benzyl 2-methylbut-3-enoate

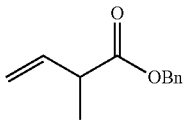

Intermediate 13

Benzyl 2-methylbut-3-enoate: To a solution of 2-methylbut-3-enoic acid (9.5 g, 95 mmol) in DCM (80 mL) was added phenylmethanol (10.26 g, 95 mmol), N,N'-methanediylidenedicyclohexanamine (19.58 g, 95 mmol) and DMAP (1.159 g, 9.49 mmol) (exothermic reaction) and the resulting mixture was stirred at rt over weekend. The reaction mixture was filtered through a pad of CELITE® to remove the solids and the filtrate was collected and concentrated. The filtrate was then concentrated and subjected to silica gel chromatography to yield the desired product as colorless oil.

Intermediate 14

(S)-1-(3-Chloro-2,6-difluorophenyl)-3-iodopropan-1-ol

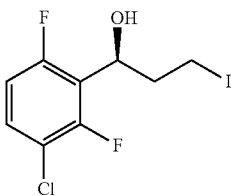 [SMILES: O[C@@H](CCI)c1c(F)ccc(Cl)c1F]

Intermediate 14

(S)-1-(3-Chloro-2,6-difluorophenyl)-3-iodopropan-1-ol: Intermediate 14 was isolated during chiral purification process of Intermediate 2. It was the early eluting enantiomer from chiral OJ column. $^1$H NMR (400 MHz, CDCl$_3$) δ 7.34 (td, J=8.5, 5.7 Hz, 1H), 6.89 (td, J=9.3, 1.8 Hz, 1H), 5.21 (td, J=8.6, 4.8 Hz, 1H), 3.31 (dd, J=7.7, 6.4 Hz, 2H), 2.61-2.50 (m, 1H), 2.34-2.22 (m, 1H), 2.19 (dt, J=8.3, 1.8 Hz, 1H) ppm.

Intermediate 15

(S)-Phenyl (1-(4-chloro-3-fluoropyridin-2-yl)-3-oxopropyl)carbamate

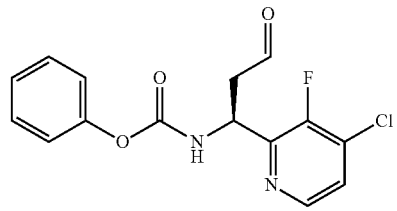 [SMILES: O=CC[C@H](NC(=O)Oc1ccccc1)c1nccc(Cl)c1F]

Intermediate 15A (S,E)-N-((4-Chloro-3-fluoropyridin-2-yl)methylene)-2-methylpropane-2-sulfinamide: A solution of (R)-2-methylpropane-2-sulfinamide (0.540 g, 4.32 mmol), 4-chloro-3-fluoropicolinaldehyde (0.627 g, 3.93 mmol) and Cs$_2$CO$_3$ (1.921 g, 5.89 mmol) in DCM (20 mL) was stirred for 1 h at rt. The reaction mixture was diluted with EtOAc and washed with brine (3×20 mL). The organic layer was dried over MgSO$_4$, filtered and concentrated in vacuo to provide the desired product (1.1 g, 100%). MS (ESI) m/z: 263.0 (M+H)$^+$.

Intermediate 15B (S)—N—((S)-1-(4-Chloro-3-fluoropyridin-2-yl)but-3-en-1-yl)-2-methylpropane-2-sulfinamide: To a solution of (S,E)-N-((4-chloro-3-fluoropyridin-2-yl)methylene)-2-methylpropane-2-sulfinamide (1.03 g, 3.92 mmol) in THF (100 mL) was added allyl magnesium bromide (1 M in ether) (4.70 mL, 4.70 mmol) dropwise and the resulting solution was stirred for 1 h at −78° C. The reaction mixture was then warmed to rt and then quenched with saturated NH$_4$Cl solution. The reaction mixture was extracted with EtOAc (3×). The combined organic layers were concentrated in vacuo, and the residue was then subjected to silica gel purification to provide a mixture of the S and R isomers. MS (ESI) m/z: 305.1 (M+H)$^+$. Chiral separation: AD column eluting with 30% isopropanol in heptane provided peak 1 as the desired (S)—N—((S)-1-(4-chloro-3-fluoropyridin-2-yl)but-3-en-1-yl)-2-methylpropane-2-sulfinamide (0.710 g, 59%) and peak 2 as (S)—N—((R)-1-(4-chloro-3-fluoropyridin-2-yl)but-3-en-1-yl)-2-methylpropane-2-sulfinamide (0.081 g, 7% yield).

Intermediate 15C (S)-Phenyl (1-(4-chloro-3-fluoropyridin-2-yl)but-3-en-1-yl)carbamate: To solution of Intermediate 15B (0.710 g, 1.329 mmol) in MeOH (10 mL) was added 4 M of HCl in dioxane (10 mL) and stirred at rt for 1 h. The reaction mixture was then concentrated and dried under vacuum. The crude product was then re-dissolved in TEA (1.623 mL, 11.65 mmol) and ACN (20 mL). To the above solution was then added phenyl chloroformate (0.321 mL, 2.56 mmol) dropwise and stirred at rt for 10 min. The reaction mixture was diluted with EtOAc and washed with water. The organic layer was concentrated and the residue was purified by silica gel chromatography to yield the desired product (0.550 g, 74%). MS (ESI) m/z: 321.0 (M+H)$^+$.

Intermediate 15

(S)-Phenyl (1-(4-chloro-3-fluoropyridin-2-yl)-3-oxopropyl)carbamate: (Reference: Hinds et al., *J. Med. Chem.*, 34(6):1778 (1991)) To a solution of Intermediate 15C (700 mg, 2.182 mmol) in MeOH (72.7 mL) and water (36.4 mL) was added osmic acid (4 wt %) in water (0.934 mL, 0.153 mmol). After 5 min, sodium periodate (1400 mg, 6.55 mmol) was added. Following the addition, the reaction mixture was stirred at rt for 1 h. After 1 h, to the reaction mixture was added water and the resulting solution was extracted with EtOAc (2×). The combined organic layers were dried over MgSO$_4$ and then concentrated to give the crude product which was purified using silica gel chromatography. The desired fractions were pooled together and combined to give (S)-phenyl (1-(4-chloro-3-fluoropyridin-2-yl)-3-oxopropyl)carbamate (569 mg, 81%) as an off white solid. MS (ESI) m/z: 323.1 (M+H)$^+$. $^1$H NMR (400 MHz, CDCl$_3$) δ 9.99-9.74 (m, 1H), 8.29 (d, J=5.3 Hz, 1H), 7.40-7.31 (m, 3H), 7.23-7.09 (m, 3H), 6.34 (d, J=7.8 Hz, 1H), 5.78-5.66 (m, 1H), 3.20-2.93 (m, 2H) ppm.

Intermediate 16

1-(3-Chloro-2-fluorophenyl)-3-iodopropan-1-ol

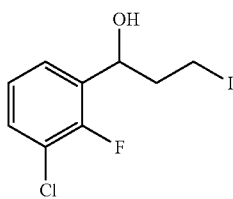 [SMILES: OC(CCI)c1cccc(Cl)c1F]

Intermediate 16A 1-(3-Chloro-2-fluorophenyl)prop-2-en-1-ol: A solution of 3-chloro-2-fluorobenzaldehyde (2.36 g, 14.88 mmol) in THF (29.8 mL) was cooled down to −78° C. under argon. To the solution was added vinyl magnesium bromide (1 M in THF) (20 mL, 20.00 mmol) via syringe pump over 30 min, while stirring was continued at −78° C. After 2 h, the reaction mixture was warmed to 0° C., quenched with 1 N HCl and adjusted the pH to 4. The aqueous layer was extracted with EtOAc (2×), and the combined organic layers were washed with brine and dried over MgSO$_4$. The solids were filtered off and the filtrate was concentrated under vacuum to yield a yellow oil as the desired product. MS (ESI) m/z: 169.1 (M+H-H$_2$O)$^+$.

Intermediate 16B 1-(3-Chloro-2-fluorophenyl)prop-2-en-1-one: To a solution of Intermediate 16A (2777 mg, 14.88 mmol) in acetone (20 mL) at 0° C. under argon was added Jones reagent (11.10 mL, 29.8 mmol) dropwise. After 30 min, the reaction mixture was quenched with i-PrOH. The solids were filtered off and the organic solution was concentrated under vacuum. The crude product was then diluted with EtOAc, washed with water and brine and dried over MgSO$_4$. The crude product was then purified by silica gel chromatography and desired fractions were pooled together and combined to yield the desired product (715 mg, 26%). MS (ESI) m/z: 185.1 (M+H)$^+$.

Intermediate 16C 1-(3-Chloro-2-fluorophenyl)-3-iodopropan-1-one: To a solution of sodium iodide (165 mg, 1.099 mmol) in ACN (1 mL) was added chlorotrimethylsilane (0.139 mL, 1.099 mmol) dropwise. To the mixture was added water (0.016 mL, 0.916 mmol), followed by Intermediate 16B (169 mg, 0.916 mmol) in 1 mL ACN. After 15 min, the reaction mixture was diluted with EtOAc and washed with water followed by 10% Na$_2$S$_2$O$_3$. The organic layer was then washed with brine and dried over MgSO$_4$. The desired product was isolated as a yellow solid (286 mg, 100%). MS (ESI) m/z: 312.9 (M+2+H)$^+$.

Intermediate 16

1-(3-Chloro-2-fluorophenyl)-3-iodopropan-1-ol: To a solution of Intermediate 16C (227 mg, 0.726 mmol) in THF (2.5 mL) and water (0.105 mL, 5.81 mmol) was added sodium borohydride (30.2 mg, 0.799 mmol) and the yellow clear solution was stirred at rt overnight. The reaction mixture was then quenched with 5 mL water, extracted with EtOAc (3×10 mL), and the combined EtOAc layers were washed with brine, dried over MgSO$_4$. The crude product was then purified using reverse phase HPLC chromatography. The desired fractions were then passed through HCO$_3$ resin cartridge (to get rid of TFA) and the filtrate was concentrated under vacuum to yield the desired product (62 mg, 27%) as a white semi-solid product. $^1$H NMR (500 MHz, CDCl$_3$) δ 7.50-7.32 (m, 2H), 7.13 (td, J=7.8, 1.1 Hz, 1H), 5.17 (t, J=6.3 Hz, 1H), 3.48-3.23 (m, 2H), 2.39-2.17 (m, 2H), 2.10-1.80 (br, 1H) ppm.

Intermediate 17

(S)-Phenyl (1-(3-chloro-2,6-difluorophenyl)-3-oxopropyl)carbamate

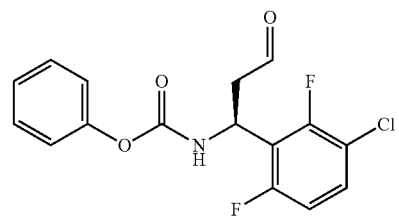

Intermediate 17A (S,E)-N-(3-Chloro-2,6-difluorobenzylidene)-2-methylpropane-2-sulfinamide: To a stirred suspension of 3-chloro- 2,6-difluorobenzaldehyde (0.615 g, 3.48 mmol) and Cs$_2$CO$_3$ (1.702 g, 5.23 mmol) in DCM (20 mL) was added a solution of (S)-2-methylpropane-2-sulfinamide (0.422 g, 3.48 mmol) in DCM (20 mL) dropwise for 10 min. The solution was then stirred at rt overnight. After overnight stirring, the reaction mixture was diluted with EtOAc and washed with brine (3×20 mL). The combined organic layers were dried over MgSO$_4$ and concentrated in vacuo to give the desired product (0.98 g, 100%) as yellow oil. MS (ESI) m/z: 282.0 (M+H)$^+$.

Intermediate 17B (S)—N—((S)-1-(3-Chloro-2,6-difluorophenyl)but-3-en-1-yl)-2-methylpropane-2-sulfinamide: To a cooled (dry ice acetone bath) solution of Intermediate 17A (0.98 g, 3.50 mmol) in THF (50 mL) was added allylmagnesium bromide 1 M in ether (4.55 mL, 4.55 mmol)-0.5 ml at a time. The resulting solution was stirred for 1 h at −78° C. followed by stirring at rt for 30 min. The reaction mixture was again cooled to −78° C. and quenched with saturated NH$_4$Cl solution. The aqueous layer was then extracted with EtOAc (3×). The combined organic layer was dried over MgSO$_4$, concentrated and purified by silica gel chromatography to yield the desired as yellow oil (1.17 g, 104%). MS (ESI) m/z: 322.1 (M+H)$^+$.

Intermediate 17C (S)-Phenyl (1-(3-chloro-2,6-difluorophenyl)but-3-en-1-yl)carbamate: To a solution of crude Intermediate 17B (1.17 g, 3.64 mmol) in MeOH (10 mL) was added HCl (5 mL, 20.00 mmol) and the reaction was stirred at rt for 1 h. After 1 h, the reaction mixture was concentrated and dried under vacuum to obtain a pale yellow solid. The solid was dissolved in ACN (25 mL) followed by addition of TEA (1.520 mL, 10.91 mmol). The above reaction mixture was cooled to 0° C. To this mixture was added phenyl chloroformate (0.502 mL, 4.00 mmol) dropwise and the resulting reaction was stirred at 0° C. for 1 h. The reaction mixture was then diluted with EtOAc and washed with water followed by brine. The crude product was then purified by silica gel chromatography to give the desired product (490 mg, 40%) as clear oil. MS (ESI) m/z: 338.1 (M+H)$^+$.

Intermediate 17

(S)-Phenyl (1-(3-chloro-2,6-difluorophenyl)-3-oxopropyl)carbamate: (Reference: Hinds et al., *J. Med. Chem.*, 34(6):1778 (1991)) To a solution of Intermediate 17C (490 mg, 1.451 mmol) in MeOH (40 mL) and water (20 mL) was added osmic acid (4 wt %) in water (0.621 mL, 0.102 mmol) followed by sodium periodate (931 mg, 4.35 mmol). The reaction mixture was stirred at rt for 2 h. After 2 h, the reaction mixture was quenched with water and extracted with EtOAc. The organic layer was concentrated and purified using silica gel chromatography to give the desired product (321 mg, 65%) as brownish oil. MS (ESI) m/z: 340.0 (M+H)$^+$. $^1$H NMR (400 MHz, CDCl$_3$) δ 9.77 (s, 1H), 7.42-7.28 (m, 3H), 7.23-7.15 (m, 1H), 7.14-7.06 (m, 2H), 6.91 (td, J=9.2, 1.6 Hz, 1H), 5.88-5.79 (m, 1H), 5.79-5.70 (m, 1H), 3.16 (dd, J=16.7, 7.2 Hz, 1H), 3.08-2.87 (m, 1H) ppm.

Intermediate 18

(S)-Phenyl (1-(3-chloro-2-fluoro-6-methoxyphenyl)-3-oxopropyl)carbamate

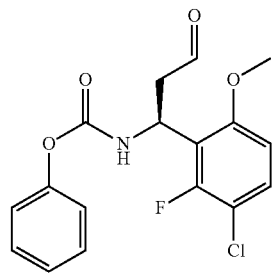

Intermediate 18

(S)-Phenyl (1-(3-chloro-2-fluoro-6-methoxyphenyl)-3-oxopropyl)carbamate: Intermediate 18 is prepared in the same way as Intermediate 17 by replacing 3-chloro-2,6-difluorobenzaldehyde with 3-chloro-2-fluoro-6-methoxybenzaldehyde. The crude product was carried on without further purification. MS (ESI) m/z: 352.0 (M+H)$^+$. $^1$H NMR (400 MHz, CDCl$_3$) δ 9.80 (br. s., 1H), 7.48-7.30 (m, 3H), 7.27-7.18 (m, 1H), 7.13 (d, J=7.8 Hz, 2H), 6.72 (dd, J=8.9, 1.1 Hz, 1H), 6.10 (br. d, J=9.3 Hz, 1H), 6.05-5.93 (m, 1H), 4.01-3.89 (m, 3H), 3.16-3.02 (m, 1H), 2.97-2.82 (m, 1H) ppm.

Intermediate 19

(S)-Phenyl (1-(3,6-dichloro-2-fluorophenyl)-3-oxopropyl)carbamate

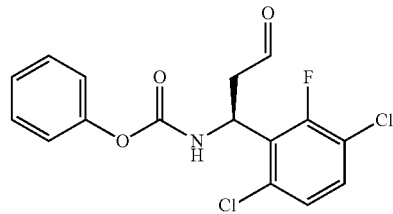 [SMILES: O=CC[C@H](NC(=O)Oc1ccccc1)c1c(F)ccc(Cl)c1F]

Intermediate 19

(S)-Phenyl (1-(3,6-dichloro-2-fluorophenyl)-3-oxopropyl)carbamate: Intermediate 19 is prepared in the same way as Intermediate 17 by replacing 3-chloro-2,6-difluoro benzaldehyde with 3,6-dichloro-2-fluorobenzaldehyde. The crude product was carried on without further purification. MS (ESI) m/z: 356.0 (M+H)$^+$. $^1$H NMR (400 MHz, CDCl$_3$) δ 9.83 (s, 1H), 7.44-7.31 (m, 3H), 7.26-7.07 (m, 3H), 6.14-6.01 (m, 1H), 5.87 (d, J=9.0 Hz, 1H), 3.20 (dd, J=16.4, 8.4 Hz, 1H), 3.11-2.95 (m, 1H) ppm.

Intermediate 20

1-(2-Fluoro-3-methoxyphenyl)-3-iodopropan-1-ol

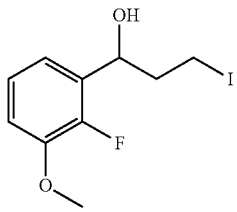

Intermediate 20A tert-Butyl 3-(2-fluoro-3-methoxyphenyl)-3-hydroxypropanoate: To a suspension of zinc (0.848 g, 12.98 mmol) in dry THF (10 mL), was added chlorotrimethylsilane (0.829 mL, 6.49 mmol). After 10 min, tert-butyl 2-bromoacetate (0.959 mL, 6.49 mmol) was added and the reaction mixture was heated at 50° C. for 10 min. The reaction mixture was then cooled to 0° C. under argon. To the cooled solution was then added 2-fluoro-3-methoxybenzaldehyde (1 g, 6.49 mmol) in THF (3 mL) and the reaction was allowed to warm to rt overnight. The reaction mixture after overnight stirring was quenched with 5% NaHCO$_3$ solution, filtered off the solids and rinsed with EtOAc. The organic layer was washed with water followed by brine and dried over MgSO$_4$ to yield the crude product. The crude product was then purified using silica gel chromatography to yield the desired product (1.02 g, 58%) as clear oil. MS (ESI) m/z: 215.1 (M-tBu)$^+$.

Intermediate 20B 1-(2-Fluoro-3-methoxyphenyl)propane-1,3-diol: (Reference: *Tetrahedron*, 64:1515-1522 (2008)) To a solution of Intermediate 20A (530 mg, 1.961 mmol) in THF (18.5 mL) at 0° C. was added lithium aluminum hydride (2.94 mL, 2.94 mmol). After completion of addition, the reaction mixture was allowed to warm to rt overnight. The reaction mixture was concentrated and to the precipitate was added 1 N HCl/EtOAc carefully to quench the reaction. The aqueous layer was extracted again with EtOAc. The combined organic layers were washed with brine, dried over MgSO$_4$ and concentrated to yield the crude product. The crude product was then purified by silica gel chromatography to isolate the desired product (281 mg, 71%) as clear oil. MS (ESI) m/z: 223.0 (M+Na)$^+$.

Intermediate 20

1-(2-Fluoro-3-methoxyphenyl)-3-iodopropan-1-ol: (Reference: *Tetrahedron*, 64:1515-1522 (2008)) To a stirred solution of Intermediate 20B (281 mg, 1.404 mmol) in PhH (14 mL) was added 1H-imidazole (96 mg, 1.404 mmol), triphenylphosphine (736 mg, 2.81 mmol), and I$_2$ (712 mg, 2.81 mmol). The reaction mixture was then stirred at rt overnight. The reaction mixture was quenched with saturated Na$_2$S$_2$O$_3$ and extracted with EtOAc (3×). The combined organic layers were washed with brine and dried over MgSO$_4$ to give the crude product. The crude product was then purified using silica gel chromatography to obtain the desired product (304 mg, 70%) as yellow oil. $^1$H NMR (500 MHz, CDCl$_3$) δ 7.15-7.01 (m, 2H), 6.98-6.86 (m, 1H), 5.15 (dd, J=7.8, 4.8 Hz, 1H), 3.91 (s, 3H), 3.38-3.23 (m, 2H), 2.37-2.23 (m, 2H) ppm.

Intermediate 21

Methyl 2-((3-chloro-2-fluorophenyl)(2-((methylsulfonyl)oxy)ethyl)amino)acetate

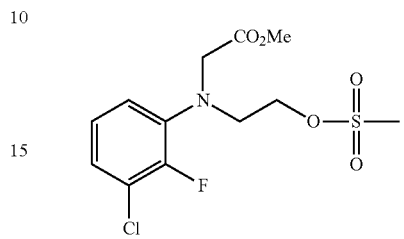

Intermediate 21A

Dimethyl 2,2'-((3-chloro-2-fluorophenyl)azanediyl)diacetate: To a solution of methyl 2-bromoacetate (5.06 mL, 55.0 mmol) and 3-chloro-2-fluoroaniline (2.0 g, 13.74 mmol) in ACN (27.5 mL) was added potassium phosphate, dibasic (4.786 g, 27.48 mmol) and potassium iodide (0.228 g, 1.374 mmol) in a thick walled glass vessel. The vessel was sealed with a Teflon O-ring and was heated to 85° C. After 20 h, the reaction mixture was allowed to cool to rt. To the reaction mixture was added additional methyl 2-bromoacetate (2.53 ml, 27.5 mmol) and potassium phosphate, dibasic (2.393 g, 13.74 mmol). After stirring at 95° C. for 48 h, the reaction mixture was filtered, washed with EtOAc, and concentrated. The residue was partitioned between EtOAc and water and the layers were separated. The organic layer was washed with brine, dried over Na$_2$SO$_4$, filtered and concentrated to obtain a peach oil. The oil was purified by normal phase chromatography which gave Intermediate 21A (1.24 g, 31%) as yellow oil. MS (ESI) m/z: 290.0 (M+H)$^+$.

Intermediate 21B 2-((3-Chloro-2-fluorophenyl)(2-methoxy-2-oxoethyl)amino)acetic acid: To a solution of Intermediate 21A (1.1115 g, 3.84 mmol) in MeOH (19.18 mL) was added 1 N NaOH (3.84 mL, 3.84 mmol). After stirring for 3 h, the reaction was concentrated to yield a yellow oil which was then partitioned between EtOAc and water. The layers were separated and the aqueous layer was washed with EtOAc and the organic layer was discarded. The aqueous layer was acidified with 1 N HCl (aqueous) to pH ~3 and then extracted with EtOAc (2×). The organic layers were combined, washed with brine, dried over Na$_2$SO$_4$, filtered and concentrated to give Intermediate 21B. MS (ESI) m/z: 276.0 (M+H)$^+$.

Intermediate 21C

Methyl N-(3-chloro-2-fluorophenyl)-N-(2-hydroxyethyl) glycinate: To a solution of Intermediate 21B (413.5 mg, 1.500 mmol) in THF (17.9 mL) was added dropwise borane-methyl sulfide complex (2.250 mL, 4.50 mmol). The reaction was allowed to stir overnight at rt under argon. After stirring overnight, the reaction was cooled to 0° C. and then it was quenched with the dropwise addition of MeOH (2 mL). The reaction was allowed to stir for 15 min and then water (2 mL) was added dropwise. The reaction was allowed to stir at 0° C.

for an additional 30 min and then the reaction was diluted with EtOAc and saturated NaHCO₃ solution. The layers were separated and the aqueous layer was extracted with EtOAc (2×). The organic layers were combined, washed with brine, dried over Na₂SO₄, filtered, and concentrated to give Intermediate 21C (374 mg, 95%) as a cloudy, yellow oil. MS (ESI) m/z: 262.0 (M+H)⁺.

Intermediate 21

Methyl 2-((3-chloro-2-fluorophenyl)(2-((methylsulfonyl)oxy)ethyl)amino) acetate: To cooled (0° C.) solution of Intermediate 21C (374.4 mg, 1.431 mmol) and pyridine (0.231 mL, 2.86 mmol) in DCM (5.723 mL) was added dropwise MsCl (0.123 mL, 1.574 mmol). The reaction was allowed to stir for 5 min at 0° C. and then the reaction was warmed to rt. After stirring at rt overnight, the reaction mixture was diluted with DCM and quenched with saturated NaHCO₃ solution. The layers were separated and the aqueous layer washed with DCM (2×). The combined organic layers were washed with brine, dried over Na₂SO₄, filtered and concentrated. Purification by normal phase chromatography gave Intermediate 21 (374 mg, 77%). MS (ESI) m/z: 340.0 (M+H)⁺. ¹H NMR (500 MHz, MeOD) δ 7.06-6.93 (m, 3H), 4.40 (t, J=5.5 Hz, 2H), 4.17 (s, 2H), 3.74-3.69 (m, 5H), 3.04 (s, 3H) ppm.

Intermediate 22

2-(5,5-Dimethyl-1,3,2-dioxaborinan-2-yl)-5-nitrophenylamine

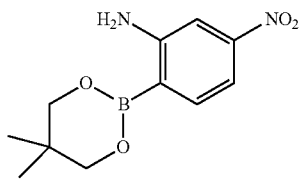 [SMILES: CC1(C)COB(c2ccc([N+](=O)[O-])cc2N)OC1]

To a flame-dried flask, equipped with a reflux condenser, containing 2-bromo-5-nitroaniline (10.0 g, 46.1 mmol), bis(neopentyl glycolato)diboron (13.01 g, 57.6 mmol), potassium acetate (13.57 g, 138 mmol), and PdCl₂(dppf)-CH₂Cl₂ adduct (0.941 g, 1.152 mmol) was added DMSO (132 mL). The resulting dark red-brown suspension was degassed with argon for 30 min and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 12 as an orange solid. MS (ESI) m/z: 183.1 (M–C₅H₈+H)⁺.

Intermediate 23

(R)-3-((tert-Butyldimethylsilyl)oxy)-3-(4-chloro-3-fluoropyridin-2-yl)propanal

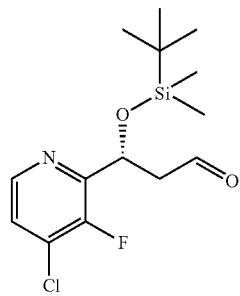 [SMILES: CC(C)(C)[Si](C)(C)O[C@H](CC=O)c1nccc(Cl)c1F]

Intermediate 23A (R)-1-(4-Chloro-3-fluoropyridin-2-yl)but-3-en-1-ol: A solution of 1 M allylbis((1S,2R,3S,5S)-2,6,6-trimethylbicyclo[3.1.1]heptan-3-yl)borane in pentane in anhydrous THF (10 mL) was cooled to −78° C. To the solution was added 4-chloro-3-fluoropicolinaldehyde (0.5 g, 3.13 mmol) in 10 mL of THF dropwise for 20 min. The resulting solution was stirred for additional 1 h. To the mixture was added MeOH (1 mL), followed addition of lithium hydroxide (0.300 g, 12.54 mmol), hydrogen peroxide (0.384 mL, 12.54 mmol) and 10 mL of 1 N NaOH. The content was allowed to warm up to rt and stirred for 1 h. The reaction mixture was diluted with EtOAc, washed with brine (2×20 mL), dried over Na₂SO₄, concentrated and purified by silica gel chromatography to provide (R)-1-(4-chloro-3-fluoropyridin-2-yl)but-3-en-1-ol (0.54 g, 85%). MS (ESI) m/z: 202.1 (M+H)⁺.

Intermediate 23B (R)-2-(1-((tert-Butyldimethylsilyl)oxy)but-3-en-1-yl)-4-chloro-3-fluoropyridine: A solution of Intermediate 23A (0.52 g, 2.58 mmol), TBS-Cl (0.466 g, 3.09 mmol), imidazole (0.211 g, 3.09 mmol) and DMAP (0.378 g, 3.09 mmol) was stirred for 12 h at rt. The reaction was diluted in EtOAc (30 mL) was washed with aq. NaHCO₃ and brine. The organic solution was concentrated in vacuo, yielding oily residue, which was purified by silica gel chromatography to provide (R)-2-(1-((tert-butyldimethylsilyl)oxy)but-3-en-1-yl)-4-chloro-3-fluoropyridine (0.42 g, 52%). ¹H NMR (400 MHz, CDCl₃) δ 8.26 (d, J=5.3 Hz, 1H), 7.23 (s, 1H), 5.88-5.60 (m, 1H), 5.12-4.91 (m, 3H), 2.74-2.43 (m, 2H), 0.84-0.76 (m, 9H), 0.00 (s, 3H), 0.12 (s, 3H).

Intermediate 23

(R)-3-((tert-Butyldimethylsilyl)oxy)-3-(4-chloro-3-fluoropyridin-2-yl)propanal: To a solution of Intermediate 23B (1.0 g, 3.17 mmol) in MeOH (20 mL) and water (10 mL) in ice bath was added osmic acid (4 wt %) in water (1.739 mL, 0.222 mmol) dropwise followed by sodium periodate (1.693 g, 7.91 mmol). Following the addition, the reaction mixture was stirred at rt for 2 h. To the reaction mixture was added water and the resulting solution was extracted with EtOAc (2×). The combined organic layers were dried over MgSO₄ and then concentrated to give the crude product which was purified using silica gel chromatography. The desired fractions were pooled together and combined to give (R)-3-((tert-butyldimethylsilyl)oxy)-3-(4-chloro-3-fluoropyridin-2-yl)propanal (0.93 g, 92%). MS (ESI) m/z: 318.1 (M+H)⁺. ¹H NMR (400 MHz, CDCl₃) δ 9.79 (s, 1H), 8.27-8.13 (m, 1H), 7.28-7.20 (m, 1H), 5.57-5.45 (m, 1H), 3.04-2.79 (m, 2H), 0.75 (s, 9H), 0.00 (s, 3H), −0.14 (s, 3H).

Intermediate 24

(R)-Phenyl 1-(2-chloro-3-fluoropyridin-4-yl)-3-oxopropylcarbamate

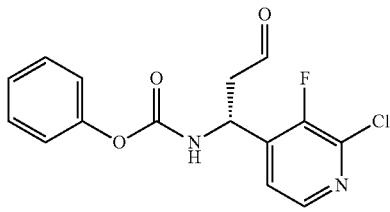 [SMILES: O=CC[C@@H](NC(=O)Oc1ccccc1)c1ccnc(Cl)c1F]

Intermediate 24A (R,E)-N-((2-Chloro-3-fluoropyridin-4-yl)methylene)-2-methylpropane-2-sulfinamide: To a stirred suspension of 2-chloro-3-fluoroisonicotinaldehyde (0.75 g, 4.70 mmol) and Cs₂CO₃ (2.297 g, 7.05 mmol) in DCM (20 mL) was added a solution of (R)-2-methylpropane-2-sulfinamide (0.570 g, 4.70 mmol) in DCM (20 mL) dropwise for 10 min. The solution was then stirred for 3.5 h at rt. The reaction mixture was diluted with EtOAc and washed with brine (3×20 mL). The organic solution was dried over MgSO₄, filtered, and concentrated in vacuo to give (R,E)-N-((2-chloro-3-fluoropyridin-4-yl)methylene)-2-methylpropane-2-sulfinamide (1.13 g, 91%) as a yellow oil which solidified upon standing. MS (ESI) m/z: 263.0 (M+H)⁺.

Intermediate 24B (R)-Phenyl (1-(2-chloro-3-fluoropyridin-4-yl)but-3-en-1-yl)carbamate: To a solution of Intermediate 24A (1.13 g, 4.30 mmol) in THF (50 mL) at was −78° C. was added allylmagnesium bromide (1 M in ether) (8 mL, 8.00 mmol). The reaction was stirred at −78° C. for 0.5 h and warmed up to rt. The mixture was stirred for 1 h at rt and quenched with saturated NH₄Cl. The mixture was extracted with EtOAc (3×). The combined organic layer was concentrated to give a 5:1 mixture of (R)—N—((R)-1-(2-chloro-3-fluoropyridin-4-yl)but-3-en-1-yl)-2-methylpropane-2-sulfinamide and (R)—N—((S)-1-(2-chloro-3-fluoropyridin-4-yl)but-3-en-1-yl)-2-methylpropane-2-sulfinamide (1.56 g, 119%) as an orange oil. The oil was taken up with methanol (10.00 mL) and treated with 4 N HCl in dioxane (3 mL, 99 mmol). The reaction was stirred at rt for 1.5 h and then concentrated to give the desired product (0.55 g, 40%) as an orange oil. MS (ESI) m/z: 321.1 (M+H)⁺.

Intermediate 24

(R)-Phenyl 1-(2-chloro-3-fluoropyridin-4-yl)-3-oxopropylcarbamate: (Reference: Hinds et al., *J. Med. Chem.*, 34(6): 1778 (1991).) To a solution of Intermediate 24B (550 mg, 1.715 mmol) in methanol (20 mL) and water (10.00 mL) was added OsO₄ (4 wt % in water) (0.734 mL, 0.120 mmol). The mixture became a clear solution after 5 min and sodium periodate (1100 mg, 5.14 mmol) was added. The reaction was stirred at rt overnight. The mixture was diluted with water and extract with EtOAc (2×). The combined organic layer was concentrated and purified by silica gel chromatography to yield the desired product (0.43 g, 78%) as clear oil that solidified upon standing. MS (ESI) m/z: 323.1 (M+H)⁺.

Intermediate 25

(R)-Phenyl 1-(5-chloropyridin-3-yl)-3-oxopropylcarbamate

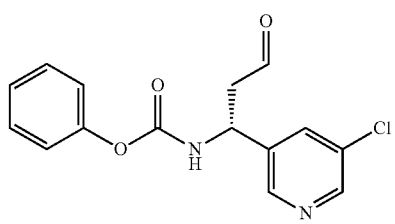 [SMILES: O=CC[C@@H](NC(=O)Oc1ccccc1)c1cncc(Cl)c1]

Intermediate 25

(R)-Phenyl 1-(5-chloropyridin-3-yl)-3-oxopropylcarbamate: Intermediate 25 was prepared in the same way as Intermediate 24 by replacing 2-chloro-3-fluoroisonicotinaldehyde with 5-chloronicotinaldehyde. MS (ESI) m/z: 550.1 (M+H)⁺. ¹H NMR (400 MHz, MeOD) δ 9.57 (s, 1H), 8.55-8.41 (m, 1H), 7.85 (s, 1H), 7.59 (s, 1H), 7.44 (d, J=14.3 Hz, 3H), 5.62-5.31 (m, 3H), 4.70 (dd, J=7.7, 4.4 Hz, 1H), 3.76 (s, 3H), 3.63-3.52 (m, 1H), 3.00-2.84 (m, 1H), 2.76 (d, J=13.3 Hz, 1H), 2.52-2.25 (m, 5H), 2.19-2.06 (m, 1H).

Intermediate 26

(S)-Phenyl 2-(3,6-dichloro-2-fluorophenyl)-4-oxobutan-2-ylcarbamate

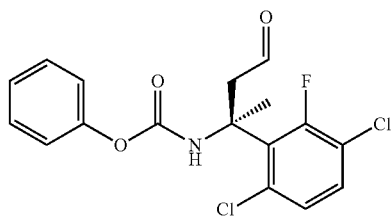 [SMILES: C[C@@](CC=O)(NC(=O)Oc1ccccc1)c1c(Cl)ccc(Cl)c1F]

Intermediate 26

(S)-Phenyl 2-(3,6-dichloro-2-fluorophenyl)-4-oxobutan-2-ylcarbamate: Intermediate 26 was prepared in the same way as Intermediate 17 by replacing 3-chloro-2,6-difluoro benzaldehyde with 1-(3-chloro-2,6-difluorophenyl)ethanone. MS (ESI) m/z: 352.1 (M+H)+.

Intermediate 27

(S)-Phenyl 1-(3-chloro-2-fluoro-6-methylphenyl)-3-oxopropylcarbamate

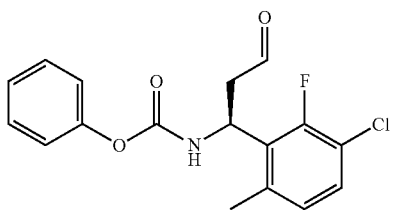 [SMILES: Cc1ccc(Cl)c(F)c1[C@H](CC=O)NC(=O)Oc1ccccc1]

Intermediate 27A

3-Chloro-2-fluoro-6-methylbenzaldehyde: (Reference: *E. J. Org. Chem.* 2005, 2116-2123) To a solution of 2,2,6,6-tetramethylpiperidine (0.642 mL, 3.80 mmol) in THF (15 mL) at −78° C. was added n-BuLi (2.162 mL, 3.46 mmol) dropwise. The resulting solution was stirred at −78° C. for 1 h and added 1-chloro-2-fluoro-4-methylbenzene (0.5 g, 3.46 mmol) dropwise. The solution was stirred for additional 0.5 h and then added DMF (0.536 mL, 6.92 mmol). The reaction was stirred at −78° C. for 1.5 h and at ambient temperature for 12 h. The mixture was diluted with water and extracted with EtOAc (3×). The combined organic layer was washed with brine and concentrated. The residue was purified by silica gel chromatography to yield the desired product (43 mg, 7%).

Intermediate 27

(S)-Phenyl 1-(3-chloro-2-fluoro-6-methylphenyl)-3-oxopropylcarbamate: Intermediate 27 was prepared in the same way as Intermediate 17 by replacing 3-chloro-2,6-difluoro benzaldehyde with Intermediate 27A. MS (ESI) m/z: 352.1 (M+H)+. $^1$H NMR (400 MHz, CDCl$_3$) δ 10.44 (s, 1H), 7.40 (t, J=7.9 Hz, 1H), 6.87-6.96 (m, 1H), 2.51 (s, 3H).

Intermediate 28

(S)-Phenyl 1-(3-fluoro-4-methylpyridin-2-yl)-3-oxopropylcarbamate

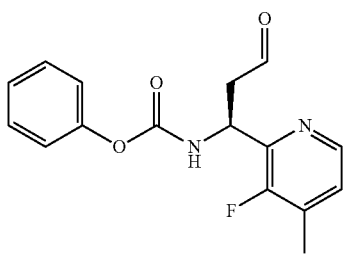 [SMILES: Cc1ccnc([C@H](CC=O)NC(=O)Oc2ccccc2)c1F]

Intermediate 28

(S)-Phenyl 1-(3-fluoro-4-methylpyridin-2-yl)-3-oxopropylcarbamate: Intermediate 28 was prepared in the same way as Intermediate 17 by replacing 3-chloro-2,6-difluoro benzaldehyde with 3-fluoro-4-methylpicolinaldehyde. MS (ESI) m/z: 303.1 (M+H)+. $^1$H NMR (400 MHz, CDCl$_3$) δ 9.88 (br. s., 1H), 8.45-8.44 (m, 1H), 8.26 (d, J=4.3 Hz, 1H), 7.26-7.08 (m, 4H), 6.52 (br. s., 1H), 5.71 (d, J=6.3 Hz, 1H), 3.27-2.83 (m, 2H), 2.38 (s, 3H).

Intermediate 29

(S)-Phenyl 1-(3-fluoro-4-(trifluoromethyl)pyridin-2-yl)-3-oxopropylcarbamate

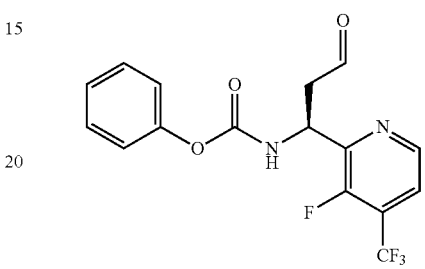

Intermediate 29

(S)-Phenyl 1-(3-fluoro-4-(trifluoromethyl)pyridin-2-yl)-3-oxopropylcarbamate: Intermediate 29 was prepared in the same way as Intermediate 17 by replacing 3-chloro-2,6-difluoro benzaldehyde with 3-fluoro-4-(trifluoromethyl)picolinaldehyde. MS (ESI) m/z: 357.0 (M+H)+. $^1$H NMR (400 MHz, CDCl$_3$) δ 9.88 (br. s., 1H), 8.45-8.44 (m, 1H), 8.26 (d, J=4.3 Hz, 1H), 7.26-7.08 (m, 4H), 6.52 (br. s., 1H), 5.71 (d, J=6.3 Hz, 1H), 3.27-2.83 (m, 2H), 2.38 (s, 3H).

Intermediate 30

(S)-tert-Butyl 1-(4-chloro-3-fluoropyridin-2-yl)-3-oxopropyl(methyl)carbamate

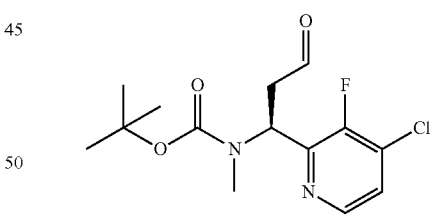

Intermediate 30A (S)—N—((S)-1-(4-Chloro-3-fluoropyridin-2-yl)but-3-en-1-yl)-N,2-dimethylpropane-2-sulfinamide: To a solution of Intermediate 15B (0.14 g, 0.459 mmol) in DMF (3 mL) was added LiHMDS (0.459 mL, 0.459 mmol) in one portion and the resulting solution was stirred at rt for 1 h. To the solution was added iodomethane (0.057 mL, 0.919 mmol) and the content was stirred for 1 h. The reaction mixture was diluted with water and extracted with EtOAc. The organic layer was concentrated and purified by silica gel chromatography to yield the desired product (0.11 g, 75%). MS (ESI) m/z: 319.1 (M+H)+.

Intermediate 30B (S)-tert-Butyl (1-(4-chloro-3-fluoropyridin-2-yl)but-3-en-1-yl)(methyl)carbamate: A solution of Intermediate 30A (0.11 g, 0.345 mmol), 4 N HCl in dioxane (3 mL), and MeOH (3.00 mL) was stirred at rt for 1 h. The reaction mixture was concentrated. The residue was re-dissolved in acetonitrile (3.00 mL) and added DIEA (0.241 mL, 1.380 mmol) followed by $BOC_2O$ (0.104 mL, 0.449 mmol). The reaction was stirred at rt for 2 h and concentrated. The residue was purified by silica gel chromatography to yield the desired product (0.11 g, 101%). MS (ESI) m/z: 314.9 $(M+H)^+$.

Intermediate 30

(S)-tert-Butyl 1-(4-chloro-3-fluoropyridin-2-yl)-3-oxopropyl(methyl)carbamate: To a solution of Intermediate 30B (0.12 g, 0.381 mmol) in MeOH (3 mL) and water (1.500 mL) was added $OsO_4$ (4% in water) (0.209 mL, 0.027 mmol) dropwise and the resulting solution was stirred at rt for 10 min. $NaIO_4$ (0.204 g, 0.953 mmol) was added and the resulting solution was stirred for 1 h at rt. The reaction mixture was diluted with EtOAc, washed with aq. $NaHCO_3$, brine, and concentrated. The residue was purified by silica gel chromatography to yield the desired product. MS (ESI) m/z: 316.9 $(M+H)^+$.

Intermediate 31

1-(3-Chloro-2,6-difluorophenyl)-3-iodo(1-$^2$H)propan-1-($^2$H)ol

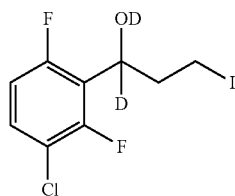

Intermediate 31

1-(3-Chloro-2,6-difluorophenyl)-3-iodo(1-$^2$H)propan-1-($^2$H)ol: To a solution of Intermediate 2C (727.0 mg, 2.200 mmol) in THF (20 mL) and deuterium oxide (374 mg, 18.70 mmol) was added sodium borodeuteride (101 mg, 2.420 mmol) and the mixture was stirred overnight at ambient temperature. Deuterium oxide (1 mL) was added and volume of the reaction solvent was reduced under vacuum. EtOAc and water were added and the phases were separated. The aqueous phase was extracted with EtOAc (3×). The combined extracts were washed with brine, dried ($Na_2SO_4$), filtered and evaporated to give a colorless oil, which was purified by silica gel chromatography to yield the desired product (342 mg, 46%) as a colorless oil. MS (ESI) m/z: 448.7 $(M+CF_3CO_2H)^+$.

Intermediate 32

1-(2,6-Difluoro-3-methylphenyl)-3-iodopropan-1-ol

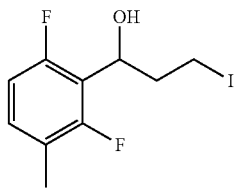

Intermediate 32A tert-Butyl 3-(2,6-difluoro-3-methylphenyl)-3-hydroxypropanoate: To a suspension of zinc (1.256 g, 19.21 mmol) in dry tetrahydrofuran (18 mL) was added chlorotrimethylsilane (1.228 mL, 9.61 mmol). After 20 min, tert-butyl 2-bromoacetate (1.420 mL, 9.61 mmol) was added. The reaction was stirred at rt for 10 min, then heated at 40° C. for 20 min. The reaction mixture was cooled to 0° C. under Ar, and 2,6-difluoro-3-methylbenzaldehyde (1.5 g, 9.61 mmol) in 3 mL of dry THF was added. The reaction was allowed to warm to rt and stirred overnight. The reaction mixture was quenched with 5% aqueous $NaHCO_3$, filtered, and rinsed with EtOAc. The filtrate was washed with water and brine, dried over $MgSO_4$, filtered, concentrated and purified by silica gel chromatography to yield the desired product (1.46 g, 56%). MS (ESI) m/z: 295.1 $(M+Na)^+$.

Intermediate 32B 1-(2,6-Difluoro-3-methylphenyl)propane-1,3-diol: Intermediate 32A (1.46 g, 5.36 mmol) in THF (26.8 mL) at 0° C. was added 2 M $LiAlH_4$ in THF (4.02 mL, 8.04 mmol). The reaction was warmed to rt and stirred overnight. The reaction was concentrated to remove some THF. 1 N HCl/EtOAc were added carefully to quench the reaction. The mixture was extracted EtOAc (2×). The combined organic layer was washed with brine, dried over $MgSO_4$, filtered and concentrated. The residue was purified by silica gel chromatography to yield the desired product (732 mg, 68%) as a white solid. MS (ESI) m/z: 225.0 $(M+Na)^+$. $^1H$ NMR (500 MHz, $CDCl_3$) δ 7.04-7.11 (m, 1H), 6.79 (ddd, J=10.0, 8.6, 1.5 Hz, 1H), 5.32 (ddd, J=9.4, 7.7, 4.4 Hz, 1H), 3.84-3.95 (m, 2H), 2.68 (d, J=7.7 Hz, 1H), 2.31-2.40 (m, 1H), 2.23-2.25 (m, 3H), 1.94-2.02 (m, 2H) ppm.

Intermediate 32

1-(2,6-Difluoro-3-methylphenyl)-3-iodopropan-1-ol: To a stirred solution of Intermediate 32B (197 mg, 0.974 mmol) in PhH (9.743 mL) was added 1H-imidazole (66.3 mg, 0.974 mmol), triphenylphosphine (511 mg, 1.949 mmol), and $I_2$ (495 mg, 1.949 mmol). The reaction was stirred at rt for 4 days. The reaction was quenched with saturated $Na_2S_2O_3$ and extracted with EtOAc (2×). The combined organic layer was washed with brine, dried over $MgSO_4$, filtered and concentrated. The residue was purified by silica gel chromatography to yield the desired product (148 mg, 49%) as colorless oil. MS (ESI) m/z: 225.0 $(M+Na)^+$. $^1H$ NMR (400 MHz, $CDCl_3$) δ 7.05-7.14 (m, 1H), 6.75-6.83 (m, 1H), 5.16 (td, J=8.7, 4.8 Hz, 1H), 3.26-3.31 (m, 2H), 2.50-2.60 (m, 1H), 2.26-2.35 (m, 2H), 2.23-2.25 (m, 3H) ppm.

Intermediate 33

1-(3-Chloro-2-fluoro-6-methoxyphenyl)-3-iodopropan-1-ol

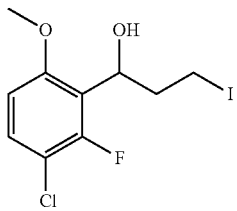

Intermediate 33

1-(3-Chloro-2-fluoro-6-methoxyphenyl)-3-iodopropan-1-ol: Intermediate 33 was prepared in the same way as Intermediate 5 by replacing 3-chloro-2-fluoro-6-(trifluoromethyl)benzaldehyde with 3-chloro-2-fluoro-6-methoxybenzaldehyde. $^1$H NMR (500 MHz, CDCl$_3$) δ 7.28 (m, J=8.8 Hz, 1H), 6.67 (dd, J=8.9, 1.5 Hz, 1H), 5.26 (dd, J=9.2, 4.8 Hz, 1H), 3.90 (s, 3H), 3.62-3.74 (m, 2H), 2.46 (ddt, J=14.5, 8.8, 5.9, 5.9 Hz, 1H), 2.09-2.18 (m, 1H) ppm.

Intermediate 34

1-(6-Bromo-3-chloro-2-fluorophenyl)-3-iodopropan-1-ol

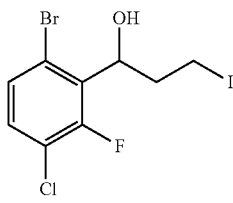

Intermediate 34

1-(6-Bromo-3-chloro-2-fluorophenyl)-3-iodopropan-1-ol: Intermediate 34 was prepared in the same way as Intermediate 5 by replacing 3-chloro-2-fluoro-6-(trifluoromethyl)benzaldehyde with 6-bromo-3-chloro-2-fluorobenzaldehyde. $^1$H NMR (500 MHz, CDCl$_3$) δ 7.33 (dd, J=8.7, 1.5 Hz, 1H), 7.21-7.26 (m, 1H), 5.32 (dd, J=9.4, 4.1 Hz, 1H), 3.31-3.41 (m, 2H), 2.53 (ddddd, J=16.1, 8.0, 6.6, 5.0, 1.4 Hz, 1H), 2.22-2.32 (m, 1H) ppm.

Intermediate 35

(R)-2-Methylbut-3-enoic acid

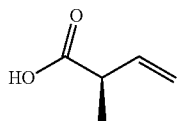

Intermediate 35A (R)-4-Benzyl-3-((R)-2-methylbut-3-enoyl)oxazolidin-2-one: To the solution of 2-methylbut-3-enoic acid (5.59 g, 55.9 mmol) and N-methylmorpholine (6.14 ml, 55.9 mmol) in THF (62 mL) at 0° C. was added pivaloyl chloride (6.87 ml, 55.9 mmol) dropwise. The reaction mixture was cooled down to −78° C., and stirred for ~2 h. In a separate flask: To the solution of (R)-4-benzyloxazolidin-2-one (8.25 g, 46.6 mmol) in THF (126 mL) at −78° C. was added N-butyllithium (2.5 M in hexane) (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with saturated NH$_4$Cl. The reaction was diluted with water and extracted with EtOAc (3×). The combined organic layers were washed with brine, dried over Na$_2$SO$_4$, filtered, and concentrated to give a yellow oil (15 g). Purification by silica gel chromatography afforded the desired product (6.59 g, 55%) as a colorless oil. MS (ESI) m/z: 282.1 (M+Na)$^+$. $^1$H NMR (500 MHz, CDCl$_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also obtained as a white solid. MS (ESI) m/z: 260.1 (M+H)$^+$.

Intermediate 35

(R)-2-Methylbut-3-enoic acid: To a clear colorless solution of Intermediate 35A (6.05 g, 23.33 mmol) in THF (146 mL) at 0° C. was added dropwise hydrogen peroxide (9.53 mL, 93 mmol) (30% aqueous) followed by 2 N lithium hydroxide (23.33 mL, 46.7 mmol). After 30 min, the reaction was quenched with 25 mL of saturated Na$_2$SO$_3$ and 25 mL of saturated NaHCO$_3$. The reaction was then concentrated to remove the THF. The residue was diluted with water and extracted with CHCl$_3$ (3×). The aqueous layer was acidified with conc. HCl to pH ~3 and then it was extracted with EtOAc (3×). The EtOAc layers were combined, washed with brine, dried over MgSO$_4$, filtered and concentrated to afford the desired product (2.15 g, 92%) as a colorless oil. $^1$H NMR (500 MHz, CDCl$_3$) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H) ppm.

Intermediate 36

Methyl 3-(3-chloro-2,6-difluorophenyl)-5-((methylsulfonyl)oxy)pentanoate

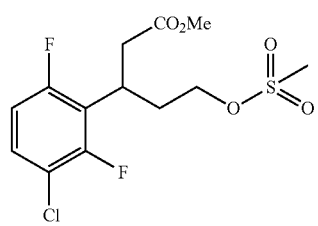 [SMILES: COC(=O)CC(CCOS(C)(=O)=O)c1c(F)ccc(Cl)c1F]

Intermediate 36

Methyl 3-(3-chloro-2,6-difluorophenyl)-5-((methylsulfonyl)oxy)pentanoate: Intermediate 36 was prepared according

Intermediate 37

Methyl 2-((3-chlorophenyl)(2-((methylsulfonyl)oxy)ethyl)amino)acetate

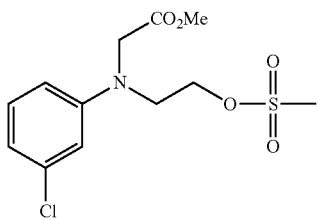 [SMILES: COC(=O)CN(CCOS(C)(=O)=O)c1cccc(Cl)c1]

Intermediate 37

Methyl 2-((3-chlorophenyl)(2-((methylsulfonyl)oxy)ethyl)amino)acetate: Intermediate 37 was prepared according to the procedures described in Intermediate 21, by replacing 3-chloro-2-fluoroaniline with 3-chloroaniline and by running the reaction at 85° C. for 45 h. MS (ESI) m/z: 321.9 (M+H)$^+$.

Intermediate 38

Methyl 2-((5-chloro-2-methylphenyl)(2-((methylsulfonyl)oxy)ethyl)amino)acetate

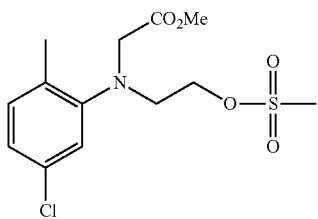 [SMILES: COC(=O)CN(CCOS(C)(=O)=O)c1cc(Cl)ccc1C]

Intermediate 38 was prepared according to the procedures described in Intermediate 21, by replacing 3-chloro-2-fluoroaniline with 5-chloro-2-methylaniline and by running the reaction at 85° C. for 48 h. MS (ESI) m/z: 336.0 (M+H)$^+$.

Intermediate 39

Methyl 2-((3-chlorophenyl)(2-((methylsulfonyl)oxy)ethyl)amino)propanoate

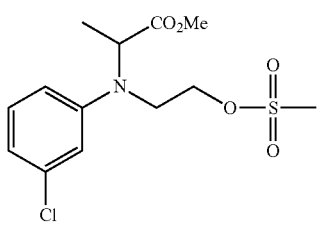 [SMILES: COC(=O)C(C)N(CCOS(C)(=O)=O)c1cccc(Cl)c1]

Intermediate 39A

Methyl 2-[(3-chlorophenyl)amino]propanoate: To a sealed tube containing a clear, slightly yellow solution of 3-chloroaniline (2.5 g, 19.60 mmol) and methyl 2-bromopropanoate (3.93 g, 23.52 mmol) in DMF (39.2 mL) was added potassium iodide (0.325 g, 1.960 mmol) and potassium carbonate (4.06 g, 29.4 mmol). The vessel was sealed with a Teflon screw cap possessing an o-ring. The resulting suspension was warmed to 100° C. After 5 h, the resulting dark brown reaction mixture was stopped and cooled to rt. The reaction was filtered to remove the solid, rinsing with EtOAc. The filtrate was partitioned between EtOAc and water and the layers were separated. The aqueous layer was extracted with EtOAc (2×). The combined organic layers were washed with brine, dried over sodium sulfate, filtered and concentrated to give a brown liquid weighing 6.30 g. Purification by normal phase chromatography gave the desired product (1.04 g, 25%) as a clear, yellow oil. MS (ESI) m/z: 214.0 (M+H)$^+$.

Intermediate 39B

2-[(3-Chlorophenyl)(1-methoxy-1-oxopropan-2-yl)amino]acetic acid: A sealed tube containing a suspension of Intermediate 39A (0.500 g, 2.340 mmol), potassium carbonate (0.485 g, 3.51 mmol), potassium iodide (0.039 g, 0.234 mmol), and tert-butyl bromoacetate (0.415 ml, 2.81 mmol) in DMA (4.68 mL) was warmed to 100° C. After 3 h, additional tert-butyl bromoacetate (0.415 mL, 2.81 mmol) was added and the reaction was heated at 100° C. After 22 h, the reaction was stopped and cooled to rt. The reaction was filtered, eluting with diethyl ether. The filtrate was partitioned between diethyl ether and water and the layers were separated. The aqueous layer was extracted with diethyl ether. The combined organic layers were washed with brine, dried over sodium sulfate, filtered and concentrated to give a clear, yellow liquid weighing 1.35 g. Purification by normal phase chromatography gave 1.2:1 mixture of Intermediate 39A and methyl 2-(2-(tert-butoxy)-2-oxoethyl)(3-chlorophenyl)amino)propanoate (0.375 g) as a clear, colorless viscous oil. MS (ESI) m/z: 350.0 (M+Na)$^+$. A clear, colorless solution of Intermediate 39A and methyl 2-((2-(tert-butoxy)-2-oxoethyl)(3-chlorophenyl)amino)propanoate (0.375 g, 1.144 mmol) in 50% TFA/DCM (16.34 mL) was stirred at rt. After 3 h, the reaction was concentrated to give a pink oil. The oil was partitioned between EtOAc and 0.5 M NaOH and the layers were separated. The organic layer was extracted with 0.5 M NaOH (2×). The combined aqueous layers were extracted with EtOAc, acidified with 1.0 N HCl to give a cloudy mixture, and then extracted with EtOAc (3×). The organic layers following acidification were combined, washed with brine, dried over sodium sulfate, filtered and concentrated to give the desired product (0.130 g) as a clear, yellow residue. MS (ESI) m/z: 272.0 (M+H)$^+$.

Intermediate 39

Methyl 2-((3-chlorophenyl)(2-((methylsulfonyl)oxy)ethyl)amino)propanoate: Intermediate 39 was prepared by following the procedures described in Intermediate 21, by replacing Intermediate 21B with Intermediate 39B. MS (ESI) m/z: 336.0 (M+H)$^+$.

Intermediate 40

Methyl 2-((3-chloro-2,6-difluorophenyl)(2-((methylsulfonyl)oxy)ethyl)amino)acetate

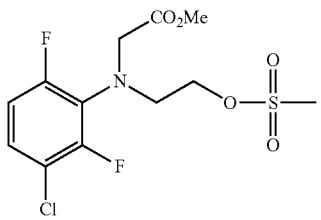 [SMILES: COC(=O)CN(CCOS(C)(=O)=O)c1c(F)ccc(Cl)c1F]

Intermediate 40

Methyl 2-((3-chloro-2,6-difluorophenyl)(2-((methylsulfonyl)oxy)ethyl)amino)acetate: Intermediate 40 was prepared according to the procedures described in Intermediate 21, by replacing 3-chloro-2-fluoroaniline with 3-chloro-2,6-difluoroaniline and by running the reaction at 100° C. for 5 days. $^1$H NMR (500 MHz, CDCl$_3$) δ 7.11 (ddd, J=9.0, 7.9, 5.4 Hz, 1H), 6.86 (ddd, J=10.9, 8.9, 2.2 Hz, 1H), 4.36 (t, J=5.5 Hz, 2H), 4.03 (s, 2H), 3.74 (s, 3H), 3.71-3.66 (m, 2H), 3.01 (s, 3H). MS (ESI) m/z: 357.9 (M+H)$^+$.

Example 1

Methyl ((12E,15S)-15-(6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, HCl salt

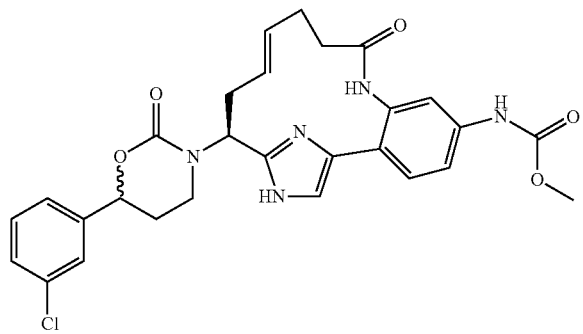 [SMILES: COC(=O)Nc1ccc2c(c1)NC(=O)CC/C=C/C[C@H](N1CCC(c3cccc(Cl)c3)OC1=O)c1nc-2c[nH]1]

1A (S)-2-(4-(Methoxycarbonylamino)-2-nitrophenyl)-2-oxoethyl 2-(tert-butoxycarbonylamino)pent-4-enoate: To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol). The reaction mixture was stirred for 20 min at rt and then cooled to 0° C. To the above mixture was then added a solution of Intermediate 11 (4.28 g, 13.50 mmol) in DMF (33.7 mL) dropwise and the reaction was allowed to warm to rt and continued to stir at rt for overnight. After 18 h, the reaction was stopped and cooled to 0° C. The reaction mixture was then poured into ice-cold water, then extracted with EtOAc (3×). The combined organic layers were washed with water, brine, dried over Na$_2$SO$_4$, filtered and concentrated. A yellow foam obtained as the desired product (6.09 g, 100%). MS (ESI) m/z: 450.5 (M−H)$^+$.

1B

Methyl (4-(2-((1S)-1-((tert-butoxycarbonyl)amino)but-3-en-1-yl)-1H-imidazol-5-yl)-3-nitrophenyl)carbamate: To a 1000 mL RBF containing 1A (6.09 g, 13.49 mmol) was added xylene (135 mL). The above mixture was sonicated to obtain a clear yellow solution. To the clear yellow solution was then added ammonium acetate (10.40 g, 135 mmol) and the flask was equipped with a Dean-Stark trap and a reflux condenser. The reaction was warmed to 110° C. for 2 h, and then 140° C. for 2 h. After stirring for 4 hours in total, the reaction was allowed to cool to rt. The reaction was diluted with EtOAc and then washed with saturated NaHCO$_3$ solution (2×) followed by brine. The organic layers were then dried over Na$_2$SO$_4$, filtered, and concentrated. The brown gum weighing 5 g was dissolved in DCM and a small amount of MeOH and then purified using silica gel chromatography. A brown foam obtained as the desired product (0.91 g, 15.6%). MS (ESI) m/z: 432.5 (M+H)$^+$.

1C

Methyl (4-(2-((1S)-1-((tert-butoxycarbonyl)amino)but-3-en-1-yl)-1-((2-(trimethylsilyl)ethoxy)methyl)-1H-imidazol-4-yl)-3-nitrophenyl)carbamate: A flame-dried 25 mL round bottom flask was charged with NaH (0.092 g, 2.295 mmol) and then THF (4.17 mL) was added to give a gray suspension. The suspension was cooled to 0° C. and then a clear, yellow solution of 1B (0.9 g, 2.086 mmol) in THF (4.17 mL) was added dropwise. The reaction mixture was stirred at 0° C. for 30 min and then allowed to warm to rt and stirring was continued at rt for additional 0.5 h. The yellow suspension was again cooled to 0° C. and then SEM-Cl (0.370 mL, 2.086 mmol) was added dropwise. The resulting cloudy reaction mixture was stirred at 0° C. After 1 h, the reaction was stopped and quenched with saturated NH$_4$Cl followed by dilution with EtOAc. The layers were separated and the aqueous layer was extracted with EtOAc. The combined organic layers were washed with saturated NaHCO$_3$, brine, dried over Na$_2$SO$_4$, filtered, and concentrated. The yellow oil weighing 1.6 g was purified by silica gel chromatography. The desired product from the reaction was obtained as yellow foam (0.424 g, 36%). MS (ESI) m/z: 562.0 (M+H)$^+$. 1D NOE confirmed the regioisomeric position of SEM on the imidazole ring.

1D tert-Butyl N-[(1S)-1-(4-{2-amino-4-[(methoxycarbonyl)amino]phenyl}-1-{[2-(trimethylsilyl)ethoxy]methyl}-1H-imidazol-2-yl)but-3-en-1-yl]carbamate: To the solution of 1C (0.424 g, 0.755 mmol) in MeOH (5 mL) was added zinc (0.494 g, 7.55 mmol) and ammonium chloride (0.404 g, 7.55 mmol). The reaction mixture was stirred at 60° C. in a sealed tube. After 4 h, the reaction was cooled to rt. The yellow suspension was diluted with DCM and then washed with water. The aqueous layer extracted with 15% IPA/CHCl$_3$. The combined organic layers were washed with brine, dried over MgSO$_4$, filtered and concentrated. The crude product was purified using silica gel chromatography to give an orange solid as the desired product (0.31 g, 77%). MS (ESI) m/z: 532.4 (M+H)$^+$.

1E tert-Butyl N-[(1S)-1-(4-{4-[(methoxycarbonyl)amino]-2-(pent-4-enamido)phenyl}-1-{[2-(trimethylsilyl)ethoxy]methyl}-1H-imidazol-2-yl)but-3-en-1-yl]carbamate: DIEA (0.148 mL, 0.846 mmol) was added to a solution of pent-4-enoic acid (0.028 g, 0.282 mmol) and 1D (0.15 g, 0.282 mmol) in ethyl acetate (8.06 mL). The reaction was allowed to cool to −10° C. under argon. To the above mixture, $T_3P$ (0.332 mL, 0.564 mmol) was added and the reaction was allowed to stir for 5 min. The reaction mixture was then warmed to rt while stirring under argon for 1 h. The reaction mixture was concentrated and then purified by silica gel chromatography to obtain a yellow solid (0.092 g, 53%). MS (ESI) m/z: 614.1 $(M+H)^+$.

1F tert-Butyl N-[(12E,15S)-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]carbamate: To a round bottom flask equipped with an argon bubbler was charged finely powdered 1E (1.0165 g, 1.656 mmol) and p-toluenesulfonic acid monohydrate (0.299 g, 1.739 mmol). The flask was purged with argon and DCM (anhydrous—degassed) (78 mL) was added followed by heating of the colorless mixture at 40° C. The mixture was rapidly stirred at this temperature until the reactants went into solution (~5 min) after which a solution of tricyclohexylphosphine[1,3-bis(2,4,6-trimethylphenyl)-4,5-dihydroimidazol-2-ylidene][benzylidine]ruthenium(IV) dichloride (0.070 g, 0.083 mmol) in DCM (anhydrous—degassed) (5.0 mL) was added at the rate of ~1 drop per second. Stirring was continued at 40° C. for 90 minutes at which time an aliquot was removed and analyzed by TLC which indicated all starting material consumed. The mixture was cooled to rt and washed with saturated $NaHCO_3$, brine, dried over $Na_2SO_4$, filtered and evaporated to give a dark solid. The residue was dissolved in a small amount of methylene chloride and purified using silica gel chromatography to give the desired product, as a mixture of the cis and trans olefin isomers. The crude product was purified by reverse phase HPLC to give two fractions, fraction 1 (trans-olefin isomer) and fraction 2 (cis-olefin isomer). Appropriate trans fractions evaporated to obtain the desired product as a colorless solid (404 mg, 42%). MS (ESI) m/z: 586.5 $(M+H)^+$.

1G

Methyl N-[(12E,15S)-15-amino-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To 1F (60.9 mg, 0.104 mmol) in DCM (anhydrous) (5 mL) was added TFA (1 mL, 12.98 mmol) and the reaction was stirred at ambient temperature under nitrogen for 1.5 h. The reaction mixture was evaporated under reduced pressure to a residue. To the residue was added ethyl acetate and an excess amount of saturated aqueous $NaHCO_3$. The aqueous layer was extracted with additional ethyl acetate and the combined organic layers were washed with brine, dried ($Na_2SO_4$) and evaporated to give the product as a solid (434 mg, 87%). MS (ESI) m/z: 486.4 $(M+H)^+$.

1H

Methyl N-[(12E,15S)-15-{[3-(3-chlorophenyl)-3 hydroxypropyl]amino}-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To a mixture of Intermediate 1 (177 mg, 0.597 mmol) and 1G (290 mg, 0.597 mmol) in ACN (anhydrous) (8 mL) was added $K_2CO_3$ (anhydrous) (825 mg, 5.97 mmol) and the mixture was placed under nitrogen and heated to 75° C. for overnight. After overnight stirring, the reaction mixture was concentrated and the crude product was purified using reverse phase HPLC and appropriate fractions evaporated to isolate the desired product (188 mg, 41%) as a colorless solid. MS (ESI) m/z: 654.3 $(M+H)^+$.

1I

Methyl N-[(12E,15S)-15-[6-(3-chlorophenyl)-2-oxo-1,3-oxazinan-3-yl]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To a microwave vial was added 1H (55.4 mg, 0.072 mmol) and 1,1'-carbonyldiimidazole (23.38 mg, 0.144 mmol). The reaction vial was then capped with a septa, purged with nitrogen, and a solution of dioxane (anhydrous) (2 mL) and TEA (0.101 mL, 0.721 mmol) was added. The reaction vial was then placed in a pre-heated oil bath (80° C.) where it was stirred for overnight. LC/MS indicated incomplete reaction with both starting material and desired product seen (ratio ~1:1). To the microwave vial was charged additional 1,1'-carbonyldiimidazole (25 mg, 0.154 mmol) as a dioxane (anhydrous) (1 mL) solution. The vial was then placed in an Al heat block (110° C.) where it was stirred for 1.5 h. The reaction mixture was then diluted with MeOH and purified by reverse phase HPLC. Appropriate fractions evaporated to give the desired product as colorless solid (7.4 mg, 45%) as a mixture of diastereomers. MS (ESI) m/z: 680.3 $(M+H)^+$.

Example 1

Methyl ((12E,15S)-15-(6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, HCl salt: To a mixture of 1I (7.4 mg, 10.88 μmol) and cysteine (6.59 mg, 0.054 mmol) was added hydrogen chloride (4 M in dioxane) (2 mL, 8.00 mmol) and the reaction stirred under nitrogen at 75° C. for 8 h followed by stirring at rt overnight. After overnight stirring at rt, the reaction mixture was evaporated under reduced pressure and the residue was diluted with MeOH, filtered and purified by reverse phase HPLC to isolate the desired product as a mixture of diastereomers as HCL salt (2.5 mg, 39%, colorless solid). $^1$H NMR (400 MHz, MeOD) δ 9.58 (s, 1H), 7.69-7.31 (m, 8H), 5.57 (s, 1H), 5.46 (d, J=10.3 Hz, 2H), 5.40-5.32 (m, 1H), 5.32-5.24 (m, 1H), 3.78 (s, 4H), 3.62 (dd, J=10.1, 4.6 Hz, 2H), 3.10-2.79 (m, 2H), 2.54-2.34 (m, 5H), 2.33-2.16 (m, 1H) ppm. MS (ESI) m/z: 550.2 $(M+H)^+$. Analytical HPLC: RT=5.49 min (Method A).

Compound 1D can be prepared by an alternative sequence described below:

1J

{3-Bromo-4-[2-((S)-1-tert-butoxycarbonylamino-but-3-enyl)-3H-imidazol-4-yl]-phenyl}-carbamic acid methyl ester: This compound was prepared following the procedure described in step 1A, by replacing Intermediate 11 with Intermediate 10; followed by step 1B. MS (ESI) m/z: 467.1 (M+2+H)$^+$.

1K

{3-Bromo-4-[2-((S)-1-tert-butoxycarbonylamino-but-3-enyl)-1-(2-trimethylsilanyl-ethoxymethyl)-1H-imidazol-4- yl]-phenyl}-carbamic acid methyl ester: To a cooled (0° C.) 1J (15 g, 32.2 mmol) in THF (77 mL) was added N,N-dicyclohexylmethylamine (7.52 mL, 35.5 mmol) followed by the dropwise addition of SEM-Cl (6.29 mL, 35.5 mmol). The reaction was stirred at 0° C. for 2 h and then it was allowed to warm slowly to rt. After 18 h, the yellow suspension was diluted with EtOAc, washed with saturated sodium bicarbonate, brine, dried over MgSO$_4$, filtered and concentrated. Purification by normal phase chromatography gave (12.24 g, 64%) of 1K as an off-white solid. MS (ESI) m/z: 595.1 (M+H)$^+$ and 597.2 (M+2H)$^+$.

1D (Alternative)

tert-Butyl N-[(1S)-1-(4-{2-amino-4-[(methoxycarbonyl)amino]phenyl}-1-{[2-(trimethylsilyl)ethoxy]methyl}-1H-imidazol-2-yl)but-3-en-1-yl]carbamate: A thick-walled vial containing 1K (2 g, 3.36 mmol), copper(I) iodide (0.128 g, 0.672 mmol), L-proline (0.155 g, 1.343 mmol) and potassium carbonate (1.392 g, 10.07 mmol) in DMSO (6.72 mL) was vacuumed and back-filled with argon three times. Then 28% aq. ammonium hydroxide (0.607 mL, 4.37 mmol) was added. The vial was sealed with a Teflon-coated screw cap and the reaction was warmed to 85° C. After 20 h, the reaction was cooled to rt, diluted with EtOAc, washed with water, brine, dried over sodium sulfate, filtered and concentrated. Purification by normal phase chromatography afforded (1.05 g, 59%) of 1D (Alternative) as a yellow solid. MS (ESI) m/z: 532.5 (M+H)$^+$.

Example 2

Methyl ((12E,15S)-15-((6S)-6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, TFA salt

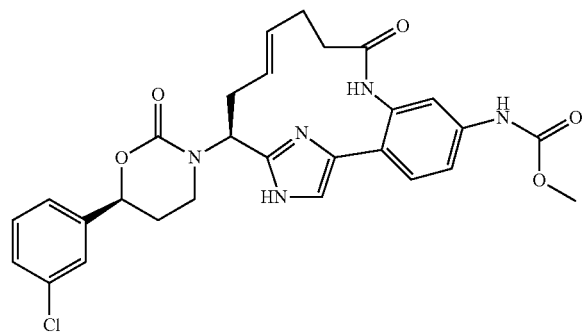 [SMILES: COC(=O)Nc1ccc2c(c1)NC(=O)CC/C=C/C[C@H](N1CC[C@@H](c3cccc(Cl)c3)OC1=O)c1nc-2c[nH]1]

Example 2

Methyl ((12E,15S)-15-((6S)-6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, TFA salt: Example 1 was subjected to chiral HPLC purification using CHIRALCEL® OJ-H, 30×250 mm ID, 5 μm at 40 mL/min, 100 bar and 40° C. using EtOH-0.1% DEA/CO$_2$ (25/75) at 219 nm and isolated the desired peak as the first peak (colorless solid) from chiral HPLC. $^1$H NMR (400 MHz, MeOD) δ 7.53-7.34 (m, 7H), 7.28-7.16 (m, 1H), 5.87-5.71 (m, 1H), 5.70-5.59 (m, 1H), 5.57-5.48 (m, 1H), 5.48-5.39 (m, 1H), 3.76 (s, 4H), 3.54-3.41 (m, 2H), 3.11-2.90 (m, 1H), 2.68-2.55 (m, 2H), 2.55-2.46 (m, 2H), 2.46-2.31 (m, 4H), 2.25-2.08 (m, 1H) ppm. MS (ESI) m/z: 550.2 (M+H)$^+$. Analytical HPLC: RT=7.44 min (Method A).

Example 3

Methyl ((12E,15S)-15-((6R)-6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, TFA salt

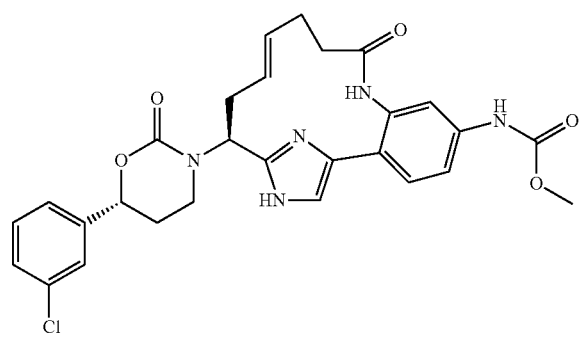

Example 3

Methyl ((12E,15S)-15-((6R)-6-(3-chlorophenyl)-2-oxo-1,3-oxazinan-3-yl)-9-oxo-8,17,19-triazatricyclo[14.2.1.0$^{2,7}$]nonadeca-1(18),2,4,6,12,16(19)-hexaen-5-yl)carbamate, TFA salt: Example 1 was subjected to chiral HPLC purification using CHIRALCEL® OJ-H, 30×250 mm ID, 5 μm at 40 mL/min, 100 bar and 40° C. using EtOH-0.1% DEA/CO$_2$ (25/75) at 219 nm and isolated the desired product as the second peak from chiral HPLC. $^1$H NMR (400 MHz, MeOD) δ 7.55-7.33 (m, 7H), 7.27-7.07 (m, 1H), 5.82-5.62 (m, 2H), 5.62-5.50 (m, 1H), 5.49-5.40 (m, 1H), 3.76 (s, 4H), 3.69-3.57 (m, 1H), 3.12-2.92 (m, 1H), 2.74-2.63 (m, 2H), 2.51 (s, 2H), 2.42 (s, 3H), 2.37-2.28 (m, 2H), 2.24-2.07 (m, 1H) ppm. MS (ESI) m/z: 550.2 (M+H)$^+$. Analytical HPLC: RT=7.37 min.

Example 4

Methyl ((14S)-14-(6-(3-chlorophenyl)-2-oxo-1,3-oxazinan-3-yl)-9-oxo-8,16,18-triazatricyclo[13.2.1.0$^{2,7}$]octadeca-1(17),2,4,6,15(18)-pentaen-5-yl)carbamate, TFA salt

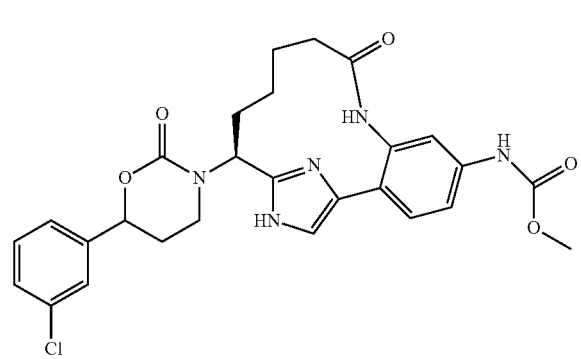 [SMILES: COC(=O)Nc1ccc2c(c1)NC(=O)CCCC[C@H](N1CCC(c3cccc(Cl)c3)OC1=O)c1nc-2c[nH]1]

4A tert-Butyl N-[(1S)-1-{4-[2-(but-3-enamido)-4-[(methoxycarbonyl)amino]phenyl]-1-{[2-(trimethylsilyl)ethoxy]methyl}-1H-imidazol-2-yl}but-3-en-1-yl]carbamate: 4A was made in the same way as 1E by using 1D and substituting but-3-enoic acid for pent-4-enoic acid (710 mg, 31%). MS (ESI) m/z: 600.5 (M+H)+.

4B tert-Butyl N-[(14S)-5-[(methoxycarbonyl)amino]-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: 4A was subjected to the macrocyclization protocol as described in 1F to obtain the unsaturated macrocyclized product. The purified product was then subjected to hydrogenation using palladium on carbon (10%) (83 mg, 0.042 mmol). The flask was purged with nitrogen and to the flask was added EtOH (absolute) (10 mL) and EtOAc (10 mL). The flask was once again purged with nitrogen (3×), evacuated and an atmosphere of hydrogen (approx. 55 psi) was introduced and the reaction stirred at ambient temperature for overnight. After overnight stirring, the reaction mixture was filtered through CELITE® with the aid of additional EtOAc and the collected solvent was evaporated. The desired product was obtained as a colorless solid (113 mg, 93%) which was used without further purification. MS (ESI) m/z: 574.5 (M+H)+.

Example 4

Methyl ((14S)-14-(6-(3-chlorophenyl)-2-oxo-1,3-oxazinan-3-yl)-9-oxo-8,16,18-triazatricyclo[13.2.1.0$^{2,7}$]octadeca-1(17),2,4,6,15(18)-pentaen-5-yl)carbamate, TFA salt: The desired product was made in a similar way as described with Example 1 starting with 4B instead of 1G. $^1$H NMR (400 MHz, CD$_3$CN) δ 9.63 (d, J=25.0 Hz, 1H), 7.90 (s, 1H), 7.44-7.22 (m, 8H), 5.29 (dt, J=10.1, 2.8 Hz, 1H), 4.99 (dd, J=12.0, 5.7 Hz, 1H), 3.66 (s, 3H), 3.57 (dd, J=8.9, 4.5 Hz, 1H), 3.51-3.45 (m, 1H), 2.54-2.37 (m, 2H), 2.27-1.92 (m, 6H), 1.58-1.43 (m, 1H), 1.25-1.01 (m, 1H), 0.81-0.51 (m, 1H) ppm. MS (ESI) m/z: 537.9 (M+H, chlorine isotope seen)+. Analytical HPLC: RT=10.04 min (Method A).

Example 5

Methyl (9R,14S)-14-(6-(3-chlorophenyl)-2-oxo-1,3-oxazinan-3-yl)-5-((methoxycarbonyl)amino)-8,16,18-triazatricyclo[13.2.1.0$^{2,7}$]octadeca-1(17),2,4,6,15(18)-pentaene-9-carboxylate, HCl salt

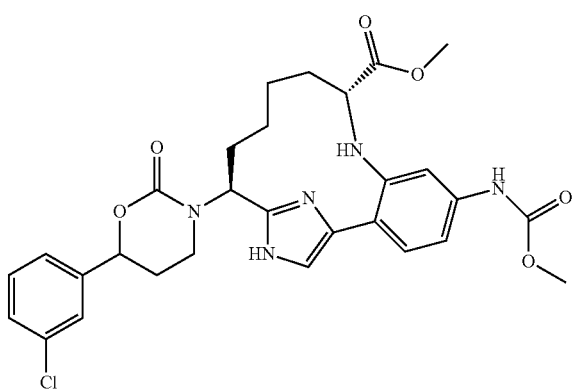 [SMILES: COC(=O)Nc1ccc2c(c1)N[C@@H](C(=O)OC)CCCC[C@H](N1CCC(c3cccc(Cl)c3)OC1=O)c1nc-2c[nH]1]

5A

Methyl (3-bromo-4-(2-((1S)-1-((tert-butoxycarbonyl)amino)but-3-en-1-yl)-1-((2-(trimethylsilyl)ethoxy)methyl)-1H-imidazol-4-yl)phenyl)carbamate: This compound was prepared following the procedures described in step 1A, by replacing Intermediate 11 with Intermediate 10; followed by step 1B and 1C. MS (ESI) m/z: 597.1 (M+2+H)+.

5B (R)-2-(2-(2-((S)-1-(tert-Butoxycarbonylamino)but-3-enyl)-1-(2-(trimethylsilyl)ethoxy)methyl)-1H-imidazol-4-yl)-5-(methoxycarbonylamino)phenylamino)pent-4-enoic acid: To a mixture of 5A (2 g, 3.36 mmol), copper(I) iodide (0.064 g, 0.336 mmol) and K$_2$CO$_3$ (1.160 g, 8.39 mmol) in a sealed tube were added (R)-2-aminopent-4-enoic acid (0.464 g, 4.03 mmol) and DMSO (6.72 ml). The reaction mixture was purged with argon, then capped and heated at 90° C. for 18 h. The reaction mixture was then cooled to rt and diluted with ethyl acetate and water. The aqueous layer was re-extracted with EtOAc (2×) and the combined organic layers were washed with brine, dried over Na$_2$SO$_4$ and concentrated to give the crude residue. A small amount of DCM (~5 mL) was added to the above crude residue to give a brown solution. To this solution was then added hexane (~300 mL) to result in a yellow suspension. The yellow suspension was then filtered and the solid rinsed with hexane and the residue was air-dried to yield the desired product as yellow solid (1.8 g, 85%). MS (ESI) m/z: 630.4 (M+H)+.

5C

Methyl (2R)-2-[(2-{2-[(1S)-1-{[(tert-butoxy)carbonyl]amino}but-3-en-1-yl]-1-{[2-(trimethylsilyl)ethoxy]methyl}-1H-imidazol-4-yl}-5-[(methoxycarbonyl)amino]phenyl)amino]pent-4-enoate: To a solution of 5B (1.8 g, 2.86 mmol) in DMF (25 mL) was added K$_2$CO$_3$ (0.395 g, 2.86 mmol) and MeI (0.179 mL, 2.86 mmol). The reaction mixture was then stirred at rt for 20 h. After 20 h, the reaction mixture was diluted with EtOAc and water. The aqueous layer was re-extracted with EtOAc and the combined organic layers were washed with water followed by brine. The organic layers were then dried over Na$_2$SO$_4$, filtered and concentrated. The crude product was then purified using silica gel chromatography to give brown foam as the desired product (0.58 g, 32%). MS (ESI) m/z: 644.3 (M+H)+.

5D

Methyl (9R,11E,14S)-14-{[(tert-butoxy)carbonyl]amino}-5-[(methoxycarbonyl)amino]-16-{[2-(trimethylsilyl)ethoxy]methyl}-8,16,18-triazatricyclo[13.2.1.0$^{2,7}$]octadeca-1(17),2,4,6,11,15(18)-hexaene-9-carboxylate: A mixture of SC (0.58 g, 0.901 mmol) and Grubbs (II) catalyst (0.306 g, 0.360 mmol) in DCE (22.52 mL) was heated at 120° C. under microwave conditions for 20 min. After 20 min, the reaction mixture was allowed to cool to rt. The reaction mixture was then diluted with EtOAc and washed with saturated NaHCO$_3$ solution followed by brine. The organic layer was then dried over MgSO$_4$, filtered and concentrated to yield the crude product. The crude product was then purified using silica gel chromatography to give a yellow solid as the desired product (0.128 g, 23%). MS (ESI) m/z: 616.4 (M+H)+.

5E

Methyl (9R,14S)-14-{[(tert-butoxy)carbonyl]amino}-5-[(methoxycarbonyl)amino]-16-{[2-(trimethylsilyl)ethoxy]methyl}-8,16,18-triazatricyclo[13.2.1.0$^{2,7}$]octadeca-1(17), 2,4,6,15(18)-pentaene-9-carboxylate: To a solution of 5D (0.128 g, 0.208 mmol) in EtOAc (5 mL) was added TFA (0.032 mL, 0.416 mmol) and 10% palladium on carbon (0.022 g, 0.021 mmol). Hydrogen was bubbled through the reaction mixture for 5 min, and then charged with a H$_2$-balloon. After 17 h, LC/MS analysis showed the major peak as desired product. The reaction mixture was filtered through a 0.45 μM GMF rinsing with MeOH (filtered twice) and concentrated to give the crude product. The crude product was then purified by reverse phase HPLC to isolate the desired product as a solid (0.113 g, 64%). MS (ESI) m/z: 618.4 (M+H)$^+$.

5F

Methyl (9R,14S)-14-amino-5-[(methoxycarbonyl)amino]-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a solution of 5E (147.2 mg, 0.238 mmol) in DCM (anhydrous) (5 mL) was added TFA (1 mL, 12.98 mmol) and the reaction mixture was stirred at rt under nitrogen for 1.5 h. After 1.5 h, HPLC analysis of the reaction mixture indicates complete consumption of the starting material. To the reaction was added an excess of saturated NaHCO$_3$ solution (20 mL). The aqueous layer was then extracted with EtOAc (2×) and the combined organic layers were washed with brine, dried (Na$_2$SO$_4$) and concentrated to give the desired product as a colorless solid (118.5 mg, 96%). MS (ESI) m/z: 518.0 (M+H)$^+$.

Example 5

Methyl (9R,14S)-14-(6-(3-chlorophenyl)-2-oxo-1,3-oxazinan-3-yl)-5-((methoxycarbonyl)amino)-8,16,18-triazatricyclo[13.2.1.0$^{2,7}$]octadeca-1(17),2,4,6,15(18)-pentaene-9-carboxylate, HCl salt: 5F was subjected to step 1H replacing 1G with 5E, followed by Step 1I and the final deprotection step as described in Example 1 to yield the desired product. $^1$H NMR (400 MHz, CD$_3$CN) δ 7.92 (s, 1H), 7.48-7.33 (m, 7H), 7.22 (dt, J=8.4, 1.9 Hz, 1H), 5.46-5.37 (m, 1H), 5.19-5.11 (m, 1H), 3.98 (s, 1H), 3.85-3.77 (m, 1H), 3.75 (s, 3H), 3.72-3.59 (m, 2H), 3.57-3.55 (m, 3H), 3.10-3.05 (m, 1H), 2.67-2.55 (m, 1H), 2.39-2.03 (m, 4H), 1.87-1.70 (m, 2H), 1.62-1.41 (m, 3H) ppm. MS (ESI) m/z: 582.0 (M+H)$^+$. Analytical HPLC: RT=6.40 min (Method A).

Example 6

Methyl ((12E,15S)-18-chloro-15-(4-(3-chlorophenyl)-2-oxo-1-piperidinyl)-9-oxo-8,17,19-triazatricyclo[14.2.1.0$^{2,7}$]nonadeca-1(18),2,4,6,12,16(19)-hexaen-5-yl)carbamate (Diastereomer mixture; 1:1), TFA salt

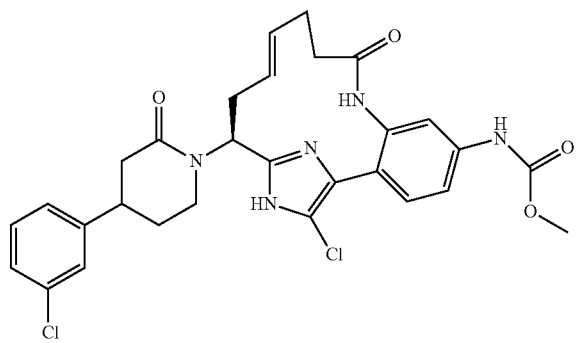 [SMILES: COC(=O)Nc1ccc2c(c1)NC(=O)CC/C=C/C[C@H](N1CCC(c3cccc(Cl)c3)CC1=O)c1nc-2c(Cl)[nH]1]

6A tert-Butyl N-[(12E,15S)-18-chloro-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]carbamate: A white suspension of 1F, as a mixture of E- and Z-alkene isomers, (2.56 g, 4.37 mmol) and NCS (0.700 g, 5.24 mmol) in CHCl$_3$ (18.36 mL) and ACN (18.36 mL) was heated to 65° C. After 10 h, the reaction mixture was cooled to rt and partitioned between DCM and water and the layers were separated. The aqueous layer was extracted with DCM (2×). The organic layers were combined, washed with saturated NaHCO$_3$, brine, dried over MgSO$_4$, filtered and concentrated to give a brown foam. The E- and Z-alkene isomers were separated by reverse phase chromatography. The fractions containing the E-alkene isomer were combined, neutralized with a solution of saturated NaHCO$_3$, and then concentrated to give a solid. The solid was partitioned between EtOAc and water and the layers were separated. The organic layer was washed with brine, dried over Na$_2$SO$_4$, filtered and concentrated to give 6A (1.15 g, 42%) as yellow foam. MS (ESI) m/z: 620.1 (M+H)$^+$.

6B

Methyl N-[(12E,15S)-15-amino-18-chloro-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To a solution of 6A (0.24 g, 0.387 mmol) in DCM (5 mL) was added TFA (1 mL, 12.98 mmol). The reaction was stirred at rt. After 1 h, the reaction was concentrated. Purification by reverse phase chromatography gave, after neutralization of the fractions with saturated NaHCO$_3$ and concentration, a solid. The solid was partitioned between EtOAc and water and the layers were separated. The organic layer was washed with brine, dried over Na$_2$SO$_4$, filtered and concentrated to give 6B (0.095 g, 47%), as a white solid. MS (ESI) m/z: 520.1 (M+H)$^+$.

6C

Methyl 5-{[(12E,15S)-18-chloro-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]amino}-3-(3-chlorophenyl)pentanoate: A sealed vial containing Intermediate 3 (0.06 g, 0.187 mmol) and 6B (0.02 g, 0.038 mmol) in THF (1 mL) and DIEA (0.098 mL, 0.561 mmol) was stirred at 120° C. After 18 h, the reaction was cooled to rt and then it was concentrated. Purification by reverse phase chromatography gave, after neutralization of the fractions with sat. NaHCO$_3$ and then concentration, a solid. The solid was partitioned between EtOAc/water and the layers were separated. The organic layer was washed with brine, dried over sodium sulfate, filtered and concentrated to give 6C (0.015 g, 11%), as a mixture of diastereomers and as a yellow solid. The material was used in the next step without further purification. MS (ESI) m/z: 744.0 (M+H)$^+$.

6D

Methyl N-[(12E,15S)-18-chloro-15-[4-(3-chlorophenyl)-2-oxopiperidin-1-yl]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: A sealed vial containing a solution of 6C (0.015 g, 0.017 mmol) in MeOH (0.5 mL) and 1 N NaOH (0.087 mL, 0.087 mmol) was stirred at 55° C. After 4 h, the reaction was cooled to rt and the reaction stirred overnight. The next day the reaction was concentrated. Purification by reverse phase chromatography gave 6D (0.005 g, 34.6%) as a white solid. MS (ESI) m/z: 712.0 (M+H)+.

Example 6

Methyl ((12E,15S)-18-chloro-15-(4-(3-chlorophenyl)-2-oxo-1-piperidinyl)-9-oxo-8,17,19-triazatricyclo[14.2.1.0$^{2,7}$]nonadeca-1(18),2,4,6,12,16(19)-hexaen-5-yl)carbamate (Diastereomer mixture; 1:1), TFA salt: A sealed vial containing a solution of 6D (0.005 g, 6.05 µmol) in 4 M HCl in 1,4-dioxane (1 mL, 32.9 mmol) was heated at 65° C. After 1 h, the reaction was cooled to rt and then it was concentrated. Purification by reverse phase chromatography gave Example 6 (0.002 g, 47%), as a mixture of diastereomers and as a white solid. $^{1}$H NMR (500 MHz, DMSO-d$_{6}$ with two drops of D$_{2}$O) δ 7.45 (d, J=6.9 Hz, 2H), 7.38-7.31 (m, 8H), 7.30-7.22 (m, 4H), 5.65-5.59 (m, 2H), 5.48-5.27 (m, 4H), 3.91-3.84 (m, J=10.7 Hz, 1H), 3.67 (s, 6H), 3.53-3.43 (m, 3H), 3.17-3.05 (m, 2H), 2.70-2.27 (m, 12H), 2.24-2.15 (m, 4H), 2.09-2.01 (m, 2H), 1.96-1.86 (m, 2H) ppm. MS (ESI) m/z: 582.0 (M+H)+. Analytical HPLC: RT=8.76 min (Method A).

Example 7

Methyl (9R,14S)-14-(6-(5-chloro-2-(difluoromethoxy)phenyl)-2-oxo-1,3-oxazinan-3-yl)-17-cyano-5-((methoxycarbonyl)amino)-8,16,18-triazatricyclo[13.2.1.0$^{2,7}$]octadeca-1(17),2,4,6,15(18)-pentaene-9-carboxylate, 2 TFA salt

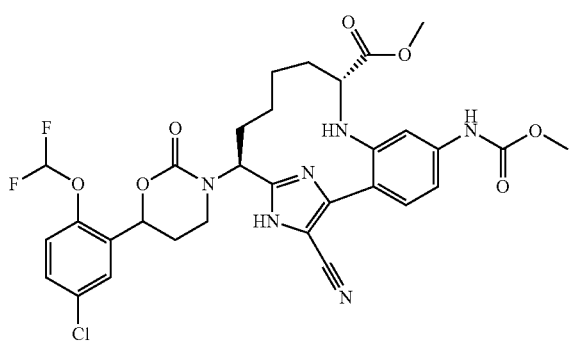 [SMILES: COC(=O)Nc1ccc2c(c1)N[C@@H](C(=O)OC)CCCC[C@H](N1CCC(c3cc(Cl)ccc3OC(F)F)OC1=O)c1nc-2c(C#N)[nH]1]

7A (R)-Methyl 2-(N-(2-(2-((S)-1-((tert-butoxycarbonyl)amino)but-3-en-1-yl)-1-((2-(trimethylsilyl)ethoxy)methyl)-1H-imidazol-4-yl)-5-((methoxycarbonyl)amino)phenyl)-2,2,2-trifluoroacetamido)pent-4-enoate: To a solution of 5C (14.75 g, 22.91 mmol) in EtOAc was added pyridine (2.78 mL, 34.4 mmol) followed by dropwise addition of TFAA (3.72 mL, 26.3 mmol) at 0° C. The reaction mixture was allowed to reach rt and stirred at rt overnight. After overnight stirring at rt, the reaction mixture was diluted with EtOAc and water. The aqueous phase was extracted with EtOAc (3×) and the combined organic phases were dried over sodium sulfate, filtered and concentrated. The crude product was purified by silica gel chromatography to give 7A as an orange solid (15.8 g, 93%). MS (ESI) m/z: 740.2 (M+H)+.

7B

Methyl (9R,14S)-14-{[(tert-butoxy)carbonyl]amino}-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,11,15(18)-hexaene-9-carboxylate: A solution of 7A (4.83 g, 6.53 mmol) dissolved in DCE (163 ml) was bubbled with Ar for 15 minutes. To the above degassed solution was then slowly added a solution of Grubbs II catalyst (0.161 g, 0.189 mmol) dissolved in 10 mL of degassed DCE. The reaction mixture was then heated to 85° C. under a reflux condenser and stirred overnight under argon. After overnight stirring, the reaction mixture was concentrated. The residue was purified by silica gel chromatography to give 7B (1.35 g, 29%) as a brown solid. MS (ESI) m/z: 712.3 (M+H)+.

7C

Methyl (9R,14S)-14-{[(tert-butoxy)carbonyl]amino}-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a degassed solution of 7B (1.35 g, 1.897 mmol) in MeOH (15 mL) was added palladium on carbon (0.202 g, 0.190 mmol), and the reaction was stirred under H$_{2}$ (3×, 55 psi) at rt for 2 days. The reaction mixture was then filtered through a pad of CELITE® and the filtrate was concentrated. The crude product was purified using silica gel chromatography to provide 7C as an orange oil (0.926 g, 68%). MS (ESI) m/z: 714.1 (M+H)+.

7D

Methyl (9R,14S)-17-bromo-14-{[(tert-butoxy)carbonyl]amino}-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a solution of 7C (0.924 g, 1.294 mmol) in CHCl$_{3}$ (20 mL) at 0° C. was added NBS (0.253 g, 1.424 mmol), and the reaction mixture was stirred at 0° C. for 1 h. The reaction mixture was then concentrated, and the residue was purified by silica gel chromatography provide 7D (850 mg, 83%) as a yellow solid. MS (ESI) m/z: 792.1 (M+H)+.

7E

Methyl (9R,14S)-14-{[(tert-butoxy)carbonyl]amino}-17-cyano-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a microwave vial was added 7D (0.850 g, 1.072 mmol) followed by DMF (11 mL). To the above solution was added zinc cyanide (0.076 g, 0.643 mmol) and the reaction mixture was flushed with argon for 20 minutes. To this mixture was finally added Pd(PPh$_{3}$)$_{4}$ (0.124 g, 0.104 mmol) under an atmosphere of argon. The reaction mixture was sealed and heated for 1 h at 120° C. in a microwave. The cooled reaction mixture was diluted with EtOAc and washed with 10% LiCl solution (4×). The organic layers were separated and further washed with brine, dried over sodium sulfate, filtered and concentrated. The residue was purified using silica gel chromatography to obtain 7E (0.769 g, 97%) as a yellow solid. MS (ESI) m/z: 739.1 (M+H)+.

7F

Methyl (9R,14S)-14-amino-17-cyano-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: (Reference: EP 2070899) To a microwave vial was added 7E (0.20 g, 0.271 mmol) followed by hexafluoroisopropanol (HFIP) (2 mL). The above solution was heated at 150° C. under microwave conditions for 1.5 h and then concentrated to yield 7F as a yellow solid. MS (ESI) m/z: 639.0 (M+H)+.

7G

Methyl (9R,14S)-14-{[(3R)-3-(3-chlorophenyl)-3-hydroxypropyl]amino}-17-cyano-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a microwave-rated vial was added Intermediate 12 (55.7 mg, 0.188 mmol), 7F (160 mg, 0.188 mmol) and ACN (2 mL), and the mixture was heated at 70° C. behind a blast shield overnight. The reaction mixture was concentrated, and the residue was redissolved in MeOH and purified by reverse phase HPLC. Desired fractions were combined and concentrated. The residue was dissolved in MeOH and run through solid supported HCO$_3$ (PL-HCO$_3$ MP SCE) cartridge to form free base. The cartridge was washed with MeOH and eluent concentrated to provide 7G (112 mg, 74%) as a white solid. MS (ESI) m/z: 807.2 (M+H)+.

7H

Methyl (9R,14S)-14-[(6R)-6-(3-chlorophenyl)-2-oxo-1,3-oxazinan-3-yl]-17-cyano-5-[(methoxycarbonyl)amino]-8-(trifluoroacetyl)-16-{[2-(trimethylsilyl)ethoxy]methyl}-8,16,18-triazatricyclo[13.2.1.0$^{2,7}$]octadeca-1(17),2,4,6,15(18)-pentaene-9-carboxylate: To a solution of 7G (0.112 g, 0.139 mmol) in THF (14 mL) was added CDI (0.112 g, 0.694 mmol), and the reaction mixture was stirred at rt. The reaction progress was monitored by LCMS and additional 3 eq of CDI was added. The reaction mixture was then cooled down to 0° C. and LHMDS (0.153 mL, 0.153 mmol) was added under argon. The reaction mixture was then allowed to warm to rt over an hour. The mixture was cooled back to 0° C. another 0.5 eq of LHMDS was added, followed by stirring for additional one hour at rt. The reaction mixture was then quenched with saturated NH$_4$Cl solution. The quenched reaction mixture was diluted with saturated NaHCO$_3$ and EtOAc. The aqueous phase was extracted with EtOAc (3×) and the combined organics were washed with brine, dried over sodium sulfate, filtered and concentrated to yield 7H (0.177 g, 153%) as a white solid. The crude product was taken on to the next step without any further purification. MS (ESI) m/z: 833.2 (M+H)+.

Example 7

Methyl (9R,14S)-14-(6-(5-chloro-2-(difluoromethoxy)phenyl)-2-oxo-1,3-oxazinan-3-yl)-17-cyano-5-((methoxycarbonyl)amino)-8,16,18-triazatricyclo[13.2.1.0$^{2,7}$]octadeca-1(17),2,4,6,15(18)-pentaene-9-carboxylate, trifluoroacetic acid salt, 2 TFA salt (Diastereomer A): To a mixture of 7H (0.04 g, 0.044 mmol) and MeOH (3 mL) in a microwave vial was added 6 M aqueous HCl (3.00 mL). The reaction mixture was sealed and heated to 75° C. behind a blast shield for 12 h. The reaction mixture was concentrated and the residue was purified by reverse phase HPLC. Example 7 was isolated as the first-eluting diastereomer (1.4 mg, 4%). $^1$H NMR (500 MHz, MeOD) δ 9.42-9.37 (m, 1H), 7.54 (d, J=2.5 Hz, 1H), 7.46 (d, J=8.5 Hz, 3H), 7.25 (d, J=8.8 Hz, 1H), 7.17 (dd, J=8.3, 2.2 Hz, 1H), 7.11-6.72 (m, 1H), 5.77 (dd, J=11.6, 6.6 Hz, 1H), 5.70 (dd, J=10.5, 2.5 Hz, 1H), 4.32-4.18 (m, 1H), 3.78 (s, 4H), 3.61 (s, 3H), 3.02-2.91 (m, 1H), 2.49-2.42 (m, 1H), 2.35-2.24 (m, 1H), 2.22-2.10 (m, 1H), 2.08-1.85 (m, 2H), 1.80-1.71 (m, 1H), 1.60-1.31 (m, 3H), 0.56-0.40 (m, 1H) ppm. MS (ESI) m/z: 673.1 (M+H)+. Analytical HPLC: RT=10.39 min (Method A).

Example 8

Methyl (9R,14S)-14-(6-(5-chloro-2-(difluoromethoxy)phenyl)-2-oxo-1,3-oxazinan-3-yl)-17-cyano-5-((methoxycarbonyl)amino)-8,16,18-triazatricyclo[13.2.1.0$^{2,7}$]octadeca-1(17),2,4,6,15(18)-pentaene-9-carboxylate, trifluoroacetic acid salt, 2 TFA salt

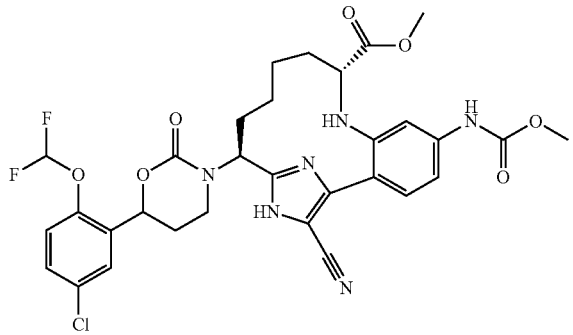 [SMILES: COC(=O)Nc1ccc2c(c1)N[C@@H](C(=O)OC)CCCC[C@H](N1CCC(c3cc(Cl)ccc3OC(F)F)OC1=O)c1nc-2c(C#N)[nH]1]

Example 8

Methyl (9R,14S)-14-(6-(5-chloro-2-(difluoromethoxy)phenyl)-2-oxo-1,3-oxazinan-3-yl)-17-cyano-5-((methoxycarbonyl)amino)-8,16,18-triazatricyclo[13.2.1.0$^{2,7}$]octadeca-1(17),2,4,6,15(18)-pentaene-9-carboxylate, 2 TFA salt (Diastereomer B): Example 8 was isolated as the second diastereomer in the above described preparation of Example 7. $^1$H NMR (500 MHz, MeOD) δ 9.42-9.35 (m, 1H), 7.55 (d, J=2.8 Hz, 1H), 7.49-7.37 (m, J=8.3 Hz, 2H), 7.26 (d, J=8.8 Hz, 1H), 7.19 (d, J=2.2 Hz, 1H), 7.11-6.70 (m, 1H), 5.81 (dd, J=11.3, 6.6 Hz, 1H), 5.71 (dd, J=10.2, 2.8 Hz, 1H), 4.01-3.91 (m, 1H), 3.90-3.84 (m, 1H), 3.78 (s, 3H), 3.61 (s, 3H), 2.99 (d, J=11.3 Hz, 1H), 2.54-2.42 (m, 1H), 2.24-2.07 (m, 2H), 2.05-1.86 (m, 2H), 1.82-1.69 (m, 1H), 1.58-1.37 (m, 3H), 0.54-0.38 (m, 1H) ppm. MS (ESI) m/z: 673.0 (M+H)+. Analytical HPLC: RT=10.5 min (Method A).

Example 9

Methyl ((12E,15S)-15-(4-(3-chlorophenyl)-2-oxo-1-piperidinyl)-9-oxo-8,17,19-triazatricyclo[14.2.1.0$^{2,7}$]nonadeca-1(18),2,4,6,12,16(19)-hexaen-5-yl)carbamate, TFA salt

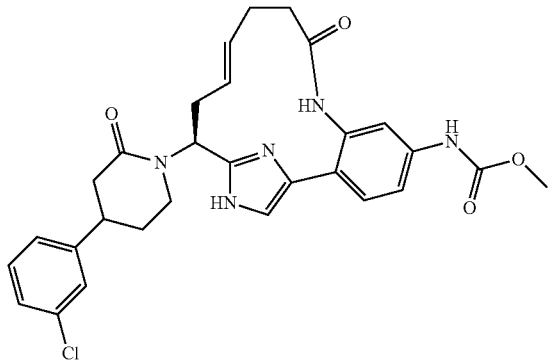 [SMILES: COC(=O)Nc1ccc2c(c1)NC(=O)CC/C=C/C[C@H](N1CCC(c3cccc(Cl)c3)CC1=O)c1nc-2c[nH]1]

127

9A

Methyl N-[(12E,15S)-15-amino-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: A solution of 1F (0.1 g, 0.171 mmol) in 1,1,1,3,3,3-hexafluoroisopropanol (1 mL) was microwaved at 150° C. for 1 h. The reaction was cooled to rt and then it was concentrated to give 9A (0.083 g, 100%) as a yellow solid. MS (ESI) m/z: 486.1 (M+H)$^+$.

9B

Methyl 3-(3-chlorophenyl)-5-{[(12E,15S)-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]amino}pentanoate, 2 TFA: A sealed vial containing Intermediate 3 (enantiomer B) (0.08 g, 0.249 mmol) and 9A (0.08 g, 0.165 mmol) in toluene (2 mL) and Hunig's base (0.086 mL, 0.494 mmol) was heated at 120° C. After 18 h, the reaction was cooled to rt and concentrated. Purification by reverse phase chromatography gave 9B (0.025 g, 18%) as a white solid and 9C (0.019 g, 14%) as a yellow solid. Compound 9B: MS (ESI) m/z: 710.2 (M+H)$^+$. Compound 9C: MS (ESI) m/z: 678.2 (M+H)$^+$.

9C

Methyl N-[(12E,15S)-15-[4-(3-chlorophenyl)-2-oxopiperidin-1-yl]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: A sealed tube containing 9B (0.025 g, 0.030 mmol) in toluene (2 mL) and Hunig's base (0.021 mL, 0.121 mmol) was heated at 150° C. After 16 h, the reaction was cooled to rt and concentrated to give the desired product (0.021 g, 100%) as a yellow solid. The material was carried onto the next step without further purification. MS (ESI) m/z: 678.1 (M+H)$^+$.

Example 9

Methyl ((12E,15S)-15-(4-(3-chlorophenyl)-2-oxo-1-piperidinyl)-9-oxo-8,17,19-triazatricyclo[14.2.1.0$^{2,7}$]nonadeca-1(18),2,4,6,12,16(19)-hexaen-5-yl)carbamate, TFA salt: Example 9 was prepared following the procedure described in Example 6 by replacing 6D with 9C and by running the reaction at 75° C. $^1$H NMR (500 MHz, CD$_3$OD) δ 7.62 (s, 1H), 7.49 (s, 1H), 7.44 (d, J=1.1 Hz, 2H), 7.37-7.32 (m, 1H), 7.31-7.26 (m, 2H), 7.22 (d, J=7.7 Hz, 1H), 5.63-5.53 (m, 2H), 5.50-5.42 (m, 1H), 3.78 (s, 3H), 3.68 (td, J=11.1, 4.7 Hz, 1H), 3.60-3.54 (m, 1H), 3.25-3.16 (m, 1H), 2.97 (td, J=12.9, 9.8 Hz, 1H), 2.86-2.78 (m, 1H), 2.74 (ddd, J=17.5, 5.2, 2.1 Hz, 1H), 2.57 (dd, J=17.5, 11.1 Hz, 1H), 2.50-2.45 (m, 2H), 2.42-2.34 (m, 2H), 2.25-2.06 (m, 2H) ppm. MS (ESI) m/z: 548.1 (M+H)$^+$. Analytical HPLC RT=5.87 min (Method A).

128

Example 10

Methyl N-[(10R,14S)-14-[(6R)-6-(3-chloro-2,6-difluorophenyl)-2-oxo-1,3-oxazinan-3-yl]-10-methyl-9-oxo-8,16,18-triazatricyclo[13.2.1.0$^{2,7}$]octadeca-1(17),2,4,6,15(18)-pentaen-5-yl]carbamate

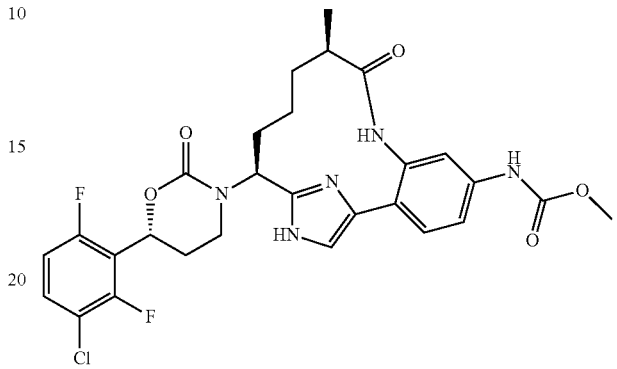

10A

Methyl (4-(2-((1S)-1-((tert-butoxycarbonyl)amino)but-3-en-1-yl)-1-((2-(trimethylsilyl)ethoxy)methyl)-1H-imidazol-4-yl)-3-((trifluoroacetyl)amino)phenyl)carbamate: A solution of 1D (10.2 g, 19.18 mmol) and TEA (3.19 mL, 23.02 mmol) in ethyl acetate (50 mL) was cooled down to 0° C. under argon. To this solution was added 2,2,2-trifluoroacetic anhydride (2.97 mL, 21.10 mmol) dropwise via a syringe pump. After completion of addition, the reaction mixture was stirred for another 30 min at 0° C. After 30 min, the reaction mixture was diluted with EtOAc. The organic layer was then washed with water followed by brine and dried over MgSO$_4$. The crude product was then filtered to remove the solids and the organic layer was concentrated and purified by silica gel chromatography. The desired fractions were combined and concentrated to yield the desired product (10.69 g, 89%) as a yellow solid. MS (ESI) m/z: 627.9 (M+H)$^+$.

10B (6S,E)-Benzyl 6-((tert-butoxycarbonyl)amino)-6-(4-((methoxycarbonyl)amino)-2-(2,2,2-trifluoroacetamido)phenyl)-1-((2-(trimethylsilyl)ethoxy)methyl)-1H-imidazol-2-yl)-2-methylhex-3-enoate: To a solution of 10A (3.3 g, 5.26 mmol) and Intermediate 13 (5.91 g, 31.1 mmol) in DCM (80 mL) was added PTSA (0.905 g, 5.26 mmol). The above solution was bubbled with Ar for 30 min. The reaction mixture was then sealed and heated to 40° C. under argon for 10 min followed by the addition of Grubbs II (1.5 g, 1.767 mmol) in degassed DCM (20 mL) dropwise via syringe pump over 3 h while maintaining the reaction temperature at 40° C. The reaction mixture was continued to be heated at the same temperature for overnight. After overnight stirring, the reaction mixture was washed with concentrated NaHCO$_3$ solution followed by brine, dried over MgSO$_4$, filtered and concentrated. The residue was purified by silica gel chromatography. Desired fractions were combined and concentrated to yield the desired product (1.93 g, 46%) as a yellow solid. MS (ESI) m/z: 790.4 (M+H)$^+$.

10C (6S)-6-((tert-Butoxycarbonyl)amino)-6-(4-(4-((methoxycarbonyl)amino)-2-(2,2,2-trifluoroacetamido)phenyl)-1-((2-(trimethylsilyl)ethoxy)methyl)-1H-imidazol-2-yl)-2-methylhexanoic acid: A solution of 10B (1.76 g, 2.228 mmol) in MeOH (40 mL) was vacuumed and refilled with Ar. To this solution under argon was added Pd/C (500 mg, 0.470 mmol), vacuumed and refilled with hydrogen gas (3×). The reaction mixture was then stirred at rt under $H_2$ balloon. After overnight stirring, the reaction mixture was filtered through CELITE®, concentrated and purified by silica gel chromatography. The desired product (1.23 g, 79%) was isolated as a beige solid. MS (ESI) m/z: 702.1 $(M+H)^+$.

10D (6S)-6-(4-(2-Amino-4-((methoxycarbonyl)amino)phenyl)-1-((2-(trimethylsilyl)ethoxy)methyl)-1H-imidazol-2-yl)-6-((tert-butoxycarbonyl)amino)-2-methylhexanoic acid: To a solution of 10C (1.656 g, 2.360 mmol) in MeOH (14 mL) was added lithium hydroxide (2 N aqueous) (7 mL, 14.00 mmol). The reaction mixture was then sealed and heated at 60° C. for 1 h. After 1 h, the reaction mixture was cooled down with an ice water bath, 1 N HCl (aqueous) was added to adjust pH to 6. The aqueous layer was extracted with EtOAc (2×60 mL). The combined organic layers were washed with brine, filtered off solids, and concentrated to yield the desired product (1.43 g, 100%) as a grayish solid. MS (ESI) m/z: 606.3 $(M+H)^+$.

10E tert-Butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: To a mixture of BOP (1141 mg, 2.58 mmol), DMAP (529 mg, 4.33 mmol) and DIEA (1.261 mL, 7.22 mmol) in DCM (300 mL) was added 10D (625 mg, 1.032 mmol) in DMF (5 mL) dropwise via syringe pump. The reaction mixture was stirred at rt for 2 days before transferring to a sealed vessel. The reaction mixture now in the sealed vessel was heated at 50° C. for 48 h before cooling down to rt. The reaction mixture was concentrated to small volume, added EtOAc, washed with 10% LiCl solution to remove DMF and dried over $MgSO_4$. The organic layer was then concentrated and purified by silica gel chromatography followed by reverse phase HPLC. Two major peaks were seen on HPLC and the first peak was identified as the desired product (second peak is the other isomer) based on previous X-ray studies and stereochemistry is assigned based on that. The desired product (132 mg, 22%) was isolated as a white solid. MS (ESI) m/z: 588.1 $(M+H)^+$.

10F

Methyl N-[(10R,14S)-14-amino-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate: To a solution of 10E (120 mg, 0.204 mmol) in DCM (4 mL) was added TFA (0.8 mL, 10.38 mmol) and the reaction was stirred at rt for 1 h. After 1 h, the reaction mixture was quenched with concentrated $Na_2CO_3$ aqueous solution followed by extraction with EtOAc. The organic layer was then washed with brine, dried over $MgSO_4$ and concentrated under vacuum to yield the desired product (71 mg, 71%) as yellow gum. MS (ESI) m/z: 488.3 $(M+H)^+$.

10G

Methyl N-[(10R,14S)-14-{[3-(3-chloro-2,6-difluorophenyl)-3-hydroxypropyl]amino}-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate: A solution of 10F (30 mg, 0.062 mmol), Intermediate 2 (36 mg, 0.108 mmol) and $K_2CO_3$ (34.0 mg, 0.246 mmol) in ACN (1 mL) was sealed and heated at 75° C. for 24 h in a 1 dram vial. The reaction mixture was cooled and filtered off the solids. The organic layer is concentrated, dissolved in MeOH and purified by reverse phase HPLC to isolate the desired product as a white solid. The solid was dissolved in MeOH, passed through $HCO_3$ resin cartridge and concentrated to get the desired product (26 mg, 61%, free base) as a white solid. MS (ESI) m/z: 692.2 $(M+H)^+$.

10H

Methyl N-[(10R,14S)-14-[6-(3-chloro-2,6-difluorophenyl)-2-oxo-1,3-oxazinan-3-yl]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate: To a solution of 10G (26 mg, 0.038 mmol) in dioxane (2 mL) was added CDI (60.9 mg, 0.376 mmol), TEA (0.262 mL, 1.878 mmol), DMAP (7.4 mg, 0.061 mmol) and sodium chloride (10.97 mg, 0.188 mmol). The reaction mixture was stirred at rt for 15 min. After 15 min, the reaction mixture was heated at 60° C. for 15 h. Aliquot LCMS shows the reaction mixture still contained the starting material and so the reaction mixture was heated at 70° C. for another 8 h. The reaction mixture was then cooled down to rt and diluted with EtOAc. The EtOAc layers were washed with water followed by brine and dried over $MgSO_4$. The organic layers were concentrated and purified by silica gel chromatography. Desired fractions were pooled together and concentrated to yield the desired product (15 mg, 55%) as white solid product. MS (ESI) m/z: 718.1 $(M+H)^+$.

Example 10

Methyl N-[(10R,14S)-14-[(6R)-6-(3-chloro-2,6-difluorophenyl)-2-oxo-1,3-oxazinan-3-yl]-10-methyl-9-oxo-8,16,18-triazatricyclo[13.2.1.0$^{2,7}$]octadeca-1(17),2,4,6,15(18)-pentaen-5-yl]carbamate: To a solid of 10H (15 mg, 0.021 mmol) in 2 dram vial was added HCl (4 M in dioxane) (1 mL, 4.00 mmol). The vial was sealed and heated at 70° C. for 2 h. The reaction mixture was concentrated under vacuum, dissolved in MeOH and passed through a $HCO_3$ resin cartridge. The cartridge was rinsed with MeOH and the filtrate was concentrated. The crude product was then purified by reverse phase HPLC. The desired product fractions were dissolved in MeOH and passed through a new $HCO_3$ resin cartridge and washed with MeOH to yield free base product. The purified product was then subjected to chiral HPLC purification using chiral OD 4.6×250 mm column with a 50:50 solvent mixture of heptane and EtOH:MeOH (50:50) at a flow rate of 20 mL/min to yield two peaks. Peak 1 (5.7 mg, 27%) was designated as Diastereomer A. $^1$H NMR (500 MHz, MeOD) δ 7.68-7.35 (m, 5H), 7.21-7.04 (m, 1H), 5.87 (dd, J=11.3, 2.8 Hz, 1H), 5.29 (dd, J=11.7, 6.2 Hz, 1H), 3.87-3.71 (m, 5H), 2.84-2.58 (m, 2H), 2.48-2.33 (m, 2H), 2.28-2.14 (m, 1H), 1.89-1.76 (m, 1H), 1.71-1.25 (m, 2H), 1.07 (d, J=6.9 Hz, 2H), 0.81 (br. s., 1H) ppm. MS (ESI) m/z: 588.1 (M+H)$^+$. Analytical HPLC RT=5.45 min (Method A).

Compound 10E can be prepared by an alternative sequence described below:

10I tert-Butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate: To a cooled (0° C.), clear yellow orange solution of 1D (Alternative) (4.83 g, 9.08 mmol) in ethyl acetate (91 mL) was added (R)-2-methylbut-3-enoic acid (1.0 g, 9.99 mmol) and Hunig's base (6.34 mL, 36.3 mmol). Next, 1-propanephosphonic acid cyclic anhydride (T$_3$P) (50% in EtOAc) (13.38 mL, 22.70 mmol) was added dropwise over 20 min. and the reaction was stirred at 0° C. After 3 h, the reaction was diluted with EtOAc and washed with saturated NaHCO$_3$. The aqueous layer was extracted with EtOAc (2×). The organic layers were combined and washed with brine, dried over sodium sulfate, filtered and concentrated to give an orange foam. Purification by normal phase chromatography gave 10I (4.53 g, 81%) as a white foam. Proton NMR indicated a 3:1 mixture of diastereomers. MS (ESI) m/z: 614.4 (M+H)$^+$.

10J tert-Butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer A) and 10K. tert-butyl N-[(10S,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer B): To a solution of 10I (4.40 g, 7.17 mmol) in dichloromethane (717 mL) was added pTsOH monohydrate (1.523 g, 7.89 mmol) and the mixture was degassed with argon for 30 min. Next, the flask was equipped with a reflux condensor and the reaction was warmed to 40° C. for 1 h. Next, a burgundy solution of Grubbs catalyst 2nd generation (2.440 g, 2.87 mmol) in 20 mL of DCM (degassed with argon) was added dropwise via syringe over 35 to 40 min. After 21.5 h, the reaction was cooled to rt. The reaction mixture was washed with saturated NaHCO$_3$, brine, dried over MgSO$_4$, filtered and concentrated to give a brown foam. Purification by normal phase chromatography gave 10J, Diastereomer A (1.71 g, 41%) as an off-white solid and a mixture of 10J, Diastereomer A and 10K, Diastereomer B (1.4 g). MS (ESI) m/z: 586.3 (M+H)$^+$.

10E (Alternative)

tert-Butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: A dark brown solution of 10J (1.71 g, 2.92 mmol) in EtOAc (97 mL) was degassed with argon for 30 minutes. Next, platinum (IV) oxide (0.066 g, 0.292 mmol) was added and hydrogen gas from a balloon was bubbled through the reaction mixture for several minutes. The reaction was stirred under a hydrogen atmosphere. After 24 h, an additional amount of platinum (IV) oxide (0.192 g, 0.876 mmol) was added and the reaction was stirred under a hydrogen atmosphere. After 21 h, the reaction was stopped. The vessel was purged with vacuum/argon three times, then CELITE® was added, and the reaction was filtered rinsing with EtOAc. The resulting clear, yellow brown filtrate was concentrated to give an off-white solid weighing 1.66 g. Recrystallization from methanol (30 mL) gave 10E (Alternative) (0.575 g, 34%) as a white solid. MS (ESI) m/z: 588.4 (M+H)$^+$.

Example 11

Methyl N-[(14S)-14-[(6S)-6-(3-chloro-2,6-difluorophenyl)-2-oxo-1,3-oxazinan-3-yl]-16-fluoro-10-methyl-9-oxo-8,17-diazatricyclo[13.3.1.0$^{2,7}$]nonadeca-1(19),2,4,6,15,17-hexaen-5-yl]carbamate, TFA salt

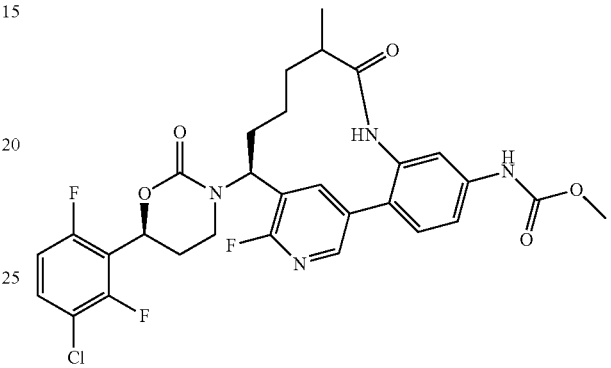

11A (R,E)-N-((5-Bromo-2-fluoropyridin-3-yl)methylene)-2-methylpropane-2-sulfinamide: To a solution of 5-bromo-2-fluoronicotinaldehyde (5 g, 24.51 mmol) and titanium (IV) ethoxide (15.42 ml, 73.5 mmol) in DCM (49.0 mL) was added (R)-2-methylpropane-2-sulfinamide (3.12 g, 25.7 mmol). The reaction mixture was then stirred at rt for 48 h. After 48 h, the reaction mixture was poured into brine at rt while rapidly stirring the mixture. The resulting suspension was filtered through a plug of CELITE®, and the filter cake was washed several times with DCM. The filtrate were separated, and the organic phase was washed with brine and dried over MgSO$_4$, filtered and concentrated to give 7.6 g of crude product which was further purified using silica gel chromatography to yield the desired product (6.97 g, 93%) as an off white solid. MS (ESI) m/z: 330.8 (M+Na)$^+$.

11B (R)—N—((S)-1-(5-Bromo-2-fluoropyridin-3-yl)but-3-en-1-yl)-2-methylpropane-2-sulfinamide: To a saturated aqueous solution of sodium bromide (420 g, 4084 mmol) (app. 420 g in 450 mL H$_2$O) was added 11A (6.97 g, 22.69 mmol) and indium (10.42 g, 91 mmol). To this mixture was then added 3-bromoprop-1-ene (7.85 mL, 91 mmol) dropwise, and the resulting cloudy white suspension was allowed to stir at rt for 10 h. The reaction mixture was quenched with saturated aqueous NaHCO$_3$ solution followed by extraction with EtOAc. The organic layers were dried over anhydrous MgSO$_4$ and the crude product was purified using silica gel chromatography to give the desired product (8.8 g, 98%) as an off white solid. MS (ESI) m/z: 350.8 (M+H)$^+$.

11C (S)-1-(5-Bromo-2-fluoropyridin-3-yl)but-3-en-1-amine, 2HCl: To a solution of 11B (8.8 g, 25.2 mmol) in MeOH (100

133 mL) was added HCl (31.5 mL, 126 mmol) (4 M in dioxane) and the reaction mixture was stirred at rt for 1 h. After 1 h, the reaction mixture was concentrated to near dryness and Et$_2$O was added to give a yellow suspension. Filtered the suspension and the solids were washed with Et$_2$O. The filtrate was concentrated and re-filtered with Et$_2$O. The solids were dried on the vacuum pump to give 11C (6.45 g, 80%) as a white solid. MS (ESI) m/z: 246.9 (M+H)$^+$.

11D (S)-tert-Butyl (1-(5-bromo-2-fluoropyridin-3-yl)but-3-en-1-yl)carbamate: To a solution of 11C (6.55 g, 20.60 mmol) in DCM (68.7 mL) at 0° C. was added TEA (11.48 mL, 82 mmol) and Boc$_2$O (4.50 g, 20.60 mmol). The reaction mixture was then stirred at 0° C. for 2 h and then allowed to warm to rt. The reaction mixture was stirred at rt overnight. After overnight stirring, the reaction mixture was diluted with DCM and washed with saturated NaHCO$_3$ solution. The aqueous layer was extracted with DCM (2×). The combined organic layers were washed with brine, dried over MgSO$_4$. The crude product was then purified using silica gel chromatography to yield the desired product (6.64 g, 87%) as a white solid. MS (ESI) m/z: 368.9 (M+Na)$^+$.

11E (S)-tert-Butyl (1-(5-(2-amino-4-nitrophenyl)-2-fluoropyridin-3-yl)but-3-en-1-yl)carbamate: To a RBF was added 11C (4.5 g, 13.04 mmol), 2-(5,5-dimethyl-1,3,2-dioxaborinan-2-yl)-5-nitroaniline (6.52 g, 26.1 mmol), PdCl$_2$(dppf)-CH$_2$Cl$_2$ adduct (1.065 g, 1.304 mmol), and potassium phosphate, tribasic (5.53 g, 26.1 mmol). The RBF was equipped with a reflux condenser and the apparatus was vacuumed and back-filled with argon. Degassed DMSO (65.2 mL) was added followed by degassed water (1.174 mL, 65.2 mmol). The dark red reaction mixture was warmed to 90° C. for 1 h, and then allowed to cool to rt. The reaction mixture was then partitioned between EtOAc and brine, and the layers were separated. The aqueous layer was extracted with EtOAc. The combined organic layers were dried over MgSO$_4$, filtered and concentrated to give the crude product as thick black oil which was subjected to silica gel chromatography to yield the desired product (5.90 g, 100%) as yellow foam. MS (ESI) m/z: 403.0 (M+H)$^+$.

11F

Methyl (3-amino-4-(5-((1S)-1-((tert-butoxycarbonyl)amino)but-3-en-1-yl)-6-fluoropyridin-3-yl)phenyl)carbamate: To a clear, orange solution of 11E (4.4 g, 9.95 mmol) in MeOH (100 mL) was added sequentially zinc (6.51 g, 99 mmol) and ammonium chloride (5.32 g, 99 mmol). The resulting yellow-orange suspension turned clear after a few minutes and was stirred at rt for 2 h. The reaction mixture was then filtered off to remove solids and the filtrate was concentrated to yield a residue. The residue was diluted with EtOAc and washed with saturated NaHCO$_3$ solution. The organic layers were dried over MgSO$_4$ and purified by silica gel chromatography to yield the desired bis amine product as a peach-colored foam. To a −78° C. clear, orange solution of the above bis amine product (5.08 g, 13.64 mmol) and pyridine (1.103 mL, 13.64 mmol) in DCM (136 mL) was added dropwise methyl chlorocarbonate (0.949 mL, 12.28 mmol). The reaction mixture was stirred at −78° C. for 1.5 h. After stirring for 1.5 h, the reaction mixture was quenched with saturated NH$_4$Cl solution and the reaction was allowed to warm to rt.

134

The reaction mixture was then diluted with DCM and the aqueous layer was extracted with DCM. The combined organic layers were washed with saturated NaHCO$_3$ followed by brine. The organic layer was then dried over MgSO$_4$, filtered and concentrated to give the crude product as a peach-colored foam. The crude product was then purified using silica gel chromatography. COSY and NOE NMR analysis confirmed the site of addition. The desired product (4.77 g, 81%) was isolated as beige foam. MS (ESI) m/z: 431.1 (M+H)$^+$.

11G tert-Butyl N-[(1S)-1-(2-fluoro-5-{4-[(methoxycarbonyl)amino]-2-(2-methylbut-3-enamido)phenyl}pyridin-3-yl)but-3-en-1-yl]carbamate: To a solution of 2-methylbut-3-enoic acid (0.216 mL, 2.091 mmol) and 11F (0.900 g, 2.091 mmol) in EtOAc (59.7 mL) was added DIEA (1.095 mL, 6.27 mmol) and the reaction was allowed to cool to −10° C. under argon. To this mixture was added 1-propanephosphonic acid cyclic anhydride in EtOAc (2.464 mL, 4.18 mmol) and the reaction was allowed to stir for 5 min, and then warmed to 0° C. while stirring under argon. The reaction was then slowly allowed to warm to rt and stirred at rt overnight. After overnight stirring, the reaction mixture was concentrated and purified by silica gel chromatography to give 11G (887 mg, 83%) as a white solid. MS (ESI) m/z: 513.1 (M+H)$^+$.

11H tert-Butyl N-[(11E,14S)-16-fluoro-5-[(methoxycarbonyl)amino]-10-methyl-9-oxo-8,17-diazatricyclo[13.3.1.0$^{2,7}$]nonadeca-1(19),2,4,6,11,15,17-heptaen-14-yl]carbamate: A clear, colorless solution of 11G (887 mg, 1.730 mmol) in DCE (100 mL) was degassed with Ar, then split into 5 microwave vials. To each of the reaction solution was added Grubbs II (588 mg, 0.692 mmol) (118 mg to each vial) and heated each vial in the microwave at 120° C. for 25 min. The reaction mixture was combined and washed with saturated sodium bicarbonate solution and brine. The organic layers were then dried over MgSO$_4$, filtered and concentrated to give the crude product which was purified by silica gel chromatography. Desired fractions were collected and concentrated to give 11H (568 mg, 68%) as a brown solid. MS (ESI) m/z: 485.1 (M+H)$^+$.

11I tert-Butyl N-[(14S)-16-fluoro-5-[(methoxycarbonyl)amino]-10-methyl-9-oxo-8,17-diazatricyclo[13.3.1.0$^{2,7}$]nonadeca-1(19),2,4,6,15,17-hexaen-14-yl]carbamate: To a solution of 11H (0.568 g, 1.172 mmol) in MeOH (39.1 mL) was added platinum (IV) oxide (0.027 g, 0.117 mmol). The reaction was mixture was then charged with H$_2$ using a H$_2$ balloon. The reaction mixture was then stirred at rt under H$_2$ for 40 h. Purified the crude product by silica gel chromatography to yield the desired product Diastereomer A (11I) (178 mg, 25%) and the undesired Diastereomer-B (95 mg, 13%) as white solids. Diastereomer A—MS (ESI) m/z: 487.1 (M+H)$^+$.

11J

Methyl N-[(14S)-14-amino-16-fluoro-10-methyl-9-oxo-8,17-diazatricyclo[13.3.1.0$^{2,7}$]nonadeca-1(19),2,4,6,15,17-hexaen-5-yl]carbamate: To a solution of 11I (95 mg, 0.158 mmol) in dioxane (1 mL) was added HCl in dioxane (5932

μL, 23.73 mmol) and the reaction mixture was stirred at rt for 1 h. After 1 h, the reaction was concentrated to give the desired product (73 mg, 100%). MS (ESI) m/z: 387.1 (M+H)+.

Example 11

Methyl N-[(14S)-14-[(6S)-6-(3-chloro-2,6-difluorophenyl)-2-oxo-1,3-oxazinan-3-yl]-16-fluoro-10-methyl-9-oxo-8,17-diazatricyclo[13.3.1.0$^{2,7}$]nonadeca-1(19),2,4,6,15,17-hexaen-5-yl]carbamate, TFA salt: Example 11 was made in the same way as Example 10 by replacing 10F with 11J and followed by the rest of the steps as in Example 10. $^1$H NMR (500 MHz, MeOD) δ 8.25 (d, J=1.4 Hz, 1H), 8.11 (dd, J=9.5, 2.1 Hz, 1H), 7.53-7.65 (m, 3H), 7.51 (s, 1H), 7.00-7.15 (m, 1H), 5.69 (dd, J=11.0, 3.0 Hz, 1H), 5.38 (dd, J=12.9, 3.3 Hz, 1H), 3.78 (s, 3H), 3.36-3.41 (m, 1H), 3.02-3.13 (m, 1H), 2.35-2.58 (m, 2H), 2.16-2.34 (m, 2H), 1.99-2.14 (m, 1H), 1.69-1.88 (m, 2H), 1.55-1.69 (m, 1H), 1.21 (d, J=6.9 Hz, 3H), 0.92 (d, J=11.6 Hz, 1H) ppm. MS (ESI) m/z: 617.1 (M+H)+. Analytical HPLC RT=9.66 min (Method A).

Example 12

Methyl ((10R,14S)-14-((6R)-6-(3-chloro-2,6-difluorophenyl)-2-oxo-1,3-oxazinan-3-yl)-10-methyl-9-oxo-8,16-diazatricyclo[13.3.1.0$^{2,7}$]nonadeca-1(19),2,4,6,15,17-hexaen-5-yl)carbamate, TFA salt

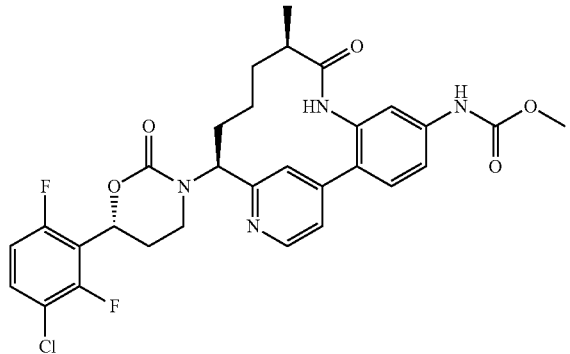 [SMILES: COC(=O)Nc1ccc2c(c1)NC(=O)[C@H](C)CCC[C@H](N1CC[C@H](c3c(F)ccc(Cl)c3F)OC1=O)c1cc-2ccn1]

12A (S,E)-N-((4-Chloropyridin-2-yl)methylene)-2-methylpropane-2-sulfinamide: Liu, G. et al., *J. Org. Chem.*, 64:1278 (1999). To a solution of S-(−)-t-butyl-sulfinamide (0.856 g, 7.06 mmol) in dichloromethane (14.13 mL) was added sequentially copper(II) sulfate (2.481 g, 15.54 mmol) and 4-chloropicolinaldehyde[1.0 g, 7.06 mmol, prepared according to a modified described by Negi (*Synthesis*, 991 (1996))]. The white suspension was stirred at rt. After 3 h, the brown suspension was filtered through CELITE®, eluting with DCM, to give a clear brown filtrate. Concentration gave a brown oil weighing 1.85 g. Purification by normal phase chromatography gave 1.31 g of 12A as a clear, yellow oil. MS (ESI) m/z: 245.0 (M+H)+.

12B (S)—N—((S)-1-(4-Chloropyridin-2-yl)but-3-enyl)-2-methylpropane-2-sulfinamide: To a cooled solution (−78° C.) of 12A (10 g, 40.9 mmol) in THF (204 mL) was added dropwise allyl magnesium bromide (44.9 mL, 44.9 mmol, 1 M in Et$_2$O). The reaction mixture was stirred at −78° C. After 2 h, the reaction mixture was quenched with the addition of saturated NH$_4$Cl (25 mL) and then the reaction mixture was allowed to warm to rt. The reaction mixture was then diluted with EtOAc and water and the layers were separated. The aqueous layer was extracted with EtOAc. The combined organic layers were washed with brine, dried over Na$_2$SO$_4$, filtered, and concentrated. Purification by normal phase chromatography gave 12B (9.23 g, 79%) as a clear, orange oil. $^1$H NMR indicated a 4.7:1 mixture of diastereomers whereby the major diastereomer corresponds to the title compound. MS (ESI) m/z: 287.1 (M+H)+.

12C (S)—N—((S)-1-(4-(2-Amino-4-nitrophenyl)pyridin-2-yl)but-3-enyl)-2-methylpropane-2-sulfinamide, Diastereomer A, and 12D. (S)—N—((R)-1-(4-(2-amino-4-nitrophenyl)pyridin-2-yl)but-3-enyl)-2-methylpropane-2-sulfinamide, Diastereomer B: To a RBF was added 12B (9.23 g, 32.2 mmol), Intermediate 22 (16.09 g, 64.4 mmol), potassium phosphate, tribasic (13.66 g, 64.4 mmol), DMSO (161 mL), and water (2.90 mL, 161 mmol). The RBF was equipped with a reflux condenser and then the apparatus was purged with argon for 30 minutes. Next, Pd(dppf)Cl$_2$—CH$_2$Cl$_2$ adduct (2.63 g, 3.22 mmol) was added and the reaction mixture was warmed to 90° C. After 4 h, the reaction was cooled to rt and then it was poured into water (1000 mL) to give a suspension. The solid was collected by filtration and then it was dissolved in EtOAc. The filtrate was extracted with EtOAc. The organic layers were combined and washed with brine, dried over sodium sulfate, filtered, and concentrated. Purification by normal phase chromatography gave 12C (3.9 g) as an orange foam. An additional 3.84 g of material was obtained as a mixture of diastereomers 12C and 12D. The diastereomers were separated by chiral SFC prep HPLC (CHIRALCEL® OD-H; 20% methanol/80% carbon dioxide) which gave 12C (2.0 g) as an orange foam and 12D (0.90 g) as an orange foam. The total amount of 12C isolated was (5.9 g, 47%) as an orange foam. MS (ESI) m/z: 389.2 (M+H)+.

12E (S)—N—((S)-1-(4-(2,4-Diaminophenyl)pyridin-2-yl)but-3-enyl)-2-methylpropane-2-sulfinamide: To a clear, orange solution of 12C (2 g, 5.15 mmol) in methanol (51.5 mL) was added sequentially zinc (3.37 g, 51.5 mmol) and ammonium chloride (2.75 g, 51.5 mmol). The resulting suspension was stirred vigorously. After 3 h, the reaction was stopped and it was filtered through a 0.45 micron GMF eluting with methanol to give a yellow filtrate. The filtrate was concentrated, then the residue was partitioned between EtOAc and water, and the layers were separated. The aqueous layer was extracted with EtOAc. The combined organic layers were washed with saturated sodium bicarbonate, brine, dried over sodium sulfate, filtered, and concentrated to give 12E (1.86 g, 101%) as a yellow foam. This material was used in the next step without further purification. MS (ESI) m/z: 359.1 (M+H)+.

12F

Methyl 3-amino-4-(2-((S)-1-((S)-1,1-dimethylethylsulfinamido)but-3-enyl)pyridin-4-yl)phenylcarbamate: To a cooled (−78° C.) clear, yellow solution of 12E (1.86 g, 5.19 mmol) and pyridine (0.420 mL, 5.19 mmol) in DCM (52 mL) was added dropwise methyl chlorocarbonate (0.361 mL, 4.67 mmol). The reaction mixture was stirred at −78° C. for 2 h. After 2 h, the reaction was quenched with saturated NH$_4$Cl and the reaction was allowed to warm to rt. The reaction mixture was then diluted with DCM and water and the layers were separated. The aqueous layer was extracted with DCM. The combined organic layers were washed with saturated NaHCO$_3$, brine, dried over sodium sulfate, filtered and concentrated to give 12F (2.3 g, 106%) as a yellow foam. This material was used in the next step without further purification. MS (ESI) m/z: 417.1 (M+H)$^+$.

12G (S)-Methyl 3-amino-4-(2-(1-aminobut-3-enyl)pyridin-4-yl)phenylcarbamate, 3HCl salt: To a clear, yellow solution of 12F (2.3 g, 5.52 mmol) in MeOH (55.2 mL) was added 4 M HCl in dioxane (13.80 mL, 55.2 mmol). The reaction mixture was stirred at rt. After 2 h, the reaction was concentrated to give a yellow residue. The residue was suspended in DCM and then it was concentrated. This was repeated one more time to give 12G (2.329 g, 100%) as a yellow solid. This material was used in the next step without further purification. MS (ESI) m/z: 313.1 (M+H)$^+$.

12H

Methyl N-(3-amino-4-{2-[(1S)-1-{[(tert-butoxy)carbonyl]amino}but-3-en-1-yl]pyridin-4-yl}phenyl)carbamate: To a yellow suspension of 12G (2.328 g, 5.52 mmol) in DCM (18.40 mL) was added Boc$_2$O (1.282 mL, 5.52 mmol) followed by TEA (3.08 mL, 22.08 mmol). The resulting orange-brown solution was stirred at rt. After 3 h, the reaction was diluted with DCM and then washed with saturated NaHCO$_3$, brine, dried over MgSO$_4$, filtered, and concentrated. Purification by normal phase chromatography gave 12H (1.91 g, 84%) as an off-white solid. MS (ESI) m/z: 413.0 (M+H)$^+$.

12I

Methyl N-(4-{2-[(1S)-1-{[(tert-butoxy)carbonyl]amino}but-3-en-1-yl]pyridin-4-yl}-3-(2-methylbut-3-enamido)phenyl)carbamate: To a cooled solution (−10° C.) of 2-methylbut-3-enoic acid (0.456 mL, 4.41 mmol) and 12H (1.82 g, 4.41 mmol) in EtOAc (126 mL) and DIEA (2.312 mL, 13.24 mmol) was added dropwise a solution of 1-propanephosphonic acid cyclic anhydride in EtOAc (5.20 mL, 8.82 mmol). After 5 min, the reaction was allowed to warm to 0° C. After 7 h, the reaction was stopped and concentrated. Purification by normal phase chromatography gave 12I (1.57 g, 72%) as a mixture of diastereomers and as a yellow solid. MS (ESI) m/z: 495.1 (M+H)$^+$.

12J ((E)-(10R,14S)-5-Methoxycarbonylamino-10-methyl-9-oxo-8,16-diaza-tricyclo[13.3.1.0$^{2,7}$]non.adeca-1(19),2(7),3,5,11,15,17-heptaen-14-yl)-carbamic acid tert-butyl ester, Diastereomer A, and 12K. ((E)-(10S,14S)-5-Methoxycarbonylamino-10-methyl-9-oxo-8,16-diaza-tricyclo[13.3.1.0$^{2,7}$]nonadeca-1(19),2(7),3,5,11,15,17-heptaen-14-yl)-carbamic acid tert-butyl ester, Diastereomer B: To a RBF was added 12I (1.57 g, 3.17 mmol), pTsOH (0.664 g, 3.49 mmol) and DCM (794 mL). The flask was then equipped with a reflux condenser and the clear yellow solution was degassed with argon for 30 min. The reaction mixture was then warmed to 40° C. for 1 h. Then a solution of Grubbs II (0.269 g, 0.317 mmol) in DCM (2 mL) was added dropwise to the reaction mixture. The reaction mixture was then stirred at 40° C. After 6 h, the reaction was cooled to rt. The reaction was washed with saturated sodium carbonate, brine, dried over magnesium sulfate, filtered, and concentrated to give the crude product as a dark brown solid. Purification by normal phase chromatography gave 12J, diastereomer A (0.374 g, 25%) as a brown solid and a mixture of 12J, diastereomer A and 12K, diastereomer B (0.44 g, 30%) as a brown solid. MS (ESI) m/z: 466.9 (M+H)$^+$.

12L

Methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate: A 500-mL hydrogenation flask was charged with 10% palladium on carbon (0.372 g, 0.349 mmol). The flask was purged with argon and then degassed methanol (72 mL) was added slowly to the flask. Next, a clear, light brown solution 12J (1.63 g, 3.49 mmol) in methanol (5 mL) was added. The flask was pressurized to 50 psi of hydrogen and the reaction was stirred overnight. After 20 h, the reaction was stopped, diluted with methanol (100 mL) and then the reaction was filtered through CELITE®, rinsing with methanol to give a clear, light brown filtrate. The filtrate was concentrated to give an off-white solid weighing 1.37 g. The off-white solid was suspended in methanol (10 mL) and sonicated. The solid was collected by filtration, rinsed with methanol (8 mL), air-dried, and dried under vacuum to give 12L (1.13 g, 69.0%) as a white solid. MS (ESI) m/z: 469.1 (M+H)$^+$.

12M

Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, 2TFA salt: To a white suspension of 12L (0.45 g, 0.960 mmol) in DCM (5 mL) was added TFA (3 mL, 38.9 mmol). The resulting clear solution was stirred at rt. After 1 h, the reaction was concentrated to give a solid. Lyophilization gave 12M (0.52 g, 91%) as a yellow solid. MS (ESI) m/z: 369.0 (M+H)$^+$.

12M (Alternative, 2HCl)

To a flask containing 12L (0.880 g, 1.878 mmol) was added 4.0 M HCl in dioxane (21.13 mL, 85 mmol). The resulting suspension was sonicated to give a clear, yellow solution. After 5 to 10 min, a precipitate formed. After 1 h, the reaction was stopped and the precipitate was collected by filtration. The solid was rinsed with dioxane and air-dried to give a hygroscopic, yellow solid. The solid was dissolved in methanol, concentrated, and lyophilized to give 12M (Alternative, 2HCl) (0.7171 g, 87%) as a yellow solid. MS (ESI) m/z: 369.3 (M+H)$^+$.

Example 12

Methyl ((10R,14S)-14-((6R)-6-(3-chloro-2,6-difluorophenyl)-2-oxo-1,3-oxazinan-3-yl)-10-methyl-9-oxo-8,16-diazatricyclo[13.3.1.0$^{2,7}$]nonadeca-1(19),2,4,6,15,17-hexaen-5-yl)carbamate, TFA salt. Example 12 was prepared following the procedures described in step 10G, by replacing 10F with 12M, followed by step 10H. $^1$H NMR (500 MHz, CD$_3$OD) δ 8.72 (d, J=5.8 Hz, 1H), 7.85 (s, 1H), 7.67 (dd, J=5.5, 1.4 Hz, 1H), 7.64-7.52 (m, 4H), 7.08 (td, J=9.5, 1.7 Hz, 1H), 5.82 (dd, J=11.6, 2.8 Hz, 1H), 5.28 (dd, J=12.7, 4.7 Hz, 1H), 3.98-3.89 (m, 1H), 3.79 (s, 3H), 3.74-3.67 (m, 1H), 2.67-2.50 (m, 2H), 2.34-2.23 (m, 2H), 2.14-2.03 (m, 4H), 1.98-1.89 (m, 1H), 1.63-1.54 (m, 1H), 1.37-1.27 (m, 1H), 1.06 (d, J=6.9 Hz, 3H), 0.99-0.88 (m, 1H) ppm. MS (ESI) m/z: 599.0 (M+H)$^+$. Analytical HPLC RT=9.37 min (Method A).

The preferred sequence for the preparation of compound 12J is described below:

12B (Alternative)

(S)—N—((S)-1-(4-Chloropyridin-2-yl)but-3-enyl)-2-methylpropane-2-sulfinamide: To a cooled (0-5° C.) mixture of indium (III) chloride (13.56 g, 61.3 mmol) in tetrahydrofuran (170 mL) was added dropwise over 30 min allylmagnesium bromide (1 M in diethylether) (62 mL, 61.3 mmol). The reaction was allowed to warm to rt. After 1 h at rt, a solution of 12A (10 g, 40.9 mmol) in ethanol (170 mL) was added. After 2-3 h, the reaction was concentrated under vacuum at 50-55° C. The crude material was partitioned between ethyl acetate (200 mL) and water (50 mL) and the layers were separated. The aqueous layer was extracted with ethyl acetate (2×50 mL). The organic layers were combined and washed with brine (100 mL), dried over sodium sulfate, filtered and concentrated to give 12B (Alternative) (13.5 g, 106%) as a yellow oil. MS (ESI) m/z: 287.2 (M+H)$^+$. This material was used in the next step without further purification.

12N (S)-tert-Butyl 1-(4-chloropyridin-2-yl)but-3-enylcarbamate: Compound 12B (Alternative) was converted to 12N in two steps by removal of the chiral auxiliary according to the procedure in step 12G and Boc-protection according to the procedure in step 12H. MS (ESI) 227.3 (M–C$_4$H$_8$+H)$^+$ and 305.4 (M+Na)$^+$.

12O (S)-tert-Butyl 1-(4-(2-amino-4-nitrophenyl)pyridin-2-yl)but-3-enylcarbamate: Compound 12O was prepared by following the procedure described in step 12C, by replacing 12B with 12N. MS (ESI) 385.1 (M+H)$^+$.

12P (S)-tert-Butyl 1-(4-(2,4-diaminophenyl)pyridin-2-yl)but-3-enylcarbamate: To a clear, orange solution of 12O (2.9 g, 7.54 mmol) in methanol (75 mL) was added sequentially zinc dust (4.93 g, 75 mmol) and ammonium chloride (4.04 g, 75 mmol). The resulting suspension was stirred vigorously for 4 h. The reaction was stopped and filtered through a 0.45 micron GMF eluting with methanol to give a clear, yellow filtrate. Concentration of the filtrate gave a yellow-black residue. The residue was partitioned between EtOAc and 0.25 M HCl (50 mL) and the layers were separated. The organic layer was extracted with 0.25 M HCl (50 mL). The combined aqueous layers were basified with 1.5 M K$_2$HPO$_4$ and then extracted with EtOAc (3×). The combined organic layers were washed with brine, dried over Na$_2$SO$_4$, filtered and concentrated to give 12P (2.63 g, 98%) as a brown foam. MS (ESI) m/z: 355.2 (M+H)$^+$.

12H (Alternative)

Methyl N-(3-amino-4-{2-[(1S)-1-{[(tert-butoxy)carbonyl]amino}but-3-en-1-yl]pyridin-4-yl}phenyl)carbamate To a cooled (–78° C.) clear, brown solution of 12P (2.63 g, 7.42 mmol) and pyridine (0.600 mL, 7.42 mmol) in dichloromethane (74.2 mL) was added dropwise over 30 min methyl chloroformate (0.516 mL, 6.68 mmol). The reaction was stirred at –78° C. After 1.5 h, the reaction was quenched with saturated NH$_4$Cl and the reaction was allowed to warm to rt. The reaction was diluted with DCM and water and the layers were separated. The aqueous layer was extracted with DCM. The combined organic layers were washed with saturated NaHCO$_3$, brine, dried over Na$_2$SO$_4$, filtered and concentrated. The residue dissolved in DCM (~10 mL) and then hexane (~300 mL) was added to give a brown suspension with brown gummy sticky substance at the bottom. The mixture was sonicated to give a mostly clear solution with the brown substance at the bottom. The solution decanted and the bottom substance rinsed with hexane, dried to give the desired product (2.7 g, 88%) as a slightly brown foam. MS (ESI) m/z: 413.2 (M+H)$^+$.

12I (Alternative)

Methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate: (R)-2-Methylbut-3-enoic acid (1.201 g, 12.00 mmol), 12H (Alternative) (3.3 g, 8.00 mmol), pyridine (1.937 mL, 24.00 mmol) in EtOAc (40.0 mL) was cooled down to –10° C. under Ar, T$_3$P (50 wt % in EtOAc) (9.52 mL, 16.00 mmol) was added dropwise and stirred at –10° C., then gradually warmed up to rt over night. The reaction mixture was washed with saturated NaHCO$_3$ twice. The combined aqueous layers were extracted with EtOAc. The combined EtOAc phase was washed with brine, dried over MgSO$_4$, filtered, concentrated. The crude product was then purified using silica gel chromatography to give the desired product (4.06 g, 97%) as a white solid. $^1$H NMR (500 MHz, MeOD) δ 8.46 (d, J=5.0 Hz, 1H), 7.64 (s, 1H), 7.47 (dd, J=8.4, 2.1 Hz, 1H), 7.35 (s, 1H), 7.29 (d, J=8.3 Hz, 1H), 7.25 (m, 1H), 5.87-5.73 (m, 2H), 5.16-5.02 (m, 4H), 4.79-4.71 (m, 1H), 3.75 (s, 3H), 3.14-3.05 (m, 1H), 2.64-2.55 (m, 1H), 2.52-2.43 (m, 1H), 1.42 (s, 9H), 1.16 (d, J=6.9 Hz, 3H). MS (ESI) m/z: 495.1 (M+H)$^+$.

12J (Alternative)

Methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate: To a RBF was added 12I (Alternative) (0.5 g, 1.011 mmol), pTsOH monohydrate (0.212 g, 1.112 mmol), and dichloromethane (84 mL). The flask was equipped with a reflux condensor and the clear yellow solution was degassed with argon for 30 min. The reaction was then warmed to reflux for 1 h. Then a solution of Grubbs II (0.172 g, 0.202 mmol) in DCM (2 mL) was added dropwise to the reaction mixture. After 4 h at reflux, the reaction was cooled to rt, washed with saturated Na$_2$CO$_3$, brine, dried over MgSO$_4$, filtered, and concentrated to give brown solid. The crude product was then purified using silica gel chromatography to give the desired product (0.336 g, 71% yield) as a yellow solid. $^1$H NMR (500 MHz, MeOD) δ 8.52 (d, J=5.2 Hz, 1H), 7.54 (d, J=1.4 Hz, 1H), 7.48-7.43 (m, 1H), 7.38 (d, J=8.3 Hz, 1H), 7.24 (dd, J=5.1, 1.5 Hz, 1H), 6.89 (s, 1H), 5.75-5.65 (m, 1H), 4.60 (dd, J=11.3, 3.6 Hz, 1H), 4.39 (dd, J=15.1, 9.6 Hz, 1H), 3.75 (s, 3H), 3.14-3.06 (m, 1H), 2.75-2.68 (m, 1H), 2.04-1.94 (m, 1H), 1.44 (s, 9H), 1.30 (br. s., 1H), 1.04 (d, J=6.6 Hz, 3H). MS (ESI) m/z: 467.2 (M+H)+.

Example 13

Methyl N-[(14S)-14-[(6R)-6-(3-chloro-2,6-difluorophenyl)-2-oxo-1,3-oxazinan-3-yl]-10-methyl-9-oxo-8,16,17-triazatricyclo[13.3.1.0$^{2,7}$]nonadeca-1(19),2(7),3,5,15,17-hexaen-5-yl]carbamate, TFA salt

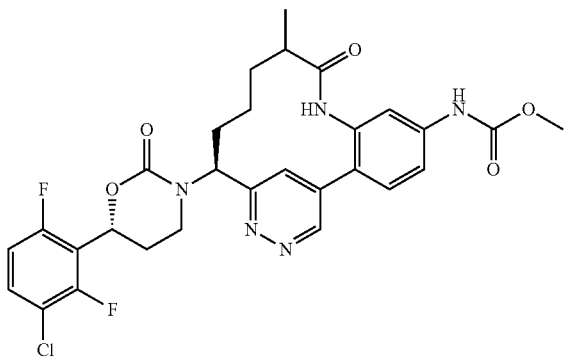 [SMILES: COC(=O)Nc1ccc2c(c1)NC(=O)C(C)CCC[C@H](N1CC[C@H](c3c(F)ccc(Cl)c3F)OC1=O)c1cc-2cnn1]

13A (S)-tert-Butyl 1-(dimethoxyphosphoryl)-2-oxohex-5-en-3-ylcarbamate: To a solution of dimethyl methylphosphonate (15.85 mL, 148 mmol) in THF (99 mL) at −78° C. was added n-butyllithium (93 mL, 148 mmol) slowly. After addition was completed, the reaction mixture was stirred for 30 min and then a solution of (S)-methyl 2-(tert-butoxycarbonylamino)pent-4-enoate (6.8 g, 29.7 mmol) in THF (15 mL) was added slowly. Stirring was continued for another 40 min at −78° C. The reaction was then quenched by adding water and diluted with EtOAc. The organic layer was washed with 1 M HCl, saturated NaHCO₃ and brine. The organic layer was then dried over MgSO₄, filtered and concentrated to give a clear oil. The crude product was then purified by silica gel chromatography to give the desired product (9.3 g, 98%) as colorless oil. MS (ESI) m/z: 599.0 (M+Na)+.

13B

Methyl 4-iodo-3-nitrophenylcarbamate: To a solution of 4-iodo-3-nitroaniline (1.320 g, 5 mmol) in DCM (50 mL) and pyridine (0.445 mL, 5.50 mmol) at 0° C. was added methyl chloroformate (0.407 mL, 5.25 mmol) dropwise. After stirring at 0° C. for 3 h, HPLC analysis showed the reaction to be complete. The reaction was then diluted with DCM, washed with brine and dried over MgSO₄ to yield the crude product. The crude product was then dissolved in minimal DCM (~20 mL) and hexane (200 mL) was added to give a yellow suspension. Filtered the solid rinsing with hexane and air-dried the solids to obtain a yellow solid as the desired product (1.51 g, 94%). MS (ESI) m/z: 322.9 (M+H)+.

13C

Methyl 4-acetyl-3-nitrophenylcarbamate: A solution of 13B (0.5 g, 1.553 mmol), tributyl(1-ethoxyvinyl)stannane (1.049 mL, 3.11 mmol), and bis(triphenylphosphine)palladium (II) chloride (0.109 g, 0.155 mmol) in toluene (3 mL) was heated at 110° C. for 3 h in a sealed tube. After 3 h, the reaction mixture was cooled to rt and concentrated to yield a residue. The residue was dissolved in THF (3 mL), followed by addition of 1 N HCl solution (5 mmol). The mixture was stirred at rt for 1 h and then diluted with EtOAc. The organic layer was then washed with brine and dried over Na₂SO₄ to give the crude product which was purified by silica gel chromatography to obtain the desired product (0.254 g, 69%) as a yellow solid. MS (ESI) m/z: 239.3 (M+H)+.

13D 2-(4-((Methoxycarbonyl)amino)-2-nitrophenyl)-2-oxoacetic acid: To a solution of 13C (11.5 g, 48.3 mmol) in pyridine (48.3 mL) was added selenium dioxide (8.04 g, 72.4 mmol) in portions. After completion of addition, the reaction mixture was stirred under argon at 60° C. overnight. After stirring overnight, the solvent was evaporated and the resulting residue was further dried under vacuum for several hours to make sure most pyridine was removed. To the residue was added 1.0 N HCl (80 mL) and the resulting solution was filtered to obtain a grayish solid which was dried in a vacuum-oven at 45° C. overnight. To the dried solid was then added MeOH (200 mL) and filtered the suspension. The filtrate was concentrated to give brownish foam (11.8 g, 79%). MS (ESI) m/z: 269.0 (M+H)+.

13E

Methyl 2-(4-((methoxycarbonyl)amino)-2-nitrophenyl)-2-oxoacetate: To a red oil of 13D (11.8 g, 38.3 mmol) in DCM (150 mL) at 0° C. was added TEA (7.47 mL, 53.6 mmol) and sonicated the mixture to dissolve into a complete solution. Methyl carbonochloridate (4.15 mL, 53.6 mmol) was added dropwise at 0° C. to the above mixture. After 20 min, the reaction mixture was diluted with DCM (300 mL), washed with 1 N HCl, saturated NaHCO₃ solution and brine. The organic layer was dried over MgSO₄, filtered and concentrated to give a red colored solid. The crude product was then purified by silica gel chromatography to yield the desired product (8.6 g, 80%) as a light grayish powder. MS (ESI) m/z: 283.0 (M+H)+.

13F

Methyl (4-(6-((1S)-1-((tert-butoxycarbonyl)amino)but-3-en-1-yl)-3-oxo-2,3-dihydropyridazin-4-yl)-3-nitrophenyl)carbamate: To a clear solution of 13A (1.16 g, 3.61 mmol) in EtOH (38.4 mL) at rt was added K₂CO₃ (0.748 g, 5.42 mmol). The reaction mixture was then stirred at rt for 2 h. After stirring for 2 h at rt, the reaction mixture was concentrated to remove the solvent followed by vacuum drying for 1 h to yield a solid. To this solid was added THF (30 mL), followed by the addition of a suspension of 13E (1.121 g, 3.97 mmol) in 8 mL of THF dropwise via an addition funnel. After 3 h, hydrazine (0.567 mL, 18.05 mmol) was added and the reaction was stirred at rt for 4 days. The reaction mixture was then diluted with EtOAc and washed with 1 N HCl followed by brine. The organic layers were then dried over MgSO₄ and concentrated to give the crude product that was purified by silica gel chromatography to give the desired product (0.48 g, 29%) as light orange solid. MS (ESI) m/z: 460.0 (M+H)+.

13G (S)-Methyl (4-(6-(1-aminobut-3-en-1-yl)-3-chloropyridazin-4-yl)-3-nitrophenyl)carbmate: To a solution of 13F (2.2 g, 4.79 mmol) in MeOH (23.94 mL) was added HCl (4 M in dioxane) (5.186 mL, 20.74 mmol) and stirred at rt for 6 h. The reaction mixture was then concentrated to yield a brownish solid. To the brownish solid was then added ACN (23.94 mL) and phosphoryl trichloride (13.39 mL, 144 mmol), and the reaction mixture was heated at 80° C. overnight. The reaction mixture was concentrated and dried under vacuum overnight. The crude mixture was cooled to 0° C. and to the cooled mixture was added 1 N HCl (20 mL) to quench the reaction. The reaction mixture was then neutralized with 1 N NaOH and extracted with EtOAc (2×). The organic layers were combined and washed with brine and dried over MgSO$_4$ to give a brownish solid as the desired product (1.03 g, 57%). MS (ESI) m/z: 377.9 (M+H)$^+$.

13H

Methyl (4-(6-(1-((tert-butoxycarbonyl)amino)but-3-en-1-yl)-3-chloropyridazin-4-yl)-3-nitrophenyl)carbamate: To a solution of 13G (1.03 g, 2.73 mmol) in DCM (27.3 mL) at 0° C. was added TEA (1.140 mL, 8.18 mmol) and Boc$_2$O (0.760 mL, 3.27 mmol). The reaction mixture was stirred at 0° C. for 10 min, then was slowly raised to rt and continued to stir at rt for overnight. The crude product was concentrated and purified by silica gel chromatography to isolate the desired product (414 mg, 36%) as orange colored foam. MS (ESI) m/z: 477.9 (M+H)$^+$.

13I

Methyl (3-amino-4-(6-((1S)-1-((tert-butoxycarbonyl)amino)but-3-en-1-yl)-3-chloropyridazin-4-yl)phenyl)carbamate: To a mixture of 13H (472 mg, 0.988 mmol) and iron powder (276 mg, 4.94 mmol) in acetic acid (7.407 mL) was added water (2.469 mL) and heated at 70° C. for 1 h. The reaction mixture was then cooled down on an ice-water bath, followed by neutralization with 10 N NaOH (aqueous). The reaction mixture was then extracted with EtOAc (3×) and the combined EtOAc layers were further washed with brine and dried over MgSO$_4$ to yield the crude product which was purified by silica gel chromatography. The purified product was then subjected to chiral HPLC separation using CHIRALPAK® AD column and 40% isopropanol/60% heptane mixture as mobile phase. Two peaks were seen eluting and the second eluting peak was collected and concentrated to yield yellow foam as the desired product (144 mg, 32%). The first peak from the chiral column was the undesired isomer. MS (ESI) m/z: 447.8 (M+H)$^+$.

13J

Methyl N-(4-{6-[(1S)-1-{[(tert-butoxy)carbonyl]amino}but-3-en-1-yl]-3-chloropyridazin-4-yl}-3-(2-methylbut-3-enamido)phenyl)carbamate: 13J was prepared in a similar way as in 12I by replacing 12H with 10I. MS (ESI) m/z: 530.0 (M+H)$^+$.

13K

Methyl N-[(11E,14S)-14-{[(tert-butoxy)carbonyl]amino}-18-chloro-10-methyl-9-oxo-8,16,17-triazatricyclo[13.3.1.0$^{2,7}$]nonadeca-1(19),2(7),3,5,11,15,17-heptaen-5-yl]carbamate: 13K was prepared in a similar way as in example 12J by replacing 12I with 13J. MS (ESI) m/z: 502.0 (M+H)$^+$.

13L

Methyl N-[(10R,14S)-14-{[(tert-butoxy)carbonyl]amino}-10-methyl-9-oxo-8,16,17-triazatricyclo[13.3.1.0$^{2,7}$] nonadeca-1(19),2(7),3,5,15,17-hexaen-5-yl]carbamate, TFA salt: To a solution of 13K (43 mg, 0.086 mmol) in ethanol (3427 µL) was added ammonium formate (108 mg, 1.713 mmol) and Pd/C (18.23 mg, 0.017 mmol). The reaction was heated at 70° C. overnight. More Pd (18 mg) and ammonium formate (54 mg) were added and the reaction was heated at 70° C. for 3 days. The mixture was filtered and rinsed with DCM, EtOAc, and MeOH. The filtrate was concentrated and purified by silica gel chromatography. The early fractions was further purified by reverse phase HPLC to afford 13L (17.8 mg, 44%). MS (ESI) m/z: 470.1 (M+H)$^+$.

Example 13

Methyl N-[(14S)-14-[(6R)-6-(3-chloro-2,6-difluorophenyl)-2-oxo-1,3-oxazinan-3-yl]-10-methyl-9-oxo-8,16,17-triazatricyclo[13.3.1.0$^{2,7}$]nonadeca-1(19),2(7),3,5,15,17-hexaen-5-yl]carbamate, TFA salt: Example 13 was made in the same way as Example 12 by replacing 12M with 13L. $^1$H NMR (400 MHz, MeOD) δ 9.56 (s, 1H), 9.22 (br. s., 1H), 7.82 (d, J=1.8 Hz, 1H), 7.67-7.46 (m, 4H), 7.14-7.01 (m, 1H), 5.81 (dd, J=11.7, 2.7 Hz, 1H), 5.40 (dd, J=12.4, 5.3 Hz, 1H), 4.42 (br. s., 1H), 3.89-3.73 (m, 1H), 3.76 (s, 3H), 2.91-2.57 (m, 3H), 2.38-2.24 (m, 1H), 2.14-1.99 (m, 1H), 1.94-1.82 (m, 1H), 1.56-1.19 (m, 2H), 0.97 (d, J=6.8 Hz, 3H), 0.67 (br. s., 1H) ppm. MS (ESI) m/z: 600.0 (M+H)$^+$. Analytical HPLC RT=8.93 min (Method A).

Example 14

Methyl ((10R,14S)-14-(4-(4-chloro-3-fluoro-2-pyridinyl)-2-oxotetrahydro-1(2H)-pyrimidinyl)-10-methyl-9-oxo-8,16,18-triazatricyclo[13.2.1.0$^{2,7}$]octadeca-1(17),2,4,6,15 (18)-pentaen-5-yl)carbamate

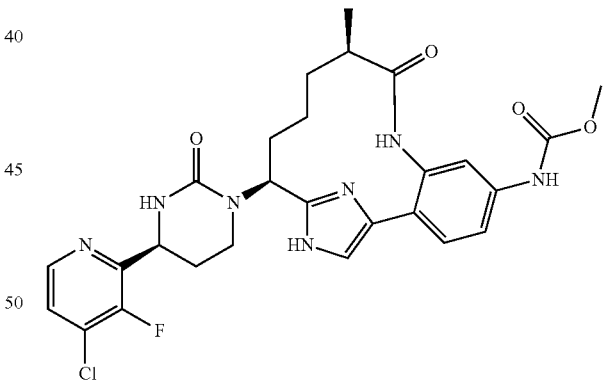

14A

Methyl N-[(10R,14S)-14-amino-10-methyl-9-oxo-8,16,18-triazatricyclo[13.2.1.0$^{2,7}$]octadeca-1(17),2,4,6,15(18)-pentaen-5-yl]carbamate: A mixture of 10E (216 mg, 0.367 mmol) and HCl (4 N in dioxane) (10 mL, 40.00 mmol) in a sealed microwave vial behind a blast shield was heated at 75° C. for 5 h. After 5 h, the reaction mixture was diluted with EtOAc and washed with saturated NaHCO$_3$ solution. The organic layers were then dried over MgSO$_4$ and concentrated to give the desired product (103 mg, 78%) as a pale yellow foam. MS (ESI) m/z: 358.1 (M+H)$^+$.

Example 14

Methyl ((10R,14S)-14-(4-(4-chloro-3-fluoro-2-pyridinyl)-2-oxotetrahydro-1(2H)-pyrimidinyl)-10-methyl-9-oxo-8,16,18-triazatricyclo[13.2.1.0$^{2,7}$]octadeca-1(17),2,4,6,15(18)-pentaen-5-yl)carbamate: (Reference: Gutierrez, C. D. et al., *Tet. Lett.*, 46:3595-3597 (2005).) To a solution of 14A (370 mg, 1.035 mmol) and Intermediate 15 (304 mg, 0.942 mmol) in MeOH (40 mL) was added sodium cyanoborohydride (89.0 mg, 1.413 mmol). The reaction was stirred for 30 min at which time additional 17 mg of intermediate 14A was added. After additional 15 min, the reaction was quenched with water and extracted with EtOAc (3×). The combined organic layer was washed with brine, dried with MgSO$_4$ and concentrated in vacuo to give a beige foam. The crude foam was dissolved in ACN (48 mL) and Et$_3$N (263 μL, 1.885 mmol), split into 4-20 ml microwave vials and microwaved for 10 min at 100° C. The crude product was then purified by reverse phase HPLC. Fractions containing product was concentrated to dryness. The residue was dissolved in EtOAc and washed with sat. NaHCO$_3$. The aqueous layer was further extracted with EtOAc (3×). The combined organic layer was concentrated in vacuo to give the desired product (140 mg, 26%) as a pale yellow foam. The free base was dissolved in dioxane and 4 N HCl in dioxane (2 mL) was added. The suspension was concentrated to dryness to give the HCl salt as a white solid. $^1$H NMR (400 MHz, MeOD) δ 8.32 (d, J=5.3 Hz, 1H), 7.64-7.36 (m, 5H), 5.25 (dd, J=11.3, 6.3 Hz, 1H), 5.03 (t, J=5.0 Hz, 1H), 3.81-3.73 (m, 3H), 3.48 (br. s., 2H), 2.73 (br. s., 1H), 2.54-2.29 (m, 2H), 2.22-1.99 (m, 2H), 1.75 (d, J=12.0 Hz, 1H), 1.65-1.42 (m, 2H), 1.03 (d, J=7.0 Hz, 3H), 0.74 (br. s., 1H). MS (ESI) m/z: 570.1 (M+H)$^+$. Analytical HPLC RT=4.25 min (Method A).

Example 15

Methyl ((10R,14S)-14-(6-(3-chloro-2-fluorophenyl)-2-oxo-1,3-oxazinan-3-yl)-10-methyl-9-oxo-8,16,18-triazatricyclo[13.2.1.0$^{2,7}$]octadeca-1(17),2,4,6,15(18)-pentaen-5-yl)carbamate, TFA salt

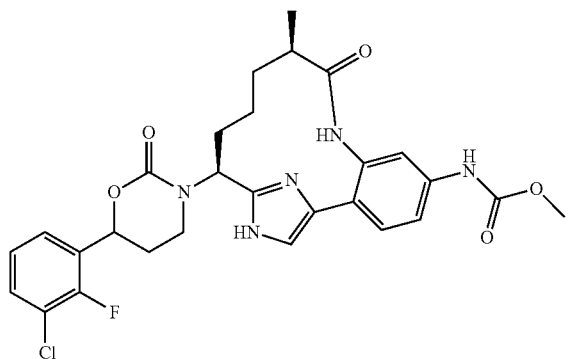 [SMILES: COC(=O)Nc1ccc2c(c1)NC(=O)[C@H](C)CCC[C@H](N1CCC(c3cccc(Cl)c3F)OC1=O)c1nc-2c[nH]1]

Example 15

Methyl ((10R,14S)-14-(6-(3-chloro-2-fluorophenyl)-2-oxo-1,3-oxazinan-3-yl)-10-methyl-9-oxo-8,16,18-triazatricyclo[13.2.1.0$^{2,7}$]octadeca-1(17),2,4,6,15(18)-pentaen-5-yl)carbamate, TFA salt: Example 15 was made in the same way as Example 10 by replacing Intermediate 2 with Intermediate 16 at step 10G. $^1$H NMR (500 MHz, MeOD) δ 7.68-7.41 (m, 6H), 7.27 (td, J=8.0, 1.1 Hz, 1H), 5.74 (dd, J=10.7, 2.5 Hz, 1H), 5.29 (dd, J=11.6, 6.1 Hz, 1H), 3.88-3.68 (m, 5H), 2.74 (td, J=6.5, 3.0 Hz, 1H), 2.53-2.10 (m, 4H), 1.85-1.44 (m, 3H), 1.07 (d, J=7.2 Hz, 3H), 0.82 (br. s., 1H) ppm. MS (ESI) m/z: 570.2 (M+H)$^+$. Analytical HPLC RT=5.35 min (Method A).

Example 16

Methyl N-[(12E,15S)-15-[(4S)-4-(3-chloro-2,6-difluorophenyl)-2-oxo-1,3-diazinan-1-yl]-18-cyano-9-oxo-8,17,19-triazatricyclo[14.2.1.0$^{2,7}$]nonadeca-1(18),2,4,6,12,16(19)-hexaen-5-yl]carbamate, TFA salt

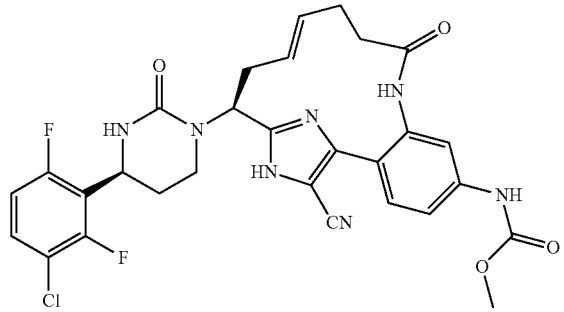 [SMILES: COC(=O)Nc1ccc2c(c1)NC(=O)CC/C=C/C[C@H](N1CC[C@@H](c3c(F)ccc(Cl)c3F)NC1=O)c1nc-2c(C#N)[nH]1]

16A tert-Butyl N-[(12E,15S)-18-bromo-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]carbamate: To a solution of 1F (0.225 g, 0.384 mmol) in CHCl$_3$ (5 mL) and ACN (5 mL) was added NBS (0.082 g, 0.461 mmol) in a portion and the resulting solution was stirred for 0.5 h at rt. The reaction mixture was then concentrated and purified by silica gel chromatography to yield the desired product (0.178 g, 70%). MS (ESI) m/z: 666.3 (M+2+H)$^+$.

16B tert-Butyl N-[(12E,15S)-18-cyano-5-[(methoxycarbonyl)amino]-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-15-yl]carbamate: A solution of 16A (0.18 g, 0.271 mmol), zinc cyanide (0.019 g, 0.162 mmol), DPPF (0.018 g, 0.032 mmol) and Pd$_2$(dba)$_3$-CHCl$_3$ (0.012 g, 0.014 mmol) in DMF (2 mL) was degassed for 0.5 h under argon bubbling. The solution was then heated at 130° C. for 0.5 h in a microwave. After 0.5 h, the reaction mixture was diluted with EtOAc and washed with NaHCO$_3$ solution, followed by brine. The organic layers were then dried over MgSO$_4$ and concentrated to yield the crude product. The crude product was then purified using reverse phase HPLC to yield the desired product (0.145 g, 88%). MS (ESI) m/z: 611.3 (M+H)$^+$.

16C

Methyl N-[(12E,15S)-15-amino-18-cyano-9-oxo-8,17,19-triazatricyclo[14.2.1.0$^{2,7}$]nonadeca-1(18),2,4,6,12,16(19)-hexaen-5-yl]carbamate: To a solution of 16B (145 mg, 0.237 mmol) dissolved in DCM (3 mL) was added TFA (0.5 mL) and the reaction mixture was stirred at rt for 2 h. After 2 h, the reaction mixture was concentrated to dryness and dissolved the brown oil in EtOAc. To the above solution was then added 0.5 mL of saturated NaHCO$_3$ solution. Extracted the aqueous layer with EtOAc (3×) and the combined organic layers were washed with brine and dried over MgSO$_4$. The organic layers were then concentrated to give the desired product (99 mg, 110%) as reddish solid. MS (ESI) m/z: 381.1 (M+H)$^+$.

Example 16

Methyl N-[(12E,15S)-15-[(4S)-4-(3-chloro-2,6-difluorophenyl)-2-oxo-1,3-diazinan-1-yl]-18-cyano-9-oxo-8,17,19-triazatricyclo[14.2.1.0$^{2,7}$]nonadeca-1(18),2,4,6,12,16(19)-hexaen-5-yl]carbamate, TFA salt: Example 16 is made in the same way as Example 14 by replacing 14A with 16B and substituting Intermediate 15 with Intermediate 17 in the last step. $^1$H NMR (400 MHz, MeOD) δ 9.56 (s, 1H), 7.66 (d, J=1.5 Hz, 1H), 7.54-7.36 (m, 3H), 7.11-6.96 (m, 1H), 5.63-5.51 (m, 2H), 5.45-5.34 (m, 1H), 3.91-3.69 (m, 4H), 3.59-3.44 (m, 1H), 2.80-2.06 (m, 9H) ppm. MS (ESI) m/z: 610.2 (M+H)$^+$. Analytical HPLC RT=6.92 min (Method A).

Example 17

Methyl N-[(10R,14S)-14-[(4S)-4-(3-chloro-2-fluoro-6-methoxyphenyl)-2-oxo-1,3-diazinan-1-yl]-10-methyl-9-oxo-8,16,18-triazatricyclo[13.2.1.0$^{2,7}$]octadeca-1(17),2,4,6,15(18)-pentaen-5-yl]carbamate, TFA salt

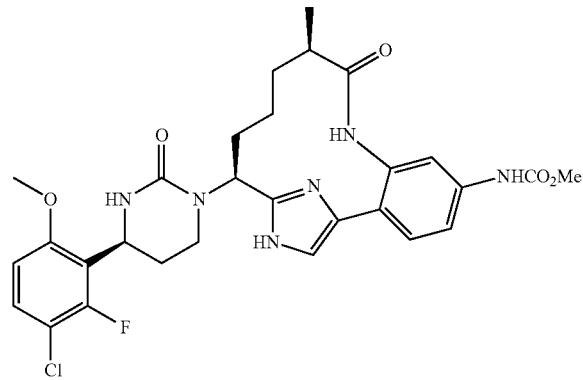

17A

Phenyl N-[(1S)-1-(3-chloro-2-fluoro-6-methoxyphenyl)-3-{[(10R,14S)-5-[(methoxycarbonyl)amino]-10-methyl-9-oxo-8,16,18-triazatricyclo[13.2.1.0$^{2,7}$]octadeca-1(17),2,4,6,15(18)-pentaen-14-yl]amino}propyl]carbamate: To a solution of Intermediate 18 (20 mg, 0.057 mmol), 14A (17 mg, 0.048 mmol) and DIEA (0.029 mL, 0.166 mmol) in MeOH (2 mL) was added decaborane (2.325 mg, 0.019 mmol) in a portion and the resulting solution was stirred for 0.5 h at rt. After stirring at rt for 0.5 h, the reaction mixture was diluted with EtOAc (30 mL) and washed with aqueous NaHCO$_3$ solution followed by brine. The organic layer was dried over Na$_2$SO$_4$ and concentrated in vacuo to yield an oily residue, which was subjected to the next step without further purification. MS (ESI) m/z: 693.2 (M+H)$^+$.

Example 17

Methyl N-[(10R,14S)-14-[(4S)-4-(3-chloro-2-fluoro-6-methoxyphenyl)-2-oxo-1,3-diazinan-1-yl]-10-methyl-9-oxo-8,16,18-triazatricyclo[13.2.1.0$^{2,7}$]octadeca-1(17),2,4,6,15(18)-pentaen-5-yl]carbamate, TFA salt The crude product from 17A (33.3 mg, 0.048 mmol) was dissolved in ACN (2 mL) followed by addition of DIEA (0.034 mL, 0.192 mmol). The resulting solution was stirred for 20 min at 100° C. The above mixture was then concentrated and purified by reverse phase HPLC to provide the desired product (2.91 mg, 8%) as a colorless solid. $^1$H NMR (400 MHz, MeOD) δ 9.58 (s, 1H), 7.58 (s, 1H), 7.52 (d, J=8.3 Hz, 1H), 7.48 (s, 1H), 7.45-7.33 (m, 2H), 6.86 (d, J=9.3 Hz, 1H), 5.23 (dd, J=11.8, 6.0 Hz, 1H), 5.14-5.04 (m, 1H), 3.83 (s, 3H), 3.76 (s, 3H), 3.55 (t, J=5.6 Hz, 2H), 2.72 (m, 1H), 2.40 (t, J=13.2 Hz, 1H), 2.33-2.15 (m, 2H), 2.07 (m, 1H), 1.80 (t, J=12.9 Hz, 1H), 1.69-1.40 (m, 2H), 1.03 (d, J=6.8 Hz, 2H), 0.74 (m, 1H) ppm. MS (ESI) m/z: 599.1 (M+H)$^+$. Analytical HPLC RT=4.94 min (Method A).

Example 18

Methyl N-[(10R,14S)-14-[4-(3,6-dichloro-2-fluorophenyl)-2-oxo-1,3-diazinan-1-yl]-10-methyl-9-oxo-8,16,18-triazatricyclo[13.2.1.0$^{2,7}$]octadeca-1(17),2,4,6,15(18)-pentaen-5-yl]carbamate, TFA salt

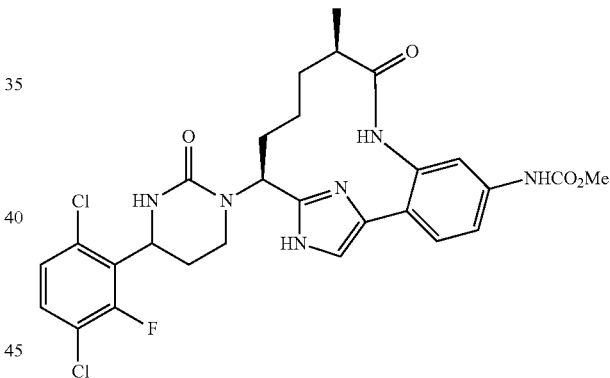

Example 18

Methyl N-[(10R,14S)-14-[4-(3,6-dichloro-2-fluorophenyl)-2-oxo-1,3-diazinan-1-yl]-10-methyl-9-oxo-8,16,18-triazatricyclo[13.2.1.0$^{2,7}$]octadeca-1(17),2,4,6,15(18)-pentaen-5-yl]carbamate, TFA salt (Diastereomer B): Example 18 was prepared in the same way as Example 17 by substituting Intermediate 19 for Intermediate 18 in Step 17A. The desired product was subjected to reverse phase HPLC followed by chiral prep HPLC using Chiral AD column with a mobile phase of IPA (0.1% DEA) and heptane (80:20) and a flow rate of 20 mL/min. Two peaks were isolated and the second eluting peak designated as Diastereomer B was identified as the desired product. $^1$H NMR (400 MHz, MeOD) δ 7.63 (br. s., 1H), 7.55-7.38 (m, 4H), 7.30 (dd, J=9.5, 8.3 Hz, 1H), 5.35 (dd, J=11.2, 5.6 Hz, 1H), 5.20 (t, J=6.3 Hz, 1H), 3.76 (s, 3H), 3.61-3.46 (m, 2H), 2.67 (br. s., 1H), 2.29 (br. s., 3H), 2.07 (br. s., 1H), 1.85-1.73 (m, 1H), 1.64 (br. s., 1H), 1.47 (br. s., 1H), 1.07 (d, J=6.8 Hz, 2H), 0.97-0.85 (m, 1H) ppm. MS (ESI) m/z: 603.1 (M+H)+. Analytical HPLC RT=4.99 min (Method A).

Example 19

Methyl N-[(10R,14S)-14-[6-(2-fluoro-3-methoxyphenyl)-2-oxo-1,3-oxazinan-3-yl]-10-methyl-9-oxo-8,16,18-triazatricyclo[13.2.1.0²,⁷]octadeca-1(17),2,4,6,15(18)-pentaen-5-yl]carbamate, TFA salt

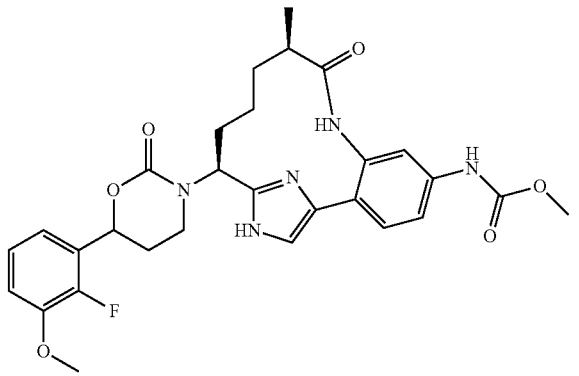 [SMILES: COC(=O)Nc1ccc2c(c1)NC(=O)[C@H](C)CCC[C@H](N1CCC(c3cccc(OC)c3F)OC1=O)c1nc-2c[nH]1]

19A

Methyl N-[(10R,14S)-14-{[3-(2-fluoro-3-methoxyphenyl)-3-hydroxypropyl]amino}-10-methyl-9-oxo-16-{[2-(trimethylsilyl)ethoxy]methyl}-8,16,18-triazatricyclo[13.2.1.0²,⁷]octadeca-1(17),2,4,6,15(18)-pentaen-5-yl]carbamate: A mixture of 10F (33 mg, 0.068 mmol), Intermediate 20 (35.7 mg, 0.115 mmol) and K₂CO₃ (37.4 mg, 0.271 mmol) in ACN (1128 μL) was sealed and heated at 75° C. overnight. The reaction mixture was concentrated and purified by silica gel chromatography to yield the desired product (31 mg, 68%) as pale yellow foam. NMR analysis confirms 1:1 diastereomer mixture. MS (ESI) m/z: 670.2 (M+H)+.

19B

Methyl N-[(10R,14S)-14-[6-(2-fluoro-3-methoxyphenyl)-2-oxo-1,3-oxazinan-3-yl]-10-methyl-9-oxo-16-{[2-(trimethylsilyl)ethoxy]methyl}-8,16,18-triazatricyclo[13.2.1.0²,⁷]octadeca-1(17),2,4,6,15(18)-pentaen-5-yl]carbamate: A mixture of 19A (30.9 mg, 0.046 mmol), CDI (37.4 mg, 0.231 mmol) in dry THF (1.5 mL) was stirred under argon overnight at rt. The reaction mixture after overnight stirring was cooled down to 0° C. under argon and to the above solution was added LiHMDS (1 M in THF) (0.161 mL, 0.161 mmol) dropwise. After 15 mins, the reaction mixture was quenched with concentrated NH₄Cl (aqueous) at 0° C. and diluted with EtOAc. The organic layer was separated and washed with water followed by brine and dried over MgSO₄. The crude product was then subjected to silica gel chromatography to yield the desired product (23 mg, 71%) as white solid. MS (ESI) m/z: 696.6 (M+H)+.

Example 19

Methyl N-[(10R,14S)-14-[6-(2-fluoro-3-methoxyphenyl)-2-oxo-1,3-oxazinan-3-yl]-10-methyl-9-oxo-8,16,18-triazatricyclo[13.2.1.0²,⁷]octadeca-1(17),2,4,6,15(18)-pentaen-5-yl]carbamate, TFA salt: A solution of HCl in dioxane (823 μL, 3.29 mmol) was added to 19B (22.9 mg, 0.033 mmol) and the reaction mixture was heated at 75° C. for 6 h. The reaction mixture after stirring for 6 h was concentrated and purified by reverse phase HPLC to yield the desired product (12 mg, 51%) as a white solid. ¹H NMR (500 MHz, MeOD) δ 9.61 (s, 1H), 7.64-7.59 (m, 1H), 7.56-7.51 (m, 2H), 7.44 (dt, J=8.4, 1.9 Hz, 1H), 7.27-7.11 (m, 2H), 7.07-7.00 (m, 1H), 5.72 (ddd, J=10.5, 5.2, 2.5 Hz, 1H), 5.27 (ddd, J=18.3, 11.7, 6.3 Hz, 1H), 3.91 (s, 3H), 3.79 (s, 3H), 3.77-3.71 (m, 1H), 3.66 (ddd, J=11.3, 5.8, 2.9 Hz, 1H), 2.74 (d, J=6.9 Hz, 1H), 2.45-2.11 (m, 4H), 1.84-1.73 (m, 1H), 1.69-1.46 (m, 2H), 1.07 (dd, J=7.0, 4.3 Hz, 3H), 0.89-0.67 (m, 1H) ppm. MS (ESI) m/z: 566.4 (M+H)+. Analytical HPLC RT=5.38 min (Method A).

Example 20

Methyl N-[(10R,14S)-14-[4-(3-chloro-2-fluorophenyl)-2-oxopiperazin-1-yl]-10-methyl-9-oxo-8,16-diazatricyclo[13.3.1.0²,⁷]nonadeca-1(19),2(7),3,5,15,17-hexaen-5-yl]carbamate, 2TFA

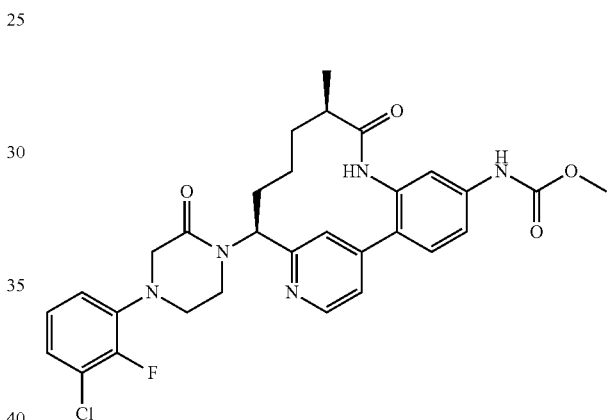

20A

Methyl N-[(10R,14S)-14-amino-10-methyl-9-oxo-8,16-diazatricyclo[13.3.1.0²,⁷]nonadeca-1(19),2(7),3,5,15,17-hexaen-5-yl]carbamate: Compound 12M (Alternative, 2HCl) was dissolved in MeOH to give a yellow solution. The solution was passed through a HCO₃ cartridge. The resulting clear filtrate was concentrated to give 20A as a white solid. MS (ESI) m/z: 369.2 (M+H)+.

Example 20

Methyl N-[(10R,14S)-14-[4-(3-chloro-2-fluorophenyl)-2-oxopiperazin-1-yl]-10-methyl-9-oxo-8,16-diazatricyclo[13.3.1.0²,⁷]nonadeca-1(19),2(7),3,5,15,17-hexaen-5-yl]carbamate, 2TFA: A sealed vial containing a solution of 20A (30 mg, 0.081 mmol) and Intermediate 21 (27.7 mg, 0.081 mmol) in DMA (0.553 mL) and DIEA (0.100 mL, 0.570 mmol) was heated to 120° C. After stirring overnight, the reaction was cooled to rt. The reaction was diluted with MeOH:ACN (1:1) and purification by reverse phase chromatography gave, after lyophilization, Example 20 (10 mg, 15%) as a yellow solid. ¹H NMR (500 MHz, CD₃OD) δ 9.67 (s, 1H), 8.76 (d, J=5.8 Hz, 1H), 8.07 (s, 1H), 7.85 (dd, J=5.9, 1.5 Hz, 1H), 7.75-7.62 (m, 1H), 7.62-7.52 (m, 2H), 7.17-7.05 (m, 2H), 7.05-6.90 (m, 1H), 5.40 (dd, J=12.7, 4.7 Hz, 1H), 3.86 (s, 2H), 3.79 (s, 3H), 3.75-3.62 (m, 2H), 3.53-3.41 (m, 2H), 2.69-2.60 (m, 1H), 2.41-2.25 (m, 1H), 2.15-2.00 (m, 1H), 2.00-1.83 (m, 1H), 1.68-1.52 (m, 1H), 1.37-1.22 (m, 1H), 1.06 (d, J=18.2 Hz, 3H), 1.04-0.96 (m, 1H). MS (ESI) m/z: 580.2 (M+H)+. Analytical HPLC: RT=6.62 min (Method A).

Example 21

Methyl N-[(10R,14S)-14-[(6R)-6-(4-chloro-3-fluoropyridin-2-yl)-2-oxo-1,3-oxazinan-3-yl]-10-methyl-9-oxo-8,16,18-triazatricyclo[13.2.1.0$^{2,7}$]octadeca-1(17),2,4,6,15(18)-pentaen-5-yl]carbamate, 2 HCl

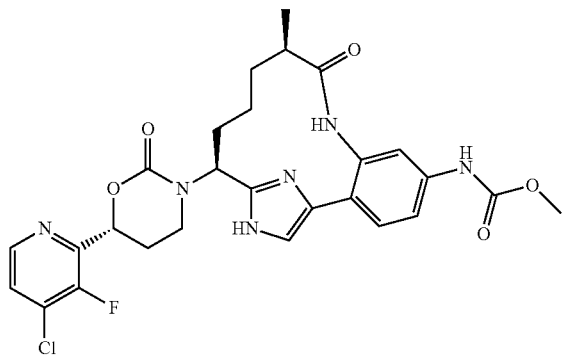 [SMILES: COC(=O)Nc1ccc2c(c1)NC(=O)[C@H](C)CCC[C@H](N1CC[C@H](c3nccc(Cl)c3F)OC1=O)c1nc-2c[nH]1]

21A

Methyl ((3R,7S)-7-(((3R)-3-((tert-butyl(dimethyl)silyl)oxy)-3-(4-chloro-3-fluoropyridin-2-yl)propyl)amino)-3-methyl-2-oxo-9-((2-(trimethylsilyl)ethoxy)methyl)-1,2,3,4,5,6,7,9-octahydro-11,8-(azeno)-1,9-benzodiazacyclotridecin-14-yl)carbamate: To a solution of Example 10F (400 mg, 0.820 mmol) and Intermediate 23 (261 mg, 0.820 mmol) in MeOH (15 mL) was added sodium cyanoborohydride (103.0 mg, 1.640 mmol). The reaction was stirred for 2 h. The reaction was quenched with water and extracted with EtOAc (3×). The combined organic layer was washed with brine, dried with MgSO$_4$ and concentrated in vacuo to give a thick brown oil. The oil was dissolved in THF (25 mL) and cooled in ice bath. To the solution was added DIEA (286 μL, 1.640 mmol) followed by phenyl chloroformate (123 μL, 0.984 mmol) dropwise. After 15 min, the reaction mixture was quenched with water, extracted with EtOAc (2×). The organic layers were concentrated and purified by silica gel chromatography to isolate the desired product (588 mg, 79%) as clear glass. MS (ESI) m/z: 909.5 (M+H)+.

21B

Phenyl ((3R)-3-((tert-butyl(dimethyl)silyl)oxy)-3-(4-chloro-3-fluoropyridin-2-yl)propyl)((10R,14S)-5-((methoxycarbonyl)amino)-10-methyl-9-oxo-16-((2-(trimethylsilyl)ethoxy)methyl)-8,16,18-triazatricyclo[13.2.1.0$^{2,7}$]octadeca-1(17),2,4,6,15(18)-pentaen-14-yl)carbamate: To a solution of 21A (588 mg, 0.646 mmol) in THF (10 mL) was added 1 M TBAF in THF solution (1.1 mL, 1.100 mmol). After 1 h, the reaction was diluted with EtOAc and washed with saturated NaHCO$_3$ solution and brine. The organic layer was dried over MgSO$_4$ and concentrated. The crude product was purified using silica gel column chromatography to provide the desired product (295 mg, 65%) as a clear glass. MS (ESI) m/z: 701.2 (M+H)+.

Example 21

Methyl N-[(10R,14S)-14-[(6R)-6-(4-chloro-3-fluoropyridin-2-yl)-2-oxo-1,3-oxazinan-3-yl]-10-methyl-9-oxo-8,16,18-triazatricyclo[13.2.1.0$^{2,7}$]octadeca-1(17),2,4,6,15(18)-pentaen-5-yl]carbamate, 2HCl: A solution of 21B in 4 mL of HCl/dioxane was stirred for 1 h at 75° C. The reaction mixture was then concentrated in vacuo, yielding a solid. It was purified by Chiral AD column (60% IPA/40% heptane) followed by reverse phase chromatography. The desired fractions were pooled together and combined to give the TFA salt. The TFA salt (100 mg, 0.125 mmol) in MeOH (5 mL) was stirred with 1.5 N aq HCl (5 mL) for 10 min. Concentrated to dryness in vacuo and repeated once more to give the desired product (80 mg, 40%) as a white solid. $^1$H NMR (400 MHz, MeOD) δ 8.34 (d, J=5.0 Hz, 1H), 7.64 (s, 1H), 7.56 (d, J=2.0 Hz, 1H), 7.54-7.47 (m, 2H), 7.46-7.41 (m, 1H), 5.92-5.83 (m, 1H), 5.27 (dd, J=11.5, 6.0 Hz, 1H), 3.76 (s, 3H), 3.68 (dd, J=12.5, 6.5 Hz, 2H), 3.35 (s, 5H), 2.81-2.71 (m, 1H), 2.59-2.35 (m, 3H), 2.21-2.08 (m, 1H), 1.87-1.75 (m, 1H), 1.67-1.55 (m, 1H), 1.54-1.42 (m, 1H), 1.03 (d, J=7.0 Hz, 3H), 0.80-0.65 (m, 1H). MS (ESI) m/z: 571.3 (M+H)+. Analytical HPLC RT=4.27 min (Method A).

Example 22

Methyl N-[(14S)-14-[(6R)-6-(3-chloro-2,6-difluorophenyl)-2-oxo-1,3-oxazinan-3-yl]-9-oxo-10-oxa-8,16-diazatricyclo[13.3.1.0$^{2,7}$]nonadeca-1(19),2,4,6,15,17-hexaen-5-yl]carbamate, TFA salt

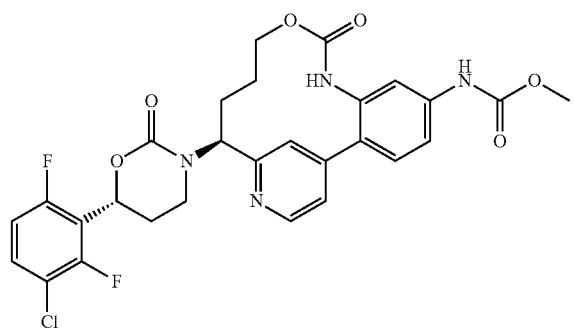 [SMILES: COC(=O)Nc1ccc2c(c1)NC(=O)OCCC[C@H](N1CC[C@H](c3c(F)ccc(Cl)c3F)OC1=O)c1cc-2ccn1]

22A tert-Butyl N-[(1S)-1-(4-{2-amino-4-[(methoxycarbonyl)amino]phenyl}pyridin-2-yl)-4-hydroxybutyl]carbamate: To a solution of 12H (0.110 g, 0.267 mmol) in THF (5 mL) was added 1.0 M borane in THF (0.533 mL, 0.533 mmol). After 3 h, the reaction mixture was cooled with an ice bath. Next, 6 N NaOH (0.089 mL, 0.533 mmol) was slowly added followed by slow addition of H$_2$O$_2$ (0.054 mL, 0.533 mmol). The reaction was allowed to warm to rt. After 1 h, the reaction was extracted with ethyl acetate (20 mL). The organic layer was washed with brine (50 mL), dried over Na₂SO₄, filtered and concentrated to give a pale yellow oil. Purification by normal phase chromatography gave the desired product (0.150 g, 27%) as a pale yellow semi-solid. MS (ESI) m/z: 431.2 (M+H)⁺. ¹H NMR (400 MHz, MeOD) δ 8.49-8.50 (m, 1H), 7.51 (s, 1H), 7.40 (d, J=5.02 Hz, 1H), 7.00-7.14 (m, 2H), 6.83 (dd, J=8.41, 2.13 Hz, 1H), 4.68 (br. s, 1H), 3.75 (s, 3H), 3.54-3.64 (m, 2H), 1.51-2.05 (m, 5H), 1.44 (s, 9H).

22B

To a cooled (0° C.) solution of 22A (0.050 g, 0.116 mol) in DCM (10 mL) and acetonitrile (10 mL) was added phosgene (20% toluene) (0.077 mL, 0.139 mmol). The reaction mixture was allowed to warm to rt. After 1 h, the reaction was concentrated by purging with nitrogen to give a residue. In a separate flask, a solution of TEA (0.113 mL, 0.813 mmol) and DMAP (0.004 g, 0.116 μmol) in DCM (25 mL) was prepared. The above residue was dissolved in DCM (10 mL) and this solution was slowly added over 2 h using a syringe pump to the TEA/DMAP solution. The reaction was concentrated. Purification by silica gel chromatography provided the desired product (0.03 g 57%) as an off white solid. MS (ESI) m/z: 457.2 (M+H)⁺. ¹H NMR (300 MHz, MeOD) δ 8.51 (d, J=5.6 Hz, 1H), 7.73 (s, 1H), 7.56-7.59 (m, 1H), 7.18-7.37 (m, 2H), 7.01 (dd, J=8.4, 2.50 Hz, 1H), 6.63 (d, J=8.3 Hz, 1H), 3.77 (s, 3H), 2.30-2.40 (m, 1H), 1.99-2.24 (m, 4H), 1.44 (d, J=42.4 Hz, 2H), 1.20-1.51 (m, 9H).

22C

Methyl N-[(14S)-14-amino-9-oxo-10-oxa-8,16-diazatricyclo[13.3.1.0²,⁷]nonadeca-1(19),2,4,6,15,17-hexaen-5-yl]carbamate, 2TFA: To a stirred solution of 22B (0.026 g, 0.057 mmol) in DCM (5 mL) at 0° C. was added TFA (0.500 mL, 6.49 mmol). The reaction was allowed to warm to rt. After 2 h, the reaction was concentrated and the crude material was washed with diethyl ether (6 mL) and dried to give the desired product (0.015 g, 73%). MS (ESI) m/z: 357.2 (M+H)⁺. ¹H NMR (400 MHz, DMSO-d₆) δ 9.94 (s, 1H), 9.35 (s, 1H), 8.61 (d, J=5.27 Hz, 1H), 8.29 (br. s, 3H), 7.74 (s, 1H), 7.57-7.59 (m, 1H), 7.48-7.51 (m, 1H), 7.39-7.40 (m, 1H), 7.35 (d, J=1.76 Hz, 1H), 4.71 (br. s, 1H), 3.91-3.94 (m, 1H), 3.69 (s, 3H), 3.66 (s, 1H), 2.11-2.32 (m, 2H), 0.94-1.40 (m, 2H).

Example 22

Methyl N-[(14S)-14-[(6R)-6-(3-chloro-2,6-difluorophenyl)-2-oxo-1,3-oxazinan-3-yl]-9-oxo-10-oxa-8,16-diazatricyclo[13.3.1.0²,⁷]nonadeca-1(19),2,4,6,15,17-hexaen-5-yl]carbamate, TFA salt: Example 22 was prepared according to the procedure described in step 10G, by replacing 10F with 22C, followed by step 10H. ¹H NMR (400 MHz, MeOD) δ 8.71 (d, J=5.27 Hz, 1H), 8.35 (br. s., 1H), 7.85 (br. s., 1H), 7.76 (d, J=8.53 Hz, 1H), 7.51-7.63 (m, 3H), 7.08 (td, J=9.47, 1.88 Hz, 1H), 5.84 (dd, J=11.17, 2.64 Hz, 1H), 5.26-5.41 (m, 1H), 4.18-4.21 (m, 1H), 3.84-3.94 (m, 1H), 3.80 (s, 3H), 2.64-2.80 (m, 1H), 2.56 (d, J=9.54 Hz, 1H), 2.28-2.38 (m, 2H), 1.98-2.14 (m, 1H), 1.65-1.77 (m, 3H). MS m/z: 587.2 (M+H)⁺. Analytical HPLC RT=8.66 min (Method A).

Example 23

Methyl N-[(11R,15S)-15-[(6R)-6-(3-chloro-2,6-difluorophenyl)-2-oxo-1,3-oxazinan-3-yl]-11-methyl-9-oxo-8,17,19-triazatricyclo[14.2.1.0²,⁷]nonadeca-1(18),2,4,6,16(19)-pentaen-5-yl]carbamate

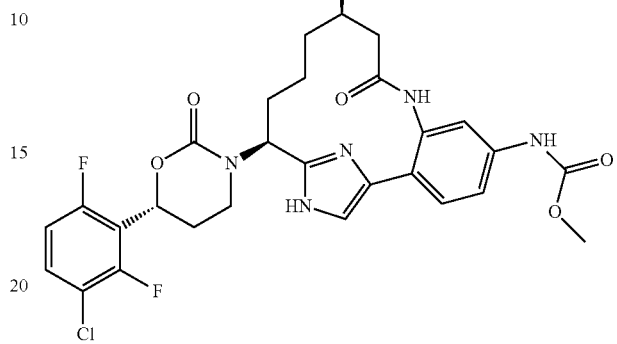

23A tert-Butyl N-[(1S)-1-(4-{4-[(methoxycarbonyl)amino]-2-(3-methylpent-4-enamido)phenyl}-1-{[2-(trimethylsilyl)ethoxy]methyl}-1H-imidazol-2-yl)but-3-en-1-yl]carbamate (mixture of diastereomers): 23A was prepared according to the procedure described in step 1E, by replacing pent-4-enoic acid with 3-methylpent-4-enoic acid. MS (ESI) m/z: 628.4 (M+H)⁺. ¹H NMR (400 MHz, MeOD) δ 8.45 (d, J=2.01 Hz, 1H), 7.51-7.58 (m, 2H), 7.35 (d, J=7.03 Hz, 1H), 5.80-5.94 (m, 2H), 5.61 (d, J=10.79 Hz, 1H), 5.36 (d, J=11.04 Hz, 1H), 5.20 (s, 1H), 5.04-5.13 (m, 2H), 4.92-5.03 (m, 2H), 3.75 (s, 3H), 3.62 (t, J=8.03 Hz, 2H), 2.73-2.87 (m, 3H), 2.40-2.57 (m, 2H), 1.45 (s, 9H), 1.14 (t, J=6.78 Hz, 3H), 0.96 (td, J=8.03, 5.52 Hz, 2H), −0.01-0.04 (m, 9H).

23B tert-Butyl N-[(12E,15S)-5-[(methoxycarbonyl)amino]-11-methyl-9-oxo-17-{[2-(trimethylsilyl)ethoxy]methyl}-8,17,19-triazatricyclo[14.2.1.0²,⁷]nonadeca-1(18),2,4,6,12,16(19)-hexaen-15-yl]carbamate and Z-isomer: A flame-dried RBF, equipped with condenser, containing a solution of 23A (1.1 g, 1.752 mmol) and p-toluenesulfonic acid monohydrate (0.367 g, 1.927 mmol) in DCM (1600 mL) was degassed for 1 h with nitrogen. The reaction mixture was refluxed for 1 h under nitrogen atmosphere. Next, a solution of tricyclohexylphosphine[1,3-bis(2,4,6-trimethylphenyl)-4,5-dihydroimidazol-2-ylidene][benzylidine]ruthenium(IV)dichloride (0.596 g, 0.701 mmol) in DCM (15 mL), purged with nitrogen for 10 min, was added slowly. The reaction was stirred overnight at 45° C. The reaction was cooled to rt. The reaction mixture was washed with saturated NaHCO₃ (2×250 mL), brine solution (250 mL), dried by Na₂SO₄, filtered and concentrated to give a gummy brown solid and as a mixture of E and Z isomers. Purification using silica gel chromatography gave the desired product (0.88 g, 84%) as a brown solid. MS (ESI) m/z: 600.4 (M+H)⁺.

23C (Diastereomer A)

tert-Butyl N-[(11R,15S)-5-[(methoxycarbonyl)amino]-11-methyl-9-oxo-17-{[2-(trimethylsilyl)ethoxy]methyl}-8, 17,19-triazatricyclo[14.2.1.0²,⁷]nonadeca-1(18),2,4,6,16 (19)-pentaen-15-yl]carbamate and 23D (Diastereomer B), tert-butyl N-[(11S,15S)-5-[(methoxycarbonyl)amino]-11- methyl-9-oxo-17-{[2-(trimethylsilyl)ethoxy]methyl}-8,17,19-triazatricyclo[14.2.1.0²,⁷]nonadeca-1(18),2,4,6,16(19)-pentaen-15-yl]carbamate: To the solution of 23B (2.1 g, 3.50 mmol) in MeOH (100 mL) was added platinum(IV) oxide (0.159 g, 0.700 mmol) and the reaction was stirred at rt under hydrogen atmosphere. After 30 h, the reaction was stopped and filtered through CELITE® washing with methanol (4×50 mL) and ethyl acetate (4×50 mL). The filtrate was concentrated to give a brown solid. The diastereomers were separated by chiral HPLC using CHIRALCEL® OD-H column to give (Diastereomer A, 0.750 g, 34%) and (Diastereomer B, 0.700 g, 33%). 23C (Diastereomer A): MS (ESI) m/z: 602.2 (M+H)⁺. [α]²⁰·⁰_D=−44.48 (c 0.5, MeOH). ¹H NMR (300 MHz, MeOD) δ 8.11 (d, J=2.17 Hz, 1H), 7.39-7.45 (m, 2H), 7.33-7.38 (m, 1H), 5.50-5.59 (m, 2H), 5.33 (d, J=10.76 Hz, 1H), 3.75 (s, 3H), 3.60 (t, J=8.12 Hz, 2H), 2.36-2.49 (m, 1H), 2.26-2.35 (m, 2H), 2.16-2.25 (m, 1H), 1.82-1.93 (m, 1H), 1.75-1.82 (m, 1H), 1.46 (s, 9H), 1.22-1.33 (m, 1H), 1.07-1.16 (m, 1H), 1.04 (d, J=6.42 Hz, 3H), 0.95 (td, J=8.14, 4.49 Hz, 2H), 0.02 (s, 9H). 23D (Diastereomer B): MS (ESI) m/z: 602.2 (M+H)⁺. [α]²⁰·⁰_D=−66.40 (c 0.5, MeOH). ¹H NMR (400 MHz, DMSO-d₆) δ 12.02 (s, 1H), 9.66 (s, 1H), 8.30 (d, J=2.26 Hz, 1H), 7.65 (s, 1H), 7.43-7.52 (m, 2H), 7.25 (dd, J=8.41, 2.13 Hz, 1H), 5.27-5.39 (m, 2H), 3.67 (s, 3H), 3.50-3.56 (m, 2H), 2.53-2.60 (m, 2H), 2.46 (s, 1H), 2.04-1.95 (m, 2H), 1.93 (dd, J=13.30, 6.02 Hz, 2H), 1.41 (s, 9H), 0.99 (d, J=6.78 Hz, 3H), 0.89 (td, J=8.16, 3.26 Hz, 2H), 0.02 (s, 9H).

Example 23

Methyl N-[(11R,15S)-15-[(6R)-6-(3-chloro-2,6-difluorophenyl)-2-oxo-1,3-oxazinan-3-yl]-11-methyl-9-oxo-8,17,19-triazatricyclo[14.2.1.0²,⁷]nonadeca-1(18),2,4,6,16(19)-pentaen-5-yl]carbamate, TFA salt: Example 23 was prepared in the same way as Example 10 by replacing 10E with 23C. ¹H NMR (400 MHz, DMSO-d₆) δ 12.52 (d, J=15.06 Hz, 2H), 9.63 (s, 1H), 8.42 (d, J=2.26 Hz, 1H), 7.68-7.83 (m, 1H), 7.51-7.64 (m, 2H), 7.17-7.33 (m, 2H), 5.78 (d, J=9.29 Hz, 1H), 5.25 (d, J=11.80 Hz, 1H), 3.66 (s, 3H), 3.42-3.56 (m, 1H), 2.94 (d, J=7.53 Hz, 1H), 2.80 (d, J=6.53 Hz, 1H), 2.34 (dd, J=3.76, 1.76 Hz, 2H), 2.16 (d, J=13.80 Hz, 1H), 1.92 (dd, J=14.18, 7.91 Hz, 1H), 1.68-1.85 (m, 2H), 1.59 (d, J=10.04 Hz, 2H), 1.31-1.48 (m, 1H), 1.06 (d, J=6.53 Hz, 3H) ppm. MS (ESI) m/z: 602.2 (M+H)⁺. Analytical HPLC RT=6.85 min (Method A).

Example 24

Methyl N-[(14S)-14-[(6R)-6-(3-chloro-2,6-difluorophenyl)-2-oxo-1,3-oxazinan-3-yl]-10,10-difluoro-9-oxo-8,16,18-triazatricyclo[13.2.1.0²,⁷]octadeca-1(17),2,4,6,15(18)-pentaen-5-yl]carbamate, TFA salt

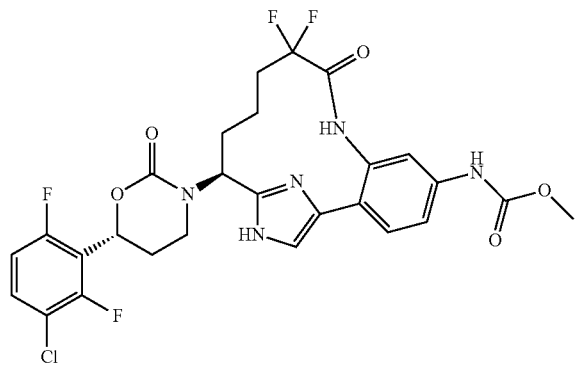 [SMILES: COC(=O)Nc1ccc2c(c1)NC(=O)C(F)(F)CCC[C@H](N1CC[C@H](c3c(F)ccc(Cl)c3F)OC1=O)c1nc-2c[nH]1]

24A

Methyl N-[(14S)-14-amino-10,10-difluoro-9-oxo-16-{[2-(trimethylsilyl)ethoxy]methyl}-8,16,18-triazatricyclo[13.2.1.0²,⁷]octadeca-1(17),2,4,6,15(18)-pentaen-5-yl]carbamate: 24A was prepared in the same way as 4B by replacing but-3-enoic acid with 2,2-difluoropent-4-enoic acid.

24B

Methyl N-[(14S)-14-[(6R)-6-(3-chloro-2,6-difluorophenyl)-2-oxo-1,3-oxazinan-3-yl]-10,10-difluoro-9-oxo-16-{[2-(trimethylsilyl)ethoxy]methyl}-8,16,18-triazatricyclo[13.2.1.0²,⁷]octadeca-1(17),2,4,6,15(18)-pentaen-5-yl]carbamate: 23B was made in the same way as Example 12 by replacing 12M with 24A. MS (ESI) m/z: 740.0 (M+H)⁺.

Example 24

Methyl N-[(14S)-14-[(6R)-6-(3-chloro-2,6-difluorophenyl)-2-oxo-1,3-oxazinan-3-yl]-10,10-difluoro-9-oxo-8,16,18-triazatricyclo[13.2.1.0²,⁷]octadeca-1(17),2,4,6,15(18)-pentaen-5-yl]carbamate, TFA salt: 24B (12 mg, 0.016 mmol) was treated with 4 M HCl in dioxane (405 μL, 1.621 mmol). The reaction was heated at 75° C. After 7 h, the reaction was cooled to rt and concentrated. The residue was purified by reverse phase HPLC to yield the desired product (8.4 mg, 70%) as a white solid. ¹H NMR (400 MHz, MeOD) δ 9.65 (s, 1H), 7.63 (d, J=2.2 Hz, 1H), 7.61-7.47 (m, 4H), 7.13-7.05 (m, 1H), 5.84 (dd, J=11.5, 2.7 Hz, 1H), 5.25 (dd, J=12.1, 5.5 Hz, 1H), 3.76 (s, 3H), 3.75-3.69 (m, 2H), 2.68-2.54 (m, 1H), 2.45-2.02 (m, 5H), 1.49-1.08 (m, 2H). MS (ESI) m/z: 610.1 (M+H)⁺. Analytical HPLC RT=7.32 min (Method A).

Example 25

Methyl (10R,14S)-14-[(6R)-6-(3-chloro-2,6-difluorophenyl)-2-oxo-1,3-oxazinan-3-yl]-10-methyl-9-oxo-8,16-diazatricyclo[13.3.1.0²,⁷]nonadeca-1(19),2,4,6,15,17-hexaene-4-carboxylate, TFA salt

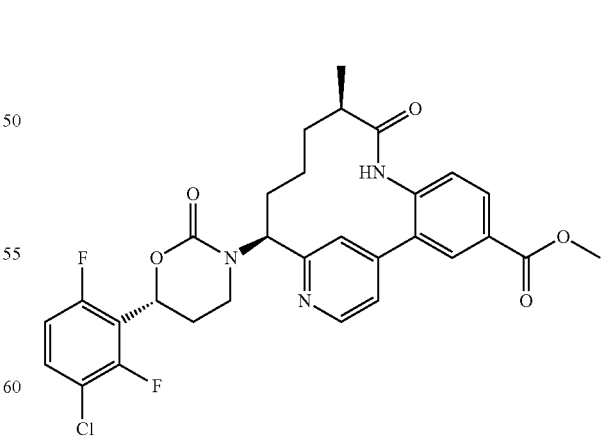

Example 25 was made in the same way as Example 12 by replacing Intermediate 22 with (2-amino-5-(methoxycarbonyl)phenyl)boronic acid in step 12C. The diastereomer mixture was separated during step 12J. Diastereomer A, the early eluting isomer on silica gel chromatography, was used to generate the homochiral final product. $^1$H NMR (500 MHz, MeOD) δ 8.84 (d, J=5.5 Hz, 1H), 8.31 (d, J=1.9 Hz, 1H), 8.19 (dd, J=8.3, 1.9 Hz, 1H), 7.95 (br. s., 1H), 7.83 (d, J=3.9 Hz, 1H), 7.57 (td, J=8.7, 5.5 Hz, 1H), 7.43 (d, J=8.3 Hz, 1H), 7.08 (td, J=9.5, 1.7 Hz, 1H), 5.83 (dd, J=11.6, 2.8 Hz, 1H), 5.26 (dd, J=12.4, 5.0 Hz, 1H), 4.09-4.02 (m, 1H), 3.97 (s, 3H), 3.74 (td, J=11.7, 4.1 Hz, 1H), 2.75-2.53 (m, 2H), 2.40-2.23 (m, 2H), 2.18-2.06 (m, 1H), 1.97-1.85 (m, 1H), 1.65-1.50 (m, 1H), 1.44-1.28 (m, 1H), 1.02 (d, J=6.9 Hz, 3H), 0.80 (m, 1H) ppm. MS (ESI) m/z: 584.2 (M+H)$^+$. Analytical HPLC RT=7.67 min (Method A).

Example 26

(10R,14S)-14-[(6R)-6-(3-chloro-2,6-difluorophenyl)-2-oxo-1,3-oxazinan-3-yl]-10-methyl-9-oxo-8,16-diazatricyclo[13.3.1.0$^{2,7}$]nonadeca-1(19),2,4,6,15,17-hexaene-4-carboxylic acid, TFA salt

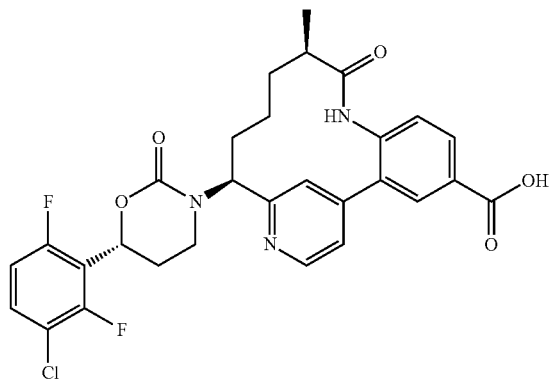 [SMILES: C[C@@H]1CCC[C@H](N2CC[C@H](c3c(F)ccc(Cl)c3F)OC2=O)c2cc(ccn2)-c2cc(C(=O)O)ccc2NC1=O]

Example 26

(10R,14S)-14-[(6R)-6-(3-chloro-2,6-difluorophenyl)-2-oxo-1,3-oxazinan-3-yl]-10-methyl-9-oxo-8,16-diazatricyclo[13.3.1.0$^{2,7}$]nonadeca-1(19),2,4,6,15,17-hexaene-4-carboxylic acid, TFA salt: To a solution of Example 25 (16 mg, 0.023 mmol) in THF (458 µL) was added LiOH (45.8 µL, 0.092 mmol). The reaction was stirred at rt for 2 h. The reaction mixture was concentrated and purified by reverse phase HPLC to yield the desired product (3 mg, 18% yield) as a white solid. $^1$H NMR (500 MHz, MeOD) δ 8.81 (d, J=5.5 Hz, 1H), 8.30 (d, J=1.9 Hz, 1H), 8.18 (dd, J=8.3, 1.9 Hz, 1H), 7.88 (s, 1H), 7.76 (dd, J=5.5, 1.1 Hz, 1H), 7.57 (td, J=8.6, 5.6 Hz, 1H), 7.42 (d, J=8.3 Hz, 1H), 7.11-7.04 (m, 1H), 5.83 (dd, J=11.6, 2.8 Hz, 1H), 5.29 (dd, J=12.5, 4.8 Hz, 1H), 4.07 (d, J=8.8 Hz, 1H), 3.73 (td, J=11.8, 4.0 Hz, 1H), 2.72-2.51 (m, 2H), 2.37-2.23 (m, 2H), 2.16-2.03 (m, 1H), 1.91 (td, J=10.0, 3.4 Hz, 1H), 1.56 (td, J=15.2, 7.0 Hz, 1H), 1.36 (d, J=4.7 Hz, 1H), 1.03 (d, J=6.9 Hz, 3H), 0.81 (m, 1H) ppm. MS (ESI) m/z: 570.1 (M+H)$^+$. Analytical HPLC RT=5.69 min (Method A).

Example 27

Methyl N-[(10R,14S)-14-[(6R)-6-(3-chloro-2,6-difluorophenyl)-2-oxo-1,3-oxazinan-3-yl]-17-methoxy-10-methyl-9-oxo-8,16-diazatricyclo[13.3.1.0$^{2,7}$]nonadeca-1(18),2,4,6,15(19),16-hexaen-5-yl]carbamate

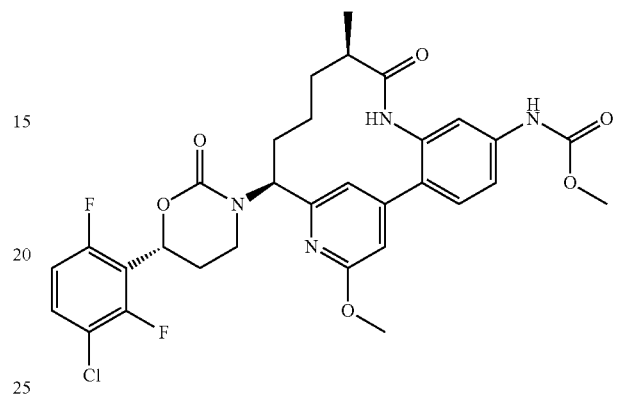

27A

Methyl 4-(1,3-dioxolan-2-yl)-3-nitrobenzoate: To a solution of methyl 4-formyl-3-nitrobenzoate (9.0 g, 43.0 mmol) in toluene (150 mL) was added ethylene glycol (7.20 mL, 129 mmol) followed by p-TsOH (0.409 g, 2.152 mmol) and the reaction mixture was heated at reflux temperature with azeotropic removal of H$_2$O using a Dean-Stark trap for 4 h. The reaction mixture was then cooled and diluted with DCM. The DCM layer was then washed with saturated NaHCO$_3$ solution. The organic layer was dried (MgSO$_4$), filtered, and concentrated to yield a residue. The residue was dissolved in minimal quantity of DCM and purified by silica gel chromatography to yield the desired product (8.53 g, 78%) as a white solid. $^1$H NMR (400 MHz, DMSO-d$_6$) δ 8.39 (s, 1H), 8.27 (d, J=8.2 Hz, 1H), 7.90 (d, J=8.2 Hz, 1H), 6.38 (s, 1H), 4.00 (dt, J=3.8, 1.9 Hz, 2H), 3.94 (dt, J=3.8, 1.9 Hz, 2H), 3.91 (s, 3H) ppm.

27B 4-(1,3-Dioxolan-2-yl)-3-nitrobenzoic acid: Lithium hydroxide monohydrate (5.67 g, 135 mmol) was added to a solution of 27A (11.4 g, 45.0 mmol) in THF (120 mL), MeOH (120 mL) and H$_2$O (40.0 mL). The above mixture was then heated to 50° C. for 1 h. After 1 h, the heating was reduced to rt and stirring was continued for overnight. To the reaction mixture was then added H$_2$O (50 mL) and the organics were concentrated. The remaining aqueous layer was made acidic with 1.0 N HCl solution to precipitate out the solids. The solids were collected by filtration, washed with H$_2$O and dried under vacuum overnight to give the desired product. $^1$H NMR (400 MHz, DMSO-d$_6$) δ 13.68 (br. s., 1H), 8.36 (d, J=1.5 Hz, 1H), 8.25 (dd, J=8.1, 1.3 Hz, 1H), 7.88 (d, J=8.1 Hz, 1H), 6.38 (s, 1H), 4.05-3.89 (m, 4H) ppm.

27C

Methyl (4-(1,3-dioxolan-2-yl)-3-nitrophenyl)carbamate: To a solution of 27B (6.77 g, 28.3 mmol) in THF (100 mL) at −5° C. was added TEA (7.89 mL, 56.6 mmol) in THF (25 mL) dropwise. The temperature was maintained at −5° C., and a solution of ethyl chloroformate (3.25 mL, 34.0 mmol) in THF (30 mL) was added dropwise over 10 minutes. After stirring for an additional 30 minutes, a cold solution of sodium azide (3.68 g, 56.6 mmol) in $H_2O$ (12.5 mL) was added dropwise. After stirring for additional 1 hour, the reaction mixture was concentrated in vacuo (without heating). The oily residue was dissolved in the $Et_2O$ (100 mL), washed with $H_2O$, brine, and dried over sodium sulfate, filtered, and concentrated (without heating) to give the acyl azide. This material was dissolved in toluene (100 mL) and heated to 110° C. After 1 h, the temperature was lowered to 80° C., MeOH (60 mL) was added, and heating was continued for overnight. The reaction mixture was concentrated and purified by silica gel chromatography to yield the desired product (5.01 g, 66%) as an amber solid. $^1H$ NMR (400 MHz, DMSO-$d_6$) δ 10.21 (s, 1H), 8.10 (d, J=1.6 Hz, 1H), 7.74-7.62 (m, 2H), 6.22 (s, 1H), 3.95-3.90 (m, 4H), 3.69 (s, 3H) ppm.

27D

Methyl (4-formyl-3-nitrophenyl)carbamate: 27C (5.00 g, 18.64 mmol) was added to a solution of TFA (27 mL) and $H_2O$ (3 mL) and stirred at rt for 3 h. After 3 h, the reaction mixture was concentrated and the residue was partitioned between $H_2O$ and EtOAc. The organic layer was then washed with saturated sodium bicarbonate solution followed by brine. The organic layer was then dried over sodium sulfate, filtered, and concentrated to give a light yellow solid as the desired product (3.83 g, 92%). $^1H$ NMR (400 MHz, DMSO-$d_6$) δ 10.59 (s, 1H), 10.09 (s, 1H), 8.23 (d, J=1.6 Hz, 1H), 7.92 (d, J=8.2 Hz, 1H), 7.86-7.81 (m, 1H), 3.74 (s, 3H) ppm.

27E (5)-tert-Butyl 1-(dimethoxyphosphoryl)-2-oxohex-5-en-3-ylcarbamate: To a solution of dimethyl methylphosphonate (13.98 mL, 131 mmol) in THF (87 mL) at −78° C. was added n-BuLi (82 mL, 131 mmol) slowly. After completion of addition, the reaction was stirred for 40 min and then a solution of (5)-methyl 2-(tert-butoxycarbonylamino)pent-4-enoate (6.0 g, 26.2 mmol) in THF (30 mL) was added slowly. Stirring was continued for another 40 min at −78° C. The reaction mixture was then quenched by adding $H_2O$ (2.357 mL, 131 mmol). The reaction mixture was diluted with EtOAc (100 mL) and the layers were separated. The organic layer was washed with 1M HCl, saturated $NaHCO_3$ solution followed by brine. The organic phase was then dried over $MgSO_4$, filtered and concentrated to give a clear oil. The crude product was finally purified using silica gel chromatography to give the desired product (7.46 g, 89%) as colorless oil. MS (ESI) m/z: 343.9 (M+Na)$^+$. $^1H$ NMR (500 MHz, CDCl$_3$) δ 5.63-5.76 (1H, m), 5.08-5.17 (2H, m), 4.33-4.43 (1H, m), 3.80 (3H, d, J=2.20 Hz), 3.77 (3H, d, J=2.20 Hz), 3.28-3.37 (1H, m), 3.05-3.16 (1H, m), 2.58-2.69 (1H, m), 2.42 (1H, dt, J=14.58, 7.29 Hz), 1.43 (9H, s) ppm.

27F

Methyl (4-((1E,4S)-4-((tert-butoxycarbonyl)amino)-3-oxohepta-1,6-dien-1-yl)-3-nitrophenyl)carbamate: To a vigorously stirred solution of 27E (4.47 g, 13.92 mmol) and 27D (2.6 g, 11.60 mmol) in THF (anhydrous) (115 mL) and EtOH (absolute) (1.148 mL) under nitrogen was added portion wise $K_2CO_3$ (anhydrous) (2.56 g, 18.56 mmol) at 0° C. The reaction mixture was allowed to raise to rt and then the mixture was heated at 55° C. The reaction mixture was then filtered with the aid of EtOAc and the filtrate evaporated to a residue which was dissolved in a small amount of methylene chloride and purified by normal phase chromatography to give the desired product (4.38 g, 90%) as yellow solid. MS (ESI) m/z: 420.2 (M+H)$^+$. $^1H$ NMR (400 MHz, DMSO-$d_6$) δ 10.36 (s, 1H), 8.22 (d, J=2.2 Hz, 1H), 7.89 (d, J=8.8 Hz, 1H), 7.83-7.73 (m, 2H), 7.21 (d, J=7.7 Hz, 1H), 7.02 (d, J=15.9 Hz, 1H), 5.77 (ddt, J=17.0, 10.2, 6.7 Hz, 1H), 5.16-5.01 (m, 2H), 4.32 (td, J=8.5, 4.9 Hz, 1H), 3.71 (s, 3H), 2.34-2.23 (m, 1H), 1.36 (s, 9H) ppm.

27G

Methyl (4-(6-(1-((tert-butoxycarbonyl)amino)but-3-en-1-yl)-2-oxo-1,2-dihydropyridin-4-yl)-3-nitrophenyl)carbamate: To a solution of 27F (3.0 g, 7.15 mmol) and 1-(2-ethoxy-2-oxoethyl)pyridinium bromide (1.189 g, 7.15 mmol) in EtOH (130 mL), was added ammonium acetate (11.03 g, 143 mmol) portion wise. After 15 min, the mixture was stirred at 75° C. The reaction mixture was then concentrated and dissolved in EtOAc. The organic layer was then washed with 1.0 N HCl, $H_2O$, saturated sodium bicarbonate solution and finally by brine. The organic phase was dried over sodium sulfate, filtered and concentrated to yield a residue which was purified by normal phase chromatography to isolate the desired product (2.2 g, 67%) as a brown solid. MS (ESI) m/z: 459.3 (M+H)$^+$.

27H

Methyl N-(4-{2-[(1S)-1-{[(tert-butoxy)carbonyl]amino}but-3-en-1-yl]-6-methoxypyridin-4-yl}-3-nitrophenyl)carbamate: To a stirred solution of 27G (3.0 g, 6.54 mmol) in chloroform (131 mL) under an argon atmosphere was added silver (I) carbonate (50% on CELITE®) (3.61 g, 6.54 mmol) and iodomethane (1.22 mL, 19.63 mmol), respectively. The reaction mixture was heated at 65° C. After stirring for 14 hours, the reaction was filtered, concentrated, and purified by normal phase chromatography to give 27H (2.69 grams, 87%) as a tan solid. MS (ESI) m/z: 473 (M+H)$^+$.

27I

Methyl N-(3-amino-4-{2-[(1S)-1-{[(tert-butoxy)carbonyl]amino}but-3-en-1-yl]-6-methoxy-pyridin-4-yl}phenyl)carbamate: 27H (2.69 g, 5.69 mmol) in MeOH (60 ml) was treated with zinc powder (3.86 g, 59.0 mmol) and ammonium chloride (0.632 g, 11.81 mmol) and heated at 65° C. overnight. The suspension was filtered hot through a plug of CELITE® and concentrated. This residue was re-dissolved in EtOAc (with 10% MeOH), washed with saturated sodium bicarbonate solution, brine, dried over sodium sulfate, filtered, and concentrated to give the desired product. MS (ESI) m/z: 443 (M+H)$^+$.

27J

Methyl N-(4-{2-[(1S)-1-{[(tert-butoxy)carbonyl]amino}but-3-en-1-yl]-6-methoxypyridin-4-yl}-3-(2-methylbut-3-enamido)phenyl)carbamate: DIPEA (3.02 mL, 17.29 mmol) was added to a solution of 2-methylbut-3-enoic acid (0.865 g, 8.64 mmol) and 27I (2.55 g, 5.76 mmol) in EtOAc (57.6 ml) at −10° C. under argon. Next, 1-propanephosphonic acid cyclic anhydride (6.79 ml, 11.53 mmol; 50% solution in EtOAc) was added dropwise and the reaction stirred for 1 h under set conditions and then allowed to come to rt. After 48

161 hours, the reaction was diluted with EtOAc, washed with saturated NaHCO$_3$, brine, dried over Na$_2$SO$_4$, filtered, and concentrated. Purification by normal phase chromatography gave the desired product (2.52 g, 83%) as a white solid. MS (ESI) m/z: 525.1 (M+H)$^+$.

27K tert-Butyl N-[(14S)-17-methoxy-5-[(methoxycarbonyl)amino]-10-methyl-9-oxo-8,16-diazatricyclo[13.3.1.0$^{2,7}$]nonadeca-1(19),2,4,6,15,17-hexaen-14-yl]carbamate: A solution of 27J (1.50 g, 2.86 mmol) and Ts-OH (0.598 g, 3.15 mmol) in DCM (337 mL) was heated for 0.5 h. The solution was cooled down to room temperature and bubbled with argon for 0.5 h. To the solution was added tricyclohexylphosphine[1,3-bis(2,4,6-trimethylphenyl)-4,5-dihydroimidazol-2-ylidene][benzylidine]ruthenium(IV)dichloride (0.728 g, 0.858 mmol) and the resulting solution bubbled with argon for additional 0.5 h before heating at 45° C. for 12 hours. The reaction mixture was washed with aqueous saturated NaHCO$_3$ solution. Aqueous layer was further extracted with DCM (2×30 mL). The combined organic extract was dried over Na$_2$SO$_4$, concentrated, and purified by normal phase chromatography. The olefin double bond was reduced by dissolution in EtOH (50 mL), treatment with platinum oxide (0.065 gram, 0.286 mmol), and subjected to a hydrogen atmosphere (55 psi) overnight. The catalyst was filtered off through a plug of CELITE® and the filtrate concentrated to give the desired product (720 mg, 51%) as a diastereomer mixture.

27L1 tert-Butyl N-[(10S,14S)-17-methoxy-5-[(methoxycarbonyl)amino]-10-methyl-9-oxo-8,16-diazatricyclo[13.3.1.0$^{2,7}$]nonadeca-1(19),2,4,6,15,17-hexaen-14-yl]carbamate and 27L2. tert-butyl N-[(10R,14S)-17-methoxy-5-[(methoxycarbonyl)amino]-10-methyl-9-oxo-8,16-diazatricyclo-[13.3.1.0$^{2,7}$]nonadeca-1(19),2,4,6,15,17-hexaen-14-yl]carbamate: Diastereomeric mixture 27K (720 mg, 1.44 mmol) was subjected to chiral SFC separation using Chiral AD-H 30×250 mm column, with a mixture of 30% EtOH and 70% CO$_2$ with a flow rate of 85 mL/min and 100 bar at 40° C. Peak 1 was designated as enantiomer A (27L1; 280 mg, 74%) and peak 2 was designated as enantiomer B (27L2; 360 mg, 100%). MS (ESI) m/z: 499.1 (M+H)$^+$ for both enantiomers.

Example 27

Methyl N-[(10R,14S)-14-[(6R)-6-(3-chloro-2,6-difluorophenyl)-2-oxo-1,3-oxazinan-3-yl]-17-methoxy-10-methyl-9-oxo-8,16-diazatricyclo[13.3.1.0$^{2,7}$]nonadeca-1(18),2,4,6,15(19),16-hexaen-5-yl]carbamate: Example 27 was prepared in the same way as Example 12 by replacing 12M with 27L2. $^1$H NMR (400 MHz, MeOD) δ 7.56 (td, J=8.7, 5.5 Hz, 1H), 7.51-7.44 (m, 3H), 7.10 (d, J=0.8 Hz, 1H), 7.09-7.04 (m, 1H), 6.76 (d, J=1.1 Hz, 1H), 5.82 (dd, J=11.4, 2.9 Hz, 1H), 5.34 (dd, J=12.4, 5.0 Hz, 1H), 4.53 (d, J=7.2 Hz, 1H), 3.93 (s, 3H), 3.78 (s, 3H), 3.72 (td, J=11.8, 4.0 Hz, 1H), 2.70-2.63 (m, 1H), 2.54 (qd, J=12.3, 5.0 Hz, 1H), 2.36-2.30 (m, 1H), 2.23-2.14 (m, 1H), 2.00-1.84 (m, 2H), 1.53-1.41 (m, 2H), 1.00 (d, J=7.2 Hz, 3H), 0.72 (br. s., 1H) ppm. MS (ESI) m/z: 628.9 (M+H)$^+$. Analytical HPLC RT=9.70 min (Method A).

Example 28

Methyl N-[(10R,14S)-14-[6-(3-chloro-2,6-difluorophenyl)-2-oxo-1,3-oxazinan-3-yl]-10-methyl-9-oxo-8,17-diazatricyclo[13.3.1.0$^{2,7}$]nonadeca-1(19),2,4,6,15,17-hexaen-5-yl]carbamate, TFA salt

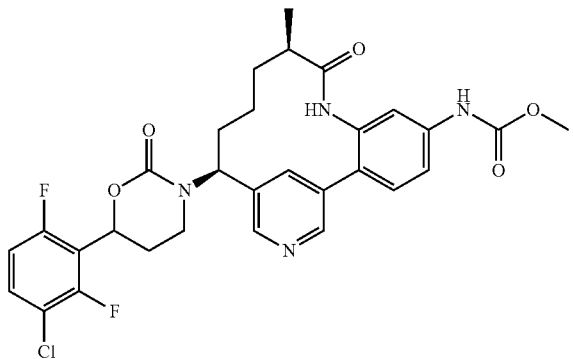 [SMILES: COC(=O)Nc1ccc2c(c1)NC(=O)[C@H](C)CCC[C@H](N1CCC(c3c(F)ccc(Cl)c3F)OC1=O)c1cncc-2c1]

Example 28

Methyl N-[(10R,14S)-14-[6-(3-chloro-2,6-difluorophenyl)-2-oxo-1,3-oxazinan-3-yl]-10-methyl-9-oxo-8,17-diazatricyclo[13.3.1.0$^{2,7}$]nonadeca-1(19),2,4,6,15,17-hexaen-5-yl]carbamate, TFA salt: Example 28 was prepared in the same way as Example 12 by replacing 4-chloropicolinaldehyde with 5-bromonicotinaldehyde 2-bromoisonicotinaldehyde in step 12A. Diastereomer A, the early eluting isomer was used to give Example 28 as a homochiral compound. $^1$H NMR (400 MHz, MeOD) δ 8.87 (s, 2H), 8.59 (s, 1H), 7.70-7.46 (m, 4H), 7.06 (td, J=9.6, 1.6 Hz, 1H), 5.79 (dd, J=11.0, 2.7 Hz, 1H), 5.35 (dd, J=12.6, 3.8 Hz, 1H), 3.77 (s, 3H), 3.67 (td, J=11.5, 4.4 Hz, 1H), 3.53-3.39 (m, 1H), 2.55-2.33 (m, 2H), 2.33-2.09 (m, 3H), 1.82 (dd, J=9.6, 6.3 Hz, 1H), 1.67-1.43 (m, 2H), 1.14 (d, J=6.6 Hz, 3H), 0.96 (m, 1H) ppm. MS (ESI) m/z: 600.3 (M+H)$^+$. Analytical HPLC RT=6.13 min (Method A).

Example 29

2-Methoxyethyl N-[(10R,14S)-14-[(6R)-6-(3-chloro-2,6-difluorophenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt

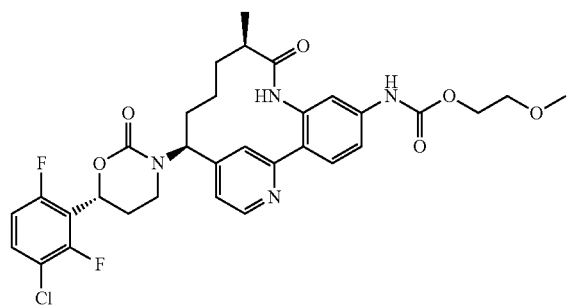 [SMILES: COCCOC(=O)Nc1ccc2c(c1)NC(=O)[C@H](C)CCC[C@H](N1CC[C@H](c3c(F)ccc(Cl)c3F)OC1=O)c1ccnc-2c1]

Example 29

2-Methoxyethyl N-[(10R,14S)-14-[(6R)-6-(3-chloro-2,6-difluorophenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt: Example 29 was prepared in the same way as Example 12 by replacing 4-chloropicolinaldehyde with 2-bromoisonicotinaldehyde in step 12A and replacing methyl chlorocarbonate with 2-methoxyethyl carbonochloridate in step 12F. $^1$H NMR (400 MHz, acetonitrile-d$_3$) δ 8.61 (d, J=5.50 Hz, 1H), 8.04 (s, 1H), 7.89 (s, 1H), 7.66 (s, 1H), 7.65 (s, 1H), 7.33-7.46 (m, 4H), 6.86-7.01 (m, 1H), 5.59 (dd, J=2.61, 11.42 Hz, 1H), 5.17 (dd, J=4.26, 12.24 Hz, 1H), 4.17 (dd, J=3.99, 5.09 Hz, 2H), 3.51 (dd, J=3.85, 5.23 Hz, 2H), 3.41 (dt, J=4.54, 11.76 Hz, 1H), 3.25 (s, 3H), 3.19 (dd, J=2.75, 11.83 Hz, 1H), 2.17-2.36 (m, 4H), 1.91-2.12 (m, 3H), 1.66-1.76 (m, 1H), 1.41 (d, J=6.33 Hz, 1H), 1.24-1.31 (m, 1H), 1.09-1.06 (m, 1H), 0.97 (d, J=6.88 Hz, 3H) ppm. MS (ESI) m/z: 642.9 (M+H)$^+$. Analytical HPLC RT=6.03 min (Method A).

Example 30

Methyl N-[(10R)-14-[(6R)-6-(3-chloro-2,6-difluorophenyl)-2-oxo-1,3-oxazinan-3-yl]-16-methoxy-10-methyl-9-oxo-8,17-diazatricyclo[13.3.1.0$^{2,7}$]nonadeca-1(19),2,4,6,15,17-hexaen-5-yl]carbamate, TFA salt

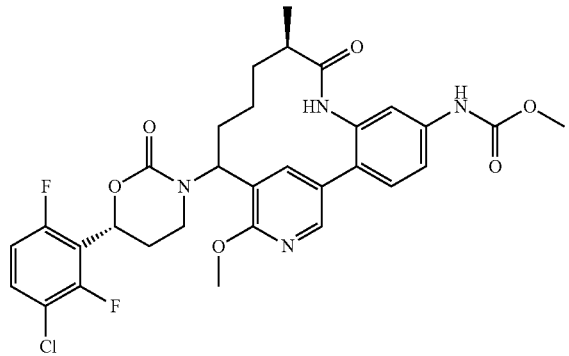 [SMILES: COC(=O)Nc1ccc2c(c1)NC(=O)[C@H](C)CCCC(N1CC[C@H](c3c(F)ccc(Cl)c3F)OC1=O)c1cc-2cnc1OC]

30A

N-(1-(5-Bromo-2-methoxypyridin-3-yl)but-3-en-1-yl)-2-methylpropane-2-sulfinamide: 30A was prepared in the same way as 12B by replacing 4-chloropicolinaldehyde with 5-bromo-2-methoxynicotinaldehyde and using t-butyl-sulfinamide instead of S-t-butyl-sulfinamide in step 12A. MS (ESI) m/z: 363.0 (M+H)$^+$.

30B tert-Butyl (1-(5-bromo-2-methoxypyridin-3-yl)but-3-en-1-yl)carbamate: To a solution of 30A (5.4 g, 14.95 mmol) in MeOH (24.91 mL) was added HCl (4.0 M in dioxane) (18.68 mL, 74.7 mmol). After 1 h, the deprotection was complete. The reaction mixture was concentrated to dryness in vacuo to give the amine HCl salt as a white solid. The amine HCl salt was taken up in acetonitrile (24.91 mL) and treated with TEA (20.83 mL, 149 mmol) followed by di-t-butyldicarbonate (6.52 g, 29.9 mmol). The reaction mixture was partitioned between EtOAc and sodium bicarbonate solution. The organic layer was separated, washed with brine followed by water, dried over sodium sulfate, filtered, and concentrated. The crude material was purified by silica gel chromatography to give the desired product (5.15 g, 96%) as a white solid. MS (ESI) m/z: 359.0 (M+H)$^+$.

30C tert-Butyl (1-(5-(2-amino-4-nitrophenyl)-2-methoxypyridin-3-yl)but-3-en-1-yl)carbamate (enantiomer A, peak 1) and 30D, tert-butyl (1-(5-(2-amino-4-nitrophenyl)-2-methoxypyridin-3-yl)but-3-en-1-yl)carbamate (enantiomer B, peak 2): A stirring suspension of 30B (3.0 g, 8.40 mmol), Intermediate 22 (2.52 g, 10.08 mmol), and Cs$_2$CO$_3$ (8.21 g, 25.2 mmol) in 1,2-dimethoxyethane (12 mL)/water (2.4 mL) was degassed with a stream of argon for 15 minutes. Tetrakis(triphenylphosphine)palladium(0) (0.970 g, 0.840 mmol) was added and the mixture irradiated at 120° C. for 20 minutes. The reaction mixtures were diluted with EtOAc (200 mL) and washed with water followed by brine. The organics were dried over MgSO$_4$, filtered, concentrated in vacuo. The crude material was purified by silica gel chromatography to give tert-butyl (1-(5-(2-amino-4-nitrophenyl)-2-methoxypyridin-3-yl)but-3-en-1-yl)carbamate as racemate. MS (ESI) m/z: 415.2 (M+H)$^+$. $^1$H NMR (400 MHz, DMSO-d$_6$) δ 8.13 (d, J=2.2 Hz, 1H), 7.76 (d, J=2.2 Hz, 1H), 7.62 (d, J=2.2 Hz, 1H), 7.47-7.42 (m, 1H), 7.39-7.34 (m, 1H), 7.19 (d, J=8.2 Hz, 1H), 5.77 (ddt, J=17.0, 10.2, 6.7 Hz, 1H), 5.10-4.98 (m, 2H), 4.88 (td, J=8.8, 4.9 Hz, 1H), 3.94 (s, 3H), 2.44-2.36 (m, 1H), 2.35-2.24 (m, 1H), 1.35 (s, 9H) ppm. The racemate was subjected to chiral HPLC separation to give 30C (enantiomer A, peak 1) and 30D (enantiomer B, peak 2).

30E tert-Butyl N-[1-(5-{2-amino-4-[(methoxycarbonyl)amino]phenyl}-2-methoxypyridin-3-yl)but-3-en-1-yl]carbamate: Zinc (0.860 g, 13.15 mmol) and NH$_4$Cl (0.352 g, 6.57 mmol) were added to a stirring solution of 30D (enantiomer B) (0.545 g, 1.315 mmol) MeOH (20 mL) and the reaction was stirred at rt overnight. The reaction was filtered through a plug of CELITE® and the filtrate was concentrated. The residue was taken up in DCM (13.15 mL) and added pyridine (0.106 ml, 1.315 mmol). The mixture was cooled to −78° C. under argon, and a solution of methyl chlorocarbonate (0.112 g, 1.183 mmol) in DCM (2 mL) was added dropwise over 10 minutes. After stirring for 1.5 h, the reaction mixture was quenched with saturated NH$_4$Cl solution. The mixture was diluted with EtOAc, washed with saturated NaHCO$_3$, brine, dried over sodium sulfate, filtered, and concentrated. The crude material was purified by silica gel chromatography to yield the desired product (0.442 g, 76%) as a white solid. $^1$H NMR (400 MHz, DMSO-d$_6$) δ 9.44 (s, 1H), 8.02 (d, J=2.3 Hz, 1H), 7.69 (d, J=2.0 Hz, 1H), 7.35 (d, J=8.6 Hz, 1H), 6.97 (d, J=2.0 Hz, 1H), 6.86 (d, J=8.3 Hz, 1H), 6.73 (dd, J=8.3, 2.0 Hz, 1H), 5.10-4.99 (m, 2H), 4.90-4.77 (m, 3H), 3.93 (s, 3H), 3.66 (s, 3H), 2.45-2.37 (m, 1H), 2.35-2.26 (m, 1H), 1.36 (s, 9H) ppm.

30F tert-Butyl N-[1-(2-methoxy-5-{4-[(methoxycarbonyl)amino]-2-[(2R)-2-methylbut-3-enamido]phenyl}pyridin-3-yl)but-3-en-1-yl]carbamate (from enantiomer B): Hunig's base (0.521 ml, 2.98 mmol) was added to a solution of (R)-2-methylbut-3-enoic acid (0.119 g, 1.193 mmol) and 30E (0.44 g, 0.994 mmol) in ethyl acetate (9.94 mL) and the reaction was allowed to cool to 0° C. under argon. Next, 1-propanephosphonic acid cyclic anhydride (50 wt % in EtOAc) (1.172 mL, 1.989 mmol) was added and the reaction was allowed warmed to rt overnight. The reaction was quenched with brine and extracted with EtOAc. The organic layer was dried over MgSO$_4$, filtered and concentrated. The residue was purified by silica gel chromatography to give the desired product (302 mg, 58%) as white foam. MS (ESI) m/z: 525.2 (M+H)$^+$.

Example 30

Methyl N-[(10R)-14-[(6R)-6-(3-chloro-2,6-difluorophenyl)-2-oxo-1,3-oxazinan-3-yl]-16-methoxy-10-methyl-9-oxo-8,17-diazatricyclo[13.3.1.0$^{2,7}$]nonadeca-1(19),2,4,6,15,17-hexaen-5-yl]carbamate, TFA salt (homochiral from enantiomer B): Example 30 was prepared in the same way as Example 12 by replacing 121 with 30F. $^1$H NMR (500 MHz, MeOD) δ 8.06 (d, J=2.2 Hz, 1H), 7.75 (d, J=2.2 Hz, 1H), 7.47-7.32 (m, 5H), 6.94 (td, J=9.4, 1.7 Hz, 1H), 5.65 (dd, J=10.5, 4.4 Hz, 1H), 5.23 (dd, J=13.1, 2.9 Hz, 1H), 3.92-3.89 (m, 3H), 3.65 (s, 3H), 2.32-2.24 (m, 1H), 2.12-1.99 (m, 4H), 1.95-1.85 (m, 2H), 1.75-1.55 (m, 3H), 1.54-1.45 (m, 2H), 1.11-1.06 (m, 3H) ppm. MS (ESI) m/z: 629.1 (M+H)$^+$. Analytical HPLC RT=10.33 min (Method A).

Example 31

Methyl N-[(10R)-14-[(6R)-6-(3-chloro-2,6-difluorophenyl)-2-oxo-1,3-oxazinan-3-yl]-10-methyl-9,16-dioxo-8,17-diazatricyclo[13.3.1.0$^{2,7}$]nonadeca-1(18),2,4,6,15(19)-pentaen-5-yl]carbamate

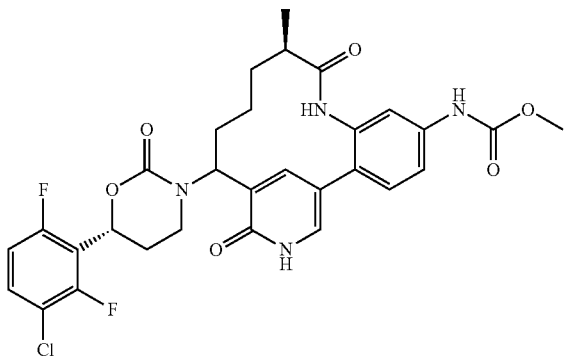 [SMILES: COC(=O)Nc1ccc2c(c1)NC(=O)[C@H](C)CCCC(N1CC[C@H](c3c(F)ccc(Cl)c3F)OC1=O)c1cc-2c[nH]c1=O]

Example 31

Methyl N-[(10R)-14-[(6R)-6-(3-chloro-2,6-difluorophenyl)-2-oxo-1,3-oxazinan-3-yl]-10-methyl-9,16-dioxo-8,17-diazatricyclo[13.3.1.0$^{2,7}$]nonadeca-1(18),2,4,6,15(19)-pentaen-5-yl]carbamate (homochiral): HCl (conc.) (0.063 mL, 0.763 mmol) was added to a suspension of Example 30 (0.008 g, 0.013 mmol) in water (0.50 mL) and the mixture was heated to 100° C. for 1 h. The reaction mixture was concentrated and purified by reverse phase HPLC to yield the desired product (1.9 mg, 22%) as a white solid. $^1$H NMR (400 MHz, MeOD) δ 7.79 (d, J=2.2 Hz, 1H), 7.55 (dd, J=8.2, 5.5 Hz, 1H), 7.50-7.46 (m, 2H), 7.44-7.39 (m, 2H), 7.05 (dd, J=9.3, 7.7 Hz, 1H), 5.71 (dd, J=11.8, 3.0 Hz, 1H), 4.98 (dd, J=13.5, 3.0 Hz, 1H), 3.75 (s, 3H), 3.56-3.48 (m, 2H), 2.54-2.39 (m, 3H), 2.32-2.13 (m, 3H), 1.98-1.93 (m, J=12.1 Hz, 1H), 1.82 (dd, J=8.8, 5.5 Hz, 1H), 1.64-1.55 (m, 2H), 1.16 (d, J=6.6 Hz, 2H) ppm. MS (ESI) m/z: 615.2 (M+H)$^+$. Analytical HPLC RT=5.68 min (Method B).

Example 32

Methyl N-[(12E,15S)-18-chloro-15-[6-(3-chloro-2,6-difluorophenyl)-6-methyl-2-oxo-1,3-oxazinan-3-yl]-9-oxo-8,17,19-triazatricyclo[14.2.1.0$^{2,7}$]nonadeca-1(18),2,4,6,12,16(19)-hexaen-5-yl]carbamate, TFA salt

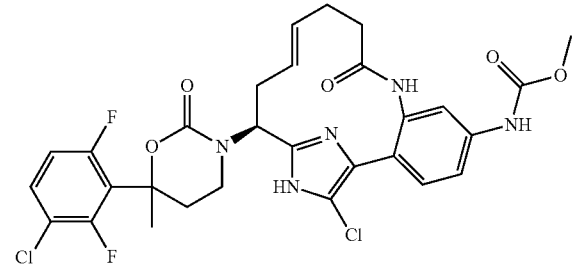 [SMILES: COC(=O)Nc1ccc2c(c1)NC(=O)CC/C=C/C[C@H](N1CCC(C)(c3c(F)ccc(Cl)c3F)OC1=O)c1nc-2c(Cl)[nH]1]

32A

Methyl N-[(12E,15S)-18-chloro-15-{[3-(3-chloro-2,6-difluorophenyl)-3-oxopropyl]amino}-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: A solution of Intermediate 2C (5.95 mg, 0.018 mmol) and 6B (33 mg, 0.063 mmol) in ACN (2 mL) was stirred for 1 h at rt. The reaction mixture was diluted with EtOAc (20 mL) and washed with aq. NaHCO$_3$ followed by brine (10 mL). The organic layer was then concentrated in vacuo, yielding an oily mixture, which was purified by silica gel chromatography to yield the desired product (18 mg, 39%). MS (ESI) m/z: 722.1 (M+H)$^+$.

32B

Methyl N-[(12E,15S)-18-chloro-15-{[3-(3-chloro-2,6-difluorophenyl)-3-hydroxybutyl]amino}-9-oxo-17-{[2-(trimethylsilyl)ethoxy]methyl}-8,17,19-triazatricyclo[14.2.1.0$^{2,7}$]nonadeca-1(18),2,4,6,12,16(19)-hexaen-5-yl]carbamate: To a solution of 32A (18 mg, 0.025 mmol) in THF at −78° C. was added 1 M methyl magnesium chloride in THF (49.8 µL, 0.050 mmol) in one portion and the resulting solution was stirred for 1 h at −78° C. and 1 h at rt. The reaction was quenched by adding drops of aq. NaHCO$_3$ into the solution. The mixture was diluted with EtOAc (20 mL) and washed with brine (2×10 mL). The organic solution was dried over Na$_2$SO$_4$ and concentrated in vacuo, yielding an oil (18 mg, 98%), which was subjected to the next reaction without further purification. MS (ESI) m/z: 738.1 (M+H)$^+$.

Example 32

Methyl N-[(12E,15S)-18-chloro-15-[6-(3-chloro-2,6-difluorophenyl)-6-methyl-2-oxo-1,3-oxazinan-3-yl]-9-oxo-8,17,19-triazatricyclo[14.2.1.0$^{2,7}$]nonadeca-1(18),2,4,6,12,16(19)-hexaen-5-yl]carbamate, TFA salt: To a solution of 32B (18.47 mg, 0.025 mmol) in DCM (2 mL) and DIEA (8.73 µL, 0.050 mmol) was added triphosgene (8.90 mg, 0.030 mmol)

and the resulting solution was stirred at ambient temp for 12 h. The reaction mixture was concentrated in vacuo, yielding oily residue, which was re-dissolved in acetonitrile (2.000 mL) and treated with $K_2CO_3$ (3.46 mg, 0.025 mmol). The reaction was stirred at 80° C. for 3 h. Separation of the reaction mixture in prep HPLC provided the desired product (2.7 mg, 13%) as a white solid. $^1$H NMR (400 MHz, MeOD) δ 7.44-7.37 (m, 3H), 7.33 (td, J=8.4, 5.5 Hz, 1H), 6.85 (t, J=9.5 Hz, 1H), 5.30-5.19 (m, 1H), 5.06 (dt, J=15.4, 7.6 Hz, 1H), 4.76 (t, J=3.3 Hz, 1H), 3.88 (dt, J=15.0, 7.7 Hz, 1H), 3.75 (s, 3H), 2.69-2.59 (m, 1H), 2.57-2.50 (m, 1H), 2.50-2.40 (m, 1H), 2.29-2.22 (m, 2H), 2.22-2.11 (m, 2H), 2.11-2.01 (m, 1H), 1.69 (s, 3H), 1.65 (m, 1H) ppm. MS (ESI) m/z: 634.0 (M+H)$^+$. Analytical HPLC RT=7.64 min (Method B).

Example 33

Methyl N-[(10R,14S)-14-[(6S)-6-(3,6-dicyano-2-fluorophenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt

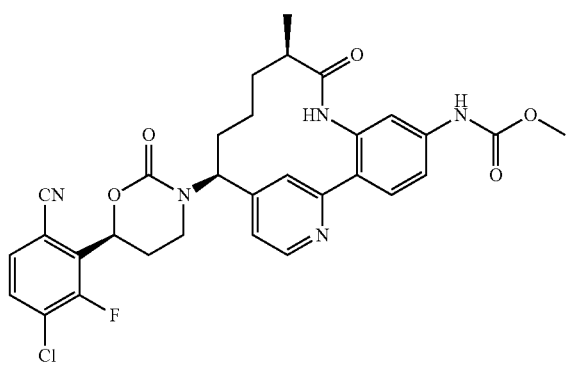 [SMILES: COC(=O)Nc1ccc2c(c1)NC(=O)[C@H](C)CCC[C@H](N1CC[C@@H](c3c(C#N)ccc(Cl)c3F)OC1=O)c1ccnc-2c1]

Example 33

Methyl N-[(10R,14S)-14-[(6S)-6-(3,6-dicyano-2-fluorophenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt: To Example 138 (4.8 mg, 7.27 mmol) in a microwave tube was added dicyanozinc (1.708 mg, 0.015 mmol), zinc (0.143 mg, 2.182 µmol), DMF (0.5 mL). The mixture was bubbled through Ar for several minutes. Bis(tri-t-butylphosphine)palladium(0) (0.372 mg, 0.727 µmol) was added. The reaction was sealed and heated at 80° C. overnight. The reaction was diluted with EtOAc, washed with saturated NaHCO$_3$, H$_2$O, brine, dried over MgSO$_4$, filtered and concentrated. Purification using reverse phase HPLC yield the title compound as an off white solid. $^1$H NMR (500 MHz, acetonitrile-d$_3$) δ 8.78 (d, J=6.1 Hz, 1H), 8.31 (s, 1H), 8.08 (s, 1H), 7.95 (d, J=1.4 Hz, 1H), 7.89 (dd, J=8.1, 6.2 Hz, 1H), 7.78-7.74 (m, 1H), 7.73-7.68 (m, 2H), 7.57 (d, J=1.9 Hz, 1H), 7.48 (dd, J=8.5, 2.2 Hz, 1H), 5.81 (dd, J=11.7, 3.2 Hz, 1H), 5.26 (dd, J=11.3, 5.2 Hz, 1H), 3.74 (s, 3H), 3.68-3.58 (m, 2H), 3.54-3.45 (m, 1H), 2.48-2.31 (m, 2H), 2.29-2.20 (m, 1H), 2.16-2.04 (m, 2H), 1.84-1.71 (m, 1H), 1.47 (td, J=14.9, 6.7 Hz, 1H), 1.21 (br. s., 2H), 1.02 (d, J=6.9 Hz, 3H) ppm. MS (ESI) m/z: 597.0 (M+H)$^+$. Analytical HPLC RT=5.21 min (Method B).

Example 34

Methyl N-[(10R,14S)-14-[6-(3-chloro-2-fluoro-6-hydroxyphenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt

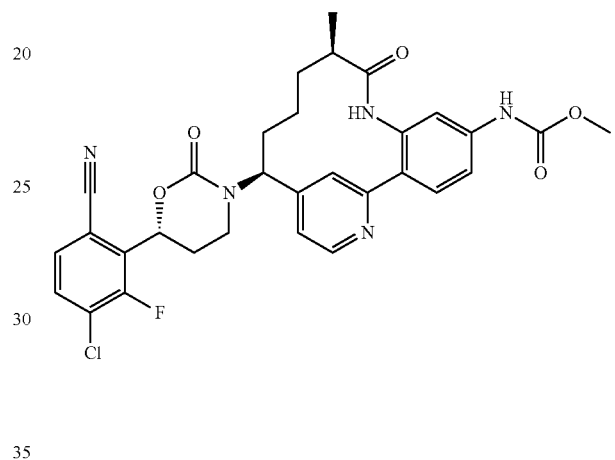

Example 34

Methyl N-[(10R,14S)-14-[6-(3-chloro-2-fluoro-6-hydroxyphenyl)-2-oxo-1,3-oxazinan-3-yl]-10-methyl-9-oxo-8,18-diazatricyclo[13.3.1.0$^{2,7}$]nonadeca-1(19),2(7),3,5,15,17-hexaen-5-yl]carbamate, TFA salt: To Example 139 (4.5 mg, 6.82 µmol) in a microwave tube was added dicyanozinc (1.601 mg, 0.014 mmol), zinc (0.134 mg, 2.046 µmol), and DMF (0.5 mL). The mixture was bubbled through Ar for several minutes. Bis(tri-t-butylphosphine)palladium(0) (0.348 mg, 0.682 µmol) was added. The reaction was sealed and heated at 80° C. overnight. The reaction was quenched with saturated NH$_4$Cl and diluted with saturated NaHCO$_3$/EtOAc. The layers were separated and the aqueous phase was extracted with EtOAc (3×). The combined organic layer was washed with brine, dried with sodium sulfate, filtered and concentrated. Purification using reverse HPLC yield the title compound (1.6 mg, 31%) as a white solid. $^1$H NMR (500 MHz, acetonitrile-d$_3$) δ 8.79 (d, J=5.8 Hz, 1H), 8.25 (s, 1H), 8.05 (s, 1H), 7.90 (s, 1H), 7.73 (d, J=8.5 Hz, 1H), 7.70-7.58 (m, 2H), 7.55 (d, J=1.9 Hz, 1H), 7.48 (dd, J=8.5, 2.2 Hz, 1H), 5.76 (dd, J=11.4, 3.2 Hz, 1H), 5.22 (dd, J=12.2, 4.5 Hz, 1H), 3.74 (s, 3H), 3.60-3.49 (m, 2H), 3.40 (td, J=11.7, 4.1 Hz, 2H), 2.49-2.34 (m, 1H), 2.24 (d, J=9.9 Hz, 1H), 2.17-2.08 (m, 1H), 2.06-1.95 (m, 2H), 1.84-1.74 (m, 1H), 1.55-1.46 (m, 1H), 1.18 (br. s., 1H), 1.01 (d, J=6.6 Hz, 3H) ppm. MS (ESI) m/z: 606.0 (M+H)$^+$. Analytical HPLC RT=5.79 min (Method B).

Example 35

Methyl N-[(10R,14S)-14-[4-(3-chloro-2,6-difluorophenyl)-2,3-dioxopiperazin-1-yl]-10-methyl-9-oxo-8,16-diazatricyclo[13.3.1.0²,⁷]nonadeca-1(19),2(7),3,5,15,17-hexaen-5-yl]carbamate, TFA salt

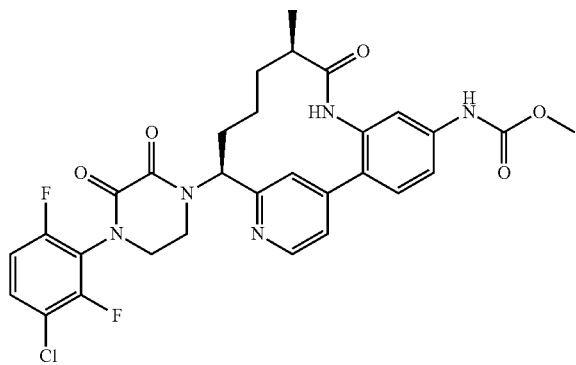 [SMILES: COC(=O)Nc1ccc2c(c1)NC(=O)[C@H](C)CCC[C@H](N1CCN(c3c(F)ccc(Cl)c3F)C(=O)C1=O)c1cc-2ccn1]

35A

Ethyl [(3-chloro-2,6-difluorophenyl)carbamoyl]formate: To a solution of 3-chloro-2,6-difluoroaniline (430 mg, 2.55 mmol) and TEA (0.5 mL, 3.59 mmol) in THF (5 mL) was added ethyl 2-chloro-2-oxoacetate (0.3 mL, 2.63 mmol). A white precipitate was formed immediately. After 30 min, the reaction mixture was filtered and rinsed with ether. The filtrate was concentrated to yield a crude yellow oil, which was purified by silica gel chromatography to yield the desired product (484 mg, 72%) as a white solid. $^1$H NMR (500 MHz, CDCl$_3$) δ 8.42 (br. s., 1H), 7.35 (m, 1H), 6.98 (m, 1H), 4.45 (q, J=7.2 Hz, 2H), 1.45 (t, J=7.2 Hz, 3H). MS (ESI) m/z: 263.9 (M+H)$^+$.

35B

Ethyl [(3-chloro-2,6-difluorophenyl)(prop-2-en-1-yl)carbamoyl]formate: 35A (484 mg, 1.836 mmol) in THF (5 mL) was cooled to 0° C. under Ar. Sodium hydride (60% in mineral oil) (81 mg, 2.020 mmol) was added portion wise to give a white turbid solution with lots of air bubbles. The reaction was warmed to rt for 1 h before cooled to 0° C. and added 3-bromoprop-1-ene (0.181 mL, 2.020 mmol). The reaction was warmed to rt and stirred for 24 h. The reaction mixture was poured onto ice and extracted with EtOAc twice. The combined EtOAc phase was washed with brine, dried over MgSO$_4$, filtered, concentrated. The residue purified by silica gel chromatography to yield desired product (381 mg, 68%) as a colorless oil. $^1$H NMR (500 MHz, CDCl$_3$) δ 7.46-7.36 (m, 1H), 7.02-6.92 (m, 1H), 5.94-5.75 (m, 1H), 5.25-5.11 (m, 2H), 4.48-4.30 (m, 2H), 4.29-4.05 (m, 2H), 1.47-1.07 (m, 3H). MS (ESI) m/z: 303.9 (M+H)$^+$.

35C

Ethyl [(3-chloro-2,6-difluorophenyl)(2-oxoethyl)carbamoyl]formate: To a solution of 35B (240 mg, 0.790 mmol) in dioxane (6 mL) and water (2 mL) was added 2,6-lutidine (0.184 mL, 1.581 mmol), osmium tetroxide (0.02 M in tBuOH) (0.790 mL, 0.016 mmol), followed by sodium periodate (676 mg, 3.16 mmol). The reaction was stirred at rt for 3 h and then diluted with DCM and water. The layers were separated and the organic phase was washed with brine, dried over MgSO$_4$, filtered, and concentrated to yield the crude product. MS (ESI) m/z: 305.9 (M+H)$^+$.

Example 35

Methyl N-[(10R,14S)-14-[4-(3-chloro-2,6-difluorophenyl)-2,3-dioxopiperazin-1-yl]-10-methyl-9-oxo-8,16-diazatricyclo[13.3.1.0²,⁷]nonadeca-1(19),2(7),3,5,15,17-hexaen-5-yl]carbamate, TFA salt: To a solution of 12M (7 mg, 0.019 mmol) in ClCH$_2$CH$_2$Cl (2 mL) was added sodium triacetoxyborohydride (6.04 mg, 0.028 mmol), AcOH (1.088 μL, 0.019 mmol), 4 Å molecular sieve (10 mg, 0.019 mmol). The mixture was cooled to 0° C., and a solution of 35B (6.97 mg, 0.023 mmol) in 0.5 mL DCE was added. After 5 min, the reaction was warmed to rt. After 3 h, the reaction mixture was filtered. The filtrate was concentrated and purified by reverse phase HPLC to yield desired product (3.3 mg, 22%) as a pale yellow solid. $^1$H NMR (500 MHz, MeOD) δ 8.68 (dd, J=5.4, 2.6 Hz, 1H), 7.83 (s, 1H), 7.64-7.55 (m, 3H), 7.54-7.48 (m, 2H), 7.22-7.14 (m, 1H), 5.56 (dd, J=12.5, 4.5 Hz, 1H), 4.13 (br. s., 1H), 4.06-3.96 (m, 2H), 3.95-3.88 (m, 1H), 3.77 (s, 3H), 2.63 (dd, J=6.6, 5.5 Hz, 1H), 2.24-2.14 (m, 1H), 2.03 (dt, J=12.0, 5.9 Hz, 1H), 1.93 (td, J=8.7, 3.2 Hz, 1H), 1.56 (td, J=14.7, 8.0 Hz, 1H), 1.34 (br. s., 1H), 1.03 (d, J=6.9 Hz, 3H), 0.91 (dd, J=13.1, 7.0 Hz, 1H). MS (ESI) m/z: 612.1 (M+H)$^+$.

Example 36

Methyl N-[(10R)-14-{4-[3-chloro-2-fluoro-6-(trifluoromethyl)phenyl]-2,5-dioxopiperazin-1-yl}-10-methyl-9-oxo-8,16-diazatricyclo[13.3.1.0²,⁷]nonadeca-1(19),2(7),3,5,15,17-hexaen-5-yl]carbamate, TFA salt

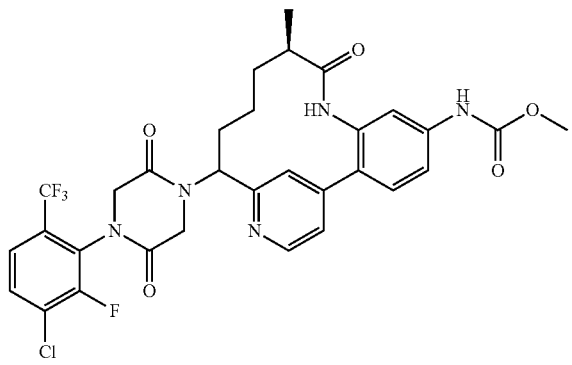 [SMILES: COC(=O)Nc1ccc2c(c1)NC(=O)[C@H](C)CCCC(N1CC(=O)N(c3c(C(F)(F)F)ccc(Cl)c3F)CC1=O)c1cc-2ccn1]

36A

2-Chloro-N-[3-chloro-2-fluoro-6-(trifluoromethyl)phenyl]acetamide: To a solution of 3-chloro-2-fluoro-6-(trifluoromethyl)aniline (250 mg, 1.136 mmol) in THF (2 mL) was added K$_2$CO$_3$ (235 mg, 1.703 mmol). The mixture was cooled to 0° C. and added 2-chloroacetyl chloride (0.099 mL, 1.249 mmol). The ice-water bath was removed and the reaction was allowed to warm to rt. After stirred at rt overnight, The reaction mixture was diluted with ether and water. The organic ether layer was separated and washed with brine, dried over MgSO$_4$, filtered and concentrated to yield a crude white solid product, which was purified by silica gel chromatography to yield desired product (280 mg, 85%) as a white solid. $^1$H NMR (500 MHz, CDCl$_3$) δ 8.06 (br. s., 1H), 7.55-7.49 (m, 1H), 7.48-7.42 (m, 1H), 4.27 (s, 2H). MS (ESI) m/z: 289.9 (M+H)$^+$.

36B

Methyl N-[(10R,14S)-14-[({[3-chloro-2-fluoro-6-(trifluoromethyl)phenyl]carbamoyl}methyl)amino]-10-methyl- 9-oxo-8,16-diazatricyclo[13.3.1.0²,⁷]nonadeca-1(19),2(7),3,5,15,17-hexaen-5-yl]carbamate: 12M (50 mg, 0.084 mmol), 36A (24.31 mg, 0.084 mmol), DIEA (0.088 mL, 0.503 mmol) in DMF (1 mL) in a seal tube was heated at 70° C. for 24 h. The reaction was cooled to rt and purified by reverse phase HPLC to yield desired product (31.4 mg, 44%) as an off white solid. ¹H NMR (500 MHz, MeOD) δ 8.76 (d, J=5.0 Hz, 1H), 7.75-7.67 (m, 1H), 7.64-7.56 (m, 2H), 7.55-7.43 (m, 4H), 4.62 (dd, J=11.0, 5.5 Hz, 1H), 4.07 (s, 2H), 3.76 (s, 3H), 2.74-2.66 (m, 1H), 2.24-2.13 (m, 1H), 1.92-1.75 (m, 2H), 1.45 (d, J=4.4 Hz, 2H), 0.93 (d, J=7.2 Hz, 3H), 0.45 (m, 1H) ppm. MS (ESI) m/z: 622.3 (M+H)⁺.

36C

Methyl N-[(10R,14S)-14-[2-chloro-N-({[3-chloro-2-fluoro-6-(trifluoromethyl)phenyl]carbamoyl}methyl)acetamido]-10-methyl-9-oxo-8,16-diazatricyclo[13.3.1.0²,⁷]nonadeca-1(19),2(7),3,5,15,17-hexaen-5-yl]carbamate: To a solution of 36B (31.4 mg, 0.050 mmol) in THF (1 mL) was added DIEA (0.044 mL, 0.252 mmol). The mixture was sonicated, cooled to 0° C., and added a solution of 2-chloroacetyl chloride (6.84 mg, 0.061 mmol) in 1 mL THF. After 10 min, the reaction mixture was diluted with 20 mL DCM and washed with water and brine. The organic phase was dried over MgSO₄, filtered, concentrated to yield the crude product, which was used in following reaction directly. MS (ESI) m/z: 622.3 (M+H)⁺.

Example 36

Methyl N-[(10R)-14-{4-[3-chloro-2-fluoro-6-(trifluoromethyl)phenyl]-2,5-dioxopiperazin-1-yl}-10-methyl-9-oxo-8,16-diazatricyclo[13.3.1.0²,⁷]nonadeca-1(19),2(7),3,5,15,17-hexaen-5-yl]carbamate, TFA salt (Diastereomer B, slow eluting isomer): 36C (34.9 mg, 0.05 mmol) in MeOH (2 mL) was cooled to 0° C., and NaOMe (25 wt % in MeOH) (54.0 mg, 0.250 mmol) was added. The reaction was gradually warmed to rt. After 1 h, the reaction was quenched with HCl (1.25 M in MeOH) (0.200 mL, 0.250 mmol) and concentrated. The residue was purified by reverse phase HPLC to yield Example 36 (Diastereomer B, the slow eluting isomer) (6.8 mg, 39%) as an off-white solid. ¹H NMR (500 MHz, MeOD) δ 8.72 (d, J=5.5 Hz, 1H), 7.87-7.78 (m, 2H), 7.69-7.61 (m, 2H), 7.61-7.56 (m, 1H), 7.54-7.49 (m, 2H), 5.54 (dd, J=12.7, 4.7 Hz, 1H), 4.62-4.50 (m, 2H), 4.45 (d, J=16.5 Hz, 1H), 4.22 (d, J=16.5 Hz, 1H), 3.77 (s, 3H), 2.63 (dd, J=7.0, 4.5 Hz, 1H), 2.30-2.19 (m, 1H), 2.00-1.88 (m, 2H), 1.64-1.53 (m, 1H), 1.41-1.27 (m, 1H), 1.02 (d, J=7.2 Hz, 3H), 0.93-0.74 (m, 1H). MS (ESI) m/z: 662.0 (M+H)⁺. Analytical HPLC RT=6.87 min (Method A).

Example 37

Methyl N-[(10R)-14-{4-[3-chloro-2-fluoro-6-(trifluoromethyl)phenyl]-2,5-dioxopiperazin-1-yl}-10-methyl-9-oxo-8,16-diazatricyclo[13.3.1.0²,⁷]nonadeca-1(19),2(7),3,5,15,17-hexaen-5-yl]carbamate, TFA salt

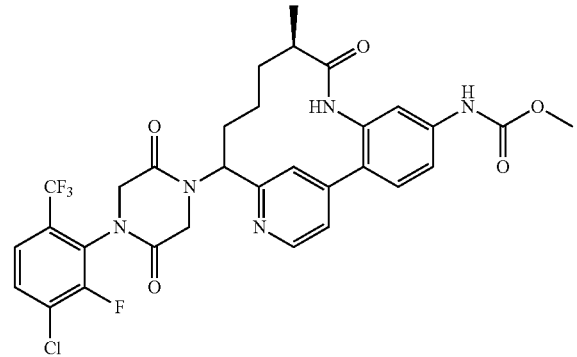 [SMILES: COC(=O)Nc1ccc2c(c1)NC(=O)[C@H](C)CCCC(N1CC(=O)N(c3c(C(F)(F)F)ccc(Cl)c3F)CC1=O)c1cc-2ccn1]

Example 37

Methyl N-[(10R)-14-{4-[3-chloro-2-fluoro-6-(trifluoromethyl)phenyl]-2,5-dioxopiperazin-1-yl}-10-methyl-9-oxo-8,16-diazatricyclo[13.3.1.0²,⁷]nonadeca-1(19),2(7),3,5,15,17-hexaen-5-yl]carbamate, TFA salt (Diastereomer A, fast eluting isomer): Example 37 was prepared in the same way as Example 36 and isolated as Diastereomer A by HPLC. ¹H NMR (500 MHz, MeOD) δ 8.70 (d, J=5.5 Hz, 1H), 7.83-7.77 (m, 2H), 7.64 (d, J=8.5 Hz, 1H), 7.61-7.56 (m, 2H), 7.54-7.48 (m, 2H), 5.55 (dd, J=12.7, 5.0 Hz, 1H), 4.79-4.70 (m, 1H), 4.52 (dd, J=16.5, 3.9 Hz, 2H), 4.15 (d, J=16.5 Hz, 1H), 3.77 (s, 3H), 2.64 (dd, J=6.7, 4.5 Hz, 1H), 2.23 (ddd, J=12.4, 7.9, 4.4 Hz, 1H), 2.02-1.87 (m, 2H), 1.62-1.51 (m, 1H), 1.41-1.29 (m, 1H), 1.01 (d, J=6.9 Hz, 3H), 0.81 (br. s., 1H). MS (ESI) m/z: 662.0 (M+H)⁺. Analytical HPLC RT=6.87 min (Method A).

The following Examples in Table 2 were prepared using the methods described in the previous Examples for preparing cyclic ureas.

TABLE 2

| Example # | Stereochemistry | Structure | M + H | RT, min Method A |
|---|---|---|---|---|
| 38 | Homochiral | 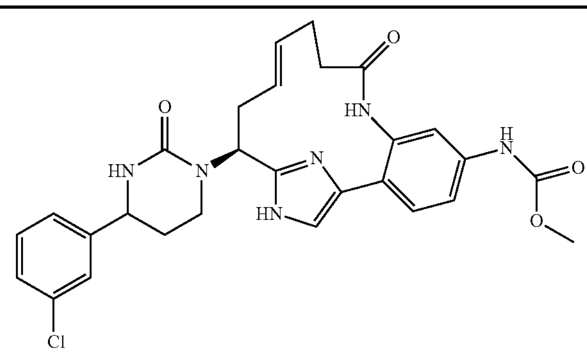 | 549.1 | 5.77 |

TABLE 2-continued

| Example # | Stereochemistry | Structure | M + H | RT, min Method A |
|---|---|---|---|---|
| 39 | Homochiral | 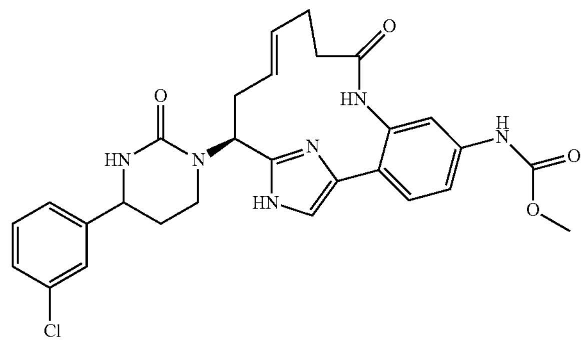 | 549.0 | 5.86 |
| 40 | Homochiral | 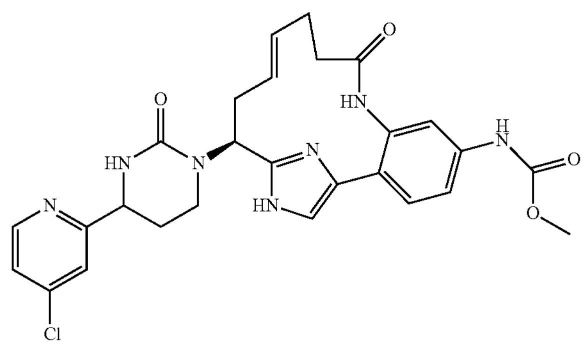 [SMILES: COC(=O)Nc1ccc2c(c1)NC(=O)CC/C=C/C[C@H](N1CCC(c3cccc(Cl)c3)NC1=O)c1nc-2c[nH]1] | 550.0 | 4.82 |
| 41 | Homochiral | 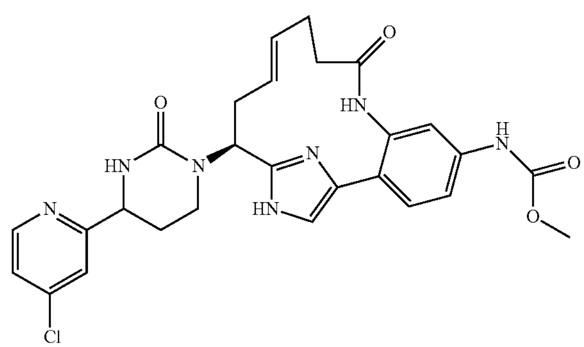 [SMILES: COC(=O)Nc1ccc2c(c1)NC(=O)CC/C=C/C[C@H](N1CCC(c3cc(Cl)ccn3)NC1=O)c1nc-2c[nH]1] | 550.0 | 4.83 |
| 42 | Homochiral | 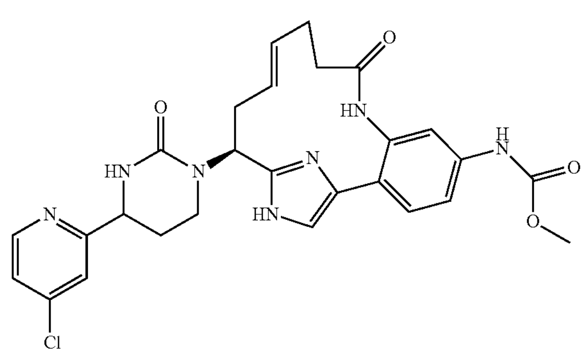 | 550.0 | 4.84 |

TABLE 2-continued

| Example # | Stereochemistry | Structure | M + H | RT, min Method A |
|---|---|---|---|---|
| 43 | Diastereomer mixture (3:1) | 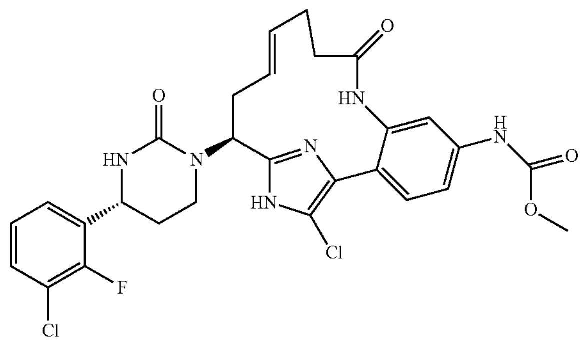 [SMILES: COC(=O)Nc1ccc2c(c1)NC(=O)CC/C=C/C[C@H](N1CC[C@H](c3cccc(Cl)c3F)NC1=O)c1nc-2c(Cl)[nH]1] | 601.0 | 7.59 |
| 44 | Diastereomer mixture (3:1) | 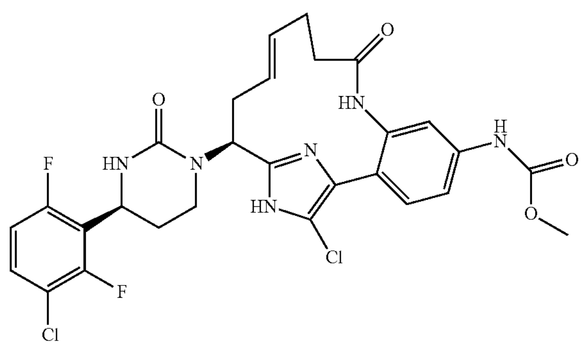 [SMILES: COC(=O)Nc1ccc2c(c1)NC(=O)CC/C=C/C[C@H](N1CC[C@@H](c3c(F)ccc(Cl)c3F)NC1=O)c1nc-2c(Cl)[nH]1] | 619.0 | 7.36 |
| 45 | Homochiral | 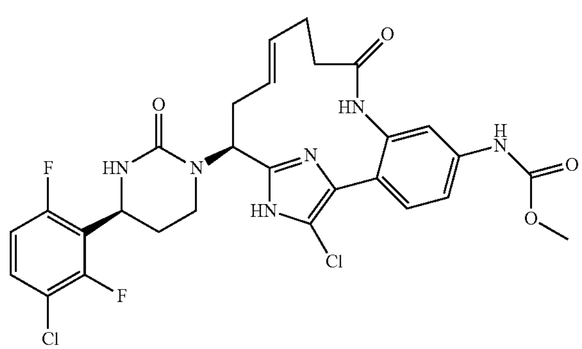 [SMILES: COC(=O)Nc1ccc2c(c1)NC(=O)CC/C=C/C[C@H](N1CC[C@@H](c3c(F)ccc(Cl)c3F)NC1=O)c1nc-2c(Cl)[nH]1] | 618.9 | 7.00 |
| 46 | Diastereomer mixture (9:1) | 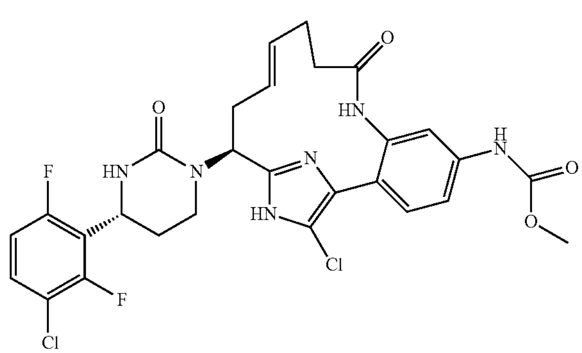 [SMILES: COC(=O)Nc1ccc2c(c1)NC(=O)CC/C=C/C[C@H](N1CC[C@H](c3c(F)ccc(Cl)c3F)NC1=O)c1nc-2c(Cl)[nH]1] | 619.0 | 7.05 |

TABLE 2-continued

| Example # | Stereochemistry | Structure | M + H | RT, min Method A |
|---|---|---|---|---|
| 47 | Homochiral | 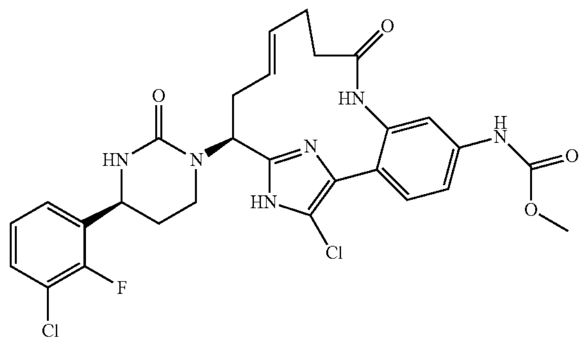 [SMILES: COC(=O)Nc1ccc2c(c1)NC(=O)CC/C=C/C[C@H](N1CC[C@@H](c3cccc(Cl)c3F)NC1=O)c1nc-2c(Cl)[nH]1] | 601.1 | 6.98 |
| 48 | Homochiral | 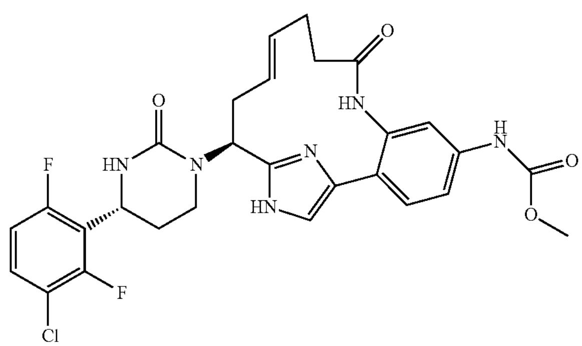 [SMILES: COC(=O)Nc1ccc2c(c1)NC(=O)CC/C=C/C[C@H](N1CC[C@H](c3c(F)ccc(Cl)c3F)NC1=O)c1nc-2c[nH]1] | 585.1 | 5.08 |
| 49 | Homochiral | 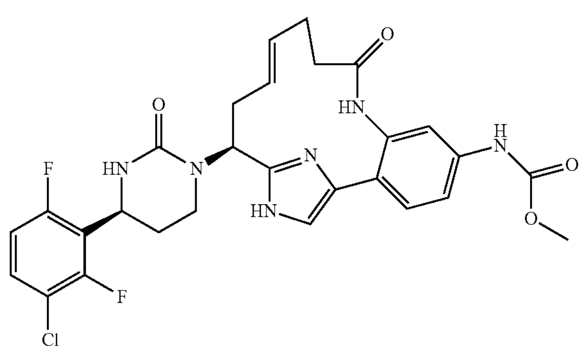 [SMILES: COC(=O)Nc1ccc2c(c1)NC(=O)CC/C=C/C[C@H](N1CC[C@@H](c3c(F)ccc(Cl)c3F)NC1=O)c1nc-2c[nH]1] | 585.0 | 5.13 |
| 50 | Diastereomer mixture (8:2) | 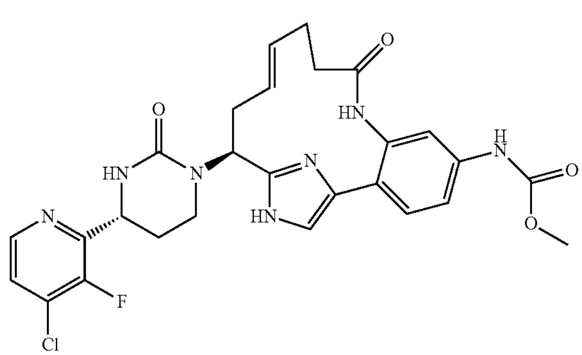 [SMILES: COC(=O)Nc1ccc2c(c1)NC(=O)CC/C=C/C[C@H](N1CC[C@H](c3nccc(Cl)c3F)NC1=O)c1nc-2c[nH]1] | 568.1 | 4.78 |

TABLE 2-continued

| Example # | Stereochemistry | Structure | M + H | RT, min Method A |
|---|---|---|---|---|
| 51 | Homochiral | 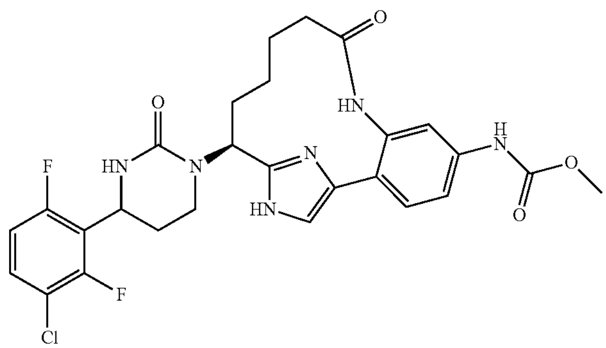 [SMILES: COC(=O)Nc1ccc2c(c1)NC(=O)CCCC[C@H](N1CCC(c3c(F)ccc(Cl)c3F)NC1=O)c1nc-2c[nH]1] | 573.1 | 5.98 |
| 52 | Diastereomer mixture (1.3:1) | 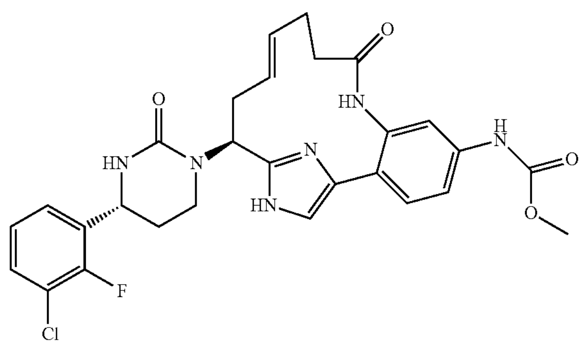 [SMILES: COC(=O)Nc1ccc2c(c1)NC(=O)CC/C=C/C[C@H](N1CC[C@H](c3cccc(Cl)c3F)NC1=O)c1nc-2c[nH]1] | 567.2 | 5.23 |
| 53 | Diastereomer mixture (3.6:1) | 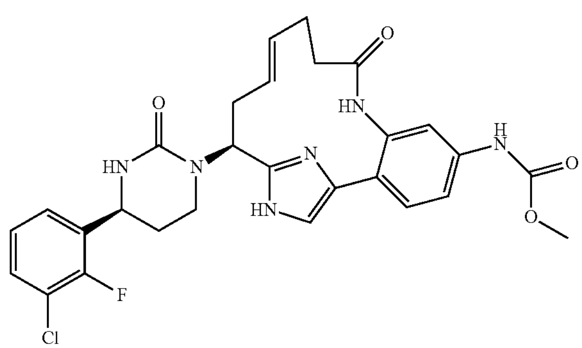 [SMILES: COC(=O)Nc1ccc2c(c1)NC(=O)CC/C=C/C[C@H](N1CC[C@@H](c3cccc(Cl)c3F)NC1=O)c1nc-2c[nH]1] | 567.2 | 5.25 |
| 54 | Homochiral | 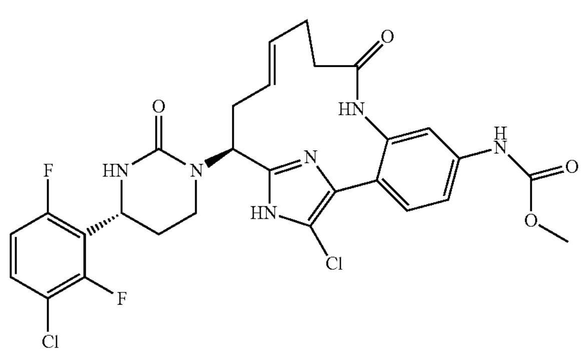 [SMILES: COC(=O)Nc1ccc2c(c1)NC(=O)CC/C=C/C[C@H](N1CC[C@H](c3c(F)ccc(Cl)c3F)NC1=O)c1nc-2c(Cl)[nH]1] | 619.1 | 6.59 |

TABLE 2-continued

| Example # | Stereochemistry | Structure | M + H | RT, min Method A |
|---|---|---|---|---|
| 55 | Diastereomer mixture (5:1) | 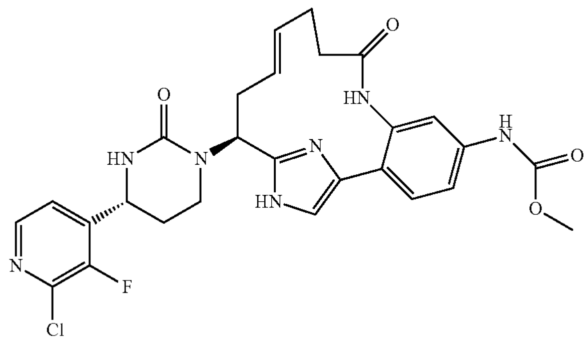 [SMILES: COC(=O)Nc1ccc2c(c1)NC(=O)CC/C=C/C[C@H](N1CC[C@H](c3ccnc(Cl)c3F)NC1=O)c1nc-2c[nH]1] | 568.2 | 6.59 |
| 56 | Homochiral | 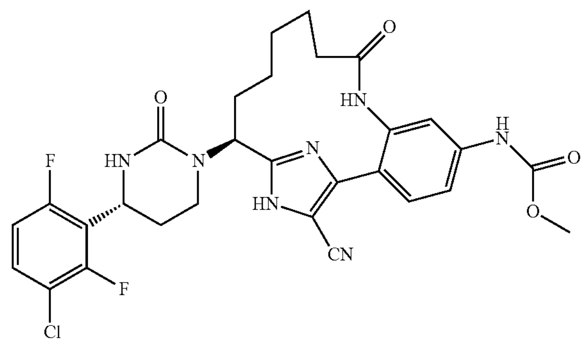 [SMILES: COC(=O)Nc1ccc2c(c1)NC(=O)CCCCC[C@H](N1CC[C@H](c3c(F)ccc(Cl)c3F)NC1=O)c1nc-2c(C#N)[nH]1] | 612.2 | 9.07 |
| 57 | Homochiral | 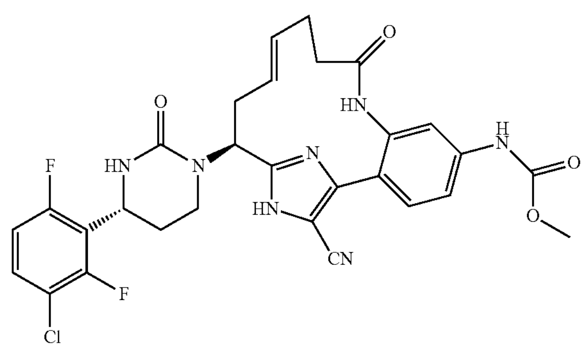 | 610.1 | 8.68 |
| 58 | Homochiral | 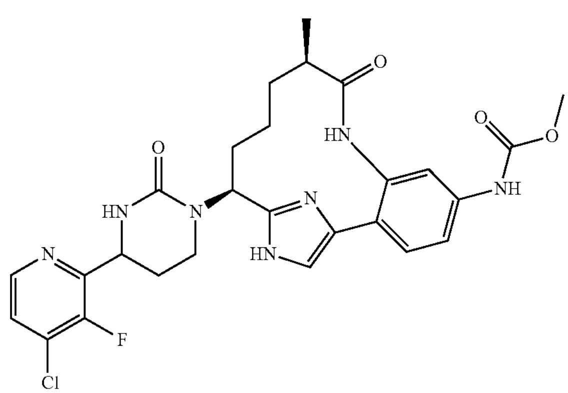 [SMILES: COC(=O)Nc1ccc2c(c1)NC(=O)[C@H](C)CCC[C@H](N1CCC(c3nccc(Cl)c3F)NC1=O)c1nc-2c[nH]1] | 570.1 | 4.38 |

TABLE 2-continued

| Example # | Stereochemistry | Structure | M + H | RT, min Method A |
|---|---|---|---|---|
| 59 | Homochiral | 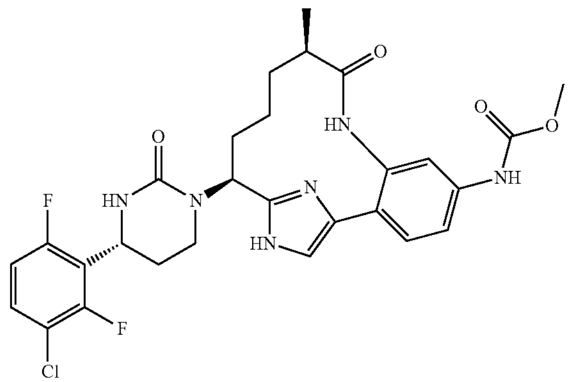 [SMILES: COC(=O)Nc1ccc2c(c1)NC(=O)[C@H](C)CCC[C@H](N1CC[C@H](c3c(F)ccc(Cl)c3F)NC1=O)c1nc-2c[nH]1] | 587.1 | 6.14 |
| 60 | Homochiral | 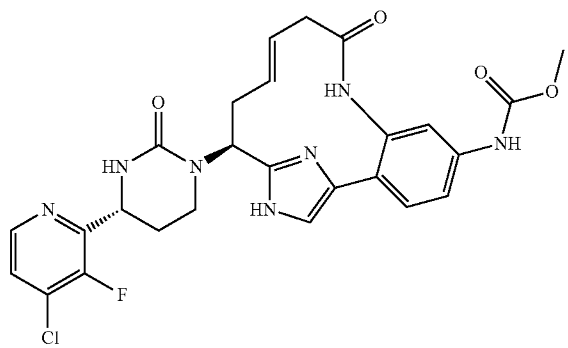 [SMILES: COC(=O)Nc1ccc2c(c1)NC(=O)C/C=C/C[C@H](N1CC[C@H](c3nccc(Cl)c3F)NC1=O)c1nc-2c[nH]1] | 550.1 | 3.51 |
| 61 | Homochiral | 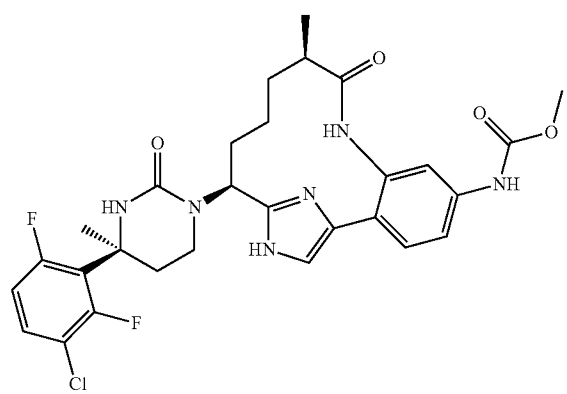 [SMILES: COC(=O)Nc1ccc2c(c1)NC(=O)[C@H](C)CCC[C@H](N1CC[C@@](C)(c3c(F)ccc(Cl)c3F)NC1=O)c1nc-2c[nH]1] | 601.2 | NA |
| 62 | Homochiral | 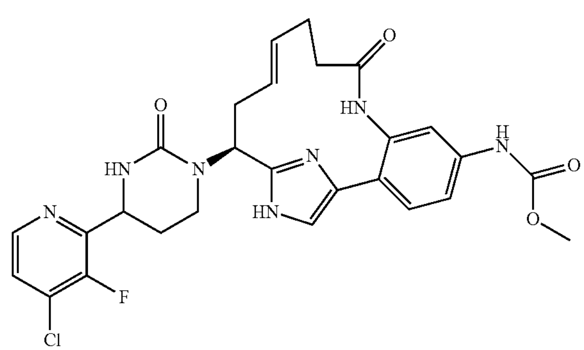 | 568.1 | 4.31 |

TABLE 2-continued

| Example # | Stereochemistry | Structure | M + H | RT, min Method A |
|---|---|---|---|---|
| 63 | Diastereomer mixture (9:1) | 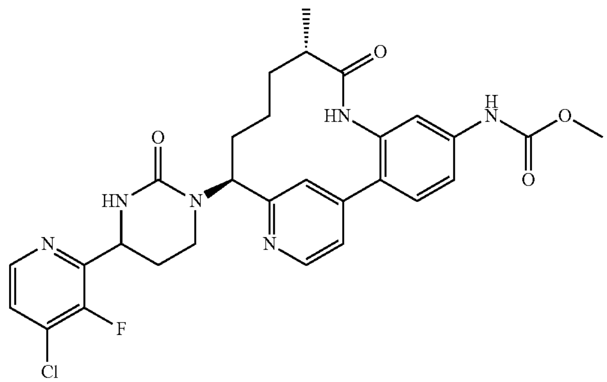 [SMILES: COC(=O)Nc1ccc2c(c1)NC(=O)[C@@H](C)CCC[C@H](N1CCC(c3nccc(Cl)c3F)NC1=O)c1cc-2ccn1] | 581.2 | 4.37 |
| 64 | Homochiral | 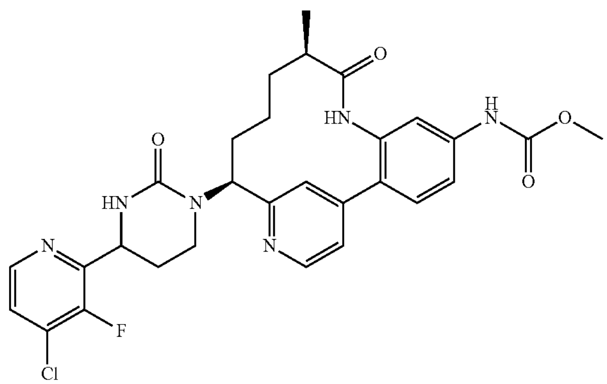 [SMILES: COC(=O)Nc1ccc2c(c1)NC(=O)[C@H](C)CCC[C@H](N1CCC(c3nccc(Cl)c3F)NC1=O)c1cc-2ccn1] | 581.1 | 4.48 |
| 65 | Homochiral | 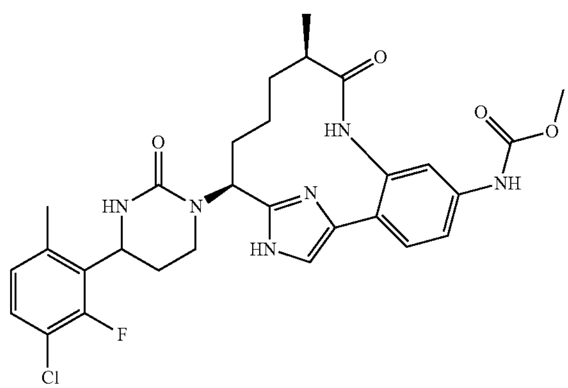 [SMILES: COC(=O)Nc1ccc2c(c1)NC(=O)[C@H](C)CCC[C@H](N1CCC(c3c(C)ccc(Cl)c3F)NC1=O)c1nc-2c[nH]1] | 583.2 | 5.03 |
| 66 | Diastereomer mixture | 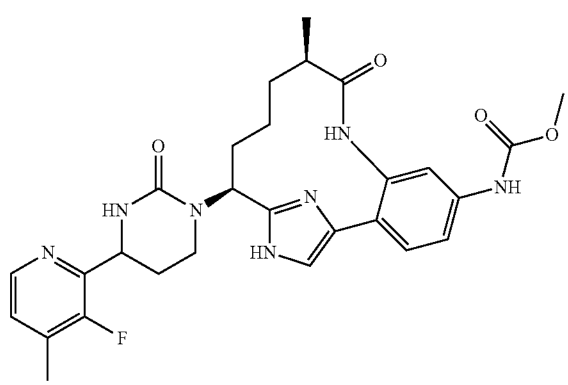 [SMILES: COC(=O)Nc1ccc2c(c1)NC(=O)[C@H](C)CCC[C@H](N1CCC(c3nccc(C)c3F)NC1=O)c1nc-2c[nH]1] | 550.2 | 3.78 |

TABLE 2-continued

| Example # | Stereochemistry | Structure | M + H | RT, min Method A |
|---|---|---|---|---|
| 67 | Homochiral | 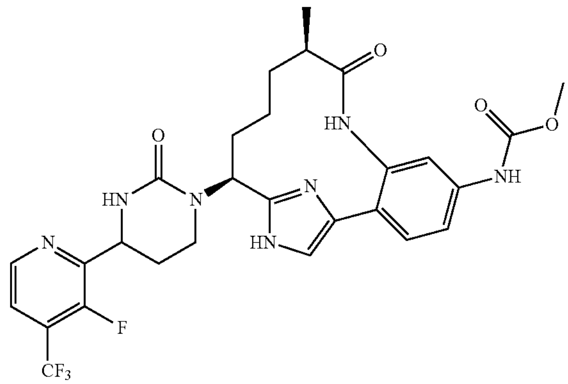 [SMILES: COC(=O)Nc1ccc2c(c1)NC(=O)[C@H](C)CCC[C@H](N1CCC(c3nccc(C(F)(F)F)c3F)NC1=O)c1nc-2c[nH]1] | 604.2 | 4.73 |
| 68 | Homochiral | 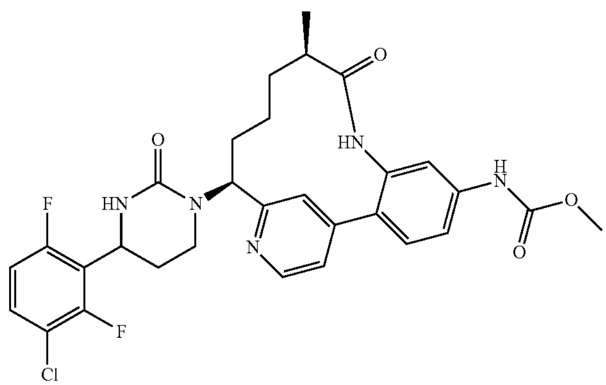 [SMILES: COC(=O)Nc1ccc2c(c1)NC(=O)[C@H](C)CCC[C@H](N1CCC(c3c(F)ccc(Cl)c3F)NC1=O)c1cc-2ccn1] | 598.3 | 4.89 |
| 69 | Homochiral | 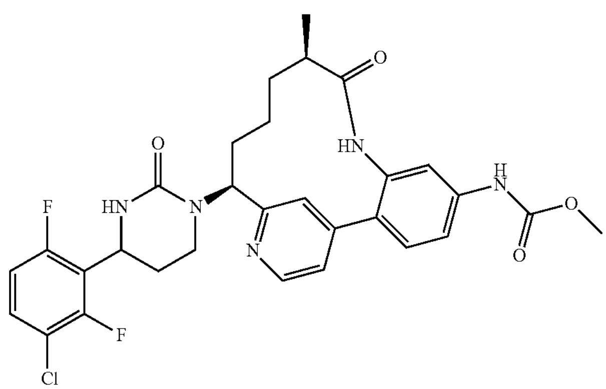 [SMILES: COC(=O)Nc1ccc2c(c1)NC(=O)[C@H](C)CCC[C@H](N1CCC(c3c(F)ccc(Cl)c3F)NC1=O)c1cc-2ccn1] | 598.3 | 4.98 |
| 70 | Homochiral | 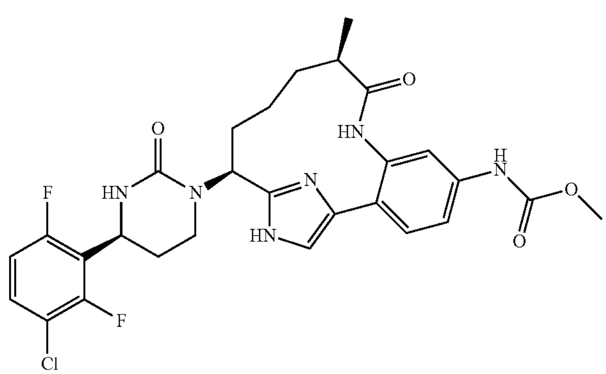 [SMILES: COC(=O)Nc1ccc2c(c1)NC(=O)[C@H](C)CCC[C@H](N1CC[C@@H](c3c(F)ccc(Cl)c3F)NC1=O)c1nc-2c[nH]1] | 587.2 | 6.12 |

TABLE 2-continued

| Example # | Stereochemistry | Structure | M + H | RT, min Method A |
|---|---|---|---|---|
| 71 | Homochiral | 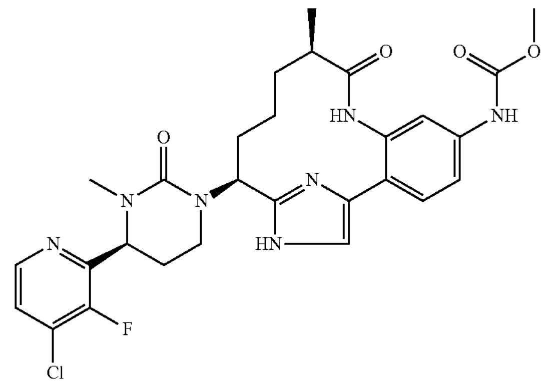 [SMILES: COC(=O)Nc1ccc2c(c1)NC(=O)[C@H](C)CCC[C@H](N1CC[C@@H](c3nccc(Cl)c3F)N(C)C1=O)c1nc-2c[nH]1] | 584.1 | 4.45 |
| 72 | Homochiral | 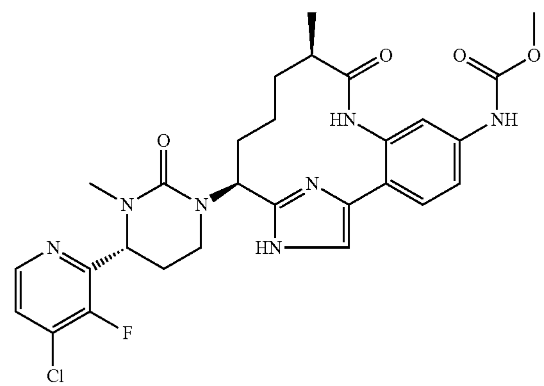 [SMILES: COC(=O)Nc1ccc2c(c1)NC(=O)[C@H](C)CCC[C@H](N1CC[C@H](c3nccc(Cl)c3F)N(C)C1=O)c1nc-2c[nH]1] | 584.1 | 4.57 |

The following Examples in Table 3 were prepared using the methods described in the previous Examples for preparing cyclic carbamates.

TABLE 3

| Example # | Stereochemistry | Structure | M + H | RT, min Method A |
|---|---|---|---|---|
| 73 | Diastereomer mixture | 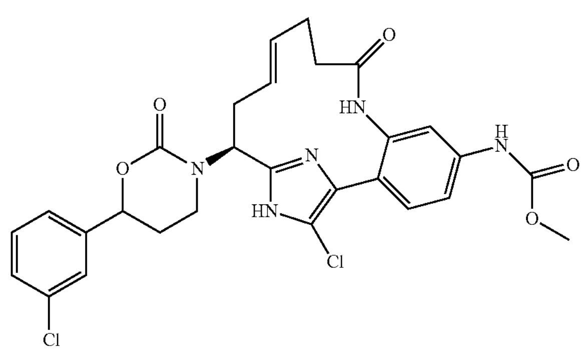 [SMILES: COC(=O)Nc1ccc2c(c1)NC(=O)CC/C=C/C[C@H](N1CCC(c3cccc(Cl)c3)OC1=O)c1nc-2c(Cl)[nH]1] | 584.1 | 7.79 |

TABLE 3-continued

| Example # | Stereochemistry | Structure | M + H | RT, min Method A |
|---|---|---|---|---|
| 74 | Diastereomer mixture | 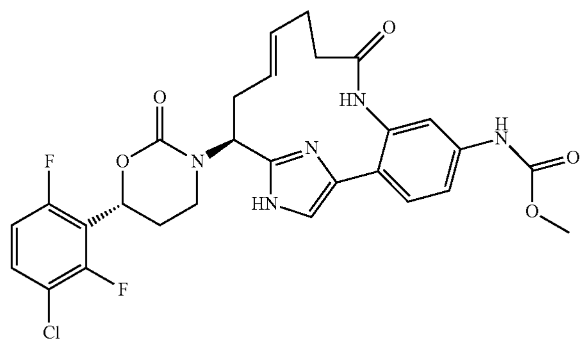 [SMILES: COC(=O)Nc1ccc2c(c1)NC(=O)CC/C=C/C[C@H](N1CC[C@H](c3c(F)ccc(Cl)c3F)OC1=O)c1nc-2c[nH]1] | 585.9 | 5.60 |
| 75 | Diastereomer mixture | 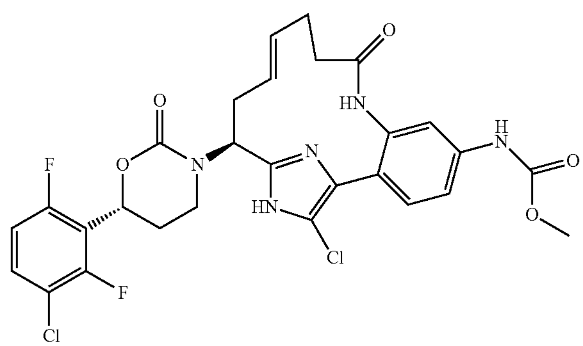 [SMILES: COC(=O)Nc1ccc2c(c1)NC(=O)CC/C=C/C[C@H](N1CC[C@H](c3c(F)ccc(Cl)c3F)OC1=O)c1nc-2c(Cl)[nH]1] | 619.8 | 7.67 |
| 76 | Diastereomer mixture | 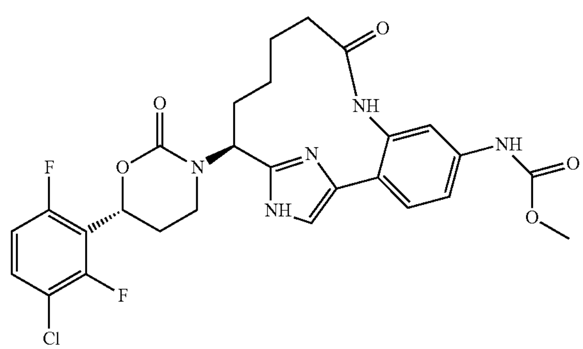 [SMILES: COC(=O)Nc1ccc2c(c1)NC(=O)CCCC[C@H](N1CC[C@H](c3c(F)ccc(Cl)c3F)OC1=O)c1nc-2c[nH]1] | 573.9 | 5.58 |
| 77 | Diastereomer mixture | 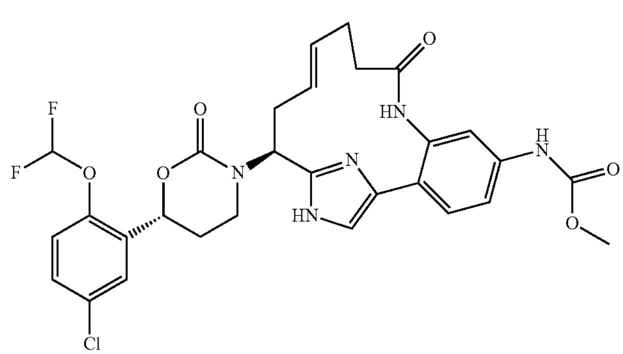 [SMILES: COC(=O)Nc1ccc2c(c1)NC(=O)CC/C=C/C[C@H](N1CC[C@H](c3cc(Cl)ccc3OC(F)F)OC1=O)c1nc-2c[nH]1] | 615.8 | 6.19 |

TABLE 3-continued

| Example # | Stereochemistry | Structure | M + H | RT, min Method A |
|---|---|---|---|---|
| 78 | Diastereomer mixture | 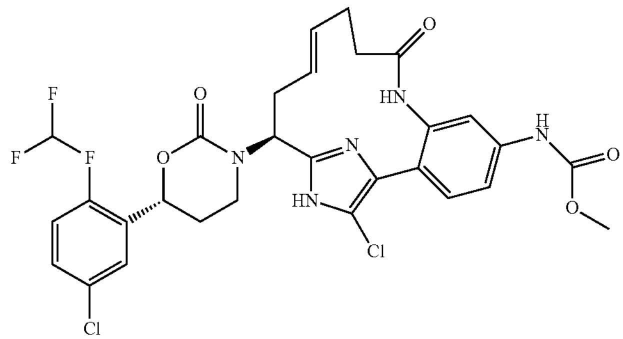 | 649.8 | 9.16 |
| 79 | Homochiral | 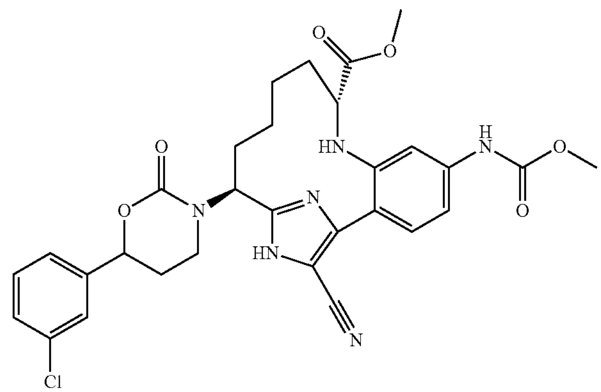 [SMILES: COC(=O)Nc1ccc2c(c1)N[C@@H](C(=O)OC)CCCC[C@H](N1CCC(c3cccc(Cl)c3)OC1=O)c1nc-2c(C#N)[nH]1] | 607.0 | 10.1 |
| 80 | Homochiral | 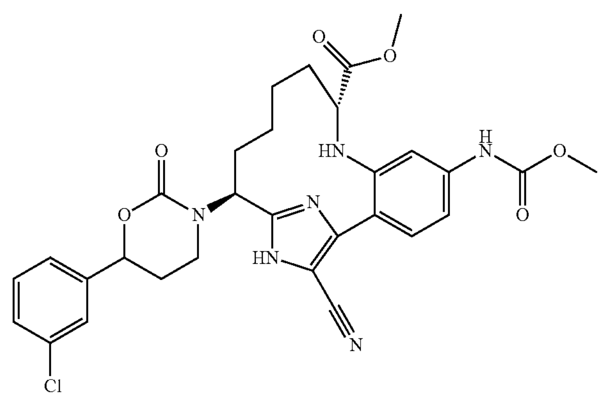 [SMILES: COC(=O)Nc1ccc2c(c1)N[C@@H](C(=O)OC)CCCC[C@H](N1CCC(c3cccc(Cl)c3)OC1=O)c1nc-2c(C#N)[nH]1] | 607.0 | 10.2 |
| 81 | Diastereomer mixture | 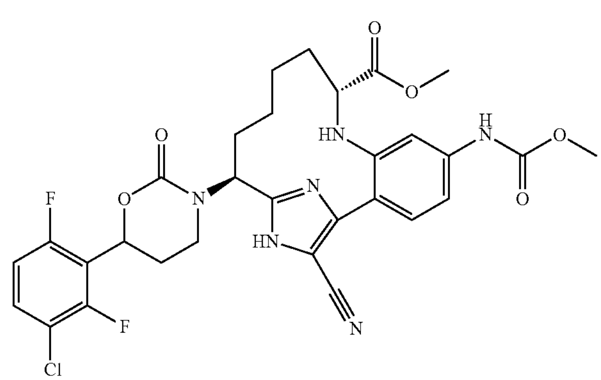 [SMILES: COC(=O)Nc1ccc2c(c1)N[C@@H](C(=O)OC)CCCC[C@H](N1CCC(c3c(F)ccc(Cl)c3F)OC1=O)c1nc-2c(C#N)[nH]1] | 643.0 | 10.11 |

TABLE 3-continued
| Example # | Stereochemistry | Structure | M + H | RT, min Method A |
|---|---|---|---|---|
| 82 | Diastereomer mixture | 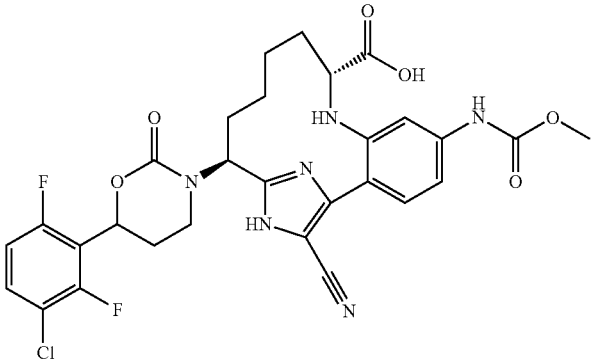 [SMILES: COC(=O)Nc1ccc2c(c1)N[C@@H](C(=O)O)CCCC[C@H](N1CCC(c3c(F)ccc(Cl)c3F)OC1=O)c1nc-2c(C#N)[nH]1] | 628.9 | 8.98 |
| 83 | Homochiral | 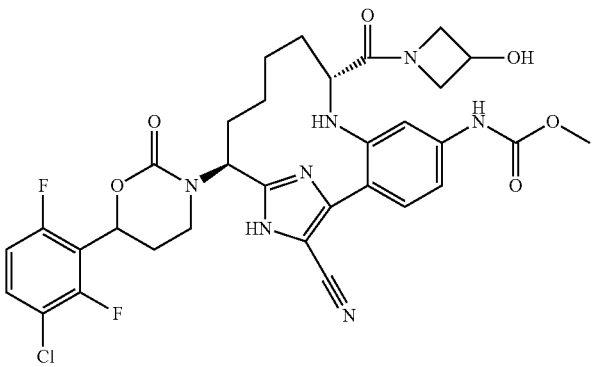 [SMILES: COC(=O)Nc1ccc2c(c1)N[C@@H](C(=O)N1CC(O)C1)CCCC[C@H](N1CCC(c3c(F)ccc(Cl)c3F)OC1=O)c1nc-2c(C#N)[nH]1] | 684.0 | 8.13 |
| 84 | Diastereomer mixture | 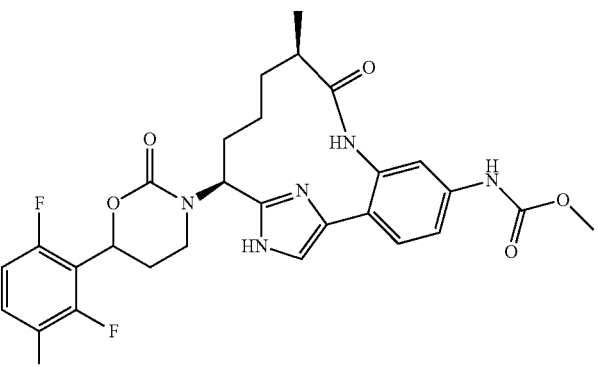 | 588.1 | 6.62 |
| 85 | Diastereomer mixture | 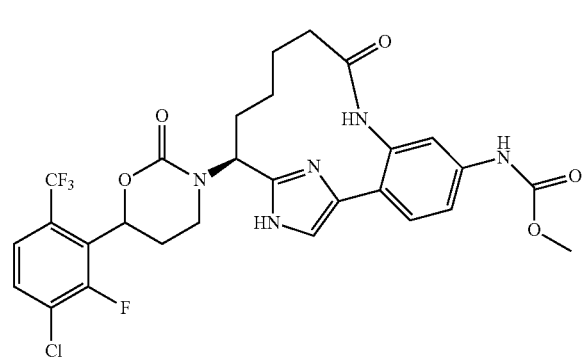 [SMILES: COC(=O)Nc1ccc2c(c1)NC(=O)CCCC[C@H](N1CCC(c3c(C(F)(F)F)ccc(Cl)c3F)OC1=O)c1nc-2c[nH]1] | 623.9 | 7.22 |

TABLE 3-continued

| Example # | Stereochemistry | Structure | M + H | RT, min Method A |
|---|---|---|---|---|
| 86 | Homochiral | 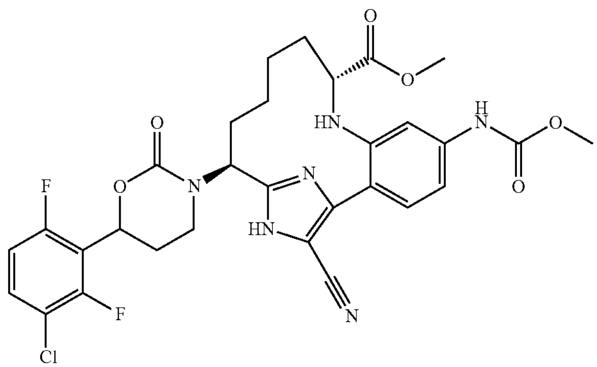 [SMILES: COC(=O)Nc1ccc2c(c1)N[C@@H](C(=O)OC)CCCC[C@H](N1CCC(c3c(F)ccc(Cl)c3F)OC1=O)c1nc-2c(C#N)[nH]1] | 643.0 | 10.0 |
| 87 | Homochiral | 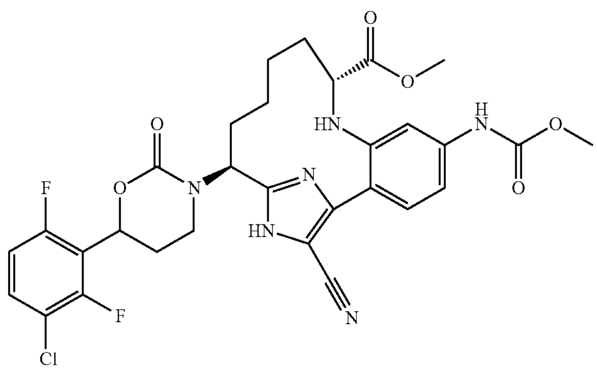 [SMILES: COC(=O)Nc1ccc2c(c1)N[C@@H](C(=O)OC)CCCC[C@H](N1CCC(c3c(F)ccc(Cl)c3F)OC1=O)c1nc-2c(C#N)[nH]1] | 643.0 | 10.1 |
| 88 | Homochiral | 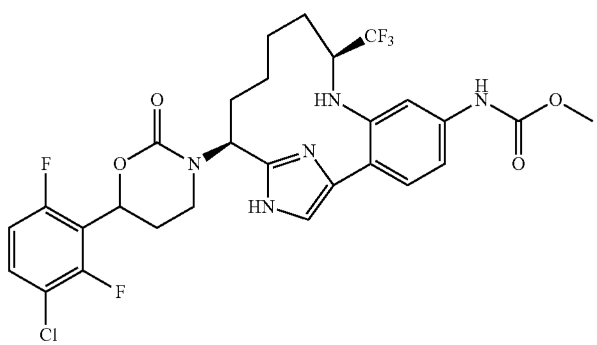 [SMILES: COC(=O)Nc1ccc2c(c1)N[C@H](C(F)(F)F)CCCC[C@H](N1CCC(c3c(F)ccc(Cl)c3F)OC1=O)c1nc-2c[nH]1] | 627.9 | 7.14 |
| 89 | Homochiral | 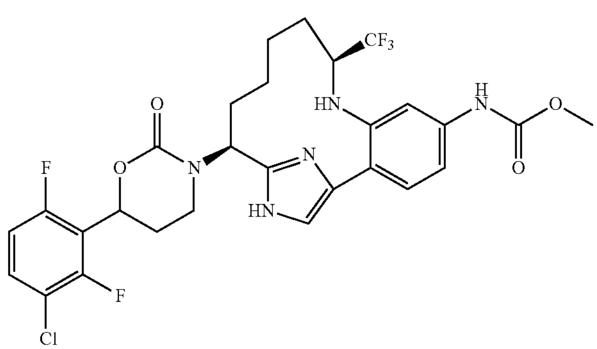 [SMILES: COC(=O)Nc1ccc2c(c1)N[C@H](C(F)(F)F)CCCC[C@H](N1CCC(c3c(F)ccc(Cl)c3F)OC1=O)c1nc-2c[nH]1] | 627.9 | 7.07 |

TABLE 3-continued
| Example # | Stereochemistry | Structure | M + H | RT, min Method A |
|---|---|---|---|---|
| 90 | Diastereomer mixture | 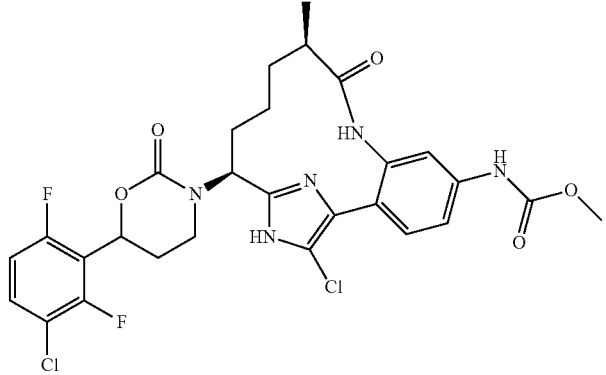 [SMILES: COC(=O)Nc1ccc2c(c1)NC(=O)[C@H](C)CCC[C@H](N1CCC(c3c(F)ccc(Cl)c3F)OC1=O)c1nc-2c(Cl)[nH]1] | 622.0 | 8.77 |
| 91 | Homochiral | 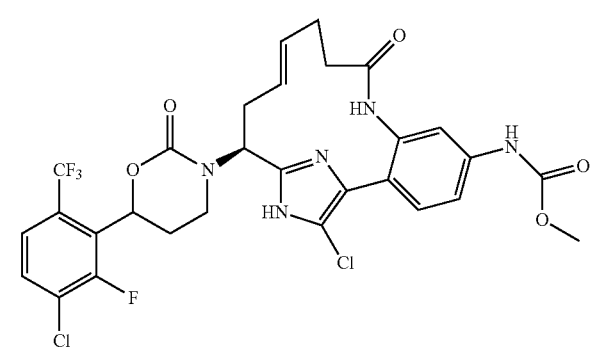 | 669.9 | 9.11 |
| 92 | Homochiral | 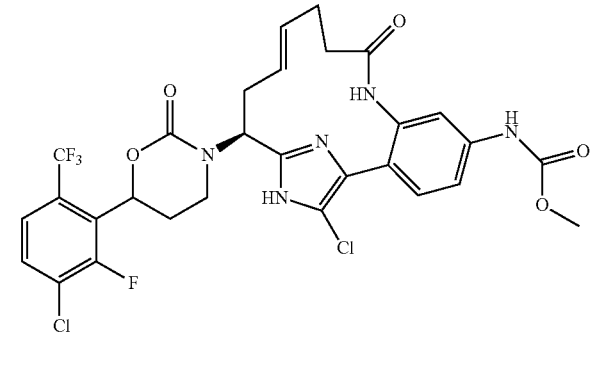 [SMILES: COC(=O)Nc1ccc2c(c1)NC(=O)CC/C=C/C[C@H](N1CCC(c3c(C(F)(F)F)ccc(Cl)c3F)OC1=O)c1nc-2c(Cl)[nH]1] | 669.9 | 9.35 |
| 93 | Homochiral | 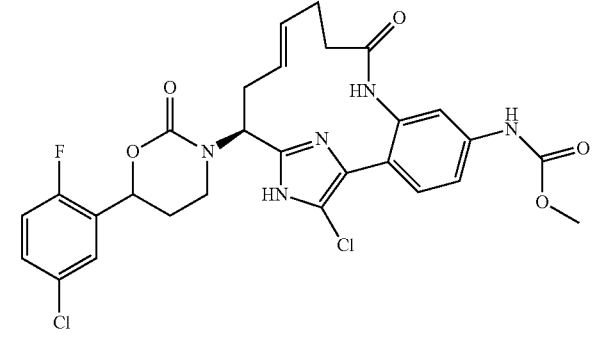 [SMILES: COC(=O)Nc1ccc2c(c1)NC(=O)CC/C=C/C[C@H](N1CCC(c3cc(Cl)ccc3F)OC1=O)c1nc-2c(Cl)[nH]1] | 601.9 | 8.57 |

TABLE 3-continued

| Example # | Stereochemistry | Structure | M + H | RT, min Method A |
|---|---|---|---|---|
| 94 | Homochiral | 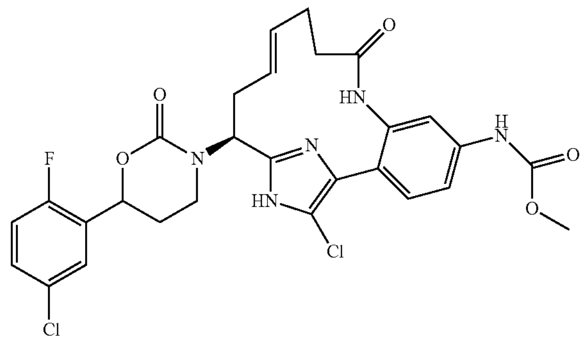 [SMILES: COC(=O)Nc1ccc2c(c1)NC(=O)CC/C=C/C[C@H](N1CCC(c3cc(Cl)ccc3F)OC1=O)c1nc-2c(Cl)[nH]1] | 601.9 | 8.71 |
| 95 | Diastereomer mixture | 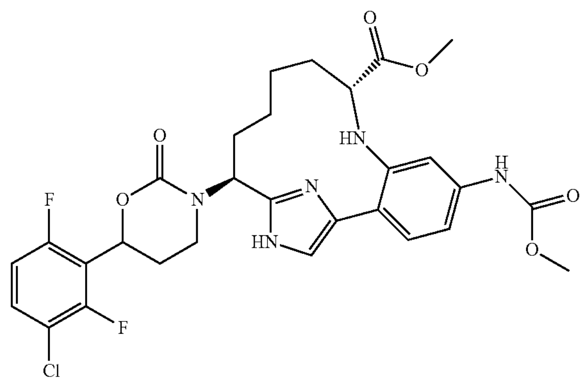 [SMILES: COC(=O)Nc1ccc2c(c1)N[C@@H](C(=O)OC)CCCC[C@H](N1CCC(c3c(F)ccc(Cl)c3F)OC1=O)c1nc-2c[nH]1] | 618.0 | 6.49 |
| 96 | Homochiral | 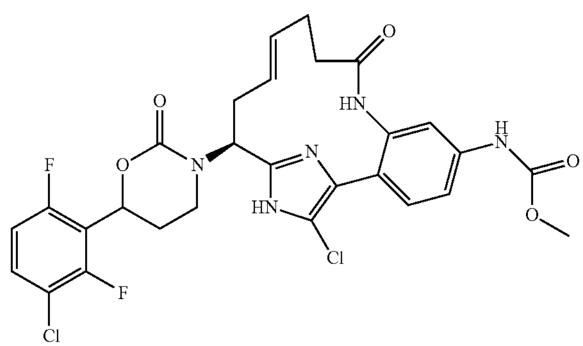 | 619.8 | 8.90 |
| 97 | Diastereomer mixture | 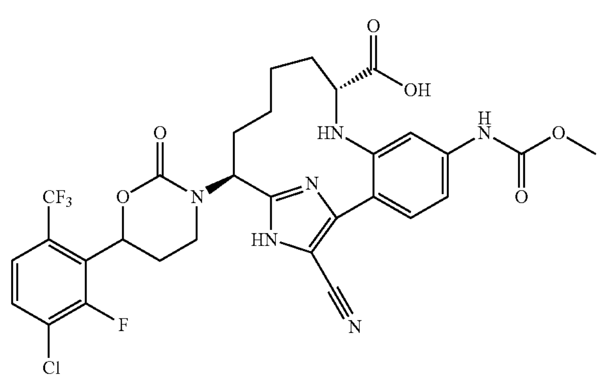 [SMILES: COC(=O)Nc1ccc2c(c1)N[C@@H](C(=O)O)CCCC[C@H](N1CCC(c3c(C(F)(F)F)ccc(Cl)c3F)OC1=O)c1nc-2c(C#N)[nH]1] | 678.9 | 9.50 |

TABLE 3-continued

| Example # | Stereochemistry | Structure | M + H | RT, min Method A |
|---|---|---|---|---|
| 98 | Diastereomer mixture | 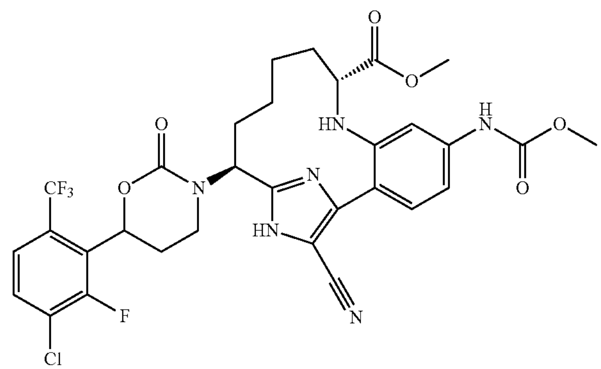 [SMILES: COC(=O)Nc1ccc2c(c1)N[C@@H](C(=O)OC)CCCC[C@H](N1CCC(c3c(C(F)(F)F)ccc(Cl)c3F)OC1=O)c1nc-2c(C#N)[nH]1] | 693.0 | 10.7 |
| 99 | Homochiral | 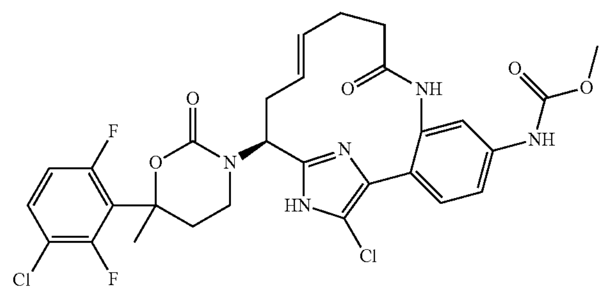 [SMILES: COC(=O)Nc1ccc2c(c1)NC(=O)CC/C=C/C[C@H](N1CCC(C)(c3c(F)ccc(Cl)c3F)OC1=O)c1nc-2c(Cl)[nH]1] | 634.0 | 7.51 |
| 100 | Homochiral | 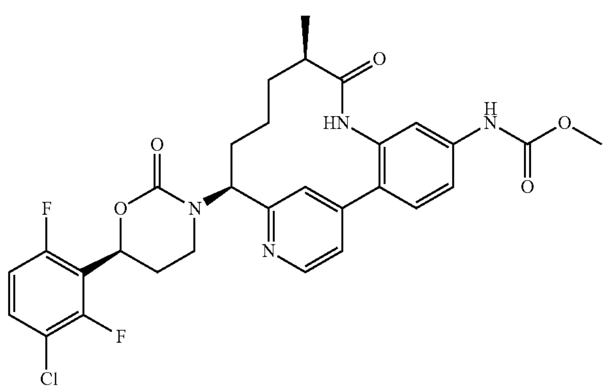 [SMILES: COC(=O)Nc1ccc2c(c1)NC(=O)[C@H](C)CCC[C@H](N1CC[C@@H](c3c(F)ccc(Cl)c3F)OC1=O)c1cc-2ccn1] | 599.0 | 6.98 |
| 101 | Homochiral | 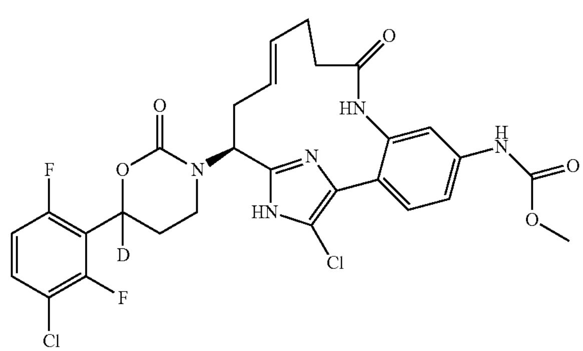 [SMILES: [2H]C1(c2c(F)ccc(Cl)c2F)CCN([C@H]2C/C=C/CCC(=O)Nc3cc(NC(=O)OC)ccc3-c3nc2[nH]c3Cl)C(=O)O1] | 620.9 | 9.13 |

TABLE 3-continued

| Example # | Stereochemistry | Structure | M + H | RT, min Method A |
|---|---|---|---|---|
| 102 | Homochiral | 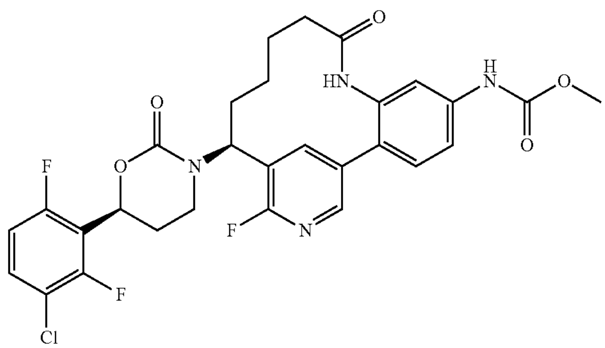 [SMILES: COC(=O)Nc1ccc2c(c1)NC(=O)CCCC[C@H](N1CC[C@@H](c3c(F)ccc(Cl)c3F)OC1=O)c1cc-2cnc1F] | 602.9 | 8.58 |
| 103 | Homochiral | 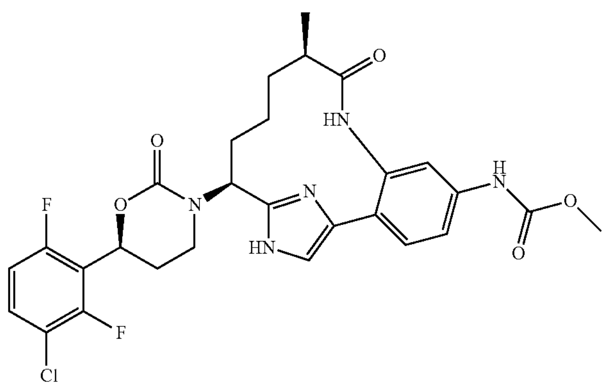 [SMILES: COC(=O)Nc1ccc2c(c1)NC(=O)[C@H](C)CCC[C@H](N1CC[C@@H](c3c(F)ccc(Cl)c3F)OC1=O)c1nc-2c[nH]1] | 588.0 | 5.88 |
| 104 | Homochiral | 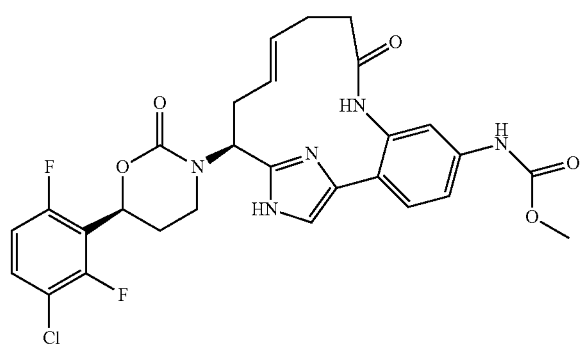 [SMILES: COC(=O)Nc1ccc2c(c1)NC(=O)CC/C=C/C[C@H](N1CC[C@@H](c3c(F)ccc(Cl)c3F)OC1=O)c1nc-2c[nH]1] | 585.9 | 6.59 |
| 105 | Homochiral | 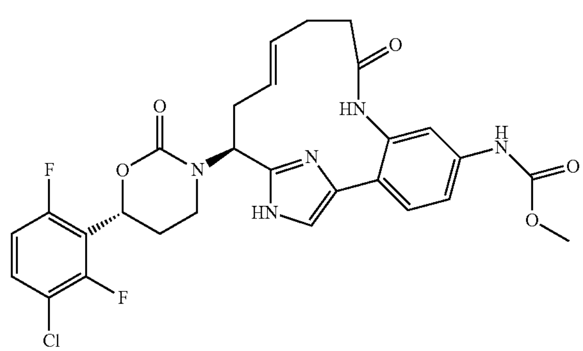 [SMILES: COC(=O)Nc1ccc2c(c1)NC(=O)CC/C=C/C[C@H](N1CC[C@H](c3c(F)ccc(Cl)c3F)OC1=O)c1nc-2c[nH]1] | 586.0 | 6.59 |

TABLE 3-continued

| Example # | Stereochemistry | Structure | M + H | RT, min Method A |
|---|---|---|---|---|
| 106 | Homochiral | 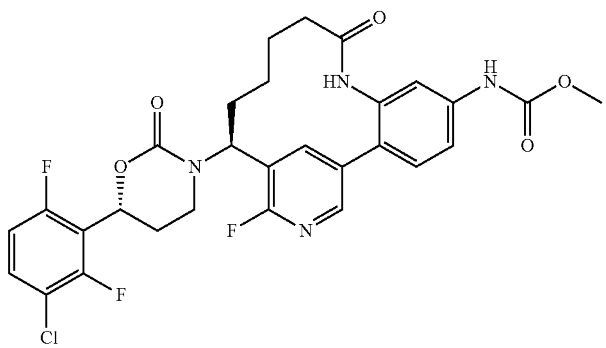 [SMILES: COC(=O)Nc1ccc2c(c1)NC(=O)CCCC[C@H](N1CC[C@H](c3c(F)ccc(Cl)c3F)OC1=O)c1cc-2cnc1F] | 603.0 | 9.16 |
| 107 | Homochiral | 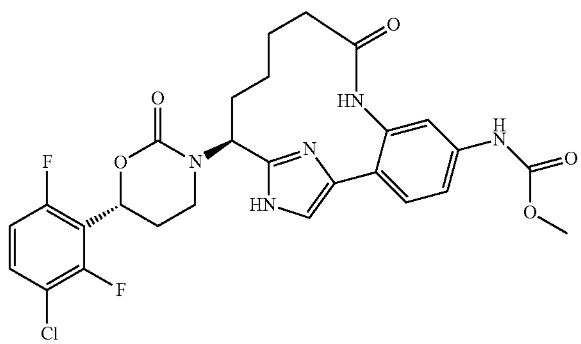 [SMILES: COC(=O)Nc1ccc2c(c1)NC(=O)CCCC[C@H](N1CC[C@H](c3c(F)ccc(Cl)c3F)OC1=O)c1nc-2c[nH]1] | 573.9 | 6.04 |
| 108 | Homochiral | 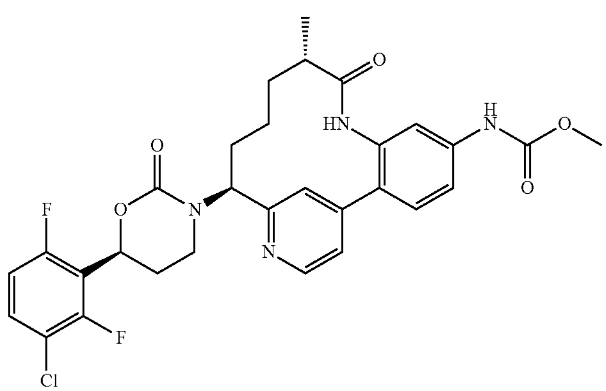 | 599.0 | 6.66 |
| 109 | Homochiral | 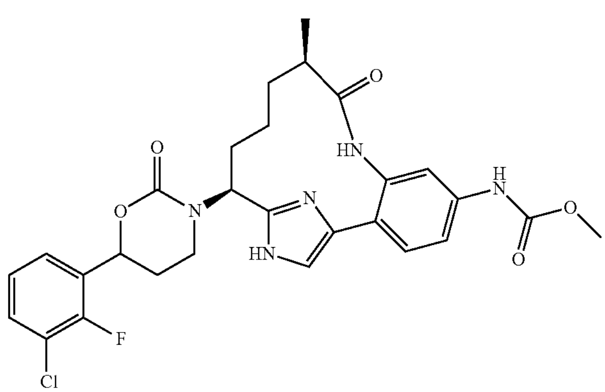 [SMILES: COC(=O)Nc1ccc2c(c1)NC(=O)[C@H](C)CCC[C@H](N1CCC(c3cccc(Cl)c3F)OC1=O)c1nc-2c[nH]1] | 570.2 | 5.99 |

TABLE 3-continued

| Example # | Stereochemistry | Structure | M + H | RT, min Method A |
|---|---|---|---|---|
| 110 | Homochiral | 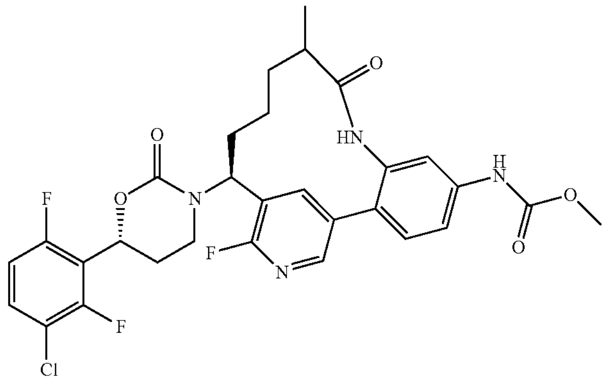 [SMILES: COC(=O)Nc1ccc2c(c1)NC(=O)C(C)CCC[C@H](N1CC[C@H](c3c(F)ccc(Cl)c3F)OC1=O)c1cc-2cnc1F] | 617.3 | 8.77 |
| 111 | Homochiral | 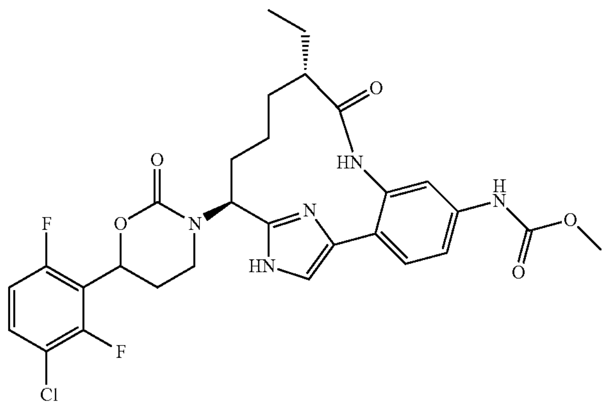 [SMILES: CC[C@H]1CCC[C@H](N2CCC(c3c(F)ccc(Cl)c3F)OC2=O)c2nc(c[nH]2)-c2ccc(NC(=O)OC)cc2NC1=O] | 602.4 | 6.06 |
| 112 | Homochiral | 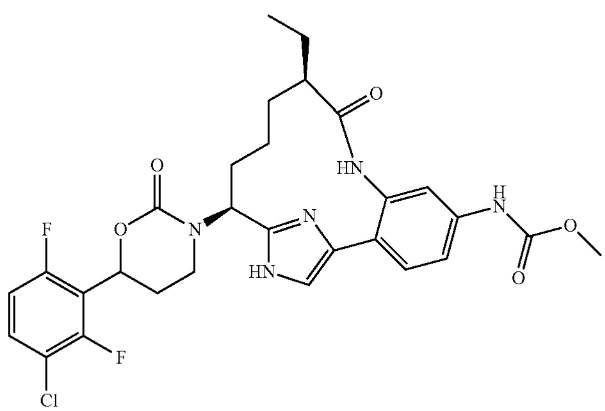 [SMILES: CC[C@@H]1CCC[C@H](N2CCC(c3c(F)ccc(Cl)c3F)OC2=O)c2nc(c[nH]2)-c2ccc(NC(=O)OC)cc2NC1=O] | 602.4 | 6.28 |
| 113 | Diastereomer mixture | 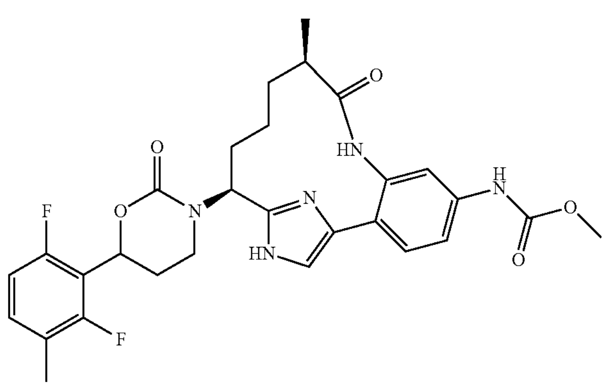 [SMILES: COC(=O)Nc1ccc2c(c1)NC(=O)[C@H](C)CCC[C@H](N1CCC(c3c(F)ccc(C)c3F)OC1=O)c1nc-2c[nH]1] | 568.3 | 6.55 |

TABLE 3-continued

| Example # | Stereochemistry | Structure | M + H | RT, min Method A |
|---|---|---|---|---|
| 114 | Homochiral | 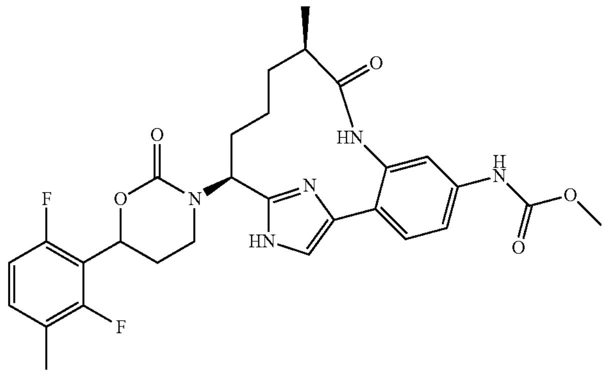 [SMILES: COC(=O)Nc1ccc2c(c1)NC(=O)[C@H](C)CCC[C@H](N1CCC(c3c(F)ccc(C)c3F)OC1=O)c1nc-2c[nH]1] | 568.3 | 5.66 |
| 115 | Homochiral | 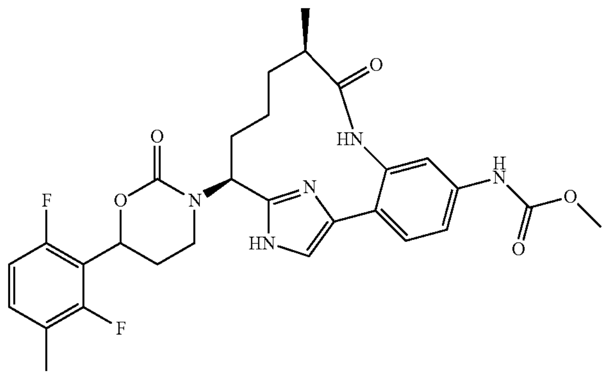 [SMILES: COC(=O)Nc1ccc2c(c1)NC(=O)[C@H](C)CCC[C@H](N1CCC(c3c(F)ccc(C)c3F)OC1=O)c1nc-2c[nH]1] | 568.3 | 5.72 |
| 116 | Homochiral | 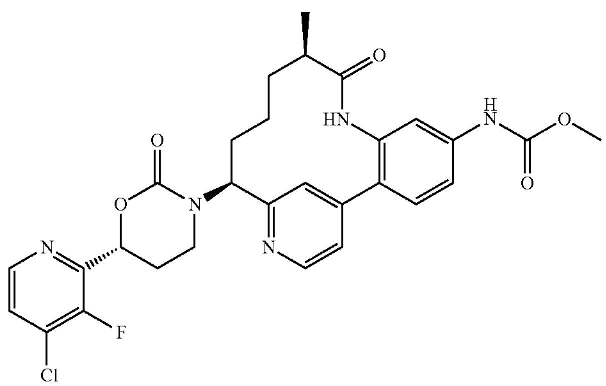 [SMILES: COC(=O)Nc1ccc2c(c1)NC(=O)[C@H](C)CCC[C@H](N1CC[C@H](c3nccc(Cl)c3F)OC1=O)c1cc-2ccn1] | 582.2 | 4.67 |
| 117 | Homochiral | 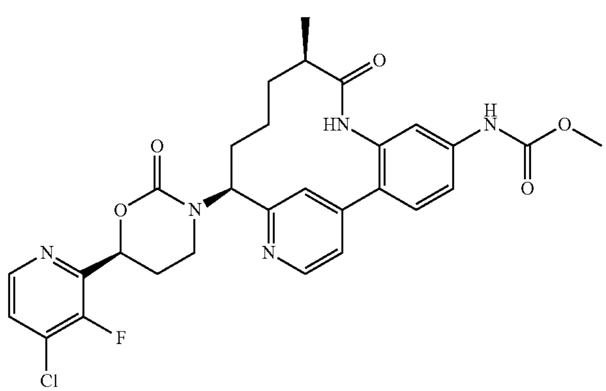 [SMILES: COC(=O)Nc1ccc2c(c1)NC(=O)[C@H](C)CCC[C@H](N1CC[C@@H](c3nccc(Cl)c3F)OC1=O)c1cc-2ccn1] | 582.1 | 4.64 |

TABLE 3-continued

| Example # | Stereochemistry | Structure | M + H | RT, min Method A |
|---|---|---|---|---|
| 118 | Homochiral | 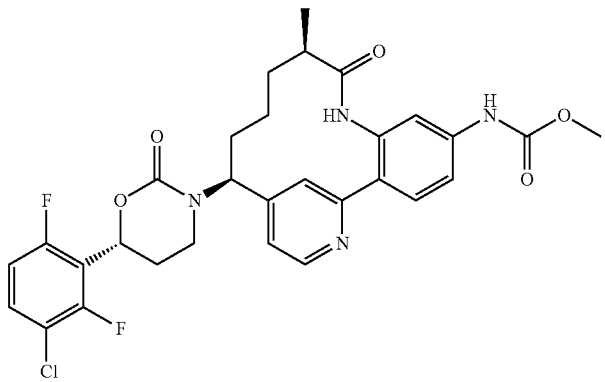 [SMILES: COC(=O)Nc1ccc2c(c1)NC(=O)[C@H](C)CCC[C@H](N1CC[C@H](c3c(F)ccc(Cl)c3F)OC1=O)c1ccnc-2c1] | 599.0 | 6.07 |
| 119 | Homochiral | 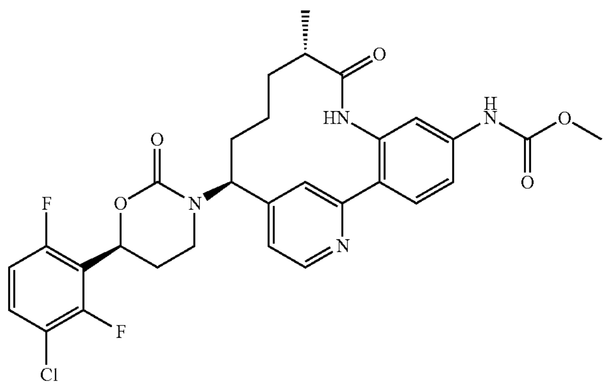 [SMILES: COC(=O)Nc1ccc2c(c1)NC(=O)[C@@H](C)CCC[C@H](N1CC[C@@H](c3c(F)ccc(Cl)c3F)OC1=O)c1ccnc-2c1] | 599.0 | 6.14 |
| 120 | Homochiral | 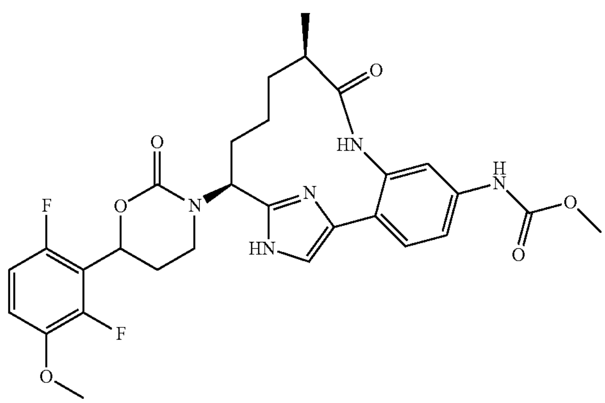 [SMILES: COC(=O)Nc1ccc2c(c1)NC(=O)[C@H](C)CCC[C@H](N1CCC(c3c(F)ccc(OC)c3F)OC1=O)c1nc-2c[nH]1] | 584.3 | 5.69 |
| 121 | Homochiral | 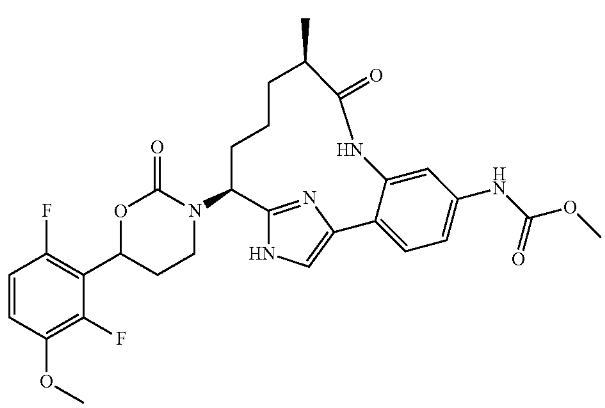 [SMILES: COC(=O)Nc1ccc2c(c1)NC(=O)[C@H](C)CCC[C@H](N1CCC(c3c(F)ccc(OC)c3F)OC1=O)c1nc-2c[nH]1] | 584.3 | 5.61 |

TABLE 3-continued

| Example # | Stereochemistry | Structure | M + H | RT, min Method A |
|---|---|---|---|---|
| 122 | Homochiral | 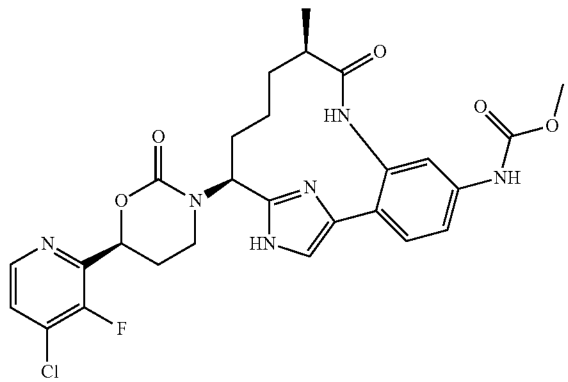 [SMILES: COC(=O)Nc1ccc2c(c1)NC(=O)[C@H](C)CCC[C@H](N1CC[C@@H](c3nccc(Cl)c3F)OC1=O)c1nc-2c[nH]1] | 571.1 | 4.67 |
| 123 | Homochiral | 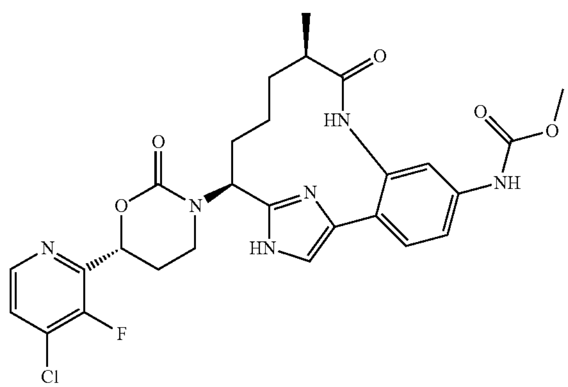 [SMILES: COC(=O)Nc1ccc2c(c1)NC(=O)[C@H](C)CCC[C@H](N1CC[C@H](c3nccc(Cl)c3F)OC1=O)c1nc-2c[nH]1] | 571.1 | 4.72 |
| 124 | Homochiral | 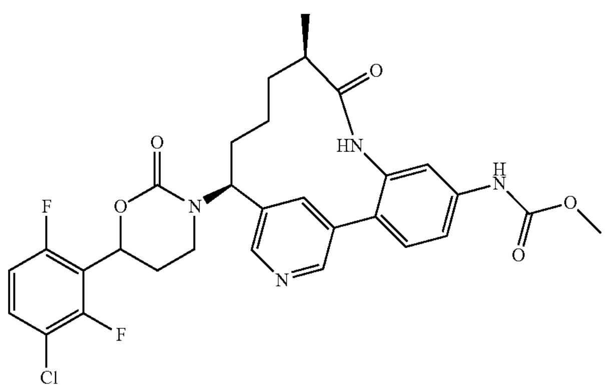 [SMILES: COC(=O)Nc1ccc2c(c1)NC(=O)[C@H](C)CCC[C@H](N1CCC(c3c(F)ccc(Cl)c3F)OC1=O)c1cncc-2c1] | 599.2 | 6.11 |
| 125 | Diastereomer mixture | 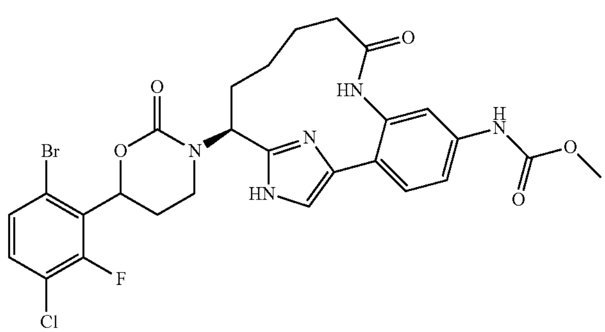 [SMILES: COC(=O)Nc1ccc2c(c1)NC(=O)CCCC[C@H](N1CCC(c3c(Br)ccc(Cl)c3F)OC1=O)c1nc-2c[nH]1] | 636.0 | 5.80 |

TABLE 3-continued

| Example # | Stereochemistry | Structure | M + H | RT, min Method A |
|---|---|---|---|---|
| 126 | Homochiral | 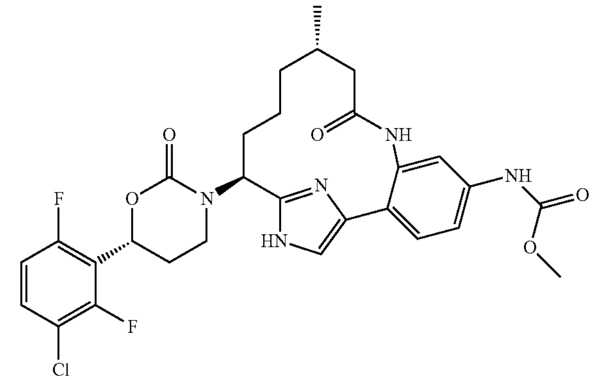 [SMILES: COC(=O)Nc1ccc2c(c1)NC(=O)C[C@@H](C)CCC[C@H](N1CC[C@H](c3c(F)ccc(Cl)c3F)OC1=O)c1nc-2c[nH]1] | 602.2 | 6.51 |
| 127 | Homochiral | 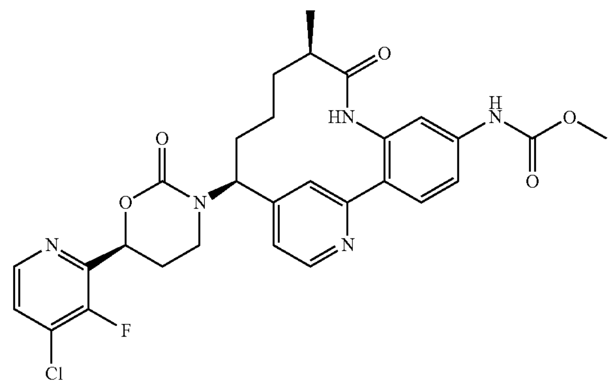 [SMILES: COC(=O)Nc1ccc2c(c1)NC(=O)[C@H](C)CCC[C@H](N1CC[C@@H](c3nccc(Cl)c3F)OC1=O)c1ccnc-2c1] | 582.0 | 5.18 |
| 128 | Homochiral | 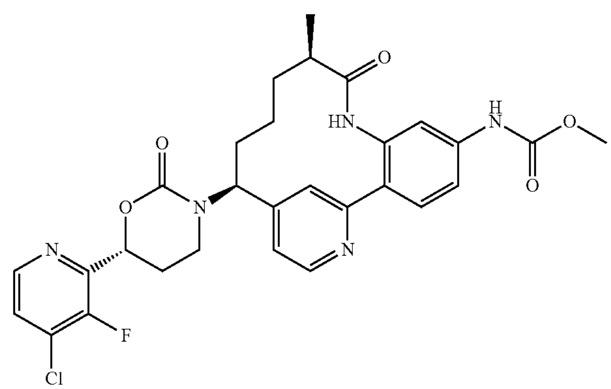 [SMILES: COC(=O)Nc1ccc2c(c1)NC(=O)[C@H](C)CCC[C@H](N1CC[C@H](c3nccc(Cl)c3F)OC1=O)c1ccnc-2c1] | 582.1 | 5.20 |
| 129 | Homochiral | Chiral | 616.9 | 8.49 |

TABLE 3-continued

| Example # | Stereochemistry | Structure | M + H | RT, min Method A |
|---|---|---|---|---|
| 130 | Homochiral | 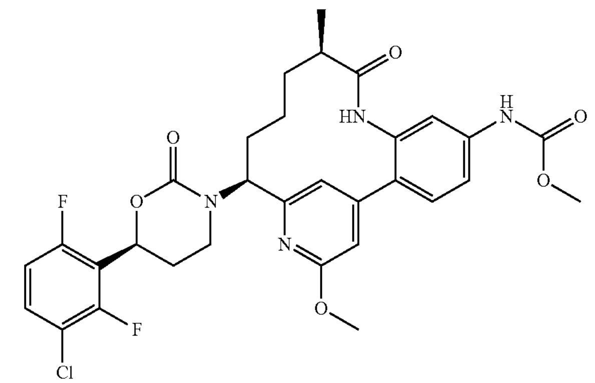 [SMILES: COC(=O)Nc1ccc2c(c1)NC(=O)[C@H](C)CCC[C@H](N1CC[C@@H](c3c(F)ccc(Cl)c3F)OC1=O)c1cc-2cc(OC)n1] | 628.9 | 9.75 |
| 131 | Homochiral | 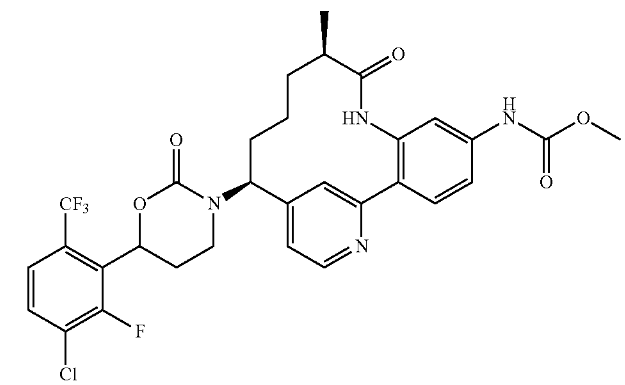 | 648.9 | 6.50 |
| 132 | Homochiral | 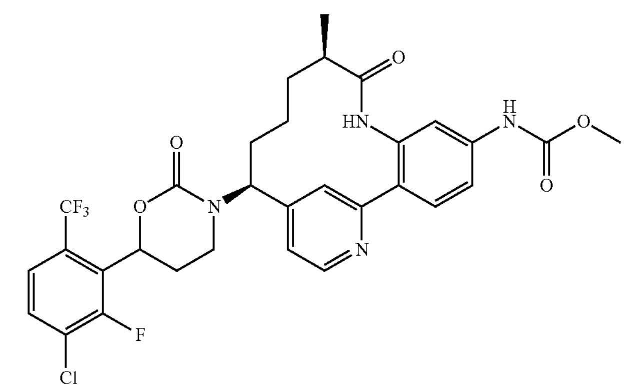 [SMILES: COC(=O)Nc1ccc2c(c1)NC(=O)[C@H](C)CCC[C@H](N1CCC(c3c(C(F)(F)F)ccc(Cl)c3F)OC1=O)c1ccnc-2c1] | 648.9 | 6.66 |
| 133 | Homochiral | 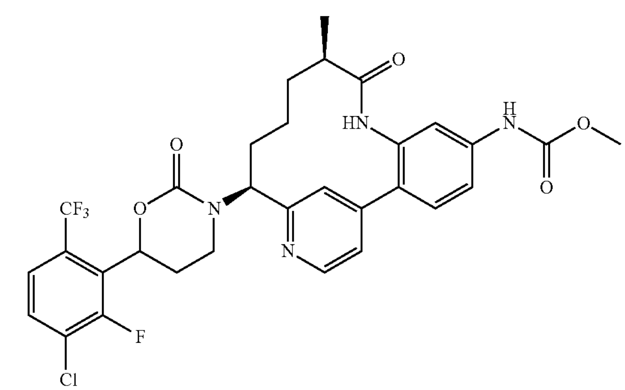 [SMILES: COC(=O)Nc1ccc2c(c1)NC(=O)[C@H](C)CCC[C@H](N1CCC(c3c(C(F)(F)F)ccc(Cl)c3F)OC1=O)c1cc-2ccn1] | 648.9 | 7.09 |

TABLE 3-continued

| Example # | Stereochemistry | Structure | M + H | RT, min Method A |
|---|---|---|---|---|
| 134 | Homochiral | 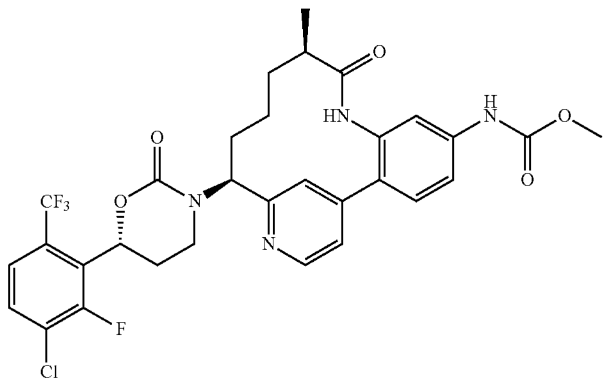 | 649.1 | 6.94 |
| 135 | Homochiral | 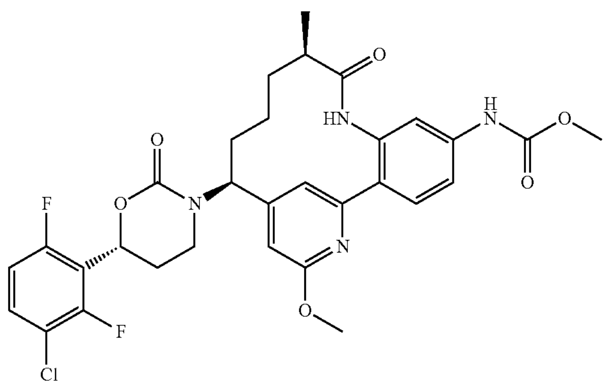 [SMILES: COC(=O)Nc1ccc2c(c1)NC(=O)[C@H](C)CCC[C@H](N1CC[C@H](c3c(F)ccc(Cl)c3F)OC1=O)c1cc(OC)nc-2c1] | 629.0 | 9.22 |
| 136 | Homochiral | 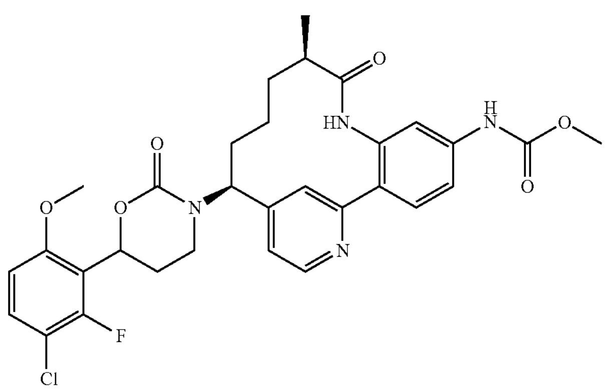 [SMILES: COC(=O)Nc1ccc2c(c1)NC(=O)[C@H](C)CCC[C@H](N1CCC(c3c(OC)ccc(Cl)c3F)OC1=O)c1ccnc-2c1] | 610.9 | 6.10 |
| 137 | Homochiral | 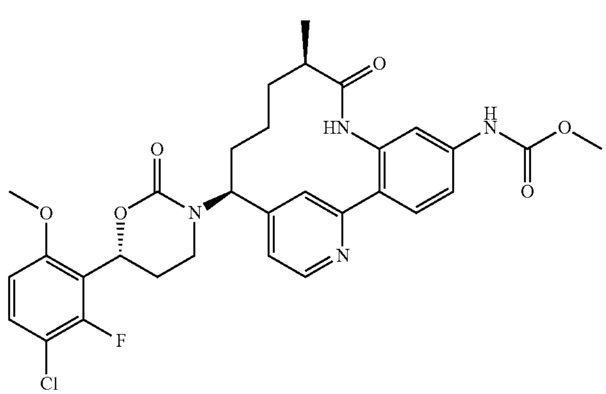 [SMILES: COC(=O)Nc1ccc2c(c1)NC(=O)[C@H](C)CCC[C@H](N1CC[C@H](c3c(OC)ccc(Cl)c3F)OC1=O)c1ccnc-2c1] | 610.9 | 6.19 |

TABLE 3-continued

| Example # | Stereochemistry | Structure | M + H | RT, min Method A |
|---|---|---|---|---|
| 138 | Homochiral | 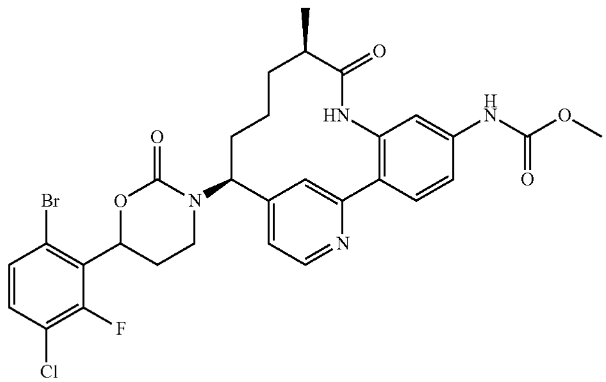 [SMILES: COC(=O)Nc1ccc2c(c1)NC(=O)[C@H](C)CCC[C@H](N1CCC(c3c(Br)ccc(Cl)c3F)OC1=O)c1ccnc-2c1] | 660.9 | 6.30 |
| 139 | Homochiral | 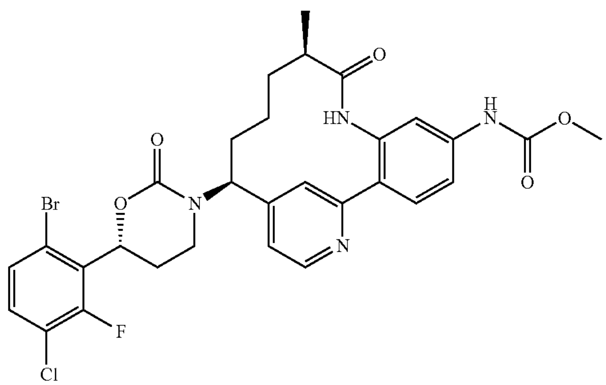 | 660.9 | 6.46 |
| 140 | Homochiral | 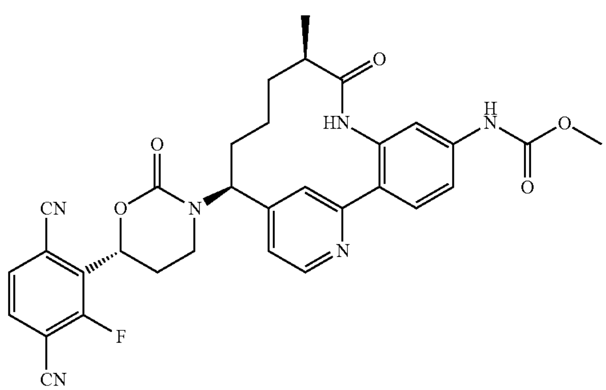 [SMILES: COC(=O)Nc1ccc2c(c1)NC(=O)[C@H](C)CCC[C@H](N1CC[C@H](c3c(C#N)ccc(C#N)c3F)OC1=O)c1ccnc-2c1] | 597.0 | 5.25 |
| 141 | Homochiral | 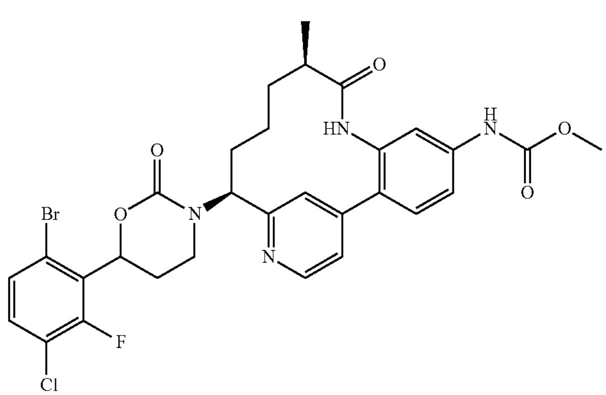 [SMILES: COC(=O)Nc1ccc2c(c1)NC(=O)[C@H](C)CCC[C@H](N1CCC(c3c(Br)ccc(Cl)c3F)OC1=O)c1cc-2ccn1] | 660.9 | 6.79 |

TABLE 3-continued

| Example # | Stereochemistry | Structure | M + H | RT, min Method A |
|---|---|---|---|---|
| 142 | Homochiral | 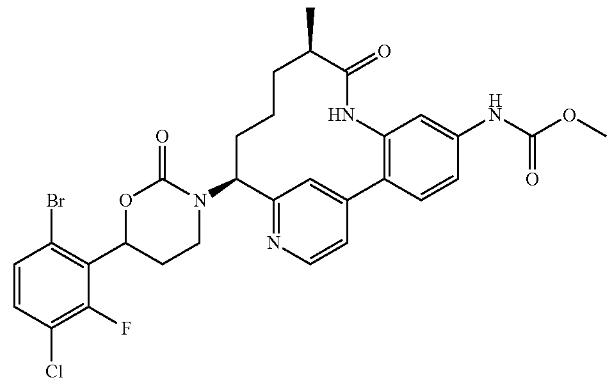 [SMILES: COC(=O)Nc1ccc2c(c1)NC(=O)[C@H](C)CCC[C@H](N1CCC(c3c(Br)ccc(Cl)c3F)OC1=O)c1cc-2ccn1] | 660.9 | 6.85 |
| 143 | Diastereomer mixture | 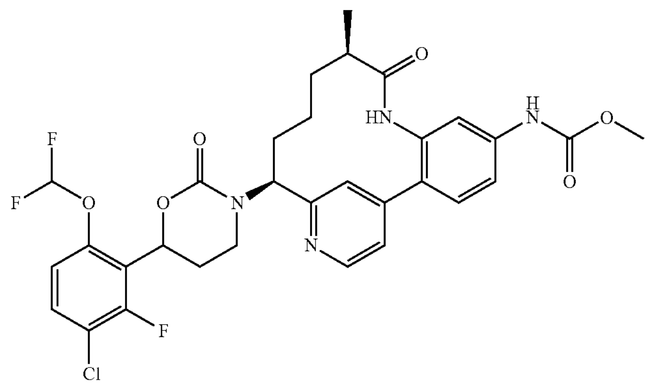 [SMILES: COC(=O)Nc1ccc2c(c1)NC(=O)[C@H](C)CCC[C@H](N1CCC(c3c(OC(F)F)ccc(Cl)c3F)OC1=O)c1cc-2ccn1] | 647.0 | 6.76 |
| 144 | Homochiral | 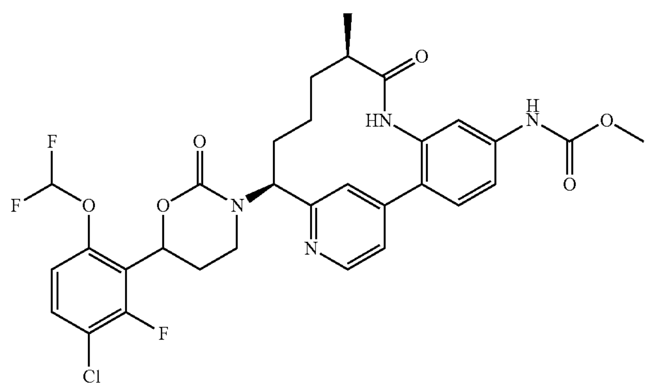 [SMILES: COC(=O)Nc1ccc2c(c1)NC(=O)[C@H](C)CCC[C@H](N1CCC(c3c(OC(F)F)ccc(Cl)c3F)OC1=O)c1cc-2ccn1] | 647.0 | 6.80 |
| 145 | Homochiral | 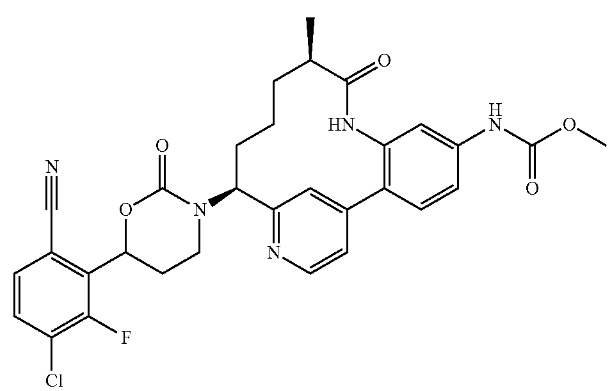 [SMILES: COC(=O)Nc1ccc2c(c1)NC(=O)[C@H](C)CCC[C@H](N1CCC(c3c(C#N)ccc(Cl)c3F)OC1=O)c1cc-2ccn1] | 606.0 | 6.04 |

TABLE 3-continued

| Example # | Stereochemistry | Structure | M + H | RT, min Method A |
|---|---|---|---|---|
| 146 | Homochiral | 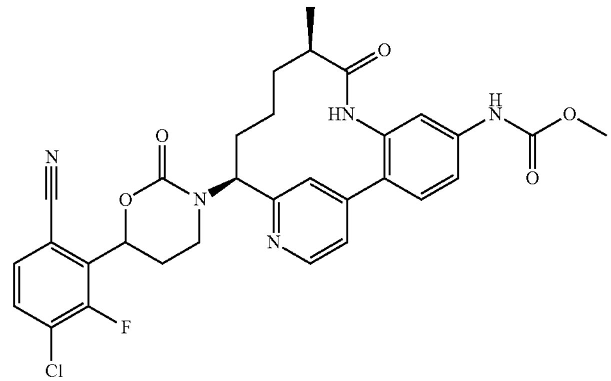 [SMILES: COC(=O)Nc1ccc2c(c1)NC(=O)[C@H](C)CCC[C@H](N1CCC(c3c(C#N)ccc(Cl)c3F)OC1=O)c1cc-2ccn1] | 606.0 | 6.00 |

The following Examples in Table 4 were prepared using the methods described in the previous Examples for preparing lactams.

TABLE 4

| Example # | Stereochemistry | Structure | M + H | RT, min Method |
|---|---|---|---|---|
| 147 | Homochiral (diastereomer A) | 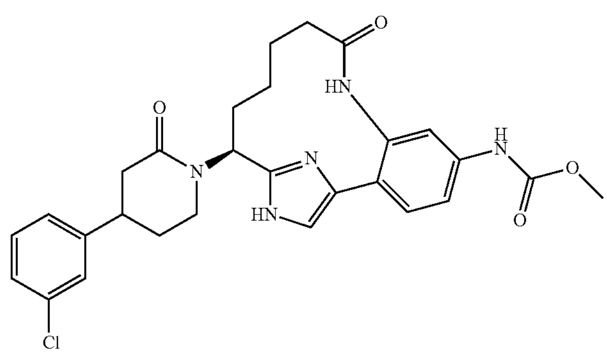 [SMILES: COC(=O)Nc1ccc2c(c1)NC(=O)CCCC[C@H](N1CCC(c3cccc(Cl)c3)CC1=O)c1nc-2c[nH]1] | 536.0 | 5.82 C |
| 148 | Homochiral (diastereomer B) | 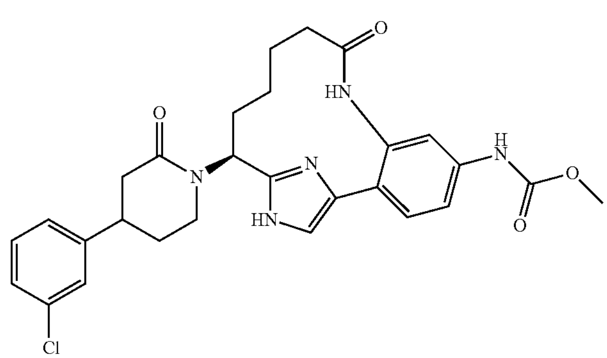 [SMILES: COC(=O)Nc1ccc2c(c1)NC(=O)CCCC[C@H](N1CCC(c3cccc(Cl)c3)CC1=O)c1nc-2c[nH]1] | 536.0 | 6.44 C |

TABLE 4-continued

| Example # | Stereochemistry | Structure | M + H | RT, min Method |
|---|---|---|---|---|
| 149 | Homochiral from Intermediate 3 (enantiomer A) | 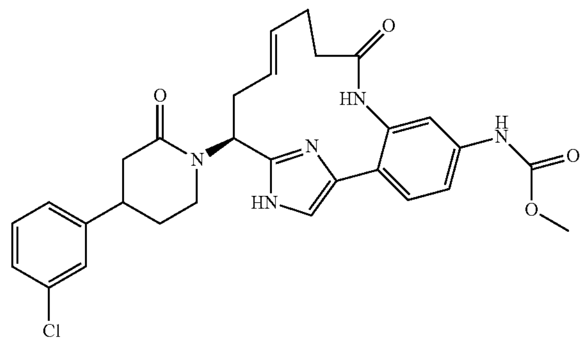 | 548.1 | 5.95 A |
| 150 | Homochiral (diastereomer A) | 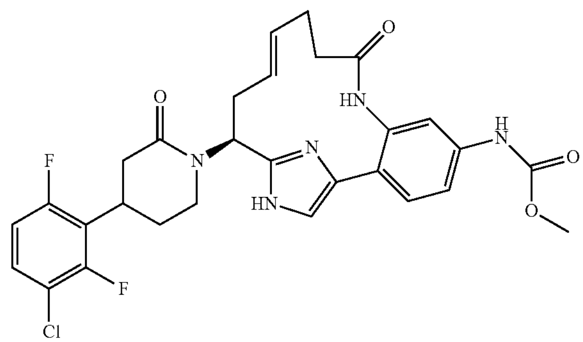 | 584.0 | 5.86 |
| 151 | Homochiral (diastereomer B) | 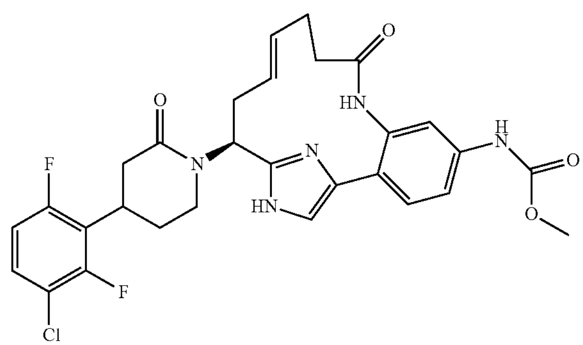 | 584.0 | 5.90 |
| 152 | Homochiral from Intermediate 3 (enantiomer B) | 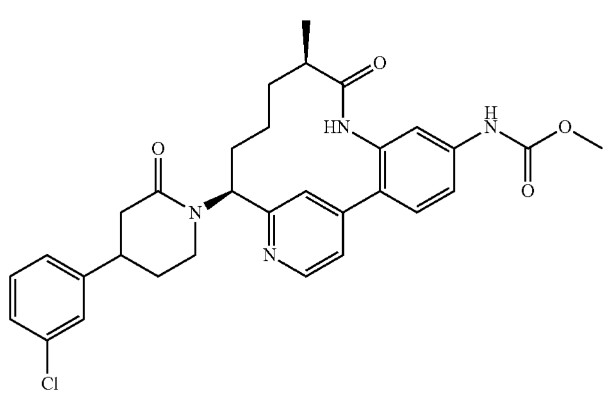 [SMILES: COC(=O)Nc1ccc2c(c1)NC(=O)[C@H](C)CCC[C@H](N1CCC(c3cccc(Cl)c3)CC1=O)c1cc-2ccn1] | 561.1 | 7.65 |

TABLE 4-continued
| Example # | Stereochemistry | Structure | M + H | RT, min Method |
|---|---|---|---|---|
| 153 | Diastereomer mixture | 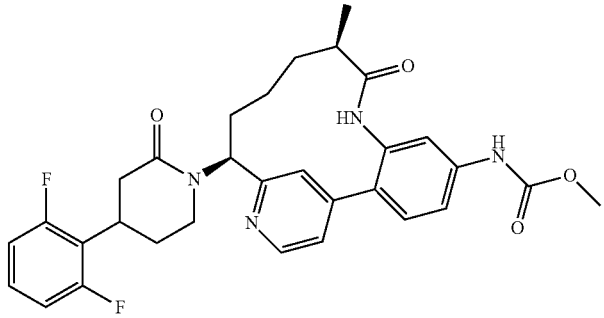 [SMILES: COC(=O)Nc1ccc2c(c1)NC(=O)[C@H](C)CCC[C@H](N1CCC(c3c(F)cccc3F)CC1=O)c1cc-2ccn1] | 563.2 | 6.67 A |
| 154 | Diastereomer mixture | 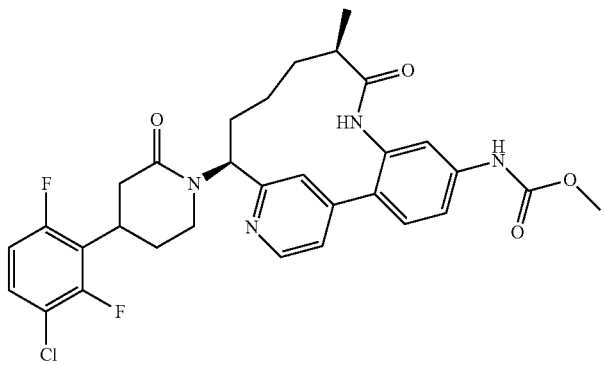 [SMILES: COC(=O)Nc1ccc2c(c1)NC(=O)[C@H](C)CCC[C@H](N1CCC(c3c(F)ccc(Cl)c3F)CC1=O)c1cc-2ccn1] | 597.1 | 7.17.2012 A |
The following Examples in Table 5 were prepared using the methods described in the previous Examples for preparing ketopiperazines and diketopiperazines.
TABLE 5
| Example # | Stereochemistry | Structure | M + H | RT, min Method |
|---|---|---|---|---|
| 155 | Homochiral | 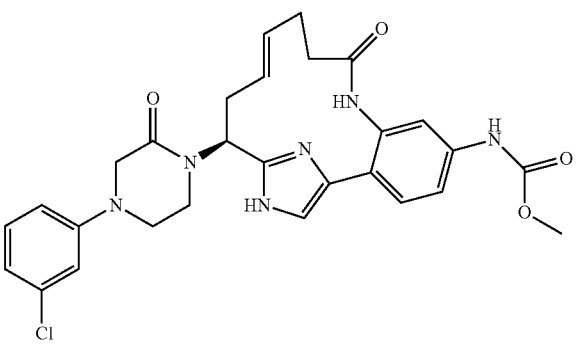 [SMILES: COC(=O)Nc1ccc2c(c1)NC(=O)CC/C=C/C[C@H](N1CCN(c3cccc(Cl)c3)CC1=O)c1nc-2c[nH]1] | 549.0 | 6.09 C |

TABLE 5-continued

| Example # | Stereochemistry | Structure | M + H | RT, min Method |
|---|---|---|---|---|
| 156 | Homochiral | 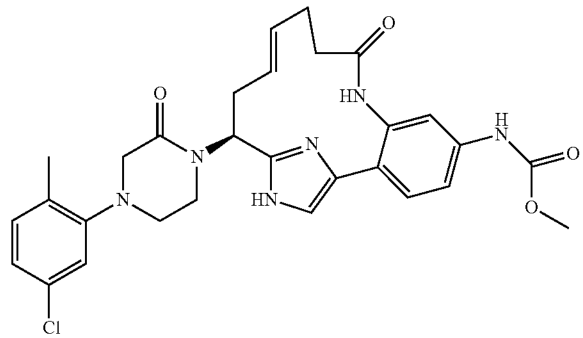 [SMILES: COC(=O)Nc1ccc2c(c1)NC(=O)CC/C=C/C[C@H](N1CCN(c3cc(Cl)ccc3C)CC1=O)c1nc-2c[nH]1] | 563.1 | 6.76 A |
| 157 | Homochiral | 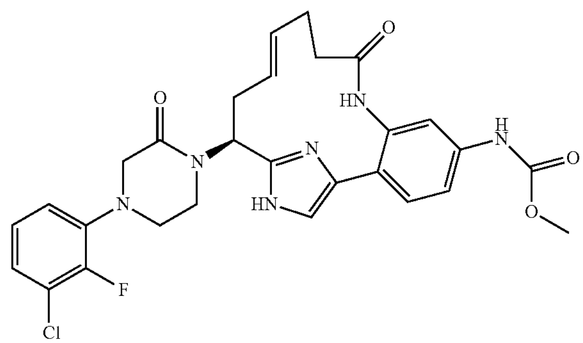 [SMILES: COC(=O)Nc1ccc2c(c1)NC(=O)CC/C=C/C[C@H](N1CCN(c3cccc(Cl)c3F)CC1=O)c1nc-2c[nH]1] | 567.2 | 6.97 A |
| 158 | Homochiral (diastereomer A) | 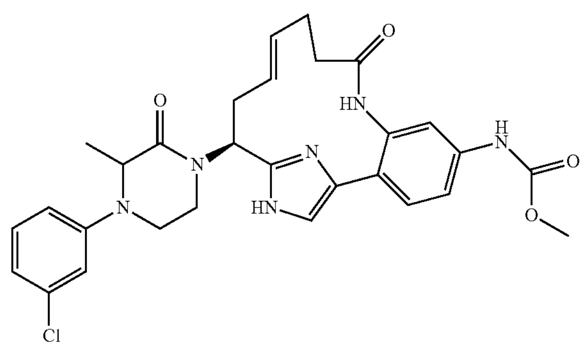 [SMILES: COC(=O)Nc1ccc2c(c1)NC(=O)CC/C=C/C[C@H](N1CCN(c3cccc(Cl)c3)C(C)C1=O)c1nc-2c[nH]1] | 563.2 | 7.19 A |
| 159 | Homochiral (diastereomer B) | 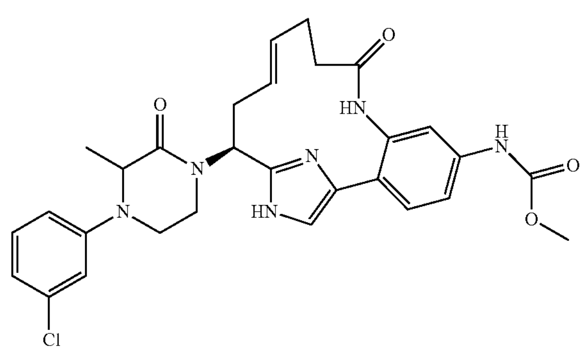 [SMILES: COC(=O)Nc1ccc2c(c1)NC(=O)CC/C=C/C[C@H](N1CCN(c3cccc(Cl)c3)C(C)C1=O)c1nc-2c[nH]1] | 563.3 | 7.29 A |

TABLE 5-continued

| Example # | Stereochemistry | Structure | M + H | RT, min Method |
|---|---|---|---|---|
| 160 | Homochiral | 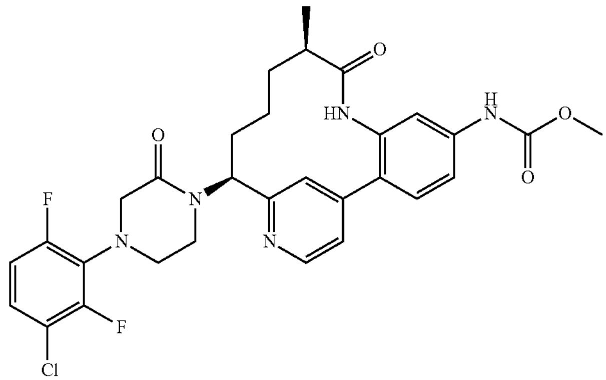 [SMILES: COC(=O)Nc1ccc2c(c1)NC(=O)[C@H](C)CCC[C@H](N1CCN(c3c(F)ccc(Cl)c3F)CC1=O)c1cc-2ccn1] | 598.2 | 5.68 C |
| 161 | Homochiral | 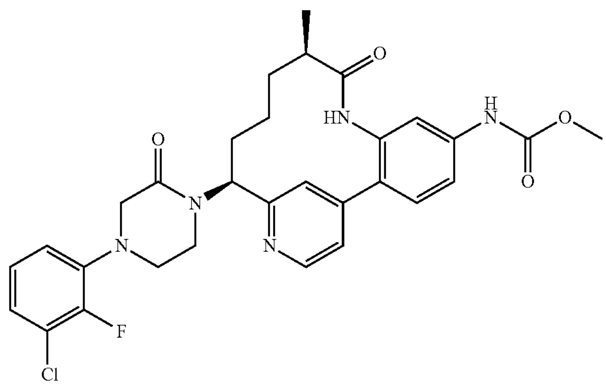 [SMILES: COC(=O)Nc1ccc2c(c1)NC(=O)[C@H](C)CCC[C@H](N1CCN(c3cccc(Cl)c3F)CC1=O)c1cc-2ccn1] | 580.2 | 6.32 B |
| 162 | Homochiral | 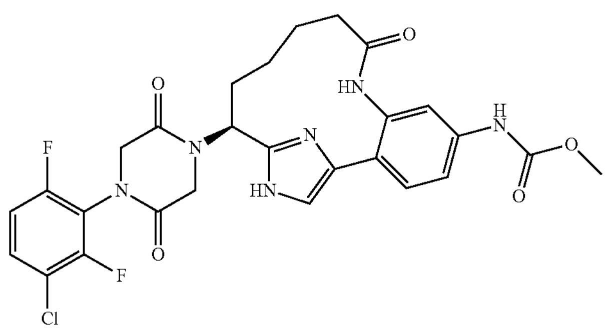 [SMILES: COC(=O)Nc1ccc2c(c1)NC(=O)CCCC[C@H](N1CC(=O)N(c3c(F)ccc(Cl)c3F)CC1=O)c1nc-2c[nH]1] | 598.2 | 5.69 C |
| 163 | Homochiral | 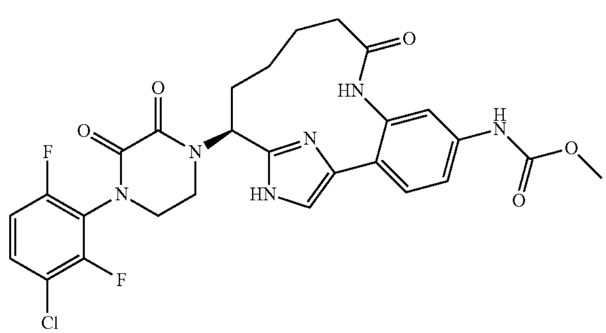 [SMILES: COC(=O)Nc1ccc2c(c1)NC(=O)CCCC[C@H](N1CCN(c3c(F)ccc(Cl)c3F)C(=O)C1=O)c1nc-2c[nH]1] | 586.8 | 4.89 A |

TABLE 5-continued

| Example # | Stereochemistry | Structure | M + H | RT, min Method |
|---|---|---|---|---|
| 164 | Homochiral | 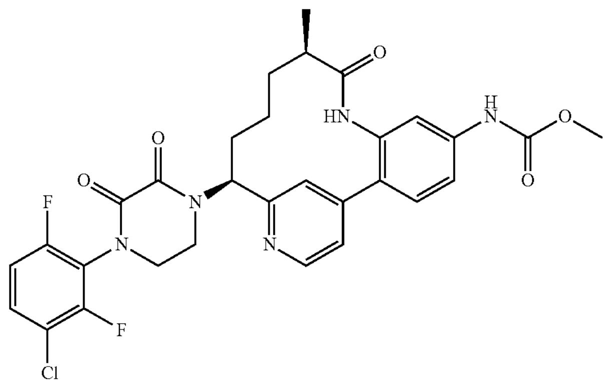 [SMILES: COC(=O)Nc1ccc2c(c1)NC(=O)[C@H](C)CCC[C@H](N1CCN(c3c(F)ccc(Cl)c3F)C(=O)C1=O)c1cc-2ccn1] | 612.1 | 6.02 A |
| 165 | Homochiral | 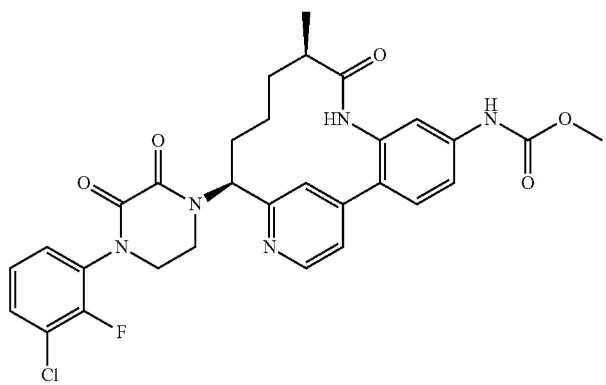 [SMILES: COC(=O)Nc1ccc2c(c1)NC(=O)[C@H](C)CCC[C@H](N1CCN(c3cccc(Cl)c3F)C(=O)C1=O)c1cc-2ccn1] | 593.9 | 5.88 A |
| 166 | Homochiral | 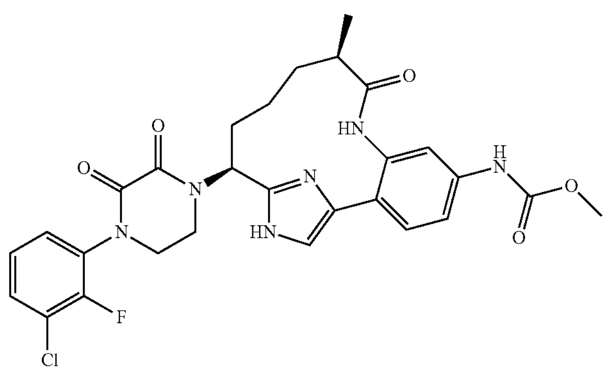 [SMILES: COC(=O)Nc1ccc2c(c1)NC(=O)[C@H](C)CCC[C@H](N1CCN(c3cccc(Cl)c3F)C(=O)C1=O)c1nc-2c[nH]1] | 583.1 | 5.01 A |
| 167 | Homochiral | 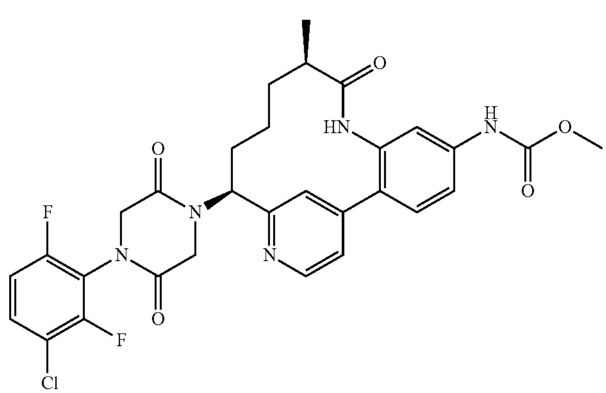 [SMILES: COC(=O)Nc1ccc2c(c1)NC(=O)[C@H](C)CCC[C@H](N1CC(=O)N(c3c(F)ccc(Cl)c3F)CC1=O)c1cc-2ccn1] | 611.9 | 5.90 A |

TABLE 5-continued

| Example # | Stereochemistry | Structure | M + H | RT, min Method |
|---|---|---|---|---|
| 168 | Diastereomer mixture | 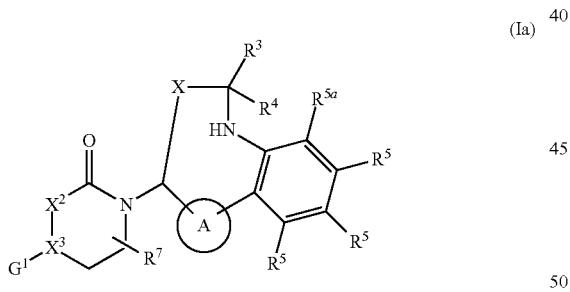 | 611.9 | 5.41<br>5.54<br>A |
| 169 | Diastereomer mixture (2:1) | 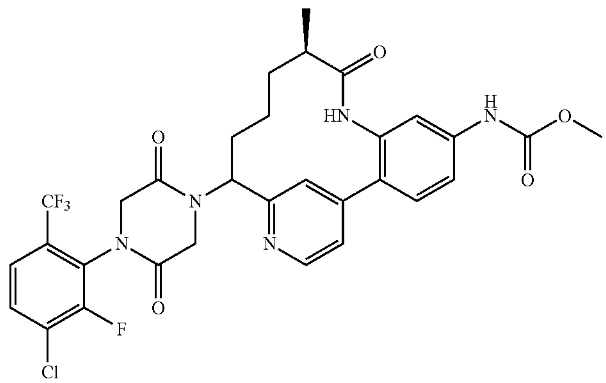 [SMILES: COC(=O)Nc1ccc2c(c1)NC(=O)[C@H](C)CCCC(N1CC(=O)N(c3c(C(F)(F)F)ccc(Cl)c3F)CC1=O)c1cc-2ccn1] | 662.0 | 6.87<br>A |

What is claimed is:
1. A compound of Formula (Ia):

(Ia)

or a stereoisomer, a tautomer, a pharmaceutically acceptable salt, thereof, wherein:
  $G^1$ is selected from the group consisting of a 6-membered aryl and a 5- to 6-membered heteroaryl wherein said aryl and heteroaryl are substituted with 1-5 $R^8$;
  ring A is selected from the group consisting of a 6-membered aryl and a 5- to 6-membered heterocycle, wherein said aryl and heterocycle are substituted with 1-3 $R^{13}$;
  X is selected from the group consisting of $C_{4-8}$ alkylene and $C_{4-8}$ alkenylene, wherein said alkylene and alkenylene are substituted with $R^1$, $R^2$, and $R^6$; alternatively one or more of the carbon atoms of said alkylene and alkenylene may be replaced by O, C=O, $S(O)_p$, NH, and $N(C_{1-4}$ alkyl);
  $X^2$ is selected from the group consisting of $CHR^{11}$, C=O, O, NH, and $N(C_{1-4}$ alkyl);
  $X^3$ is $CR^{12}$ or N; provided $X^3$ is $CR^{12}$ when $X^2$ is O, NH, or $N(C_{1-4}$ alkyl);
  $R^1$ and $R^2$ are independently selected from the group consisting of H, halogen, $C_{1-6}$ alkyl, OH, $NH_2$, —$CH_2NH_2$, $C_{1-4}$ haloalkyl, —$OCH_2F$, —$OCHF_2$, —$OCF_3$, $NH(C_{1-4}$ alkyl), $N(C_{1-4}$ alkyl)$_2$, $C_{1-4}$ alkoxy, —$CH_2OH$, and —$CH_2O(C_{1-4}$ alkyl); alternatively, $R^1$ and $R^2$ are taken together with the carbon atoms to which they are attached to form a carbocycle;
  $R^3$ is selected from the group consisting of H, haloalkyl, —C(=O)OH, —C(=O)O—$C_{1-4}$ alkyl, and —C(=O)$NR^9R^{10}$;
  $R^4$ is selected from the group consisting of H and $C_{1-6}$ alkyl; alternatively, $R^3$ and $R^4$ together are =O;
  $R^5$ is independently selected from the group consisting of H, halogen, $C_{1-4}$ alkyl, OH, CN, $NR^9R^{10}$, $NO_2$, $C_{1-4}$ alkoxy, —C(=O)OH, —C(=O)O($C_{1-4}$ alkyl), —C(=O)$NH_2$, C(=O)$NR^9(C_{1-4}$ alkyl), —C(=O)$NR^9$—$C_{1-4}$ alkylene-O($C_{1-4}$ alkyl), —$NR^9C$(=O)$C_{1-4}$ alkyl, —$NR^9C$(=O)O$C_{1-4}$ alkyl, —$NR^9C$(=O)$C_{1-4}$ alkylene-O($C_{1-4}$ alkyl), —$NR^9C$(=O)O$C_{1-4}$ alkylene-O($C_{1-4}$ alkyl), —$NR^9C$(=O)NH($C_{1-4}$ alkyl), $R^{15}$, —C(=O)$OR^{15}$, —C(=O)$NR^9R^{15}$, —$NR^9R^{15}$, —$NR^9C$(=O)$R^{15}$, and —$NR^9C$(=O)$OR^{15}$;
  $R^{5a}$ is selected from the group consisting of H, halogen, and methyl;
  $R^6$ is selected from the group consisting of H, $C_{1-6}$ alkyl, and OH;
  $R^7$ is selected from the group consisting of H, $^2H$, F, =O, OH, and $C_{1-4}$ alkyl;

241

$R^8$ is selected from the group consisting of H, halogen, OH, CN, $C_{1-6}$ alkyl, haloalkyl, alkoxy, haloalkoxy, and —C(=O)$C_{1-3}$ alkyl;

$R^9$ is selected from the group consisting of H and $C_{1-6}$ alkyl;

$R^{10}$ is selected from the group consisting of H and $C_{1-6}$ alkyl;

alternatively, $R^9$ and $R^{10}$ are taken together with the nitrogen atom to which they are attached to form a 4- to 7-membered heterocycle substituted with $R^{14}$;

$R^{11}$ is selected from the group consisting of H and $C_{1-6}$ alkyl;

$R^{12}$ is selected from the group consisting of H, $^2$H, and $C_{1-6}$ alkyl;

$R^{13}$ is selected from the group consisting of H, OH, halogen, CN, $C_{1-6}$ alkyl, alkoxy, haloalkyl, haloalkoxy, and $C_{3-6}$ cycloalkyl;

$R^{14}$ is selected from the group consisting of H, OH, halogen, and $C_{1-6}$ alkyl;

$R^{15}$ is selected from the group consisting of: —(CH$_2$)$_n$—$C_{3-10}$ carbocycle and —(CH$_2$)$_n$-4-10 membered heterocycle, wherein said carbocycle and heterocycle are optionally substituted with $C_{1-6}$ alkyl, $C_{3-6}$ cycloalkyl, —(CH$_2$)$_n$—C(=O)O$C_{1-4}$ alkyl, —(CH$_2$)$_n$—O$C_{1-4}$ alkyl, and =O;

n, at each occurrence, is selected from 0, 1, 2, 3 and 4; and p, at each occurrence, is selected from 0, 1, and 2.

2. The compound of claim 1 having Formula (IIa):

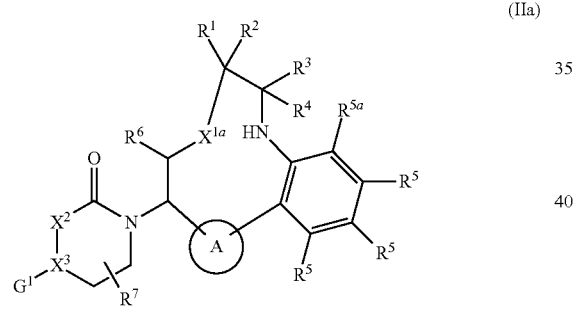

(IIa)

or a stereoisomer, a tautomer, a pharmaceutically acceptable salt, thereof, wherein:

$G^1$ is selected from the group consisting of a 6-membered aryl and heteroaryl comprising carbon atoms and 1-2 heteroatoms selected from N, NH, and N($C_{1-4}$ alkyl), wherein said aryl and heterocycle are substituted with 1-4 $R^8$;

$X^{1a}$ is selected from the group consisting of $C_{2-4}$ alkylene and $C_{2-4}$ alkenylene wherein said $C_{2-4}$ alkylene and $C_{2-4}$ alkenylene are optionally substituted with $R^1$ and $R^2$; alternatively one or more of the carbon atoms of said alkylene may be replaced by O and C=O;

$R^1$ and $R^2$ are independently selected from the group consisting of H, halogen, $C_{1-6}$ alkyl, OH, NH$_2$, $C_{1-4}$ haloalkyl, —OCHF$_2$, —OCF$_3$;

$R^3$ is selected from the group consisting of H, haloalkyl, —C(=O)OH, —C(=O)O—$C_{1-4}$ alkyl, and —C(=O)NR$^9$R$^{10}$;

$R^4$ is selected from the group consisting of H and $C_{1-4}$ alkyl; optionally, $R^3$ and $R^4$ together are =O;

$R^5$ is independently selected from the group consisting of H, halogen, —NHC(=O)O—$C_{1-4}$ alkyl, —NHC

242

(=O)O(CH$_2$)$_{1-4}$—O$C_{1-4}$ alkyl, —C(=O)NH$_2$, —C(=O)O—$C_{1-4}$ alkyl, —C(=O)OH, CN, OH, and —O—$C_{1-4}$ alkyl, $R^{15}$, and —NR$^9$R$^{15}$;

$R^{5a}$ is selected from the group consisting of H, halogen, and methyl;

$R^7$ is selected from the group consisting of H, $^2$H, F, =O, OH, methyl, ethyl, and isopropyl;

$R^8$ is selected from the group consisting of H, halogen, OH, CN, $C_{1-4}$ alkyl, haloalkyl, alkoxy, haloalkoxy, and —C(=O)$C_{1-3}$ alkyl;

$R^9$ is selected from the group consisting of H and $C_{1-6}$ alkyl;

$R^{10}$ is selected from the group consisting of H and $C_{1-6}$ alkyl;

$R^9$ and $R^{10}$ are taken together with the nitrogen atom to which they are attached to form a 4- to 7-membered heterocycle; and $R^{15}$ is selected from the group consisting of —(CH$_2$)$_n$—$C_{3-10}$ carbocycle and —(CH$_2$)$_n$-4-10 membered heterocycle comprising carbon atoms and 1-4 heteroatoms selected from the group consisting of N, NH, N($C_{1-4}$ alkyl), O, and S(O)$_p$; wherein said carbocycle and heterocycle are optionally substituted with $C_{1-6}$ alkyl, $C_{3-6}$ cycloalkyl, —(CH$_2$)$_n$—C(=O)O$C_{1-4}$ alkyl, —(CH$_2$)$_n$—O$C_{1-4}$ alkyl, and =O.

3. The compound of claim 2 or a stereoisomer, a tautomer, a pharmaceutically acceptable salt, thereof, wherein:

$G^1$ is selected from the group consisting of

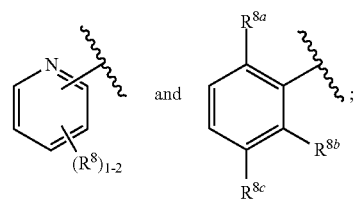

$R^8$ is selected from the group consisting of H, halogen, $C_{1-4}$ alkyl, and haloalkyl;

$R^{8a}$ and $R^{8c}$ are each independently selected from the group consisting of H, halogen, CN, $C_{1-4}$ alkyl, haloalkyl, alkoxy, haloalkoxy, and —C(=O)$C_{1-3}$ alkyl; and $R^{8b}$ is selected from the group consisting of H and halogen.

4. The compound of claim 2, wherein:

ring A is selected from the group consisting of phenyl, imidazole, pyridine, pyridazine, pyrimidine, pyridone, and pyridazinone.

5. The compound of claim 4 having Formula (IIIa):

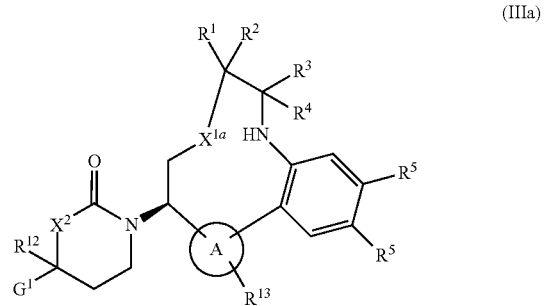

(IIIa)

or a stereoisomer, a tautomer, a pharmaceutically acceptable salt, thereof, wherein:

G¹ is selected from the group consisting of

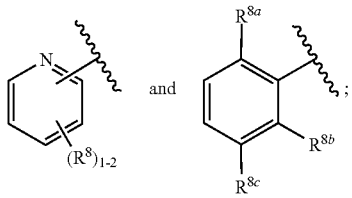

ring A is selected from the group consisting of

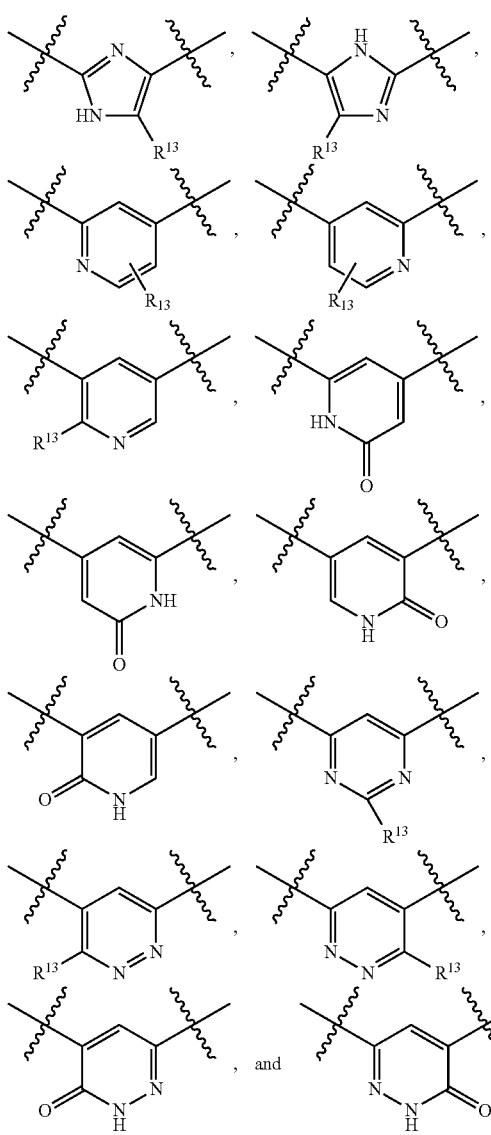

$X^{1a}$ is selected from the group consisting of —CR¹R²—CR¹R²—, —CR¹R²—CR¹R²—CR¹R²—, and —CR¹=CR²CR¹R²—, wherein one or more —CR¹R²— may be replaced by O or C=O;

$X^2$ is selected from the group consisting of CH₂, O, NH, and N(C₁₋₄ alkyl);

R¹ and R² are independently selected from the group consisting of H, F, C₁₋₆ alkyl, OH, CF₃, OCHF₂, OCF₃;

R³ is selected from the group consisting of H, haloalkyl, C(=O)OH, C(=O)O—C₁₋₄ alkyl, and C(=O)NR⁹R¹⁰;

R⁴ is selected from the group consisting of H and C₁₋₆ alkyl; optionally, R³ and R⁴ together are =O;

R⁵ is selected from the group consisting of H, halogen, NHC(=O)O—C₁₋₄ alkyl, NHC(=O)O(CH₂)₂—OC₁₋₄ alkyl, C(=O)NH₂, C(=O)O—C₁₋₄ alkyl, C(=O)OH, R¹⁵, and —NHR¹⁵;

R⁸ is selected from the group consisting of H, F, Cl, Br, CH₃ and CF₃;

$R^{8a}$ and $R^{8c}$ are each independently selected from the group consisting of H, halogen, CN, CH₃, OCH₃, CF₃, and OCHF₂;

$R^{8b}$ is selected from the group consisting of H, F, and Cl;

R⁹ is selected from the group consisting of H and C₁₋₆ alkyl;

R¹⁰ is selected from the group consisting of H and C₁₋₆ alkyl;

alternatively, R⁹ and R¹⁰ are taken together with the nitrogen atom to which they are attached to form a 4- to 7-membered heterocycle optionally substituted with R¹⁴; and R¹² is selected from the group consisting of H, ²H, and methyl;

R¹³ is selected from the group consisting of H, OH, halogen, CN, C₁₋₄ alkyl, and OC₁₋₄ alkyl;

R¹⁴ is selected from the group consisting of H, OH, halogen, and C₁₋₆ alkyl;

R¹⁵ is a 4- to 10-membered heterocycle comprising carbon atoms and 1-4 heteroatoms selected from the group consisting of N, NH, N(C₁₋₄ alkyl), O, and S(O)ₚ optionally substituted with C₁₋₆ alkyl, C₃₋₆ cycloalkyl, —(CH₂)ₙ—C(=O)OC₁₋₄ alkyl, —(CH₂)ₙOC₁₋₄ alkyl, and =O.

6. The compound of claim 5 having Formula (IVa):

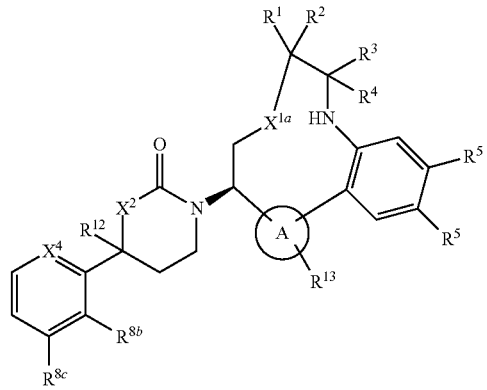

(IVa)

or a stereoisomer, a tautomer, a pharmaceutically acceptable salt, thereof, wherein:

ring A is selected from the group consisting of

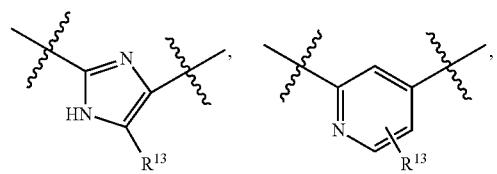

245

-continued

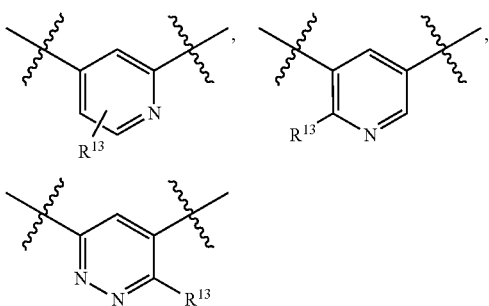

and;

X$^{1a}$ is selected from the group consisting of CH$_2$CH$_2$ and CH═CHCH$_2$;

X$^2$ is selected from the group consisting of CH$_2$, O, and NH;

X$^4$ is selected from the group consisting of CR$^{8a}$ and N;

R$^1$ is selected from the group consisting of H, F, methyl, ethyl, and isopropyl;

R$^2$ is selected from the group consisting of H and F;

R$^{12}$ is selected from the group consisting of H, $^2$H, and methyl;

R$^5$ is selected from the group consisting of H, halogen, —NHC(═O)O—C$_{1-4}$ alkyl, —NHC(═O)O(CH$_2$)$_2$—OC$_{1-4}$ alkyl, —C(═O)NH$_2$, —C(═O)O—C$_{1-4}$ alkyl, —C(═O)OH, and NH—R$^{15}$;

R$^{8a}$ is selected from the group consisting of H, F, Cl, Br, CN, OCH$_3$, CF$_3$, and OCHF$_2$;

R$^{8b}$ is selected from the group consisting of H and F;

R$^{8c}$ is selected from the group consisting of H, F, Cl, OH, CH$_3$, OCH$_3$, and CF$_3$;

R$^{12}$ is selected from the group consisting of H and $^2$H;

R$^{13}$ is selected from the group consisting of H, OH, F, Cl, OC$_{1-4}$ alkyl, and CN;

R$^{15}$ is a 5- to 10-membered heterocycle comprising carbon atoms and 1-4 heteroatoms selected from the group consisting of N, NH, N(C$_{1-4}$ alkyl), O, and S(O)$_p$ optionally substituted with C$_{1-6}$ alkyl, C$_{3-6}$ cycloalkyl, —CH$_2$C(═O)OC$_{1-4}$ alkyl, —CH$_2$OC$_{1-4}$ alkyl, and ═O.

7. The compound of claim 2 having Formula (Va):

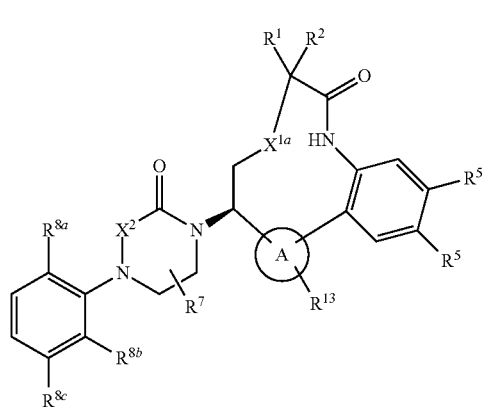

(Va)

or a stereoisomer, a tautomer, a pharmaceutically acceptable salt, thereof, wherein:

246 ring A is selected from the group consisting of

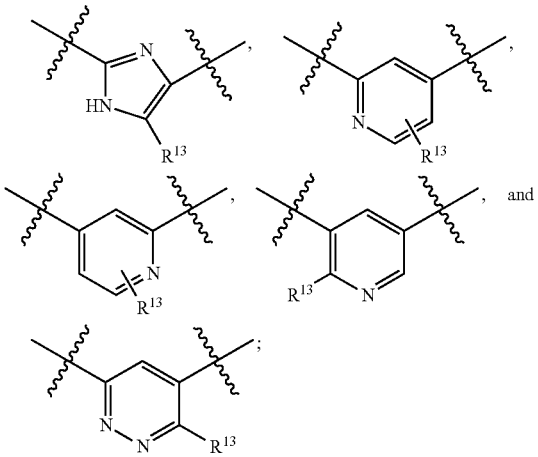

X$^{1a}$ is selected from the group consisting of CH$_2$CH$_2$ and CH═CHCH$_2$;

X$^2$ is selected from the group consisting of CHR$^{11}$, and C═O;

R$^1$ is selected from the group consisting of H, methyl, ethyl;

R$^2$ is H;

R$^5$ is selected from the group consisting of NHC(O)OMe, C(O)OH and NH—R$^{15}$;

R$^7$ is selected from the group consisting of H, ═O, OH, and methyl;

R$^{8a}$ is selected from the group consisting of H, F, Cl, methyl, and CF$_3$;

R$^{8b}$ is selected from the group consisting of H and F;

R$^{8c}$ is selected from the group consisting of H and Cl;

R$^{11}$ is selected from the group consisting of H and C$_{1-4}$ alkyl;

R$^{13}$ is selected from the group consisting of H, F, Cl, and CN; and

R$^{15}$ is a 5- to 10-membered heterocycle comprising carbon atoms and 1-4 heteroatoms selected from the group consisting of N, NH, N(C$_{1-4}$ alkyl), O, and S(O)$_p$ optionally substituted with C$_{1-6}$ alkyl, C$_{3-6}$ cycloalkyl, —CH$_2$C(═O)OC$_{1-4}$ alkyl, —CH$_2$OC$_{1-4}$ alkyl, and ═O.

8. The compound of claim 2, wherein:

G$^1$ is selected from the group consisting of

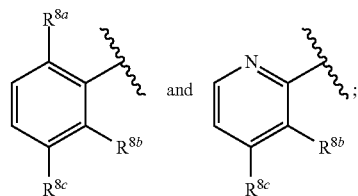

ring A is selected from the group consisting of

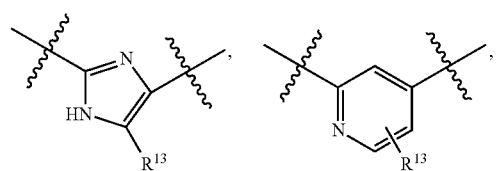

-continued

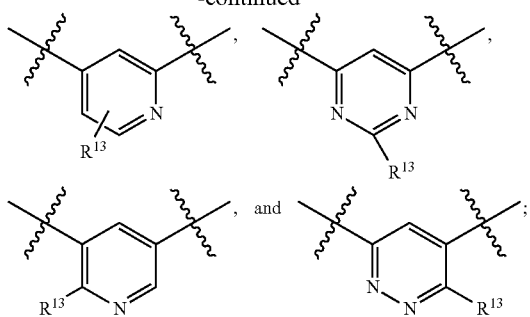

$X^{1a}$ is selected from the group consisting of $CH_2CH_2$ and $CH=CHCH_2$;

$X^2$ is selected from the group consisting of $CH_2$, $C=O$, $O$, and NH;

$X^3$ is CH or N; provided when $X^2$ is O or NH, $X^3$ is CH;

$R^1$ is selected from the group consisting of H, methyl, and ethyl;

$R^2$ is H;

$R^3$ is selected from the group consisting of $C(=O)OH$ and $C(=O)OMe$;

$R^4$ is H; or $R^3$ and $R^4$ together are $=O$;

$R^5$ is selected from the group consisting of $NHC(=O)OMe$, $C(=O)OH$, and $NHC(=O)O(CH_2)_2OCH_3$;

$R^7$ is selected from the group consisting of H, methyl, $=O$, and OH;

$R^{8a}$ is selected from the group consisting of H, F, Cl, Br, CN, $CH_3$, $OCH_3$, $CF_3$, and $OCHF_2$;

$R^{8b}$ is selected from the group consisting of H and F;

$R^{8c}$ is selected from the group consisting of H, Cl, $CH_3$, and $OCH_3$;

$R^{12}$ is selected from the group consisting of H, and $^2H$; and $R^{13}$ is selected from the group consisting of H, F, Cl, $OCH_3$, and CN.

9. A pharmaceutical composition comprising one or more compounds according to claim 1 and a pharmaceutically acceptable carrier or diluent.

10. A method for the treatment and/or prophylaxis of a thromboembolic disorder, comprising: administering to a patient in need thereof a therapeutically effective amount of a compound of claim 1, or a stereoisomer, a tautomer, or a pharmaceutically acceptable salt thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

12. A method according to claim 11, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

* * * * *